(12) United States Patent
Sommer et al.

(10) Patent No.: US 11,747,351 B2
(45) Date of Patent: Sep. 5, 2023

(54) ASSAYS TO MONITOR BLEEDING DISORDERS

(71) Applicant: BIOVERATIV THERAPEUTICS INC., Waltham, MA (US)

(72) Inventors: Jurg Sommer, Wayland, MA (US); Haiyan Jiang, Belmont, MA (US); Xin Zhang, Weston, MA (US); Buyue Yang, Arlington, MA (US); Glenn Pierce, Rancho Santa Fe, CA (US)

(73) Assignee: BIOVERATIV THERAPEUTICS INC., Waltham, MA (US)

( * ) Notice: Subject to any disclaimer, the term of this patent is extended or adjusted under 35 U.S.C. 154(b) by 697 days.

(21) Appl. No.: 16/848,445

(22) Filed: Apr. 14, 2020

(65) Prior Publication Data

US 2020/0386774 A1 Dec. 10, 2020

Related U.S. Application Data

(62) Division of application No. 14/234,789, filed as application No. PCT/US2012/048191 on Jul. 25, 2012, now Pat. No. 10,656,167.

(60) Provisional application No. 61/668,911, filed on Jul. 6, 2012, provisional application No. 61/596,902, filed on Feb. 9, 2012, provisional application No. 61/568,986, filed on Dec. 9, 2011, provisional application No. 61/522,560, filed on Aug. 11, 2011, provisional application No. 61/511,207, filed on Jul. 25, 2011.

(51) Int. Cl.
*G01N 33/86* (2006.01)
*C12N 9/64* (2006.01)

(52) U.S. Cl.
CPC ............. *G01N 33/86* (2013.01); *C12N 9/644* (2013.01); *G01N 2333/755* (2013.01); *G01N 2333/9645* (2013.01); *G01N 2333/974* (2013.01)

(58) Field of Classification Search
None
See application file for complete search history.

(56) References Cited

U.S. PATENT DOCUMENTS

| | | | |
|---|---|---|---|
| 4,757,006 A | 7/1988 | Toole, Jr. et al. |
| 4,868,112 A | 9/1989 | Toole, Jr. |
| 4,965,199 A | 10/1990 | Capon et al. |
| 4,994,371 A | 2/1991 | Davie et al. |
| 5,004,803 A | 4/1991 | Kaufman et al. |
| 5,112,950 A | 5/1992 | Meulien et al. |
| 5,171,844 A | 12/1992 | Van Ooyen et al. |
| 5,364,771 A | 11/1994 | Lollar et al. |
| 5,543,502 A | 4/1996 | Nordfang et al. |
| 5,595,886 A | 1/1997 | Chapman et al. |
| 5,610,278 A | 3/1997 | Nordfang et al. |
| 5,789,203 A | 8/1998 | Chapman et al. |
| 5,859,204 A | 1/1999 | Lollar |
| 5,972,885 A | 10/1999 | Spira et al. |
| 6,048,720 A | 4/2000 | Dalborg et al. |
| 6,060,447 A | 5/2000 | Chapman et al. |
| 6,228,620 B1 | 5/2001 | Chapman et al. |
| 6,251,632 B1 | 6/2001 | Lillicrap et al. |
| 6,316,226 B1 | 11/2001 | Van Ooyen et al. |
| 6,346,513 B1 | 2/2002 | Van Ooyen et al. |
| 6,376,463 B1 | 4/2002 | Lollar |
| 6,458,563 B1 | 10/2002 | Lollar |
| 6,686,179 B2 | 2/2004 | Fleer et al. |
| 7,041,635 B2 | 5/2006 | Kim et al. |
| 7,348,004 B2 | 3/2008 | Peters et al. |
| 7,381,408 B2 | 6/2008 | Mezo et al. |
| 7,404,956 B2 | 7/2008 | Peters et al. |
| 7,592,010 B2 | 9/2009 | Rosen et al. |
| 7,820,162 B2 | 10/2010 | Mezo et al. |
| 7,862,820 B2 | 1/2011 | Peters et al. |
| 8,329,182 B2 | 12/2012 | Peters et al. |
| 8,449,884 B2 | 5/2013 | Rivera et al. |
| 8,455,439 B2 | 6/2013 | Lu et al. |
| 8,815,250 B2 | 8/2014 | Rivera et al. |
| 10,656,167 B2 | 5/2020 | Sommer et al. |
| 2005/0100990 A1 | 5/2005 | Saenko et al. |
| 2005/0147618 A1 | 7/2005 | Rivera et al. |
| 2009/0092582 A1 | 4/2009 | Bogin et al. |
| 2009/0163699 A1 | 6/2009 | Chamberlain et al. |
| 2009/0264627 A1 | 10/2009 | Gillies et al. |
| 2010/0189682 A1 | 7/2010 | Schellenberger et al. |
| 2010/0292130 A1 | 11/2010 | Skerra et al. |

(Continued)

FOREIGN PATENT DOCUMENTS

| AU | 609829 B2 | 5/1991 |
|---|---|---|
| EP | 0295597 A2 | 12/1988 |

(Continued)

OTHER PUBLICATIONS

Buyue et al., "The Effect of Factor Xa on Thrombin Generation Activity Determination: rFIXFc Vs. BeneFIX®" Blood Nov. 18, 2011 118:2266; 2 page printout downloaded Dec. 9, 2022 from bloodjournal.org DOI: https://doi.org/10.1182/blood.V118.21.2266. 2266.*

(Continued)

*Primary Examiner* — Michael Szperka
(74) *Attorney, Agent, or Firm* — LATHROP GPM LLP; James H. Velema; James V. DeGiulio

(57) ABSTRACT

The present invention provides methods of dosing Factor VIII or Factor IX chimeric and hybrid polypeptides. The present invention further provides high-sensitivity methods of quantifying an amount of activated FIX protein in a test sample.

15 Claims, 27 Drawing Sheets

Specification includes a Sequence Listing.

(56) References Cited

U.S. PATENT DOCUMENTS

| | | |
|---|---|---|
| 2011/0046060 A1 | 2/2011 | Schellenberger et al. |
| 2011/0159540 A1 | 6/2011 | Mezo et al. |
| 2013/0108629 A1 | 5/2013 | Dumont et al. |
| 2013/0171138 A1 | 7/2013 | Peters et al. |
| 2013/0171175 A1 | 7/2013 | Pierce et al. |
| 2013/0202595 A1 | 8/2013 | Pierce et al. |
| 2013/0274194 A1 | 10/2013 | Dumont et al. |
| 2015/0044207 A1 | 2/2015 | Rivera et al. |
| 2015/0079072 A1 | 3/2015 | Sommer et al. |
| 2015/0139947 A1 | 5/2015 | Peters et al. |

FOREIGN PATENT DOCUMENTS

| | | | |
|---|---|---|---|
| EP | | 2737311 A1 | 6/2014 |
| EP | | 2950597 A1 | 12/2015 |
| WO | WO 1987/004187 A1 | | 7/1987 |
| WO | WO 1988/000831 A1 | | 7/1987 |
| WO | WO 1988/003558 A1 | | 11/1987 |
| WO | WO 1988/008035 A1 | | 4/1988 |
| WO | WO 1991/009122 A1 | | 12/1990 |
| WO | WO 1993/020093 A1 | | 4/1993 |
| WO | WO 1994/011503 A2 | | 10/1993 |
| WO | WO 2002/040544 A2 | | 5/2002 |
| WO | WO 2002/040544 A3 | | 10/2002 |
| WO | WO 2003/020764 A2 | | 3/2003 |
| WO | WO 2004/101740 A2 | | 11/2004 |
| WO | WO 2005/001025 A2 | | 1/2005 |
| WO | WO 2006/074199 A1 | | 7/2006 |
| WO | WO 2007/103515 A2 | | 9/2007 |
| WO | WO 2007/149406 A2 | | 12/2007 |
| WO | WO 2008/118507 A2 | | 10/2008 |
| WO | WO 2008/155134 A1 | | 12/2008 |
| WO | WO 2009/023270 A2 | | 2/2009 |
| WO | WO 2009/023538 A1 | | 2/2009 |
| WO | WO 2009/051717 A2 | | 4/2009 |
| WO | WO 2009/130198 A2 | | 10/2009 |
| WO | WO 2009/137254 A2 | | 11/2009 |
| WO | WO 2009/140015 A2 | | 11/2009 |
| WO | WO 2010/012451 A1 | | 2/2010 |
| WO | WO 2010/091122 A1 | | 8/2010 |
| WO | WO 2011/014570 A1 | | 2/2011 |
| WO | WO 2011/028229 A1 | | 3/2011 |
| WO | WO 2011/069164 A2 | | 6/2011 |
| WO | WO 2012/006624 A2 | | 1/2012 |
| WO | WO 2013/016454 A1 | | 1/2013 |

OTHER PUBLICATIONS

Van Veen et al., Br J Haematol. Sep. 2008;142(6):889-903. doi: 10.1111/j.1365-2141.2008.07267.x. Epub Jun. 28, 2008. PMID: 18564356.*

Depasse et al., J Thromb Haemost. Dec. 2021;19(12):2907-2917. doi: 10.1111/jth.15529. Epub Sep. 26, 2021. PMID: 34525255.*

Andersson, et al., (1975) "Purification and Characterization of Human Factor IX", Thrombosis Research, vol. 7, Issue 3, pp. 451-459.

Armour, et al., (1999) "Recombinant Human IgG Molecules Lacking Fc Gamma Receptor I Binding and Monocyte Triggering Activities", European Journal of Immunology, vol. 29, No. 8, pp. 2613-2624.

Bassus, et al., (2004) "Monitoring of FVIII Replacement Therapy with Cell-Based Monitoring Tests", Blood, vol. 104, No. 11, Part 1, pp. 3098-3098.

Brutlag, et al., (1990) "Improved Sensitivity of Biological Sequence Database Searches", Computer Applications in the Biosciences: CABIOS, vol. 6, No. 3, pp. 237-245.

Burmeister, et al., (1994) "Crystal Structure of the Complex of Rat Neonatal Fc Receptor with Fc", Nature, vol. 372, No. 6504, pp. 379-383.

Buyue, et al., (2008) "The Heparin-Binding Exosite of Factor IXa Is a Critical Regulator of Plasma Thrombin Generation and Venous Thrombosis", Blood, vol. 112, No. 8, pp. 3234-3241.

Buyue, et al., (2011) "The Effect of Factor IXa on Thrombin Generation Activity Determination: rFIXFc Vs. BeneFIX", Blood Journal vol. 118, No. 21, p. 2266.

Cameron, et al., (1998) "The Canine Factor VIII cDNA and 5' Flanking Sequence", Journal of Thrombosis and Haemostasis, vol. 79, No. 2, pp. 317-322.

Carr, et al., (2002) "Delayed, Reduced or Inhibited Thrombin Production Reduces Platelet Contractile Force and Results in Weaker Clot Formation", Blood, Coagulation and Fibrinolysis, vol. 13, No. 3, pp. 193-197.

Cutler, et al., (2002) "The Identification and Classification of 41 Novel Mutations in the Factor VIII Gene (F8c)", Human Mutation, vol. 19, No. 3, pp. 274-278.

Dobeli, et al., (1988) "Role of the Carboxy-Terminal Sequence on the Biological Activity of Human Immune Interferon (IFN-y)", Journal of Biotechnology, vol. 7, No. 3, pp. 199-216.

Eaton, et al., (1986) "Construction and Characterization of an Active Factor VIII Variant Lacking the Central One-Third of the Molecule", Biochemistry, vol. 25, No. 26, pp. 8343-8347.

Extended European Search Report received for European Patent Application No. 12817042, dated Mar. 4, 2015. 11 pages.

Friend, et al., (1999) "Phase I Study of an Engineered Aglycosylated Humanized CD3 Antibody in Renal Transplant Rejection", Transplantation, vol. 68, Issue 11, pp. 1632-1637.

Gayle, et al., (1993) "Identification of Regions in Interleukin-1 Alpha Important for Activity", Journal of Biological Chemistry, vol. 268, No. 29, pp. 22105-22111.

Gitschier, et al., (1984) "Characterization of the Human Factor VIII Gene", Nature, vol. 312, No. 5992, pp. 326-330.

Gray, et al., (1995) "Measurement of Activated Factor IX in Factor IX Concentrates: Correlation with In Vivo Thrombogenicity", Thrombosis and Haemostasis, vol. 74, No. 04, pp. 675-679.

Healey, et al., (1996) "The cDNA and Derived Amino Acid Sequence of Porcine Factor VIII", Blood, vol. 88, No. 11, pp. 4209-4214.

Hoeben, et al., (1990) "Expression of Functional Factor VIII in Primary Human Skin Fibroblasts After Retrovirus-Mediated Gene Transfer", Journal of Biological Chemistry, vol. 265, No. 13, pp. 7318-7323.

Hoffman, et al., (1995) "Factors IXa and Xa Play Distinct Roles in Tissue Factor-Dependent Initiation of Coagulation", Blood, vol. 86, No. 5, pp. 1794-1801.

International Preliminary Report on Patentability received for PCT Patent Application PCT/US2012/48191, dated Jan. 28, 2014, 7 pages.

International Search Report and Written Opinion received for PCT Patent Application PCT/US2012/48191, dated Oct. 26, 2012, 9 pages.

Kasuda, et al., (2008) "Establishment of Embryonic Stem Cells Secreting Human Factor VIII for Cell-Based Treatment of Hemophilia A", Journal of Thrombosis and Haemostasis, vol. 6, No. 8, pp. 1352-1359.

Kravtsov, et al., (2009) "Factor XI Contributes to Thrombin Generation in the Absence of Factor XII", Blood, vol. 114, No. 2, pp. 452-458.

Langner, et al., (1988) "Synthesis of Biologically Active Deletion Mutants of Human Factor VIII:C", Behring Institute Mitteilungen, No. 82, pp. 16-25.

Lundblad, et al., (2000) "Issues with the Assay of Factor VIII Activity in Plasma and Factor VIII Concentrates", Thrombosis and Haemostasis, vol. 84, No. 12, pp. 942-948.

Mannucci, et al., (2001) "The Hemophilias—From Royal Genes to Gene Therapy", New England Journal of Medicine, vol. 344, No. 23, pp. 1773-1779.

Matsumoto, et al., (2006) "The Measurement of Low Levels of Factor VIII or Factor IX in Hemophilia A and Hemophilia B Plasma by Clot Waveform Analysis and Thrombin Generation Assay", Journal of Thrombosis and Haemostasis, vol. 4, No. 2, pp. 377-384.

McCue, et al., (2009) "Application of a Novel Affinity Adsorbent for the Capture and Purification of Recombinant Factor VIII Compounds", Journal of Chromatography A, vol. 1216, No. 45, pp. 7824-7830.

(56) References Cited

OTHER PUBLICATIONS

Meulien, et al., (1988) "A New Recombinant Procoagulant Protein Derived from the cDNA Encoding Human Factor VIII", Protein Engineering, Design and Selection, vol. 2, No. 4, pp. 301-306.
Miao, et al., (2004) "Bioengineering of Coagulation Factor VIII for Improved Secretion", Blood, vol. 103, No. 9, pp. 3412-3419.
Oganesyan, et al., (2009) "Structural Characterization of a Human Fc Fragment Engineered for Extended Serum Half-Life", Molecular Immunology, vol. 46, No. 8-9, pp. 1750-1755.
Peters, et al., (2010) "Prolonged Activity of Factor IX as a Monomeric Fc Fusion Protein", Blood, vol. 115, No. 10, pp. 2057-2064.
Pipe, et al., (2011) "Functional Factor VIII Made with Von Willebrand Factor at High Levels in Transgenic Milk", Journal of Thrombosis and Haemostasis, vol. 9, No. 11, pp. 2235-2242.
Rodriguez-Merchan, Carlos E., (2003) "Management of Musculoskeletal Complications of Hemophilia", Seminars in Thrombosis and Hemostasis., vol. 29, No. 01, pp. 87-96.
Ron, et al., (1993) "Expression of Biologically Active Recombinant Keratinocyte Growth Factor. Structure/Function Analysis of Amino-Terminal Truncation Mutants", Journal of Biological Chemistry, vol. 268, No. 4, pp. 2984-2988.
Routledge, et al., (1995) "The Effect of Aglycosylation on the Immunogenicity of a Humanized Therapeutic CD3 Monoclonal Antibody", Transplantation, vol. 60, No. 8, pp. 847-853.
Sarver, et al., (1987) "Stable Expression of Recombinant Factor VIII Molecules Using a Bovine Papillomavirus Vector", DNA, vol. 6, No. 6, pp. 553-564.
Schellenberger, et al., (2009) "A Recombinant Polypeptide Extends the In Vivo Half-Life of Peptides and Proteins in a Tunable Manner", Nature Biotechnology, vol. 27, No. 12, pp. 1186-1190.
Schulte, Stefan, (2009) "Half-Life Extension Through Albumin Fusion Technologies", Thrombosis Research, vol. 124, Supplement 2, pp. S6-S8.
Shields, et al., (2001) "High Resolution Mapping of the Binding Site on Human IgG1 for Fc Gamma RI, Fc Gamma RII, Fc Gamma RIII, and FcRn and Design of IgG1 Variants with Improved Binding to the Fc Gamma R", Journal of Biological Chemistry, vol. 276, No. 9, pp. 6591-6604.
Shima, et al., (2008), "New Assays for Monitoring Haemophilia Treatment", Haemophilia, vol. 14, Suppl. 3, pp. 83-92.
Sommermeyer, et al., (1987) "Klinisch Verwendete Hydroxyethylstärke: Physikalischchemische Charakterisierung", Krankenhauspharmazie, vol. 8, No. 8, Deutscher Apotheker, pp. 271-278.
Story, et al., (1994) "A Major Histocompatibility Complex Class I-like Fc Receptor Cloned from Human Placenta: Possible Role in Transfer of Immunoglobulin G from Mother to Fetus", Journal of Experimental Medicine, vol. 180, No. 6, pp. 2377-2381.
Toole, et al., (1984) "Molecular Cloning of a cDNA Encoding Human Antihaemophilic Factor", Nature, vol. 312, No. 5992, pp. 342-347.
Toole, et al., (1986) "A Large Region (Approximately Equal to 95 kDa) of Human Factor VIII Is Dispensable for In Vitro Procoagulant Activity", Proceedings of the National Academy of Sciences, vol. 83, No. 16, pp. 5939-5942.
U.S. Appl. No. 61/668,889, filed Jul. 6, 2012.
Vaccaro, et al., (2005) "Engineering the Fc Region of Immunoglobulin G to Modulate In Vivo Antibody Levels", Nature Biotechnology, vol. 23, No. 10, pp. 1283-1288.
Vehar, et al., (1984) "Structure of Human Factor VIII", Nature, vol. 312, No. 5992, pp. 337-342.
Ward, et al., (1995) "The Effector Functions of Immunoglobulins: Implications for Therapy", Therapeutic immunology, vol. 2, No. 2, pp. 77-94.
Weidler, et al., (1991) "Pharmacokinetic Parameters as Criteria for Clinical Use of Hydroxyethyl Starch Preparations", Arzneimittelforschung/Drug Research, vol. 41, No. 5, pp. 494-498.
Wood, et al., (1984) "Expression of Active Human Factor VIII from Recombinant DNA Clones", Nature, vol. 312, No. 5992, pp. 330-337.

\* cited by examiner

In standard TGA: 1 IU/mL rFIXFc + 20 pM FIXa has same peak thrombin generation as 1 IU/mL BeneFIX

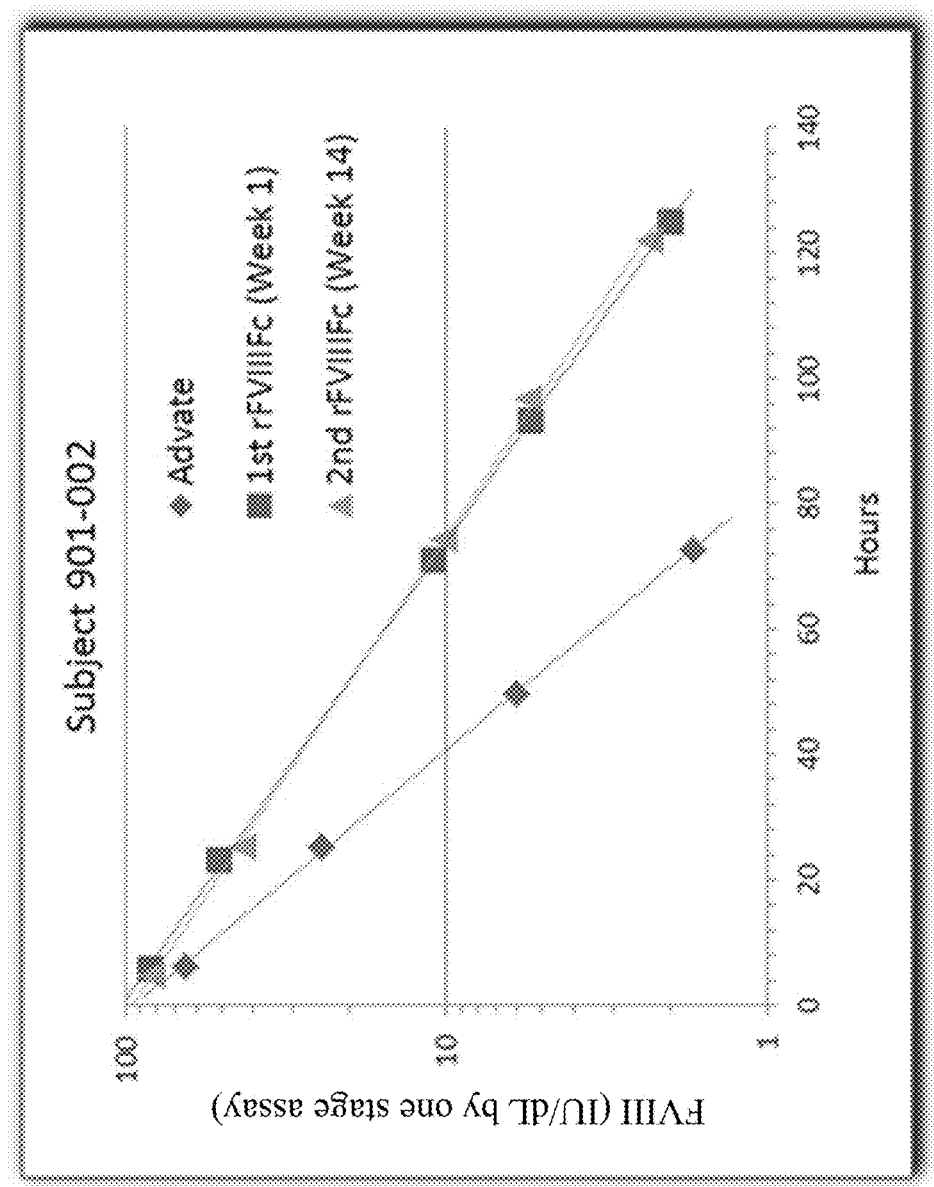
FIG. 5: Pharmacokinetics of rFVIIIFc by Activity (One-stage Assay)

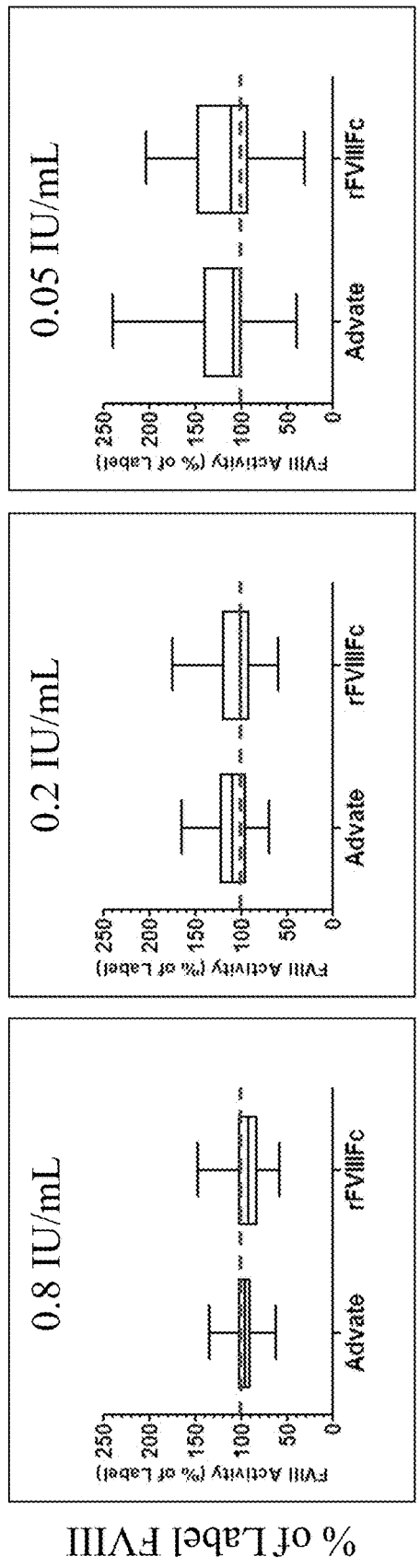
Figure 14: Performance of rFVIIIFc in Field Studies (One-Stage Clotting Assay, n=30 labs)
N = 30 labs x 3 replicate tests. Median result, 25% and 75 percentile and Min/Max as percent of nominal (label) activity.
|  | Label Activity (IU/mL) | Mean Recovery (n=90) | Mean Intra-lab %CV (n=3 per lab) | Inter-Lab %CV (n=30) |
|---|---|---|---|---|
| Advate | 0.8 | 96.7% | 6.3% | 10% |
|  | 0.2 | 110.2% | 7.8% | 19% |
|  | 0.05 | 118.1% | 7.4% | 34% |
| rFVIIIFc | 0.87 | 94.6% | 6.0% | 16% |
|  | 0.22 | 106.0% | 8.7% | 17% |
|  | 0.054 | 115.7% | 10.3% | 31% |

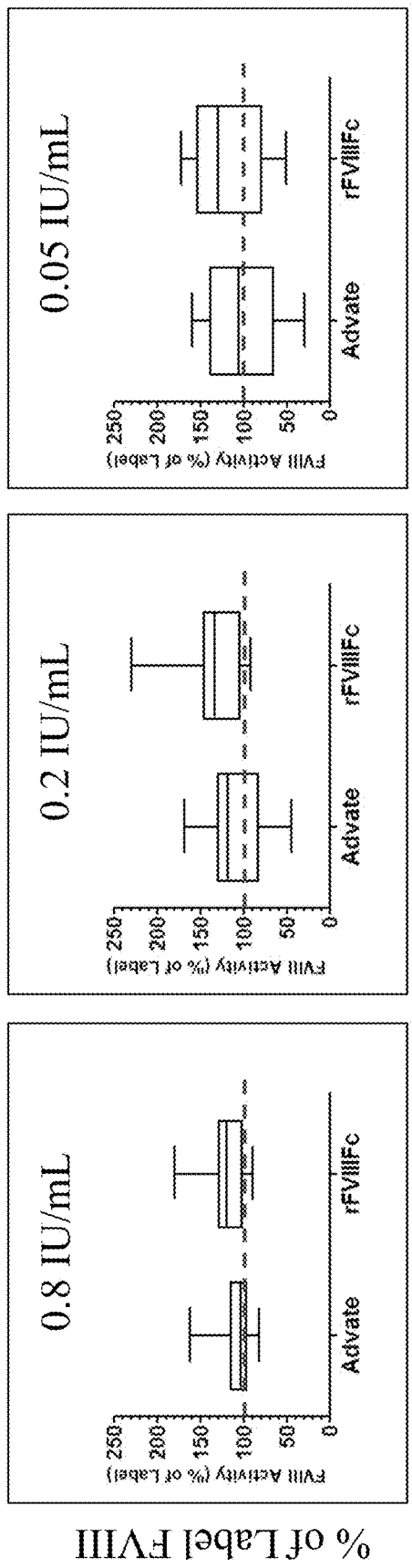
Figure 15 Performance of rFVIIIFc in Field Studies (Chromogenic Assay, n=11 labs)
N = 11 labs x 3 replicate tests. Median result, 25% and 75 percentile and Min/Max as percent of nominal (label) activity.
| | Label Activity (IU/mL) | Mean Recovery (n=33) | Mean Intra-Lab %CV (n=3 per lab) | Inter-Lab %CV (n=11) |
|---|---|---|---|---|
| Advate | 0.8 | 108% | 4.4% | 18% |
| | 0.2 | 112% | 11.7% | 26% |
| | 0.05 | 102% | 12.5% | 38% |
| rFVIIIFc | 0.87 | 119% | 2.9% | 19% |
| | 0.22 | 133% | 7.0% | 23% |
| | 0.054 | 120% | 8.3% | 31% |

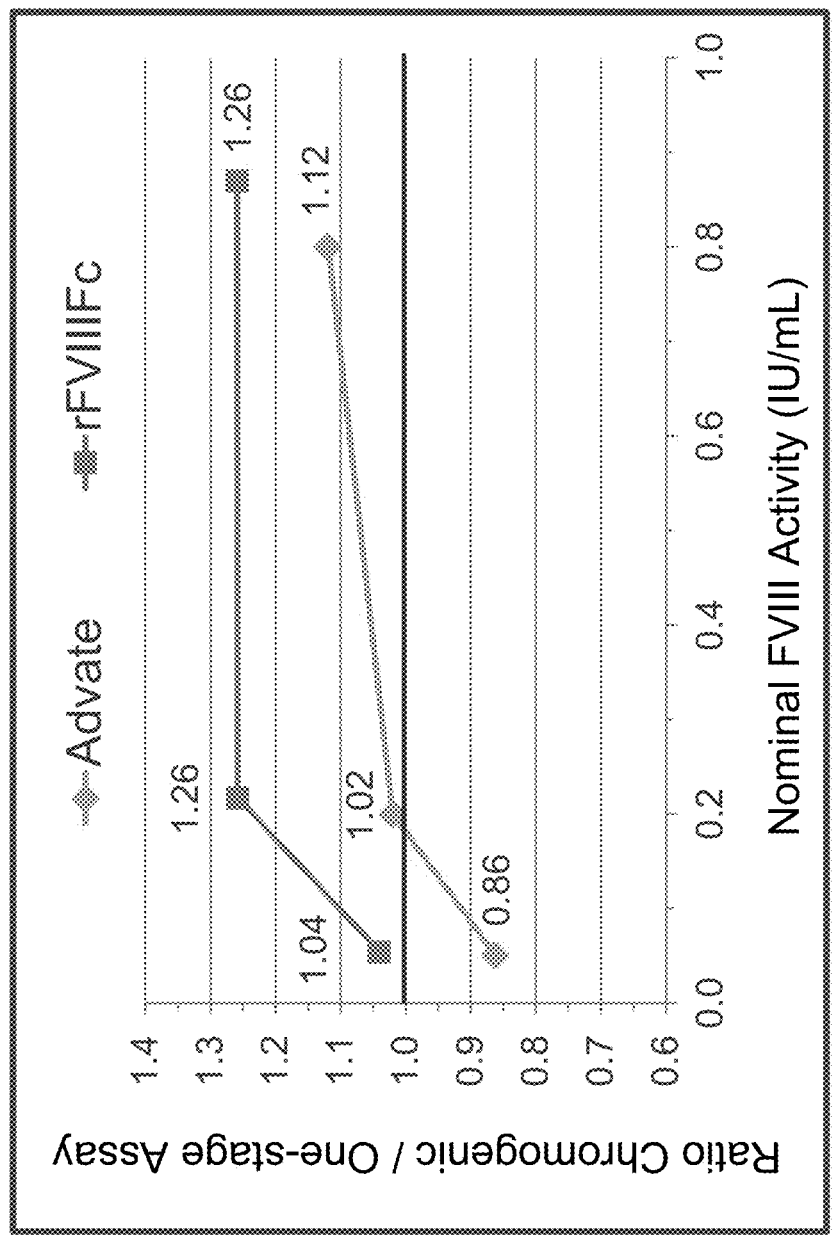
Figure 16: Chromogenic / One-Stage Assay Ratio in Clinical Assays

SEQUENCE LISTING

```
<160> NUMBER OF SEQ ID NOS: 21

<210> SEQ ID NO 1
<211> LENGTH: 5052
<212> TYPE: DNA
<213> ORGANISM: Artificial Sequence
<220> FEATURE:
<223> OTHER INFORMATION: B-Domain Deleted FVIIIFc Chain
<220> FEATURE:
<221> NAME/KEY: misc_feature
<222> LOCATION: (1)..(57)
<223> OTHER INFORMATION: FVIII signal
<220> FEATURE:
<221> NAME/KEY: misc_feature
<222> LOCATION: (4372)..(5052)
<223> OTHER INFORMATION: Fc region

<400> SEQUENCE: 1
atgcaaatag agctctccac ctgcttcttt ctgtgccttt gcgattctg ctttagtgcc      60 accagaagat actacctggg tgcagtggaa ctgtcatggg actatatgca aagtgatctc    120
ggtgagctgc ctgtggacgc aagatttcct cctagagtgc caaatctttt ccattcaac    180 acctcagtcg tgtacaaaaa gactctgttt gtagaattca cggatcacct tttcaacatc    240
gctaagccaa ggccaccctg gatgggtctg ctaggtccta ccatccaggc tgaggtttat    300
gatacagtgg tcattacact taagaacatg gcttcccatc ctgtcagtct tcatgctgtt    360
ggtgtatcct actggaaagc ttctgaggga gctgaatatg atgatcagac cagtcaaagg    420
gagaaagaag atgataaagt cttccctggt ggaagccata catatgtctg gcaggtcctg    480
```

```
aaagagaatg gtccaatggc ctctgaccca ctgtgcctta cctactcata tctttctcat    540
gtggacctgg taaaagactt gaattcaggc ctcattggag ccctactagt atgtagagaa    600
gggagtctgg ccaaggaaaa gacacagacc ttgcacaaat ttatactact ttttgctgta    660
tttgatgaag ggaaaagttg gcactcagaa acaaagaact ccttgatgca ggatagggat    720
gctgcatctg ctcgggcctg gcctaaaatg cacacagtca atggttatgt aaacaggtct    780
ctgccaggtc tgattggatg ccacaggaaa tcagtctatt ggcatgtgat tggaatgggc    840
accactcctg aagtgcactc aatattcctc gaaggtcaca catttcttgt gaggaaccat    900
cgccaggcgt ccttggaaat ctcgccaata actttcctta ctgctcaaac actcttgatg    960
gaccttggac agtttctact gttttgtcat atctcttccc accaacatga tggcatggaa   1020
gcttatgtca aagtagacag ctgtccagag aaccccaac tacgaatgaa aaataatgaa    1080
gaagcggaag actatgatga tgatcttact gattctgaaa tggatgtggt caggtttgat   1140
gatgacaact ctccttcctt tatccaaatt cgctcagttg ccaagaagca tcctaaaact   1200
tgggtacatt acattgctgc tgaagaggag gactgggact atgctcccett agtcctcgcc   1260
cccgatgaca gaagttataa aagtcaatat ttgaacaatg gccctcagcg gattggtagg   1320
aagtacaaaa aagtccgatt tatggcatac acagatgaaa cctttaagac tcgtgaagct   1380
attcagcatg aatcaggaat cttgggacct ttactttatg gggaagttgg agacacactg   1440
ttgattatat ttaagaatca agcaagcaga ccatataaca tctaccctca cggaatcact   1500
gatgtccgtc ctttgtattc aaggagatta ccaaaaggtg taaaacattt gaaggatttt   1560
ccaattctgc caggagaaat attcaaatat aaatggacag tgactgtaga agatgggcca   1620
actaaatcag atcctcggtg cctgacccgc tattactcta gtttcgttaa tatggagaga   1680
gatctagctt caggactcat tggccctctc ctcatctgct acaaagaatc tgtagatcaa   1740
agaggaaacc agataatgtc agacaagagg aatgtcatcc tgttttctgt atttgatgag   1800
aaccgaagct ggtacctcac agagaatata caacgctttc tccccaatcc agctggagtg   1860
cagcttgagg atccagagtt ccaagcctcc aacatcatgc acagcatcaa tggctatgtt   1920
tttgatagtt tgcagttgtc agtttgtttg catgaggtgg catactggta cattctaagc   1980
attggagcac agactgactt cctttctgtc ttcttctctg gatataccett caaacacaaa   2040
atggtctatg aagacacact caccctattc ccattctcag agaaactgt cttcatgtcg   2100
atggaaaacc caggtctatg gattctgggg tgccacaact cagactttcg gaacagaggc   2160
atgaccgcct tactgaaggt ttctagttgt gacaagaaca ctggtgatta ttacgaggac   2220
agttatgaag atatttcagc atacttgctg agtaaaaaca atgccattga accaagaagc   2280
ttctctcaaa acccaccagt cttgaaacgc atcaacggg aaataactcg tactactctt   2340
cagtcagatc aagaggaaat tgactatgat gataccatat cagttgaaat gaagaaggaa   2400
gattttgaca tttatgatga ggatgaaaat cagagccccc gcagctttca aaagaaaaca   2460
cgacactatt ttattgctgc agtggagagg ctctgggatt atgggatgag tagctcccca   2520
catgttctaa gaaacagggc tcagagtggc agtgtccctc agttcaagaa agttgttttc   2580
caggaattta ctgatggctc ctttactcag ccccttatacc gtggagaact aaatgaacat   2640
ttgggactcc tggggccata tataagagca gaagttgaag ataatatcat ggtaactttc   2700
agaaatcagg cctctcgtcc ctattccttc tattctagcc ttatttctta tgaggaagat   2760
cagaggcaag gagcagaacc tagaaaaaac tttgtcaagc ctaatgaaac caaaacttac   2820
```

-continued

```
ttttggaaag tgcaacatca tatggcaccc actaaagatg agtttgactg caaagcctgg   2880
gcttatttct ctgatgttga cctggaaaaa gatgtgcact caggcctgat tggacccctt   2940
ctggtctgcc acactaacac actgaaccct gctcatggga gacaagtgac agtacaggaa   3000
tttgctctgt tttcaccat ctttgatgag accaaaagct ggtacttcac tgaaaatatg   3060
gaaagaaact gcagggctcc ctgcaatatc cagatggaag atcccacttt taaagagaat   3120
tatcgcttcc atgcaatcaa tggctacata atggatacac tacctggctt agtaatggct   3180
caggatcaaa ggattcgatg gtatctgctc agcatgggca gcaatgaaaa catccattct   3240
attcatttca gtggacatgt gttcactgta cgaaaaaaag aggagtataa aatggcactg   3300
tacaatctct atccaggtgt ttttgagaca gtggaaatgt taccatccaa agctggaatt   3360
tggcgggtgg aatgccttat tggcgagcat ctacatgctg ggatgagcac actttttctg   3420
gtgtacagca ataagtgtca gactcccctg ggaatggctt ctggacacat tagagatttt   3480
cagattacag cttcaggaca atatggacag tgggccccaa agctggccag acttcattat   3540
tccggatcaa tcaatgcctg gagcaccaag gagccctttt cttggatcaa ggtggatctg   3600
ttggcaccaa tgattattca cggcatcaag acccagggtg cccgtcagaa gttctccagc   3660
ctctacatct ctcagtttat catcatgtat agtcttgatg ggaagaagtg gcagacttat   3720
cgaggaaatt ccactggaac cttaatggtc ttctttggca atgtggattc atctgggata   3780
aaacacaata tttttaaccc tccaattatt gctcgataca tccgtttgca cccaactcat   3840
tatagcattc gcagcactct tcgcatggag ttgatgggct gtgatttaaa tagttgcagc   3900
atgccattgg gaatggagag taaagcaata tcagatgcac agattactgc ttcatcctac   3960
tttaccaata tgtttgccac ctggtctcct tcaaaagctc gacttcacct ccaagggagg   4020
agtaatgcct ggagacctca ggtgaataat ccaaaagagt ggctgcaagt ggacttccag   4080
aagacaatga aagtcacagg agtaactact cagggagtaa aatctctgct taccagcatg   4140
tatgtgaagg agttcctcat ctccagcagt caagatggcc atcagtggac tctctttttt   4200
cagaatggca aagtaaaggt ttttcaggga aatcaagact ccttcacacc tgtggtgaac   4260
tctctagacc caccgttact gactcgctac cttcgaattc acccccagag ttgggtgcac   4320
cagattgccc tgaggatgga ggttctgggc tgcgaggcac aggacctcta cgacaaaact   4380
cacacatgcc caccgtgccc agctccagaa ctcctgggcg gaccgtcagt cttcctcttc   4440
cccccaaaac ccaaggacac cctcatgatc tcccggaccc ctgaggtcac atgcgtggtg   4500
gtggacgtga gccacgaaga ccctgaggtc aagttcaact ggtacgtgga cggcgtggag   4560
gtgcataatg ccaagacaaa gccgcgggag gagcagtaca acagcacgta ccgtgtggtc   4620
agcgtcctca ccgtcctgca ccaggactgg ctgaatggca aggagtacaa gtgcaaggtc   4680
tccaacaaag ccctcccagc ccccatcgag aaaaccatct ccaaagccaa agggcagccc   4740
cgagaaccac aggtgtacac cctgccccca tcccgggatg agctgaccaa gaaccaggtc   4800
agcctgacct gcctggtcaa aggcttctat cccagcgaca tcgccgtgga gtgggagagc   4860
aatgggcagc cggagaacaa ctacaagacc acgcctcccg tgttggactc cgacggctcc   4920
ttcttcctct acagcaagct caccgtggac aagagcaggt ggcagcaggg gaacgtcttc   4980
tcatgctccg tgatgcatga ggctctgcac aaccactaca cgcagaagag cctctccctg   5040
tctccgggta aa                                                        5052
```

<210> SEQ ID NO 2
<211> LENGTH: 1684

```
<212> TYPE: PRT
<213> ORGANISM: Artificial Sequence
<220> FEATURE:
<223> OTHER INFORMATION: B domain deleted FVIII-Fc chain
<220> FEATURE:
<221> NAME/KEY: MISC_FEATURE
<222> LOCATION: (1)..(19)
<223> OTHER INFORMATION: Signal
<220> FEATURE:
<221> NAME/KEY: MISC_FEATURE
<222> LOCATION: (20)..(753)
<223> OTHER INFORMATION: Heavy chain (HC)
<220> FEATURE:
<221> NAME/KEY: MISC_FEATURE
<222> LOCATION: (760)..(773)
<223> OTHER INFORMATION: B domain
<220> FEATURE:
<221> NAME/KEY: MISC_FEATURE
<222> LOCATION: (1457)..(1684)
<223> OTHER INFORMATION: Fc region

<400> SEQUENCE: 2
```

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
            85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

```
Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
                420                 425                 430

Asn Gly Pro Gln Arg Ile Gly Arg Lys Tyr Lys Lys Val Arg Phe Met
            435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
            515                 520                 525

Lys Tyr Lys Trp Thr Val Thr Val Glu Asp Gly Pro Thr Lys Ser Asp
530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
            675                 680                 685

Leu Phe Pro Phe Ser Gly Glu Thr Val Phe Met Ser Met Glu Asn Pro
        690                 695                 700

Gly Leu Trp Ile Leu Gly Cys His Asn Ser Asp Phe Arg Asn Arg Gly
705                 710                 715                 720
```

-continued

```
Met Thr Ala Leu Leu Lys Val Ser Ser Cys Asp Lys Asn Thr Gly Asp
                725                 730                 735
Tyr Tyr Glu Asp Ser Tyr Glu Asp Ile Ser Ala Tyr Leu Leu Ser Lys
            740                 745                 750
Asn Asn Ala Ile Glu Pro Arg Ser Phe Ser Gln Asn Pro Pro Val Leu
        755                 760                 765
Lys Arg His Gln Arg Glu Ile Thr Arg Thr Thr Leu Gln Ser Asp Gln
    770                 775                 780
Glu Glu Ile Asp Tyr Asp Asp Thr Ile Ser Val Glu Met Lys Lys Glu
785                 790                 795                 800
Asp Phe Asp Ile Tyr Asp Glu Asp Glu Asn Gln Ser Pro Arg Ser Phe
                805                 810                 815
Gln Lys Lys Thr Arg His Tyr Phe Ile Ala Ala Val Glu Arg Leu Trp
            820                 825                 830
Asp Tyr Gly Met Ser Ser Ser Pro His Val Leu Arg Asn Arg Ala Gln
        835                 840                 845
Ser Gly Ser Val Pro Gln Phe Lys Lys Val Val Phe Gln Glu Phe Thr
    850                 855                 860
Asp Gly Ser Phe Thr Gln Pro Leu Tyr Arg Gly Glu Leu Asn Glu His
865                 870                 875                 880
Leu Gly Leu Leu Gly Pro Tyr Ile Arg Ala Glu Val Glu Asp Asn Ile
                885                 890                 895
Met Val Thr Phe Arg Asn Gln Ala Ser Arg Pro Tyr Ser Phe Tyr Ser
            900                 905                 910
Ser Leu Ile Ser Tyr Glu Glu Asp Gln Arg Gln Gly Ala Glu Pro Arg
        915                 920                 925
Lys Asn Phe Val Lys Pro Asn Glu Thr Lys Thr Tyr Phe Trp Lys Val
    930                 935                 940
Gln His His Met Ala Pro Thr Lys Asp Glu Phe Asp Cys Lys Ala Trp
945                 950                 955                 960
Ala Tyr Phe Ser Asp Val Asp Leu Glu Lys Asp Val His Ser Gly Leu
                965                 970                 975
Ile Gly Pro Leu Leu Val Cys His Thr Asn Thr Leu Asn Pro Ala His
            980                 985                 990
Gly Arg Gln Val Thr Val Gln Glu Phe Ala Leu Phe Phe Thr Ile Phe
        995                 1000                1005
Asp Glu Thr Lys Ser Trp Tyr Phe Thr Glu Asn Met Glu Arg Asn
    1010                1015                1020
Cys Arg Ala Pro Cys Asn Ile Gln Met Glu Asp Pro Thr Phe Lys
    1025                1030                1035
Glu Asn Tyr Arg Phe His Ala Ile Asn Gly Tyr Ile Met Asp Thr
    1040                1045                1050
Leu Pro Gly Leu Val Met Ala Gln Asp Gln Arg Ile Arg Trp Tyr
    1055                1060                1065
Leu Leu Ser Met Gly Ser Asn Glu Asn Ile His Ser Ile His Phe
    1070                1075                1080
Ser Gly His Val Phe Thr Val Arg Lys Lys Glu Glu Tyr Lys Met
    1085                1090                1095
Ala Leu Tyr Asn Leu Tyr Pro Gly Val Phe Glu Thr Val Glu Met
    1100                1105                1110
Leu Pro Ser Lys Ala Gly Ile Trp Arg Val Glu Cys Leu Ile Gly
    1115                1120                1125
Glu His Leu His Ala Gly Met Ser Thr Leu Phe Leu Val Tyr Ser
```

```
            1130                1135                1140
Asn Lys Cys Gln Thr Pro Leu Gly Met Ala Ser Gly His Ile Arg
    1145                1150                1155
Asp Phe Gln Ile Thr Ala Ser Gly Gln Tyr Gly Gln Trp Ala Pro
    1160                1165                1170
Lys Leu Ala Arg Leu His Tyr Ser Gly Ser Ile Asn Ala Trp Ser
    1175                1180                1185
Thr Lys Glu Pro Phe Ser Trp Ile Lys Val Asp Leu Leu Ala Pro
    1190                1195                1200
Met Ile Ile His Gly Ile Lys Thr Gln Gly Ala Arg Gln Lys Phe
    1205                1210                1215
Ser Ser Leu Tyr Ile Ser Gln Phe Ile Ile Met Tyr Ser Leu Asp
    1220                1225                1230
Gly Lys Lys Trp Gln Thr Tyr Arg Gly Asn Ser Thr Gly Thr Leu
    1235                1240                1245
Met Val Phe Phe Gly Asn Val Asp Ser Ser Gly Ile Lys His Asn
    1250                1255                1260
Ile Phe Asn Pro Pro Ile Ile Ala Arg Tyr Ile Arg Leu His Pro
    1265                1270                1275
Thr His Tyr Ser Ile Arg Ser Thr Leu Arg Met Glu Leu Met Gly
    1280                1285                1290
Cys Asp Leu Asn Ser Cys Ser Met Pro Leu Gly Met Glu Ser Lys
    1295                1300                1305
Ala Ile Ser Asp Ala Gln Ile Thr Ala Ser Ser Tyr Phe Thr Asn
    1310                1315                1320
Met Phe Ala Thr Trp Ser Pro Ser Lys Ala Arg Leu His Leu Gln
    1325                1330                1335
Gly Arg Ser Asn Ala Trp Arg Pro Gln Val Asn Asn Pro Lys Glu
    1340                1345                1350
Trp Leu Gln Val Asp Phe Gln Lys Thr Met Lys Val Thr Gly Val
    1355                1360                1365
Thr Thr Gln Gly Val Lys Ser Leu Leu Thr Ser Met Tyr Val Lys
    1370                1375                1380
Glu Phe Leu Ile Ser Ser Ser Gln Asp Gly His Gln Trp Thr Leu
    1385                1390                1395
Phe Phe Gln Asn Gly Lys Val Lys Val Phe Gln Gly Asn Gln Asp
    1400                1405                1410
Ser Phe Thr Pro Val Val Asn Ser Leu Asp Pro Pro Leu Leu Thr
    1415                1420                1425
Arg Tyr Leu Arg Ile His Pro Gln Ser Trp Val His Gln Ile Ala
    1430                1435                1440
Leu Arg Met Glu Val Leu Gly Cys Glu Ala Gln Asp Leu Tyr Asp
    1445                1450                1455
Lys Thr His Thr Cys Pro Pro Cys Pro Ala Pro Glu Leu Leu Gly
    1460                1465                1470
Gly Pro Ser Val Phe Leu Phe Pro Pro Lys Pro Lys Asp Thr Leu
    1475                1480                1485
Met Ile Ser Arg Thr Pro Glu Val Thr Cys Val Val Val Asp Val
    1490                1495                1500
Ser His Glu Asp Pro Glu Val Lys Phe Asn Trp Tyr Val Asp Gly
    1505                1510                1515
Val Glu Val His Asn Ala Lys Thr Lys Pro Arg Glu Glu Gln Tyr
    1520                1525                1530
```

```
Asn Ser Thr Tyr Arg Val Val Ser Val Leu Thr Val Leu His Gln
    1535                1540                1545

Asp Trp Leu Asn Gly Lys Glu Tyr Lys Cys Lys Val Ser Asn Lys
1550                1555                1560

Ala Leu Pro Ala Pro Ile Glu Lys Thr Ile Ser Lys Ala Lys Gly
1565                1570                1575

Gln Pro Arg Glu Pro Gln Val Tyr Thr Leu Pro Pro Ser Arg Asp
1580                1585                1590

Glu Leu Thr Lys Asn Gln Val Ser Leu Thr Cys Leu Val Lys Gly
1595                1600                1605

Phe Tyr Pro Ser Asp Ile Ala Val Glu Trp Glu Ser Asn Gly Gln
1610                1615                1620

Pro Glu Asn Asn Tyr Lys Thr Thr Pro Pro Val Leu Asp Ser Asp
1625                1630                1635

Gly Ser Phe Phe Leu Tyr Ser Lys Leu Thr Val Asp Lys Ser Arg
1640                1645                1650

Trp Gln Gln Gly Asn Val Phe Ser Cys Ser Val Met His Glu Ala
1655                1660                1665

Leu His Asn His Tyr Thr Gln Lys Ser Leu Ser Leu Ser Pro Gly
1670                1675                1680

Lys
```

<210> SEQ ID NO 3
<211> LENGTH: 741
<212> TYPE: DNA
<213> ORGANISM: Artificial Sequence
<220> FEATURE:
<223> OTHER INFORMATION: Fc region
<220> FEATURE:
<221> NAME/KEY: misc_signal
<222> LOCATION: (1)..(60)
<223> OTHER INFORMATION: Mouse Ig kappa signal

<400> SEQUENCE: 3

```
atggagacag acacactcct gctatgggta ctgctgctct ggttccagg ttccactggt    60 gacaaaactc acacatgccc accgtgccca gcacctgaac tcctgggagg accgtcagtc   120
ttcctcttcc ccccaaaacc caaggacacc ctcatgatct cccggacccc tgaggtcaca   180
tgcgtggtgg tggacgtgag ccacgaagac cctgaggtca agttcaactg gtacgtggac   240
ggcgtggagg tgcataatgc caagacaaag ccgcgggagg agcagtacaa cagcacgtac   300
cgtgtggtca gcgtcctcac cgtcctgcac caggactggc tgaatggcaa ggagtacaag   360
tgcaaggtct ccaacaaagc cctcccagcc cccatcgaga aaccatctc caaagccaaa    420 gggcagcccc gagaaccaca ggtgtacacc ctgcccccat cccgcgatga gctgaccaag   480
aaccaggtca gcctgacctg cctggtcaaa ggcttctatc ccagcgacat cgccgtggag   540
tgggagagca atgggcagcc ggagaacaac tacaagacca cgcctcccgt gttggactcc   600
gacggctcct tcttcctcta cagcaagctc accgtggaca agagcaggtg gcagcagggg   660
aacgtcttct catgctccgt gatgcatgag gctctgcaca accactacac gcagaagagc   720
ctctccctgt ctccgggtaa a                                             741
```

<210> SEQ ID NO 4
<211> LENGTH: 247
<212> TYPE: PRT
<213> ORGANISM: Artificial Sequence
<220> FEATURE:

```
<223> OTHER INFORMATION: Fc chain
<220> FEATURE:
<221> NAME/KEY: MISC_FEATURE
<222> LOCATION: (1)..(20)
<223> OTHER INFORMATION: heterologous signal from Mouse Ig kappa chain

<400> SEQUENCE: 4

Met Glu Thr Asp Thr Leu Leu Leu Trp Val Leu Leu Leu Trp Val Pro
1               5                   10                  15

Gly Ser Thr Gly Asp Lys Thr His Thr Cys Pro Pro Cys Pro Ala Pro
            20                  25                  30

Glu Leu Leu Gly Gly Pro Ser Val Phe Leu Phe Pro Pro Lys Pro Lys
        35                  40                  45

Asp Thr Leu Met Ile Ser Arg Thr Pro Glu Val Thr Cys Val Val Val
    50                  55                  60

Asp Val Ser His Glu Asp Pro Glu Val Lys Phe Asn Trp Tyr Val Asp
65                  70                  75                  80

Gly Val Glu Val His Asn Ala Lys Thr Lys Pro Arg Glu Glu Gln Tyr
                85                  90                  95

Asn Ser Thr Tyr Arg Val Val Ser Val Leu Thr Val Leu His Gln Asp
            100                 105                 110

Trp Leu Asn Gly Lys Glu Tyr Lys Cys Lys Val Ser Asn Lys Ala Leu
        115                 120                 125

Pro Ala Pro Ile Glu Lys Thr Ile Ser Lys Ala Lys Gly Gln Pro Arg
    130                 135                 140

Glu Pro Gln Val Tyr Thr Leu Pro Pro Ser Arg Asp Glu Leu Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
    210                 215                 220

Cys Ser Val Met His Glu Ala Leu His Asn His Tyr Thr Gln Lys Ser
225                 230                 235                 240

Leu Ser Leu Ser Pro Gly Lys
                245

<210> SEQ ID NO 5
<211> LENGTH: 7734
<212> TYPE: DNA
<213> ORGANISM: Artificial Sequence
<220> FEATURE:
<223> OTHER INFORMATION: Full length FVIIIFc
<220> FEATURE:
<221> NAME/KEY: misc_signal
<222> LOCATION: (1)..(57)
<223> OTHER INFORMATION: FVIII signal
<220> FEATURE:
<221> NAME/KEY: misc_feature
<222> LOCATION: (7054)..(7734)
<223> OTHER INFORMATION: Fc region

<400> SEQUENCE: 5
atgcaaatag agctctccac ctgcttcttt ctgtgccttt tgcgattctg ctttagtgcc      60
accagaagat actacctggg tgcagtggaa ctgtcatggg actatatgca aagtgatctc     120
ggtgagctgc ctgtggacgc aagatttcct cctagagtgc caaaatcttt tccattcaac     180
```

```
acctcagtcg tgtacaaaaa gactctgttt gtagaattca cggatcacct tttcaacatc    240
gctaagccaa ggccaccctg gatgggtctg ctaggtccta ccatccaggc tgaggtttat    300
gatacagtgg tcattacact taagaacatg gcttcccatc ctgtcagtct tcatgctgtt    360
ggtgtatcct actggaaagc ttctgaggga gctgaatatg atgatcagac cagtcaaagg    420
gagaaagaag atgataaagt cttccctggt ggaagccata catatgtctg gcaggtcctg    480
aaagagaatg gtccaatggc ctctgaccca ctgtgcctta cctactcata tctttctcat    540
gtggacctgg taaaagactt gaattcaggc ctcattggag ccctactagt atgtagagaa    600
gggagtctgg ccaaggaaaa gacacagacc ttgcacaaat ttatactact ttttgctgta    660
tttgatgaag ggaaaagttg gcactcagaa acaaagaact ccttgatgca ggatagggat    720
gctgcatctg ctcgggcctg gcctaaaatg cacacagtca atggttatgt aaacaggtct    780
ctgccaggtc tgattggatg ccacaggaaa tcagtctatt ggcatgtgat tggaatgggc    840
accactcctg aagtgcactc aatattcctc gaaggtcaca catttcttgt gaggaaccat    900
cgccaggcgt ccttggaaat ctcgccaata actttcctta ctgctcaaac actcttgatg    960
gaccttggac agtttctact gttttgtcat atctcttccc accaacatga tggcatggaa   1020
gcttatgtca agtagacag ctgtccagag aaccccaac tacgaatgaa aaataatgaa     1080
gaagcggaag actatgatga tgatcttact gattctgaaa tggatgtggt caggtttgat   1140
gatgacaact ctccttcctt tatccaaatt cgctcagttg ccaagaagca tcctaaaact   1200
tgggtacatt acattgctgc tgaagaggag gactgggact atgctcccct agtcctcgcc   1260
cccgatgaca gaagttataa aagtcaatat ttgaacaatg gccctcagcg gattggtagg   1320
aagtacaaaa aagtccgatt tatggcatac acagatgaaa cctttaagac tcgtgaagct   1380
attcagcatg aatcaggaat cttgggacct ttactttatg gggaagttgg agacacactg   1440
ttgattatat ttaagaatca agcaagcaga ccatataaca tctaccctca cggaatcact   1500
gatgtccgtc ctttgtattc aaggagatta ccaaaaggtg taaaacattt gaaggatttt   1560
ccaattctgc caggagaaat attcaaatat aaatggacag tgactgtaga agatgggcca   1620
actaaatcag atcctcggtg cctgacccgc tattactcta gtttcgttaa tatggagaga   1680
gatctagctt caggactcat tggccctctc ctcatctgct acaaagaatc tgtagatcaa   1740
agaggaaacc agataatgtc agacaagagg aatgtcatcc tgttttctgt atttgatgag   1800
aaccgaagct ggtacctcac agagaatata caacgctttc tccccaatcc agctggagtg   1860
cagcttgagg atccagagtt ccaagcctcc aacatcatgc acagcatcaa tggctatgtt   1920
tttgatagtt tgcagttgtc agtttgtttg catgaggtgg catactggta cattctaagc   1980
attggagcac agactgactt cctttctgtc ttcttctctg gatataccct caaacacaaa   2040
atggtctatg aagacacact caccctattc ccattctcag agaaactgt cttcatgtcg    2100 atggaaaacc caggtctatg gattctgggg tgccacaact cagactttcg gaacagaggc   2160
atgaccgcct tactgaaggt ttctagttgt gacaagaaca ctggtgatta ttacgaggac   2220
agttatgaag atatttcagc atacttgctg agtaaaaaca atgccattga accaagaagc   2280 ttctctcccaga attcaagaca ccctagcact aggcaaaagc aatttaatgc caccacaatt  2340
ccagaaaatg acatagagaa gactgaccct tggtttgcac acagaacacc tatgcctaaa   2400
atacaaaatg tctcctctag tgatttgttg atgctcttgc gacagagtcc tactccacat   2460
gggctatcct tatctgatct ccaagaagcc aaatatgaga cttttctga tgatccatca    2520
```

```
cctggagcaa tagacagtaa taacagcctg tctgaaatga cacacttcag gccacagctc    2580
catcacagtg gggacatggt atttacccct gagtcaggcc tccaattaag attaaatgag    2640
aaactgggga caactgcagc aacagagttg aagaaacttg atttcaaagt ttctagtaca    2700
tcaaataatc tgatttcaac aattccatca gacaatttgg cagcaggtac tgataataca    2760
agttccttag gacccccaag tatgccagtt cattatgata gtcaattaga taccactcta    2820
tttggcaaaa agtcatctcc ccttactgag tctggtggac ctctgagctt gagtgaagaa    2880
aataatgatt caaagttgtt agaatcaggt ttaatgaata gccagaaaag ttcatgggga    2940
aaaaatgtat cgtcaacaga gagtggtagg ttatttaaag ggaaaagagc tcatggacct    3000
gctttgttga ctaaagataa tgccttattc aaagttagca tctctttgtt aaagacaaac    3060
aaaacttcca ataattcagc aactaataga aagactcaca ttgatggccc atcattatta    3120
attgagaata gtccatcagt ctggcaaaat atattagaaa gtgacactga gtttaaaaaa    3180
gtgacacctt tgattcatga cagaatgctt atggacaaaa atgctacagc tttgaggcta    3240
aatcatatgt caaataaaac tacttcatca aaaaacatgg aaatggtcca acagaaaaaa    3300
gagggcccca ttccaccaga tgcacaaaat ccagatatgt cgttctttaa gatgctattc    3360
ttgccagaat cagcaaggtg gatacaaagg actcatggaa agaactctct gaactctggg    3420
caaggcccca gtccaaagca attagtatcc ttaggaccag aaaaatctgt ggaaggtcag    3480
aatttcttgt ctgagaaaaa caagtggta gtaggaaagg gtgaatttac aaaggacgta    3540
ggactcaaag agatggtttt tccaagcagc agaaacctat ttcttactaa cttggataat    3600
ttacatgaaa ataatacaca caatcaagaa aaaaaaattc aggaagaaat agaaaagaag    3660
gaaacattaa tccaagagaa tgtagttttg cctcagatac atacagtgac tggcactaag    3720
aatttcatga agaaccttt cttactgagc actaggcaaa atgtagaagg ttcatatgac    3780
ggggcatatg ctccagtact tcaagatttt aggtcattaa atgattcaac aaatagaaca    3840
aagaaacaca cagctcattt ctcaaaaaaa ggggaggaag aaaacttgga aggcttggga    3900 aatcaaaacca agcaaattgt agagaaatat gcatgcacca caggatatc tcctaataca    3960 agccagcaga attttgtcac gcaacgtagt aagagagctt tgaaacaatt cagactccca    4020
ctagaagaaa cagaacttga aaaaaggata attgtggatg cacctcaac ccagtggtcc    4080 aaaaacatga acatttgac cccgagcacc ctcacacaga tagactacaa tgagaaggag    4140
aaaggggcca ttactcagtc tcccttatca gattgcctta cgaggagtca tagcatccct    4200
caagcaaata gatctccatt acccattgca aaggtatcat catttccatc tattagacct    4260
atatatctga ccagggtcct attccaagac aactcttctc atcttccagc agcatcttat    4320
agaaagaaag attctgggt ccaagaaagc agtcatttct tacaaggagc caaaaaaaat    4380
aacctttctt tagccattct aaccttggag atgactggta tcaaagaga ggttggctcc    4440 ctggggacaa gtgccacaaa ttcagtcaca tacaagaaag ttgagaacac tgttctcccg    4500
aaaccagact tgcccaaaac atctggcaaa gttgaattgc ttccaaaagt tcacatttat    4560
cagaaggacc tattccctac ggaaactagc aatgggtctc ctggccatct ggatctcgtg    4620
gaagggagcc ttcttcaggg aacagaggga gcgattaagt ggaatgaagc aaacagacct    4680
ggaaaagttc cctttctgag agtagcaaca gaaagctctg caaagactcc ctccaagcta    4740
ttggatcctc ttgcttggga taaccactat ggtactcaga taccaaaaga agagtggaaa    4800
tcccaagaga agtcaccaga aaaaacagct tttaagaaaa aggataccat tttgtccctg    4860
aacgcttgtg aaagcaatca tgcaatagca gcaataaatg agggacaaaa taagcccgaa    4920
```

```
atagaagtca cctgggcaaa gcaaggtagg actgaaaggc tgtgctctca aaacccacca    4980
gtcttgaaac gccatcaacg ggaaataact cgtactactc ttcagtcaga tcaagaggaa    5040
attgactatg atgataccat atcagttgaa atgaagaagg aagattttga catttatgat    5100
gaggatgaaa atcagagccc ccgcagcttt caaaagaaaa cacgacacta ttttattgct    5160
gcagtggaga ggctctggga ttatgggatg agtagctccc cacatgttct aagaaacagg    5220
gctcagagtg gcagtgtccc tcagttcaag aaagttgttt tccaggaatt tactgatggc    5280
tcctttactc agcccttata ccgtggagaa ctaaatgaac atttgggact cctggggcca    5340
tatataagag cagaagttga agataatatc atggtaactt tcagaaatca ggcctctcgt    5400
ccctattcct tctattctag ccttatttct tatgaggaag atcagaggca aggagcagaa    5460
cctagaaaaa actttgtcaa gcctaatgaa accaaaactt acttttggaa agtgcaacat    5520
catatggcac ccactaaaga tgagtttgac tgcaaagcct gggcttattt ctctgatgtt    5580
gacctggaaa agatgtgcac ctcaggcctg attggacccc ttctggtctg ccacactaac    5640
acactgaacc ctgctcatgg gagacaagtg acagtacagg aatttgctct gttttttcacc   5700
atctttgatg agaccaaaag ctggtacttc actgaaaata tggaaagaaa ctgcagggct    5760
ccctgcaata tccagatgga agatcccact tttaaagaga attatcgctt ccatgcaatc    5820
aatggctaca taatggatac actacctggc ttagtaatgg ctcaggatca aaggattcga    5880
tggtatctgc tcagcatggg cagcaatgaa acatccatt ctattcattt cagtggacat     5940
gtgttcactg tacgaaaaaa agaggagtat aaaatggcac tgtacaatct ctatccaggt    6000
gttttttgaga cagtggaaat gttaccatcc aaagctggaa tttggcgggt ggaatgcctt    6060
attggcgagc atctacatgc tgggatgagc acactttttc tggtgtacag caataagtgt    6120
cagactcccc tgggaatggc ttctggacac attagagatt tcagattac agcttcagga    6180
caatatggac agtgggcccc aaagctggcc agacttcatt attccggatc aatcaatgcc    6240
tggagcacca aggagccctt tcttggatc aaggtggatc tgttggcacc aatgattatt    6300
cacggcatca agacccaggg tgcccgtcag aagttctcca gcctctacat ctctcagttt    6360
atcatcatgt atagtcttga tgggaagaag tggcagactt atcgaggaaa ttccactgga    6420
accttaatgg tcttctttgg caatgtggat tcatctggga taaaacacaa tattttttaac   6480
cctccaatta ttgctcgata catccgtttg cacccaactc attatagcat tcgcagcact    6540
cttcgcatgg agttgatggg ctgtgattta aatagttgca gcatgccatt gggaatggag    6600
agtaaagcaa tatcagatgc acagattact gcttcatcct actttaccaa tatgtttgcc    6660
acctggtctc cttcaaaagc tcgacttcac ctccaaggga ggagtaatgc ctggagacct    6720
caggtgaata atccaaaaga gtggctgcaa gtggacttcc agaagacaat gaaagtcaca    6780
ggagtaacta ctcagggagt aaaatctctg cttaccagca tgtatgtgaa ggagttcctc    6840
atctccagca gtcaagatgg ccatcagtgg actctctttt ttcagaatgg caaagtaaag    6900
gttttttcagg gaaatcaaga ctccttcaca cctgtggtga actctctaga cccaccgtta    6960
ctgactcgct accttcgaat tcaccccag agttgggtgc accagattgc cctgaggatg     7020
gaggttctgg gctgcgaggc acaggacctc tacgacaaaa ctcacacatg cccacgtgc     7080
ccagctccag aactcctggg cggaccgtca gtcttcctct tccccccaaa acccaaggac    7140
accctcatga tctcccggac ccctgaggtc acatgcgtgg tggtgacgt gagccacgaa     7200
gaccctgagg tcaagttcaa ctggtacgtg gacggcgtgg aggtgcataa tgccaagaca    7260
```

-continued

| aagccgcggg aggagcagta caacagcacg taccgtgtgg tcagcgtcct caccgtcctg | 7320 |
| caccaggact ggctgaatgg caaggagtac aagtgcaagg tctccaacaa agccctccca | 7380 |
| gcccccatcg agaaaaccat ctccaaagcc aagggcagc cccgagaacc acaggtgtac | 7440 |
| accctgcccc catcccggga tgagctgacc aagaaccagg tcagcctgac ctgcctggtc | 7500 |
| aaaggcttct atcccagcga catcgccgtg gagtgggaga gcaatgggca gccggagaac | 7560 |
| aactacaaga ccacgcctcc cgtgttggac tccgacggct ccttcttcct ctacagcaag | 7620 |
| ctcaccgtgg acaagagcag gtggcagcag gggaacgtct tctcatgctc cgtgatgcat | 7680 |
| gaggctctgc acaaccacta cacgcagaag agcctctccc tgtctccggg taaa | 7734 |

<210> SEQ ID NO 6
<211> LENGTH: 2578
<212> TYPE: PRT
<213> ORGANISM: Artificial Sequence
<220> FEATURE:
<223> OTHER INFORMATION: Full length FVIIIFc chain
<220> FEATURE:
<221> NAME/KEY: MISC_FEATURE
<222> LOCATION: (1)..(19)
<223> OTHER INFORMATION: FVIII signal
<220> FEATURE:
<221> NAME/KEY: MISC_FEATURE
<222> LOCATION: (20)..(759)
<223> OTHER INFORMATION: HC
<220> FEATURE:
<221> NAME/KEY: MISC_FEATURE
<222> LOCATION: (760)..(1667)
<223> OTHER INFORMATION: B domain
<220> FEATURE:
<221> NAME/KEY: MISC_FEATURE
<222> LOCATION: (2352)..(2578)
<223> OTHER INFORMATION: Fc region

<400> SEQUENCE: 6

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
```

-continued

```
            195                 200                 205
Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620
```

```
Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
            645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
            675                 680                 685

Leu Phe Pro Phe Ser Gly Glu Thr Val Phe Met Ser Met Glu Asn Pro
        690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Ser Arg His Pro
            755                 760                 765

Ser Thr Arg Gln Lys Gln Phe Asn Ala Thr Thr Ile Pro Glu Asn Asp
770                 775                 780

Ile Glu Lys Thr Asp Pro Trp Phe Ala His Arg Thr Pro Met Pro Lys
785                 790                 795                 800

Ile Gln Asn Val Ser Ser Ser Asp Leu Leu Met Leu Leu Arg Gln Ser
                805                 810                 815

Pro Thr Pro His Gly Leu Ser Leu Ser Asp Leu Gln Glu Ala Lys Tyr
            820                 825                 830

Glu Thr Phe Ser Asp Asp Pro Ser Pro Gly Ala Ile Asp Ser Asn Asn
            835                 840                 845

Ser Leu Ser Glu Met Thr His Phe Arg Pro Gln Leu His His Ser Gly
850                 855                 860

Asp Met Val Phe Thr Pro Glu Ser Gly Leu Gln Leu Arg Leu Asn Glu
865                 870                 875                 880

Lys Leu Gly Thr Thr Ala Ala Thr Glu Leu Lys Lys Leu Asp Phe Lys
                885                 890                 895

Val Ser Ser Thr Ser Asn Asn Leu Ile Ser Thr Ile Pro Ser Asp Asn
            900                 905                 910

Leu Ala Ala Gly Thr Asp Asn Thr Ser Ser Leu Gly Pro Pro Ser Met
        915                 920                 925

Pro Val His Tyr Asp Ser Gln Leu Asp Thr Thr Leu Phe Gly Lys Lys
        930                 935                 940

Ser Ser Pro Leu Thr Glu Ser Gly Gly Pro Leu Ser Leu Ser Glu Glu
945                 950                 955                 960

Asn Asn Asp Ser Lys Leu Leu Glu Ser Gly Leu Met Asn Ser Gln Glu
            965                 970                 975

Ser Ser Trp Gly Lys Asn Val Ser Ser Thr Glu Ser Gly Arg Leu Phe
            980                 985                 990

Lys Gly Lys Arg Ala His Gly Pro Ala Leu Leu Thr Lys Asp Asn Ala
        995                 1000                1005

Leu Phe Lys Val Ser Ile Ser Leu Leu Lys Thr Asn Lys Thr Ser
    1010                1015                1020

Asn Asn Ser Ala Thr Asn Arg Lys Thr His Ile Asp Gly Pro Ser
    1025                1030                1035
```

-continued

| | | | | | | | | | | | |
|---|---|---|---|---|---|---|---|---|---|---|---|
| Leu | Leu | Ile | Glu | Asn | Ser | Pro | Ser | Val | Trp | Gln | Asn | Ile | Leu | Glu |
| 1040 | | | | | 1045 | | | | | 1050 | | | | |

Ser Asp Thr Glu Phe Lys Lys Val Thr Pro Leu Ile His Asp Arg
 1055                    1060                    1065

Met Leu Met Asp Lys Asn Ala Thr Ala Leu Arg Leu Asn His Met
 1070                    1075                    1080

Ser Asn Lys Thr Thr Ser Ser Lys Asn Met Glu Met Val Gln Gln
 1085                    1090                    1095

Lys Lys Glu Gly Pro Ile Pro Pro Asp Ala Gln Asn Pro Asp Met
 1100                    1105                    1110

Ser Phe Phe Lys Met Leu Phe Leu Pro Glu Ser Ala Arg Trp Ile
 1115                    1120                    1125

Gln Arg Thr His Gly Lys Asn Ser Leu Asn Ser Gly Gln Gly Pro
 1130                    1135                    1140

Ser Pro Lys Gln Leu Val Ser Leu Gly Pro Glu Lys Ser Val Glu
 1145                    1150                    1155

Gly Gln Asn Phe Leu Ser Glu Lys Asn Lys Val Val Val Gly Lys
 1160                    1165                    1170

Gly Glu Phe Thr Lys Asp Val Gly Leu Lys Glu Met Val Phe Pro
 1175                    1180                    1185

Ser Ser Arg Asn Leu Phe Leu Thr Asn Leu Asp Asn Leu His Glu
 1190                    1195                    1200

Asn Asn Thr His Asn Gln Glu Lys Lys Ile Gln Glu Glu Ile Glu
 1205                    1210                    1215

Lys Lys Glu Thr Leu Ile Gln Glu Asn Val Val Leu Pro Gln Ile
 1220                    1225                    1230

His Thr Val Thr Gly Thr Lys Asn Phe Met Lys Asn Leu Phe Leu
 1235                    1240                    1245

Leu Ser Thr Arg Gln Asn Val Glu Gly Ser Tyr Asp Gly Ala Tyr
 1250                    1255                    1260

Ala Pro Val Leu Gln Asp Phe Arg Ser Leu Asn Asp Ser Thr Asn
 1265                    1270                    1275

Arg Thr Lys Lys His Thr Ala His Phe Ser Lys Lys Gly Glu Glu
 1280                    1285                    1290

Glu Asn Leu Glu Gly Leu Gly Asn Gln Thr Lys Gln Ile Val Glu
 1295                    1300                    1305

Lys Tyr Ala Cys Thr Thr Arg Ile Ser Pro Asn Thr Ser Gln Gln
 1310                    1315                    1320

Asn Phe Val Thr Gln Arg Ser Lys Arg Ala Leu Lys Gln Phe Arg
 1325                    1330                    1335

Leu Pro Leu Glu Glu Thr Glu Leu Glu Lys Arg Ile Ile Val Asp
 1340                    1345                    1350

Asp Thr Ser Thr Gln Trp Ser Lys Asn Met Lys His Leu Thr Pro
 1355                    1360                    1365

Ser Thr Leu Thr Gln Ile Asp Tyr Asn Glu Lys Glu Lys Gly Ala
 1370                    1375                    1380

Ile Thr Gln Ser Pro Leu Ser Asp Cys Leu Thr Arg Ser His Ser
 1385                    1390                    1395

Ile Pro Gln Ala Asn Arg Ser Pro Leu Pro Ile Ala Lys Val Ser
 1400                    1405                    1410

Ser Phe Pro Ser Ile Arg Pro Ile Tyr Leu Thr Arg Val Leu Phe
 1415                    1420                    1425

Gln Asp Asn Ser Ser His Leu Pro Ala Ala Ser Tyr Arg Lys Lys

```
                1430               1435               1440
Asp Ser Gly Val Gln Glu Ser Ser His Phe Leu Gln Gly Ala Lys
    1445               1450               1455
Lys Asn Asn Leu Ser Leu Ala Ile Leu Thr Leu Glu Met Thr Gly
    1460               1465               1470
Asp Gln Arg Glu Val Gly Ser Leu Gly Thr Ser Ala Thr Asn Ser
    1475               1480               1485
Val Thr Tyr Lys Lys Val Glu Asn Thr Val Leu Pro Lys Pro Asp
    1490               1495               1500
Leu Pro Lys Thr Ser Gly Lys Val Glu Leu Leu Pro Lys Val His
    1505               1510               1515
Ile Tyr Gln Lys Asp Leu Phe Pro Thr Glu Thr Ser Asn Gly Ser
    1520               1525               1530
Pro Gly His Leu Asp Leu Val Glu Gly Ser Leu Leu Gln Gly Thr
    1535               1540               1545
Glu Gly Ala Ile Lys Trp Asn Glu Ala Asn Arg Pro Gly Lys Val
    1550               1555               1560
Pro Phe Leu Arg Val Ala Thr Glu Ser Ser Ala Lys Thr Pro Ser
    1565               1570               1575
Lys Leu Leu Asp Pro Leu Ala Trp Asp Asn His Tyr Gly Thr Gln
    1580               1585               1590
Ile Pro Lys Glu Glu Trp Lys Ser Gln Glu Lys Ser Pro Glu Lys
    1595               1600               1605
Thr Ala Phe Lys Lys Lys Asp Thr Ile Leu Ser Leu Asn Ala Cys
    1610               1615               1620
Glu Ser Asn His Ala Ile Ala Ala Ile Asn Glu Gly Gln Asn Lys
    1625               1630               1635
Pro Glu Ile Glu Val Thr Trp Ala Lys Gln Gly Arg Thr Glu Arg
    1640               1645               1650
Leu Cys Ser Gln Asn Pro Pro Val Leu Lys Arg His Gln Arg Glu
    1655               1660               1665
Ile Thr Arg Thr Thr Leu Gln Ser Asp Gln Glu Glu Ile Asp Tyr
    1670               1675               1680
Asp Asp Thr Ile Ser Val Glu Met Lys Lys Glu Asp Phe Asp Ile
    1685               1690               1695
Tyr Asp Glu Asp Glu Asn Gln Ser Pro Arg Ser Phe Gln Lys Lys
    1700               1705               1710
Thr Arg His Tyr Phe Ile Ala Ala Val Glu Arg Leu Trp Asp Tyr
    1715               1720               1725
Gly Met Ser Ser Ser Pro His Val Leu Arg Asn Arg Ala Gln Ser
    1730               1735               1740
Gly Ser Val Pro Gln Phe Lys Lys Val Val Phe Gln Glu Phe Thr
    1745               1750               1755
Asp Gly Ser Phe Thr Gln Pro Leu Tyr Arg Gly Glu Leu Asn Glu
    1760               1765               1770
His Leu Gly Leu Leu Gly Pro Tyr Ile Arg Ala Glu Val Glu Asp
    1775               1780               1785
Asn Ile Met Val Thr Phe Arg Asn Gln Ala Ser Arg Pro Tyr Ser
    1790               1795               1800
Phe Tyr Ser Ser Leu Ile Ser Tyr Glu Glu Asp Gln Arg Gln Gly
    1805               1810               1815
Ala Glu Pro Arg Lys Asn Phe Val Lys Pro Asn Glu Thr Lys Thr
    1820               1825               1830
```

-continued

```
Tyr Phe Trp Lys Val Gln His His Met Ala Pro Thr Lys Asp Glu
1835                1840                1845

Phe Asp Cys Lys Ala Trp Ala Tyr Phe Ser Asp Val Asp Leu Glu
1850                1855                1860

Lys Asp Val His Ser Gly Leu Ile Gly Pro Leu Leu Val Cys His
1865                1870                1875

Thr Asn Thr Leu Asn Pro Ala His Gly Arg Gln Val Thr Val Gln
1880                1885                1890

Glu Phe Ala Leu Phe Phe Thr Ile Phe Asp Glu Thr Lys Ser Trp
1895                1900                1905

Tyr Phe Thr Glu Asn Met Glu Arg Asn Cys Arg Ala Pro Cys Asn
1910                1915                1920

Ile Gln Met Glu Asp Pro Thr Phe Lys Glu Asn Tyr Arg Phe His
1925                1930                1935

Ala Ile Asn Gly Tyr Ile Met Asp Thr Leu Pro Gly Leu Val Met
1940                1945                1950

Ala Gln Asp Gln Arg Ile Arg Trp Tyr Leu Leu Ser Met Gly Ser
1955                1960                1965

Asn Glu Asn Ile His Ser Ile His Phe Ser Gly His Val Phe Thr
1970                1975                1980

Val Arg Lys Lys Glu Glu Tyr Lys Met Ala Leu Tyr Asn Leu Tyr
1985                1990                1995

Pro Gly Val Phe Glu Thr Val Glu Met Leu Pro Ser Lys Ala Gly
2000                2005                2010

Ile Trp Arg Val Glu Cys Leu Ile Gly Glu His Leu His Ala Gly
2015                2020                2025

Met Ser Thr Leu Phe Leu Val Tyr Ser Asn Lys Cys Gln Thr Pro
2030                2035                2040

Leu Gly Met Ala Ser Gly His Ile Arg Asp Phe Gln Ile Thr Ala
2045                2050                2055

Ser Gly Gln Tyr Gly Gln Trp Ala Pro Lys Leu Ala Arg Leu His
2060                2065                2070

Tyr Ser Gly Ser Ile Asn Ala Trp Ser Thr Lys Glu Pro Phe Ser
2075                2080                2085

Trp Ile Lys Val Asp Leu Leu Ala Pro Met Ile Ile His Gly Ile
2090                2095                2100

Lys Thr Gln Gly Ala Arg Gln Lys Phe Ser Ser Leu Tyr Ile Ser
2105                2110                2115

Gln Phe Ile Ile Met Tyr Ser Leu Asp Gly Lys Lys Trp Gln Thr
2120                2125                2130

Tyr Arg Gly Asn Ser Thr Gly Thr Leu Met Val Phe Phe Gly Asn
2135                2140                2145

Val Asp Ser Ser Gly Ile Lys His Asn Ile Phe Asn Pro Pro Ile
2150                2155                2160

Ile Ala Arg Tyr Ile Arg Leu His Pro Thr His Tyr Ser Ile Arg
2165                2170                2175

Ser Thr Leu Arg Met Glu Leu Met Gly Cys Asp Leu Asn Ser Cys
2180                2185                2190

Ser Met Pro Leu Gly Met Glu Ser Lys Ala Ile Ser Asp Ala Gln
2195                2200                2205

Ile Thr Ala Ser Ser Tyr Phe Thr Asn Met Phe Ala Thr Trp Ser
2210                2215                2220
```

Pro Ser Lys Ala Arg Leu His Leu Gln Gly Arg Ser Asn Ala Trp
2225                2230                2235

Arg Pro Gln Val Asn Asn Pro Lys Glu Trp Leu Gln Val Asp Phe
2240                2245                2250

Gln Lys Thr Met Lys Val Thr Gly Val Thr Thr Gln Gly Val Lys
2255                2260                2265

Ser Leu Leu Thr Ser Met Tyr Val Lys Glu Phe Leu Ile Ser Ser
2270                2275                2280

Ser Gln Asp Gly His Gln Trp Thr Leu Phe Phe Gln Asn Gly Lys
2285                2290                2295

Val Lys Val Phe Gln Gly Asn Gln Asp Ser Phe Thr Pro Val Val
2300                2305                2310

Asn Ser Leu Asp Pro Pro Leu Leu Thr Arg Tyr Leu Arg Ile His
2315                2320                2325

Pro Gln Ser Trp Val His Gln Ile Ala Leu Arg Met Glu Val Leu
2330                2335                2340

Gly Cys Glu Ala Gln Asp Leu Tyr Asp Lys Thr His Thr Cys Pro
2345                2350                2355

Pro Cys Pro Ala Pro Glu Leu Leu Gly Gly Pro Ser Val Phe Leu
2360                2365                2370

Phe Pro Pro Lys Pro Lys Asp Thr Leu Met Ile Ser Arg Thr Pro
2375                2380                2385

Glu Val Thr Cys Val Val Val Asp Val Ser His Glu Asp Pro Glu
2390                2395                2400

Val Lys Phe Asn Trp Tyr Val Asp Gly Val Glu Val His Asn Ala
2405                2410                2415

Lys Thr Lys Pro Arg Glu Glu Gln Tyr Asn Ser Thr Tyr Arg Val
2420                2425                2430

Val Ser Val Leu Thr Val Leu His Gln Asp Trp Leu Asn Gly Lys
2435                2440                2445

Glu Tyr Lys Cys Lys Val Ser Asn Lys Ala Leu Pro Ala Pro Ile
2450                2455                2460

Glu Lys Thr Ile Ser Lys Ala Lys Gly Gln Pro Arg Glu Pro Gln
2465                2470                2475

Val Tyr Thr Leu Pro Pro Ser Arg Asp Glu Leu Thr Lys Asn Gln
2480                2485                2490

Val Ser Leu Thr Cys Leu Val Lys Gly Phe Tyr Pro Ser Asp Ile
2495                2500                2505

Ala Val Glu Trp Glu Ser Asn Gly Gln Pro Glu Asn Asn Tyr Lys
2510                2515                2520

Thr Thr Pro Pro Val Leu Asp Ser Asp Gly Ser Phe Phe Leu Tyr
2525                2530                2535

Ser Lys Leu Thr Val Asp Lys Ser Arg Trp Gln Gln Gly Asn Val
2540                2545                2550

Phe Ser Cys Ser Val Met His Glu Ala Leu His Asn His Tyr Thr
2555                2560                2565

Gln Lys Ser Leu Ser Leu Ser Pro Gly Lys
2570                2575

<210> SEQ ID NO 7
<211> LENGTH: 2958
<212> TYPE: DNA
<213> ORGANISM: Artificial Sequence
<220> FEATURE:
<223> OTHER INFORMATION: Heavy Chain (HC)-Fc DNA sequence

```
<220> FEATURE:
<221> NAME/KEY: misc_feature
<222> LOCATION: (1)..(57)
<223> OTHER INFORMATION: signal peptide

<400> SEQUENCE: 7
```

| | | | | |
|---|---|---|---|---|
| atgcaaatag | agctctccac | ctgcttcttt | ctgtgccttt | tgcgattctg ctttagtgcc | 60 |
| accagaagat | actacctggg | tgcagtggaa | ctgtcatggg | actatatgca aagtgatctc | 120 |
| ggtgagctgc | ctgtggacgc | aagatttcct | cctagagtgc | caaaatcttt tccattcaac | 180 |
| acctcagtcg | tgtacaaaaa | gactctgttt | gtagaattca | cggatcacct tttcaacatc | 240 |
| gctaagccaa | ggccaccctg | gatgggtctg | ctaggtccta | ccatccaggc tgaggtttat | 300 |
| gatacagtgg | tcattacact | taagaacatg | gcttcccatc | ctgtcagtct tcatgctgtt | 360 |
| ggtgtatcct | actggaaagc | ttctgaggga | gctgaatatg | atgatcagac cagtcaaagg | 420 |
| gagaaagaag | atgataaagt | cttccctggt | ggaagccata | catatgtctg gcaggtcctg | 480 |
| aaagagaatg | gtccaatggc | ctctgaccca | ctgtgcctta | cctactcata tctttctcat | 540 |
| gtggacctgg | taaaagactt | gaattcaggc | ctcattggag | ccctactagt atgtagagaa | 600 |
| gggagtctgg | ccaaggaaaa | gacacagacc | ttgcacaaat | ttatactact ttttgctgta | 660 |
| tttgatgaag | ggaaaagttg | gcactcagaa | acaaagaact | ccttgatgca ggatagggat | 720 |
| gctgcatctg | ctcgggcctg | gcctaaaatg | cacacagtca | atggttatgt aaacaggtct | 780 |
| ctgccaggtc | tgattggatg | ccacaggaaa | tcagtctatt | ggcatgtgat tggaatgggc | 840 |
| accactcctg | aagtgcactc | aatattcctc | gaaggtcaca | catttcttgt gaggaaccat | 900 |
| cgccaggcgt | ccttggaaat | ctcgccaata | actttcctta | ctgctcaaac actcttgatg | 960 |
| gaccttggac | agtttctact | gttttgtcat | atctcttccc | accaacatga tggcatggaa | 1020 |
| gcttatgtca | agtagacag | ctgtccagag | gaaccccaac | tacgaatgaa aaataatgaa | 1080 |
| gaagcggaag | actatgatga | tgatcttact | gattctgaaa | tggatgtggt caggtttgat | 1140 |
| gatgacaact | ctccttcctt | tatccaaatt | cgctcagttg | ccaagaagca tcctaaaact | 1200 |
| tgggtacatt | acattgctgc | tgaagaggag | gactgggact | atgctcccct agtcctcgcc | 1260 |
| cccgatgaca | gaagttataa | aagtcaatat | ttgaacaatg | gccctcagcg gattggtagg | 1320 |
| aagtacaaaa | aagtccgatt | tatggcatac | acagatgaaa | cctttaagac tcgtgaagct | 1380 |
| attcagcatg | aatcaggaat | cttgggacct | ttactttatg | gggaagttgg agacacactg | 1440 |
| ttgattatat | ttaagaatca | agcaagcaga | ccatataaca | tctaccctca cggaatcact | 1500 |
| gatgtccgtc | ctttgtattc | aaggagatta | ccaaaaggtg | taaaacattt gaaggatttt | 1560 |
| ccaattctgc | caggagaaat | attcaaatat | aaatggacag | tgactgtaga agatgggcca | 1620 |
| actaaatcag | atcctcggtg | cctgacccgc | tattactcta | gtttcgttaa tatggagaga | 1680 |
| gatctagctt | caggactcat | tggccctctc | ctcatctgct | acaaagaatc tgtagatcaa | 1740 |
| agaggaaacc | agataatgtc | agacaagagg | aatgtcatcc | tgttttctgt atttgatgag | 1800 |
| aaccgaagct | ggtacctcac | agagaatata | caacgctttc | tccccaatcc agctggagtg | 1860 |
| cagcttgagg | atccagagtt | ccaagcctcc | aacatcatgc | acagcatcaa tggctatgtt | 1920 |
| tttgatagtt | tgcagttgtc | agtttgtttg | catgaggtgg | catactggta cattctaagc | 1980 |
| attggagcac | agactgactt | cctttctgtc | ttcttctctg | gatataccttt caaacacaaa | 2040 |
| atggtctatg | aagacacact | caccctattc | ccattctcag | agaaactgt cttcatgtcg | 2100 |
| atggaaaacc | caggtctatg | gattctgggg | tgccacaact | cagactttcg gaacagaggc | 2160 |

```
atgaccgcct tactgaaggt ttctagttgt gacaagaaca ctggtgatta ttacgaggac    2220
agttatgaag atatttcagc atacttgctg agtaaaaaca atgccattga accaagagac    2280
aaaactcaca catgcccacc gtgcccagct ccagaactcc tgggcggacc gtcagtcttc    2340
ctcttccccc caaaacccaa ggacaccctc atgatctccc ggacccctga ggtcacatgc    2400
gtggtggtgg acgtgagcca cgaagaccct gaggtcaagt tcaactggta cgtggacggc    2460
gtggaggtgc ataatgccaa gacaaagccg cgggaggagc agtacaacag cacgtaccgt    2520
gtggtcagcg tcctcaccgt cctgcaccag gactggctga atggcaagga gtacaagtgc    2580
aaggtctcca acaaagccct cccagccccc atcgagaaaa ccatctccaa agccaaaggg    2640
cagccccgag aaccacaggt gtacaccctg cccccatccc gggatgagct gaccaagaac    2700
caggtcagcc tgacctgcct ggtcaaaggc ttctatccca gcgacatcgc cgtggagtgg    2760
gagagcaatg ggcagccgga gaacaactac aagaccacgc ctcccgtgtt ggactccgac    2820
ggctccttct tcctctacag caagctcacc gtggacaaga gcaggtggca gcaggggaac    2880
gtcttctcat gctccgtgat gcatgaggct ctgcacaacc actacacgca gaagagcctc    2940
tccctgtctc cgggtaaa                                                  2958
```

<210> SEQ ID NO 8
<211> LENGTH: 986
<212> TYPE: PRT
<213> ORGANISM: Artificial Sequence
<220> FEATURE:
<223> OTHER INFORMATION: Heavy Chain (HC)-Fc Peptide
<220> FEATURE:
<221> NAME/KEY: MISC_FEATURE
<222> LOCATION: (1)..(19)
<223> OTHER INFORMATION: signal peptide
<220> FEATURE:
<221> NAME/KEY: MISC_FEATURE
<222> LOCATION: (760)..(986)
<223> OTHER INFORMATION: Fc sequence

<400> SEQUENCE: 8

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
                20                  25                  30

Trp Asp Tyr Met Gln Ser Asp Leu Gly Glu Leu Pro Val Asp Ala Arg
            35                  40                  45

Phe Pro Pro Arg Val Pro Lys Ser Phe Pro Phe Asn Thr Ser Val Val
        50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175
```

-continued

```
Tyr Leu Ser His Val Asp Leu Val Lys Asp Leu Asn Ser Gly Leu Ile
            180                 185                 190
Gly Ala Leu Leu Val Cys Arg Glu Gly Ser Leu Ala Lys Glu Lys Thr
        195                 200                 205
Gln Thr Leu His Lys Phe Ile Leu Leu Phe Ala Val Phe Asp Glu Gly
    210                 215                 220
Lys Ser Trp His Ser Glu Thr Lys Asn Ser Leu Met Gln Asp Arg Asp
225                 230                 235                 240
Ala Ala Ser Ala Arg Ala Trp Pro Lys Met His Thr Val Asn Gly Tyr
                245                 250                 255
Val Asn Arg Ser Leu Pro Gly Leu Ile Gly Cys His Arg Lys Ser Val
            260                 265                 270
Tyr Trp His Val Ile Gly Met Gly Thr Thr Pro Glu Val His Ser Ile
        275                 280                 285
Phe Leu Glu Gly His Thr Phe Leu Val Arg Asn His Arg Gln Ala Ser
    290                 295                 300
Leu Glu Ile Ser Pro Ile Thr Phe Leu Thr Ala Gln Thr Leu Leu Met
305                 310                 315                 320
Asp Leu Gly Gln Phe Leu Leu Phe Cys His Ile Ser Ser His Gln His
                325                 330                 335
Asp Gly Met Glu Ala Tyr Val Lys Val Asp Ser Cys Pro Glu Glu Pro
            340                 345                 350
Gln Leu Arg Met Lys Asn Asn Glu Glu Ala Glu Asp Tyr Asp Asp Asp
        355                 360                 365
Leu Thr Asp Ser Glu Met Asp Val Val Arg Phe Asp Asp Asp Asn Ser
    370                 375                 380
Pro Ser Phe Ile Gln Ile Arg Ser Val Ala Lys Lys His Pro Lys Thr
385                 390                 395                 400
Trp Val His Tyr Ile Ala Ala Glu Glu Glu Asp Trp Asp Tyr Ala Pro
                405                 410                 415
Leu Val Leu Ala Pro Asp Asp Arg Ser Tyr Lys Ser Gln Tyr Leu Asn
            420                 425                 430
Asn Gly Pro Gln Arg Ile Gly Arg Lys Tyr Lys Lys Val Arg Phe Met
        435                 440                 445
Ala Tyr Thr Asp Glu Thr Phe Lys Thr Arg Glu Ala Ile Gln His Glu
    450                 455                 460
Ser Gly Ile Leu Gly Pro Leu Leu Tyr Gly Glu Val Gly Asp Thr Leu
465                 470                 475                 480
Leu Ile Ile Phe Lys Asn Gln Ala Ser Arg Pro Tyr Asn Ile Tyr Pro
                485                 490                 495
His Gly Ile Thr Asp Val Arg Pro Leu Tyr Ser Arg Arg Leu Pro Lys
            500                 505                 510
Gly Val Lys His Leu Lys Asp Phe Pro Ile Leu Pro Gly Glu Ile Phe
        515                 520                 525
Lys Tyr Lys Trp Thr Val Thr Val Glu Asp Gly Pro Thr Lys Ser Asp
    530                 535                 540
Pro Arg Cys Leu Thr Arg Tyr Tyr Ser Ser Phe Val Asn Met Glu Arg
545                 550                 555                 560
Asp Leu Ala Ser Gly Leu Ile Gly Pro Leu Leu Ile Cys Tyr Lys Glu
                565                 570                 575
Ser Val Asp Gln Arg Gly Asn Gln Ile Met Ser Asp Lys Arg Asn Val
            580                 585                 590
Ile Leu Phe Ser Val Phe Asp Glu Asn Arg Ser Trp Tyr Leu Thr Glu
```

```
                        595                 600                 605
Asn Ile Gln Arg Phe Leu Pro Asn Pro Ala Gly Val Gln Leu Glu Asp
            610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Asp Lys Thr His Thr Cys Pro Pro Cys
        755                 760                 765

Pro Ala Pro Glu Leu Leu Gly Gly Pro Ser Val Phe Leu Phe Pro Pro
    770                 775                 780

Lys Pro Lys Asp Thr Leu Met Ile Ser Arg Thr Pro Glu Val Thr Cys
785                 790                 795                 800

Val Val Val Asp Val Ser His Glu Asp Pro Glu Val Lys Phe Asn Trp
                805                 810                 815

Tyr Val Asp Gly Val Glu Val His Asn Ala Lys Thr Lys Pro Arg Glu
            820                 825                 830

Glu Gln Tyr Asn Ser Thr Tyr Arg Val Val Ser Val Leu Thr Val Leu
        835                 840                 845

His Gln Asp Trp Leu Asn Gly Lys Glu Tyr Lys Cys Lys Val Ser Asn
    850                 855                 860

Lys Ala Leu Pro Ala Pro Ile Glu Lys Thr Ile Ser Lys Ala Lys Gly
865                 870                 875                 880

Gln Pro Arg Glu Pro Gln Val Tyr Thr Leu Pro Pro Ser Arg Asp Glu
                885                 890                 895

Leu Thr Lys Asn Gln Val Ser Leu Thr Cys Leu Val Lys Gly Phe Tyr
            900                 905                 910

Pro Ser Asp Ile Ala Val Glu Trp Glu Ser Asn Gly Gln Pro Glu Asn
        915                 920                 925

Asn Tyr Lys Thr Thr Pro Pro Val Leu Asp Ser Asp Gly Ser Phe Phe
    930                 935                 940

Leu Tyr Ser Lys Leu Thr Val Asp Lys Ser Arg Trp Gln Gln Gly Asn
945                 950                 955                 960

Val Phe Ser Cys Ser Val Met His Glu Ala Leu His Asn His Tyr Thr
                965                 970                 975

Gln Lys Ser Leu Ser Leu Ser Pro Gly Lys
            980                 985

<210> SEQ ID NO 9
<211> LENGTH: 2973
<212> TYPE: DNA
<213> ORGANISM: Artificial Sequence
```

```
<220> FEATURE:
<223> OTHER INFORMATION: Heavy Chain (HC)-Fc DNA sequence
<220> FEATURE:
<221> NAME/KEY: misc_feature
<222> LOCATION: (1)..(57)
<223> OTHER INFORMATION: signal peptide
<220> FEATURE:
<221> NAME/KEY: misc_feature
<222> LOCATION: (2278)..(2292)
<223> OTHER INFORMATION: 5 amino acid linker

<400> SEQUENCE: 9
atgcaaatag agctctccac ctgcttcttt ctgtgccttt tgcgattctg ctttagtgcc      60
accagaagat actacctggg tgcagtggaa ctgtcatggg actatatgca aagtgatctc     120
ggtgagctgc ctgtggacgc aagatttcct cctagagtgc aaaatctttt ccattcaac     180
acctcagtcg tgtacaaaaa gactctgttt gtagaattca cggatcacct tttcaacatc     240
gctaagccaa ggccacccctg gatgggtctg ctaggtccta ccatccaggc tgaggtttat     300
gatacagtgg tcattacact taagaacatg gcttcccatc ctgtcagtct tcatgctgtt     360
ggtgtatcct actggaaagc ttctgaggga gctgaatatg atgatcagac cagtcaaagg     420
gagaaagaag atgataaagt cttccctggt ggaagccata catatgtctg gcaggtcctg     480
aaagagaatg gtccaatggc ctctgaccca ctgtgcctta cctactcata tctttctcat     540
gtggacctgg taaaagactt gaattcaggc ctcattggag ccctactagt atgtagagaa     600
gggagtctgg ccaaggaaaa gacacagacc ttgcacaaat ttatactact ttttgctgta     660
tttgatgaag ggaaaagttg gcactcagaa acaaagaact ccttgatgca ggataggat     720
gctgcatctg ctcgggcctg gcctaaaatg cacacagtca atggttatgt aaacaggtct     780
ctgccaggtc tgattggatg ccacaggaaa tcagtctatt ggcatgtgat tggaatgggc     840
accactcctg aagtgcactc aatattcctc gaaggtcaca catttcttgt gaggaaccat     900
cgccaggcgt ccttggaaat ctcgccaata actttcctta ctgctcaaac actcttgatg     960
gaccttggac agtttctact gttttgtcat atctcttccc accaacatga tggcatggaa    1020
gcttatgtca agtagacag ctgtccagag gaaccccaac tacgaatgaa aaataatgaa    1080
gaagcggaag actatgatga tgatcttact gattctgaaa tggatgtggt caggtttgat    1140
gatgacaact ctccttcctt tatccaaatt cgctcagttg ccaagaagca tcctaaaact    1200
tgggtacatt acattgctgc tgaagaggag gactgggact atgctccctt agtcctcgcc    1260
cccgatgaca aagttataa aagtcaatat ttgaacaatg ccctcagcg gattggtagg    1320
aagtacaaaa aagtccgatt tatggcatac acagatgaaa cctttaagac tcgtgaagct    1380
attcagcatg aatcaggaat cttgggacct ttactttatg gggaagttgg agacacactg    1440
ttgattatat ttaagaatca agcaagcaga ccatataaca tctaccctca cggaatcact    1500
gatgtccgtc ctttgtattc aaggagatta ccaaaaggtg taaacatttt gaaggatttt    1560
ccaattctgc aggagaaat attcaaatat aaatggacag tgactgtaga agatgggcca    1620
actaaatcag atcctcggtg cctgacccgc tattactcta gtttcgttaa tatggagaga    1680
gatctagctt caggactcat ggcccctctc ctcatctgct acaaagaatc tgtagatcaa    1740
agaggaaacc agataatgtc agacaagagg aatgtcatcc tgtttcctgt atttgatgag    1800
aaccgaagct ggtacctcac agagaatata caacgctttc tccccaatcc agctggagtg    1860
cagcttgagg atccagagtt ccaagcctcc aacatcatgc acagcatcaa tggctatgtt    1920
tttgatagtt tgcagttgtc agtttgtttg catgaggtgg catactggta cattctaagc    1980
```

-continued

```
attggagcac agactgactt cctttctgtc ttcttctctg gatatacctt caaacacaaa    2040
atggtctatg aagacacact caccctattc ccattctcag gagaaactgt cttcatgtcg    2100
atggaaaacc caggtctatg gattctgggg tgccacaact cagactttcg aacagaggc     2160 atgaccgcct tactgaaggt ttctagttgt gacaagaaca ctggtgatta ttacgaggac    2220
agttatgaag atatttcagc atacttgctg agtaaaaaca atgccattga accaagaagc    2280
ttctcccaga atgacaaaac tcacacatgc ccaccgtgcc cagctccaga actcctgggc    2340
ggaccgtcag tcttcctctt ccccccaaaa cccaaggaca cctcatgat  ctcccggacc    2400 cctgaggtca catgcgtggt ggtggacgtg agccacgaag accctgaggt caagttcaac    2460
tggtacgtgg acggcgtgga ggtgcataat gccaagacaa agccgcggga ggagcagtac    2520
aacagcacgt accgtgtggt cagcgtcctc accgtcctgc accaggactg gctgaatggc    2580
aaggagtaca agtgcaaggt ctccaacaaa gccctcccag cccccatcga gaaaaccatc    2640
tccaaagcca aagggcagcc ccgagaacca caggtgtaca ccctgccccc atcccgggat    2700
gagctgacca agaaccaggt cagcctgacc tgcctggtca aaggcttcta tcccagcgac    2760
atcgccgtgg agtgggagag caatgggcag ccggagaaca actacaagac cacgcctccc    2820
gtgttggact ccgacggctc cttcttcctc tacagcaagc tcaccgtgga caagagcagg    2880
tggcagcagg ggaacgtctt ctcatgctcc gtgatgcatg aggctctgca caaccactac    2940
acgcagaaga gcctctccct gtctccgggt aaa                                 2973
```

<210> SEQ ID NO 10
<211> LENGTH: 991
<212> TYPE: PRT
<213> ORGANISM: Artificial Sequence
<220> FEATURE:
<223> OTHER INFORMATION: Heavy Chain (HC)-Fc Peptide
<220> FEATURE:
<221> NAME/KEY: MISC_FEATURE
<222> LOCATION: (1)..(19)
<223> OTHER INFORMATION: signal peptide
<220> FEATURE:
<221> NAME/KEY: MISC_FEATURE
<222> LOCATION: (760)..(764)
<223> OTHER INFORMATION: 5 amino acid linker
<220> FEATURE:
<221> NAME/KEY: MISC_FEATURE
<222> LOCATION: (765)..(991)
<223> OTHER INFORMATION: Fc sequence

<400> SEQUENCE: 10

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125
```

```
Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540
```

-continued

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
            565                 570                 575

Ser Val Asp Gln Arg Gly Asn Gln Ile Met Ser Asp Lys Arg Asn Val
        580                 585                 590

Ile Leu Phe Ser Val Phe Asp Glu Asn Arg Ser Trp Tyr Leu Thr Glu
    595                 600                 605

Asn Ile Gln Arg Phe Leu Pro Asn Pro Ala Gly Val Gln Leu Glu Asp
610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Asp Lys Thr His
        755                 760                 765

Thr Cys Pro Pro Cys Pro Ala Pro Glu Leu Leu Gly Gly Pro Ser Val
    770                 775                 780

Phe Leu Phe Pro Pro Lys Pro Lys Asp Thr Leu Met Ile Ser Arg Thr
785                 790                 795                 800

Pro Glu Val Thr Cys Val Val Val Asp Val Ser His Glu Asp Pro Glu
                805                 810                 815

Val Lys Phe Asn Trp Tyr Val Asp Gly Val Glu Val His Asn Ala Lys
            820                 825                 830

Thr Lys Pro Arg Glu Glu Gln Tyr Asn Ser Thr Tyr Arg Val Val Ser
        835                 840                 845

Val Leu Thr Val Leu His Gln Asp Trp Leu Asn Gly Lys Glu Tyr Lys
850                 855                 860

Cys Lys Val Ser Asn Lys Ala Leu Pro Ala Pro Ile Glu Lys Thr Ile
865                 870                 875                 880

Ser Lys Ala Lys Gly Gln Pro Arg Glu Pro Gln Val Tyr Thr Leu Pro
                885                 890                 895

Pro Ser Arg Asp Glu Leu Thr Lys Asn Gln Val Ser Leu Thr Cys Leu
            900                 905                 910

Val Lys Gly Phe Tyr Pro Ser Asp Ile Ala Val Glu Trp Glu Ser Asn
        915                 920                 925

Gly Gln Pro Glu Asn Asn Tyr Lys Thr Thr Pro Pro Val Leu Asp Ser
    930                 935                 940

Asp Gly Ser Phe Phe Leu Tyr Ser Lys Leu Thr Val Asp Lys Ser Arg
945                 950                 955                 960

Trp Gln Gln Gly Asn Val Phe Ser Cys Ser Val Met His Glu Ala Leu

His Asn His Tyr Thr Gln Lys Ser Leu Ser Leu Ser Pro Gly Lys
   965               970                 975
                980              985                990

<210> SEQ ID NO 11
<211> LENGTH: 2793
<212> TYPE: DNA
<213> ORGANISM: Artificial Sequence
<220> FEATURE:
<223> OTHER INFORMATION: Light Chain (LC)-Fc DNA sequence
<220> FEATURE:
<221> NAME/KEY: misc_feature
<222> LOCATION: (1)..(60)
<223> OTHER INFORMATION: signal peptide

<400> SEQUENCE: 11

| | | | | | |
|---|---|---|---|---|---|
| atggagacag | acacactcct | gctatgggta | ctgctgctct | gggttccagg | ttccactggt | 60 |
| gaaataactc | gtactactct | tcagtcagat | caagaggaaa | ttgactatga | tgataccata | 120 |
| tcagttgaaa | tgaagaagga | agattttgac | atttatgatg | aggatgaaaa | tcagagcccc | 180 |
| cgcagctttc | aaagaaaac | acgacactat | tttattgctg | cagtggagag | gctctgggat | 240 |
| tatgggatga | gtagctcccc | acatgttcta | agaaacaggg | ctcagagtgg | cagtgtccct | 300 |
| cagttcaaga | agttgttttt | ccaggaattt | actgatggct | cctttactca | gcccttatac | 360 |
| cgtggagaac | taaatgaaca | tttgggactc | ctggggccat | atataagagc | agaagttgaa | 420 |
| gataatatca | tggtaacttt | cagaaatcag | gcctctcgtc | cctattcctt | ctattctagc | 480 |
| cttatttctt | atgaggaaga | tcagaggcaa | ggagcagaac | ctagaaaaaa | ctttgtcaag | 540 |
| cctaatgaaa | ccaaaactta | cttttggaaa | gtgcaacatc | atatggcacc | cactaaagat | 600 |
| gagtttgact | gcaaagcctg | gcttatttc | tctgatgttg | acctggaaaa | agatgtgcac | 660 |
| tcaggcctga | ttggacccct | tctggtctgc | cacactaaca | cactgaaccc | tgctcatggg | 720 |
| agacaagtga | cagtacagga | atttgctctg | ttttttcacca | tctttgatga | gaccaaaagc | 780 |
| tggtacttca | ctgaaaatat | ggaaagaaac | tgcagggctc | cctgcaatat | ccagatggaa | 840 |
| gatcccactt | ttaaagagaa | ttatcgcttc | catgcaatca | atggctacat | aatggatacac | 900 |
| ctacctggct | tagtaatggc | tcaggatcaa | aggattcgat | ggtatctgct | cagcatgggc | 960 |
| agcaatgaaa | acatccattc | tattcatttc | agtggacatg | tgttcactgt | acgaaaaaaa | 1020 |
| gaggagtata | aaatggcact | gtacaatctc | tatccaggtg | ttttttgagac | agtggaaatg | 1080 |
| ttaccatcca | agctggaat | tggcgggtg | gaatgcctta | ttggcgagca | tctacatgct | 1140 |
| gggatgagca | cacttttct | ggtgtacagc | aataagtgtc | agactcccct | gggaatggct | 1200 |
| tctggacaca | ttagagattt | tcagattaca | gcttcaggac | aatatggaca | gtgggcccca | 1260 |
| aagctggcca | gacttcatta | ttccggatca | atcaatgcct | ggagcaccaa | ggagcccttt | 1320 |
| tcttggatca | aggtggatct | gttggcacca | atgattattc | acggcatcaa | gacccagggt | 1380 |
| gcccgtcaga | agttctccag | cctctacatc | tctcagttta | tcatcatgta | tagtcttgat | 1440 |
| gggaagaagt | ggcagactta | tcgaggaaat | tccactggaa | ccttaatggt | cttctttggc | 1500 |
| aatgtggatt | catctgggat | aaaacacaat | attttaacc | ctccaattat | tgctcgatac | 1560 |
| atccgtttgc | acccaactca | ttatagcatt | cgcagcactc | ttcgcatgga | gttgatgggc | 1620 |
| tgtgatttaa | atagttgcag | catgccattg | ggaatggaga | gtaaagcaat | atcagatgca | 1680 |
| cagattactg | cttcatccta | ctttaccaat | atgtttgcca | cctggtctcc | ttcaaaagct | 1740 |
| cgacttcacc | tccaagggag | gagtaatgcc | tggagaccte | aggtgaataa | tccaaaagag | 1800 |

```
tggctgcaag tggacttcca gaagacaatg aaagtcacag gagtaactac tcagggagta   1860
aaatctctgc ttaccagcat gtatgtgaag gagttcctca tctccagcag tcaagatggc   1920
catcagtgga ctctcttttt tcagaatggc aaagtaaagg tttttcaggg aaatcaagac   1980
tccttcacac ctgtggtgaa ctctctagac ccaccgttac tgactcgcta ccttcgaatt   2040
cacccccaga gttgggtgca ccagattgcc ctgaggatgg aggttctggg ctgcgaggca   2100
caggacctct acgacaaaac tcacacatgc ccaccgtgcc cagctccaga actcctgggc   2160
ggaccgtcag tcttcctctt ccccccaaaa cccaaggaca ccctcatgat ctcccggacc   2220
cctgaggtca catgcgtggt ggtggacgtg agccacgaag accctgaggt caagttcaac   2280
tggtacgtgg acggcgtgga ggtgcataat gccaagacaa agccgcggga ggagcagtac   2340
aacagcacgt accgtgtggt cagcgtcctc accgtcctgc accaggactg gctgaatggc   2400
aaggagtaca agtgcaaggt ctccaacaaa gccctcccag cccccatcga gaaaaccatc   2460
tccaaagcca agggcagccc cgagaaccca caggtgtaca ccctgccccc atcccgggat   2520
gagctgacca agaaccaggt cagcctgacc tgcctggtca aaggcttcta tcccagcgac   2580
atcgccgtgg agtgggagag caatgggcag ccggagaaca actacaagac cacgcctccc   2640
gtgttggact ccgacggctc cttcttcctc tacagcaagc tcaccgtgga caagagcagg   2700
tggcagcagg ggaacgtctt ctcatgctcc gtgatgcatg aggctctgca caaccactac   2760
acgcagaaga gcctctccct gtctccgggt aaa                                2793
```

```
<210> SEQ ID NO 12
<211> LENGTH: 931
<212> TYPE: PRT
<213> ORGANISM: Artificial Sequence
<220> FEATURE:
<223> OTHER INFORMATION: Light Chain (LC)-Fc Peptide
<220> FEATURE:
<221> NAME/KEY: MISC_FEATURE
<222> LOCATION: (1)..(20)
<223> OTHER INFORMATION: signal peptide
<220> FEATURE:
<221> NAME/KEY: MISC_FEATURE
<222> LOCATION: (705)..(931)
<223> OTHER INFORMATION: Fc sequence

<400> SEQUENCE: 12

Met Glu Thr Asp Thr Leu Leu Leu Trp Val Leu Leu Leu Trp Val Pro
1               5                   10                  15

Gly Ser Thr Gly Glu Ile Thr Arg Thr Thr Leu Gln Ser Asp Gln Glu
            20                  25                  30

Glu Ile Asp Tyr Asp Asp Thr Ile Ser Val Glu Met Lys Lys Glu Asp
        35                  40                  45

Phe Asp Ile Tyr Asp Glu Asp Glu Asn Gln Ser Pro Arg Ser Phe Gln
    50                  55                  60

Lys Lys Thr Arg His Tyr Phe Ile Ala Ala Val Glu Arg Leu Trp Asp
65                  70                  75                  80

Tyr Gly Met Ser Ser Pro His Val Leu Arg Asn Arg Ala Gln Ser
                85                  90                  95

Gly Ser Val Pro Gln Phe Lys Lys Val Val Phe Gln Glu Phe Thr Asp
            100                 105                 110

Gly Ser Phe Thr Gln Pro Leu Tyr Arg Gly Glu Leu Asn Glu His Leu
        115                 120                 125

Gly Leu Leu Gly Pro Tyr Ile Arg Ala Glu Val Glu Asp Asn Ile Met
    130                 135                 140
```

```
Val Thr Phe Arg Asn Gln Ala Ser Arg Pro Tyr Ser Phe Tyr Ser Ser
145                 150                 155                 160

Leu Ile Ser Tyr Glu Glu Asp Gln Arg Gln Gly Ala Glu Pro Arg Lys
                165                 170                 175

Asn Phe Val Lys Pro Asn Glu Thr Lys Thr Tyr Phe Trp Lys Val Gln
            180                 185                 190

His His Met Ala Pro Thr Lys Asp Glu Phe Asp Cys Lys Ala Trp Ala
        195                 200                 205

Tyr Phe Ser Asp Val Asp Leu Glu Lys Asp Val His Ser Gly Leu Ile
    210                 215                 220

Gly Pro Leu Leu Val Cys His Thr Asn Thr Leu Asn Pro Ala His Gly
225                 230                 235                 240

Arg Gln Val Thr Val Gln Glu Phe Ala Leu Phe Phe Thr Ile Phe Asp
                245                 250                 255

Glu Thr Lys Ser Trp Tyr Phe Thr Glu Asn Met Glu Arg Asn Cys Arg
                260                 265                 270

Ala Pro Cys Asn Ile Gln Met Glu Asp Pro Thr Phe Lys Glu Asn Tyr
            275                 280                 285

Arg Phe His Ala Ile Asn Gly Tyr Ile Met Asp Thr Leu Pro Gly Leu
        290                 295                 300

Val Met Ala Gln Asp Gln Arg Ile Arg Trp Tyr Leu Leu Ser Met Gly
305                 310                 315                 320

Ser Asn Glu Asn Ile His Ser Ile His Phe Ser Gly His Val Phe Thr
                325                 330                 335

Val Arg Lys Lys Glu Glu Tyr Lys Met Ala Leu Tyr Asn Leu Tyr Pro
                340                 345                 350

Gly Val Phe Glu Thr Val Glu Met Leu Pro Ser Lys Ala Gly Ile Trp
            355                 360                 365

Arg Val Glu Cys Leu Ile Gly Glu His Leu His Ala Gly Met Ser Thr
        370                 375                 380

Leu Phe Leu Val Tyr Ser Asn Lys Cys Gln Thr Pro Leu Gly Met Ala
385                 390                 395                 400

Ser Gly His Ile Arg Asp Phe Gln Ile Thr Ala Ser Gly Gln Tyr Gly
                405                 410                 415

Gln Trp Ala Pro Lys Leu Ala Arg Leu His Tyr Ser Gly Ser Ile Asn
            420                 425                 430

Ala Trp Ser Thr Lys Glu Pro Phe Ser Trp Ile Lys Val Asp Leu Leu
        435                 440                 445

Ala Pro Met Ile Ile His Gly Ile Lys Thr Gln Gly Ala Arg Gln Lys
    450                 455                 460

Phe Ser Ser Leu Tyr Ile Ser Gln Phe Ile Ile Met Tyr Ser Leu Asp
465                 470                 475                 480

Gly Lys Lys Trp Gln Thr Tyr Arg Gly Asn Ser Thr Gly Thr Leu Met
                485                 490                 495

Val Phe Phe Gly Asn Val Asp Ser Ser Gly Ile Lys His Asn Ile Phe
            500                 505                 510

Asn Pro Pro Ile Ile Ala Arg Tyr Ile Arg Leu His Pro Thr His Tyr
        515                 520                 525

Ser Ile Arg Ser Thr Leu Arg Met Glu Leu Met Gly Cys Asp Leu Asn
    530                 535                 540

Ser Cys Ser Met Pro Leu Gly Met Glu Ser Lys Ala Ile Ser Asp Ala
545                 550                 555                 560

Gln Ile Thr Ala Ser Ser Tyr Phe Thr Asn Met Phe Ala Thr Trp Ser
```

Pro Ser Lys Ala Arg Leu His Leu Gln Gly Arg Ser Asn Ala Trp Arg
    565                 570                 575
Pro Gln Val Asn Asn Pro Lys Glu Trp Leu Gln Val Asp Phe Gln Lys
580                 585                 590
Thr Met Lys Val Thr Gly Val Thr Thr Gln Gly Val Lys Ser Leu Leu
595                 600                 605
Thr Ser Met Tyr Val Lys Glu Phe Leu Ile Ser Ser Ser Gln Asp Gly
610                 615                 620
His Gln Trp Thr Leu Phe Phe Gln Asn Gly Lys Val Lys Val Phe Gln
625                 630                 635                 640
Gly Asn Gln Asp Ser Phe Thr Pro Val Val Asn Ser Leu Asp Pro Pro
        645                 650                 655
Leu Leu Thr Arg Tyr Leu Arg Ile His Pro Gln Ser Trp Val His Gln
            660                 665                 670
Ile Ala Leu Arg Met Glu Val Leu Gly Cys Glu Ala Gln Asp Leu Tyr
        675                 680                 685
Asp Lys Thr His Thr Cys Pro Pro Cys Pro Ala Pro Glu Leu Leu Gly
    690                 695                 700
Gly Pro Ser Val Phe Leu Phe Pro Pro Lys Pro Lys Asp Thr Leu Met
705                 710                 715                 720
Ile Ser Arg Thr Pro Glu Val Thr Cys Val Val Val Asp Val Ser His
        725                 730                 735
Glu Asp Pro Glu Val Lys Phe Asn Trp Tyr Val Asp Gly Val Glu Val
            740                 745                 750
His Asn Ala Lys Thr Lys Pro Arg Glu Glu Gln Tyr Asn Ser Thr Tyr
        755                 760                 765
Arg Val Val Ser Val Leu Thr Val Leu His Gln Asp Trp Leu Asn Gly
    770                 775                 780
Lys Glu Tyr Lys Cys Lys Val Ser Asn Lys Ala Leu Pro Ala Pro Ile
785                 790                 795                 800
Glu Lys Thr Ile Ser Lys Ala Lys Gly Gln Pro Arg Glu Pro Gln Val
        805                 810                 815
Tyr Thr Leu Pro Pro Ser Arg Asp Glu Leu Thr Lys Asn Gln Val Ser
            820                 825                 830
Leu Thr Cys Leu Val Lys Gly Phe Tyr Pro Ser Asp Ile Ala Val Glu
        835                 840                 845
Trp Glu Ser Asn Gly Gln Pro Glu Asn Asn Tyr Lys Thr Thr Pro Pro
    850                 855                 860
Val Leu Asp Ser Asp Gly Ser Phe Phe Leu Tyr Ser Lys Leu Thr Val
865                 870                 875                 880
Asp Lys Ser Arg Trp Gln Gln Gly Asn Val Phe Ser Cys Ser Val Met
        885                 890                 895
His Glu Ala Leu His Asn His Tyr Thr Gln Lys Ser Leu Ser Leu Ser
            900                 905                 910
Pro Gly Lys
    915                 920                 925

Pro Gly Lys
    930

<210> SEQ ID NO 13
<211> LENGTH: 7583
<212> TYPE: DNA
<213> ORGANISM: Artificial Sequence
<220> FEATURE:
<223> OTHER INFORMATION: FIX-Fc Chain DNA Sequence

<400> SEQUENCE: 13

```
gcgcgcgttg acattgatta ttgactagtt attaatagta atcaattacg gggtcattag     60
ttcatagccc atatatggag ttccgcgtta cataacttac ggtaaatggc ccgcctggct    120
gaccgcccaa cgaccccgc ccattgacgt caataatgac gtatgttccc atagtaacgc    180
caatagggac tttccattga cgtcaatggg tggagtattt acggtaaact gcccacttgg    240
cagtacatca agtgtatcat atgccaagta cgccccctat tgacgtcaat gacggtaaat    300
ggcccgcctg gcattatgcc cagtacatga ccttatggga ctttcctact tggcagtaca    360
tctacgtatt agtcatcgct attaccatgg tgatgcggtt ttggcagtac atcaatgggc    420
gtggatagcg gtttgactca cggggatttc caagtctcca ccccattgac gtcaatggga    480
gtttgttttg gcaccaaaat caacgggact ttccaaaatg tcgtaacaac tccgccccat    540
tgacgcaaat gggcggtagg cgtgtacggt gggaggtcta tataagcaga gctctctggc    600
taactagaga acccactgct tactggctta tcgaaattaa tacgactcac tatagggaga    660
cccaagcttc gcgacgtacg gccgccacca tgcagcgcgt gaacatgatc atggcagaat    720
caccaggcct catcaccatc tgccttttag gatatctact cagtgctgaa tgtacaggtt    780
tgtttccttt ttttaaaatac attgagtatg cttgcctttt agatatagaa atatctgatg    840
ctgtcttctt cactaaattt tgattacatg atttgacagc aatattgaag agtctaacag    900
ccagcacgca ggttggtaag tactgtggga acatcacaga ttttggctcc atgccctaaa    960
gagaaattgg ctttcagatt atttggatta aaaacaaaga ctttcttaag agatgtaaaa   1020
ttttcatgat gttttctttt ttgctaaaac taaagaatta ttcttttaca tttcagtttt   1080
tcttgatcat gaaaacgcca acaaaattct gaatcggcca agaggtata attcaggtaa    1140
attggaagag tttgttcaag ggaatctaga gagagaatgt atggaagaaa agtgtagttt   1200
tgaagaagca cgagaagttt ttgaaaacac tgaaagaaca actgaatttt ggaagcagta   1260
tgttgatgga gatcagtgtg agtccaatcc atgttttaaat ggcggcagtt gcaaggatga   1320
cattaattcc tatgaatgtt ggtgtccctt tggatttgaa ggaagaact gtgaattaga    1380
tgtaacatgt aacattaaga atggcagatg cgagcagttt tgtaaaaata gtgctgataa    1440
caaggtggtt tgctcctgta ctgagggata tcgacttgca gaaaaccaga gtcctgtga   1500
accagcagtg ccatttccat gtggaagagt ttctgtttca caaacttcta agctcacccg   1560
tgctgagact gttttcctg atgtggacta tgtaaattct actgaagctg aaaccatttt   1620
ggataacatc actcaaagca cccaatcatt taatgacttc actcgggttg ttggtggaga   1680
agatgccaaa ccaggtcaat tcccttggca ggttgttttg aatggtaaag ttgatgcatt   1740
ctgtggaggc tctatcgtta tgaaaaatg gattgtaact gctgcccact gtgttgaaac   1800
tggtgttaaa attacagttg tcgcaggtga acataatatt gaggagacag aacatacaga   1860
gcaaaagcga aatgtgattc gaattattcc tcaccacaac tacaatgcag ctattaataa   1920
gtacaaccat gacattgccc ttctggaact ggacgaaccc ttagtgctaa acagctacgt   1980
tacacctatt tgcattgctg acaaggaata cacgaacatc ttcctcaaat tggatctgg    2040
ctatgtaagt ggctggggaa gagtcttcca caaaggggaga tcagctttag ttcttcagta   2100
ccttagagtt ccacttgttg accgagccac atgtcttcga tctacaaagt tcaccatcta   2160
taacaacatg ttctgtgctg gcttccatga aggaggtaga gattcatgtc aaggagatag   2220
tgggggaccc catgttactg aagtggaagg gaccagtttc ttaactgaa ttattagctg   2280
gggtgaagag tgtgcaatga aaggcaaata tggaatatat accaaggtgt cccggtatgt   2340
```

```
caactggatt aaggaaaaaa caaagctcac tgacaaaact cacacatgcc caccgtgccc    2400
agctccggaa ctcctgggcg gaccgtcagt cttcctcttc cccccaaaac ccaaggacac    2460
cctcatgatc tcccggaccc ctgaggtcac atgcgtggtg gtggacgtga gccacgaaga    2520 cccctgaggtc aagttcaact ggtacgtgga cggcgtggag gtgcataatg ccaagacaaa    2580
gccgcgggag gagcagtaca acagcacgta ccgtgtggtc agcgtcctca ccgtcctgca    2640
ccaggactgg ctgaatggca aggagtacaa gtgcaaggtc tccaacaaag ccctcccagc    2700
ccccatcgag aaaaccatct ccaaagccaa agggcagccc cgagaaccac aggtgtacac    2760
cctgccccca tcccgggatg agctgaccaa gaaccaggtc agcctgacct gcctggtcaa    2820
aggcttctat cccagcgaca tcgccgtgga gtgggagagc aatgggcagc cggagaacaa    2880
ctacaagacc acgcctcccg tgttggactc cgacggctcc ttcttcctct acagcaagct    2940
caccgtggac aagagcaggt ggcagcaggg gaacgtcttc tcatgctccg tgatgcatga    3000
ggctctgcac aaccactaca cgcagaagag cctctccctg tctccgggta atgagaatt    3060 cagacatgat aagatacatt gatgagtttg gacaaaccac aactagaatg cagtgaaaaa    3120
aatgctttat ttgtgaaatt tgtgatgcta ttgctttatt tgtaaccatt ataagctgca    3180
ataaacaagt tggggtgggc gaagaactcc agcatgagat ccccgcgctg gaggatcatc    3240
cagccggcgt cccggaaaac gattccgaag cccaaccttt catagaaggc ggcggtggaa    3300
tcgaaatctc gtagcacgtg tcagtcctgc tcctcggcca cgaagtgcac gcagttgccg    3360
gccgggtcgc gcagggcgaa ctcccgcccc cacggctgct cgccgatctc ggtcatggcc    3420
ggcccggagg cgtcccggaa gttcgtggac acgacctccg accactcggc gtacagctcg    3480
tccaggccgc gcacccacac ccaggccagg gtgttgtccg gcaccacctg gtcctggacc    3540
gcgctgatga acagggtcac gtcgtcccgg accacaccgg cgaagtcgtc ctccacgaag    3600
tcccgggaga cccgagccg gtcggtccag aactcgaccg ctccggcgac gtcgcgcgcg    3660
gtgagcaccg gaacggcact ggtcaacttg gccatggttt agttcctcac cttgtcgtat    3720
tatactatgc cgatatacta tgccgatgat taattgtcaa cacgtgctga tcagatccga    3780
aaatggatat acaagctccc gggagctttt tgcaaaagcc taggcctcca aaaaagcctc    3840
ctcactactt ctggaatagc tcagaggcag aggcggcctc ggcctctgca taaataaaaa    3900
aaattagtca gccatgggc ggagaatggg cggaactggg cggagttagg ggcgggatgg    3960
gcggagttag ggcgggact atggttgctg actaattgag atgcatgctt tgcatacttc    4020
tgcctgctgg ggagcctggg gactttccac acctggttgc tgactaattg agatgcatgc    4080
tttgcatact tctgcctgct ggggagcctg ggactttcc acaccctcgt cgagctagct    4140
tcgtgaggct ccggtgcccg tcagtgggca gagcgcacat cgcccacagt ccccgagaag    4200 ttgggggga ggggtcggca attgaaccggt gcctagagaa ggtggcgcgg ggtaaactgg    4260
gaaagtgatg tcgtgtactg gctccgcctt tttcccgagg gtgggggaga accgtatata    4320
agtgcagtag tcgccgtgaa cgttcttttt cgcaacgggt ttgccgccag aacacaggta    4380
agtgccgtgt gtggttcccg cgggcctggc ctctttacgg gttatggccc ttgcgtgcct    4440
tgaattactt ccacctggct ccagtacgtg attcttgatc ccgagctgga gccaggggcg    4500
ggccttgcgc tttaggagcc ccttcgcctc gtgcttgagt tgaggcctgg cctgggcgct    4560
ggggccgccg cgtgcgaatc tggtggcacc ttcgcgcctg tctcgctgct tcgataagt    4620 ctctagccat ttaaaatttt tgatgacctg ctgcgacgct ttttttctgg caagatagtc    4680
```

```
ttgtaaatgc gggccaggat ctgcacactg gtatttcggt ttttggggcc gcgggcggcg    4740
acggggcccg tgcgtcccag cgcacatgtt cggcgaggcg gggcctgcga gcgcggccac    4800
cgagaatcgg acggggtag tctcaagctg gccggcctgc tctggtgcct ggcctcgcgc    4860
cgccgtgtat cgccccgccc tgggcggcaa ggctggcccg gtcggcacca gttgcgtgag    4920
cggaaagatg gccgcttccc ggccctgctc caggggctc aaaatggagg acgcggcgct    4980
cgggagagcg ggcgggtgag tcacccacac aaaggaaagg ggcctttccg tcctcagccg    5040
tcgcttcatg tgactccacg gagtaccggg cgccgtccag gcacctcgat tagttctgga    5100
gcttttggag tacgtcgtct ttaggttggg gggagggggtt ttatgcgatg gagtttcccc    5160
acactgagtg ggtggagact gaagttaggc cagcttggca cttgatgtaa ttctccttgg    5220
aatttgccct ttttgagttt ggatcttggt tcattctcaa gcctcagaca gtggttcaaa    5280
gttttttttct tccatttcag gtgtcgtgaa cacgtggtcg cggccgcgcc gccaccatgg    5340
agacagacac actcctgcta tgggtactgc tgctctgggt tccaggttcc actggtgaca    5400
aaactcacac atgcccaccg tgcccagcac ctgaactcct gggaggaccg tcagtcttcc    5460
tcttccccc aaaacccaag gacaccctca tgatctcccg gacccctgag gtcacatgcg    5520
tggtggtgga cgtgagccac gaagaccctg aggtcaagtt caactggtac gtggacggcg    5580
tggaggtgca taatgccaag acaaagccgc gggaggagca gtacaacagc acgtaccgtg    5640
tggtcagcgt cctcaccgtc ctgcaccagg actggctgaa tggcaaggag tacaagtgca    5700
aggtctccaa caaagccctc ccagccccca tcgagaaaac catctccaaa gccaagggc    5760
agcccccgaga accacaggtg tacaccctgc cccatcccg cgatgagctg accaagaacc    5820
aggtcagcct gacctgcctg gtcaaaggct tctatcccag cgacatcgcc gtggagtggg    5880
agagcaatgg gcagccggag aacaactaca agaccacgcc tcccgtgttg gactccgacg    5940
gctccttctt cctctacagc aagctcaccg tggacaagag caggtggcag caggggaacg    6000
tcttctcatg ctccgtgatg catgaggctc tgcacaacca ctacacgcag aagagcctct    6060
ccctgtctcc gggtaaatga ctcgagagat ctggccggct gggcccgttt cgaaggtaag    6120
cctatcccta accctctcct cggtctcgat tctacgcgta ccggtcatca tcaccatcac    6180
cattgagttt aaacccgctg atcagcctcg actgtgcctt ctagttgcca gccatctgtt    6240
gtttgcccct cccccgtgcc ttccttgacc ctggaaggtg ccactcccac tgtcctttcc    6300
taataaaatg aggaaattgc atcgcattgt ctgagtaggt gtcattctat tctggggggt    6360
ggggtggggc aggacagcaa gggggaggat tgggaagaca atagcaggca tgctggggat    6420
gcggtgggct ctatggcttc tgaggcggaa agaaccagtg gcggtaatac ggttatccac    6480
agaatcaggg gataacgcag gaaagaacat gtgagcaaaa ggccagcaaa aggccaggaa    6540
ccgtaaaaag gccgcgttgc tggcgttttt ccataggctc cgcccccctg acgagcatca    6600
caaaaatcga cgctcaagtc agaggtggcg aaacccgaca ggactataaa gataccaggc    6660
gtttccccct agaagctccc tcgtgcgctc tcctgttccg accctgccgc ttaccggata    6720
cctgtccgcc tttctccctt cgggaagcgt ggcgctttct catagctcac gctgtaggta    6780
tctcagttcg gtgtaggtcg ttcgctccaa gctgggctgt gtgcacgaac cccccgttca    6840
gcccgaccgc tgcgccttat ccggtaacta tcgtcttgag tccaacccgg taagacacga    6900
cttatcgcca ctggcagcag ccactggtaa caggattagc agagcgaggt atgtaggcgg    6960
tgctacagag ttcttgaagt ggtggcctaa ctacggctac actagaagaa cagtatttgg    7020
tatctgcgct ctgctgaagc cagttacctt cggaaaaaga gttggtagct cttgatccgg    7080
```

```
caaacaaacc accgctggta gcggtggttt ttttgtttgc aagcagcaga ttacgcgcag    7140
aaaaaaagga tctcaagaag atcctttgat cttttctacg gggtctgacg ctcagtggaa    7200
cgaaaactca cgttaaggga ttttggtcat gacattaacc tataaaaata ggcgtatcac    7260
gaggcccttt cgtctcgcgc gtttcggtga tgacggtgaa aacctctgac acatgcagct    7320
cccggagacg gtcacagctt gtctgtaagc ggatgccggg agcagacaag cccgtcaggg    7380
cgcgtcagcg ggtgttggcg ggtgtcgggg ctggcttaac tatgcggcat cagagcagat    7440
tgtactgaga gtgcaccata tatgcggtgt gaaataccgc acagatgcgt aaggagaaaa    7500
taccgcatca ggcgccattc gccattcagg ctgcgcaact gttgggaagg gcgatcggtg    7560
cgggcctctt cgctattacg cca                                            7583
```

<210> SEQ ID NO 14
<211> LENGTH: 688
<212> TYPE: PRT
<213> ORGANISM: Artificial Sequence
<220> FEATURE:
<223> OTHER INFORMATION: FIX-Fc Chain Peptide
<220> FEATURE:
<221> NAME/KEY: MISC_FEATURE
<222> LOCATION: (1)..(28)
<223> OTHER INFORMATION: FIX Signal Peptide
<220> FEATURE:
<221> NAME/KEY: MISC_FEATURE
<222> LOCATION: (29)..(46)
<223> OTHER INFORMATION: FIX Propeptide
<220> FEATURE:
<221> NAME/KEY: MISC_FEATURE
<222> LOCATION: (416)..(688)
<223> OTHER INFORMATION: Fc Region

<400> SEQUENCE: 14

```
Met Gln Arg Val Asn Met Ile Met Ala Glu Ser Pro Gly Leu Ile Thr
 1               5                  10                  15

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg Tyr Asn
        35                  40                  45

Ser Gly Lys Leu Glu Glu Phe Val Gln Gly Asn Leu Glu Arg Glu Cys
    50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125

Glu Leu Asp Val Thr Cys Asn Ile Lys Asn Gly Arg Cys Glu Gln Phe
    130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190

Glu Thr Val Phe Pro Asp Val Asp Tyr Val Asn Ser Thr Glu Ala Glu
        195                 200                 205
```

-continued

Thr Ile Leu Asp Asn Ile Thr Gln Ser Thr Gln Ser Phe Asn Asp Phe
    210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                245                 250                 255

Val Asn Glu Lys Trp Ile Val Thr Ala Ala His Cys Val Glu Thr Gly
            260                 265                 270

Val Lys Ile Thr Val Val Ala Gly Glu His Asn Ile Glu Glu Thr Glu
        275                 280                 285

His Thr Glu Gln Lys Arg Asn Val Ile Arg Ile Ile Pro His His Asn
    290                 295                 300

Tyr Asn Ala Ala Ile Asn Lys Tyr Asn His Asp Ile Ala Leu Leu Glu
305                 310                 315                 320

Leu Asp Glu Pro Leu Val Leu Asn Ser Tyr Val Thr Pro Ile Cys Ile
                325                 330                 335

Ala Asp Lys Glu Tyr Thr Asn Ile Phe Leu Lys Phe Gly Ser Gly Tyr
            340                 345                 350

Val Ser Gly Trp Gly Arg Val Phe His Lys Gly Arg Ser Ala Leu Val
        355                 360                 365

Leu Gln Tyr Leu Arg Val Pro Leu Val Asp Arg Ala Thr Cys Leu Arg
    370                 375                 380

Ser Thr Lys Phe Thr Ile Tyr Asn Asn Met Phe Cys Ala Gly Phe His
385                 390                 395                 400

Glu Gly Gly Arg Asp Ser Cys Gln Gly Asp Ser Gly Gly Pro His Val
                405                 410                 415

Thr Glu Val Glu Gly Thr Ser Phe Leu Thr Gly Ile Ile Ser Trp Gly
            420                 425                 430

Glu Glu Cys Ala Met Lys Gly Lys Tyr Gly Ile Tyr Thr Lys Val Ser
        435                 440                 445

Arg Tyr Val Asn Trp Ile Lys Glu Lys Thr Lys Leu Thr Asp Lys Thr
    450                 455                 460

His Thr Cys Pro Pro Cys Pro Ala Pro Glu Leu Leu Gly Gly Pro Ser
465                 470                 475                 480

Val Phe Leu Phe Pro Pro Lys Pro Lys Asp Thr Leu Met Ile Ser Arg
                485                 490                 495

Thr Pro Glu Val Thr Cys Val Val Asp Val Ser His Glu Asp Pro
            500                 505                 510

Glu Val Lys Phe Asn Trp Tyr Val Asp Gly Val Glu Val His Asn Ala
        515                 520                 525

Lys Thr Lys Pro Arg Glu Glu Gln Tyr Asn Ser Thr Tyr Arg Val Val
    530                 535                 540

Ser Val Leu Thr Val Leu His Gln Asp Trp Leu Asn Gly Lys Glu Tyr
545                 550                 555                 560

Lys Cys Lys Val Ser Asn Lys Ala Leu Pro Ala Pro Ile Glu Lys Thr
                565                 570                 575

Ile Ser Lys Ala Lys Gly Gln Pro Arg Glu Pro Gln Val Tyr Thr Leu
            580                 585                 590

Pro Pro Ser Arg Asp Glu Leu Thr Lys Asn Gln Val Ser Leu Thr Cys
        595                 600                 605

Leu Val Lys Gly Phe Tyr Pro Ser Asp Ile Ala Val Glu Trp Glu Ser
    610                 615                 620

```
Asn Gly Gln Pro Glu Asn Asn Tyr Lys Thr Thr Pro Pro Val Leu Asp
625                 630                 635                 640

Ser Asp Gly Ser Phe Phe Leu Tyr Ser Lys Leu Thr Val Asp Lys Ser
            645                 650                 655

Arg Trp Gln Gln Gly Asn Val Phe Ser Cys Ser Val Met His Glu Ala
        660                 665                 670

Leu His Asn His Tyr Thr Gln Lys Ser Leu Ser Leu Ser Pro Gly Lys
    675                 680                 685

<210> SEQ ID NO 15
<211> LENGTH: 20
<212> TYPE: PRT
<213> ORGANISM: Artificial Sequence
<220> FEATURE:
<223> OTHER INFORMATION: PAS Sequence

<400> SEQUENCE: 15

Ala Ser Pro Ala Ala Pro Ala Pro Ala Ser Pro Ala Ala Pro Ala Pro
1               5                   10                  15

Ser Ala Pro Ala
            20

<210> SEQ ID NO 16
<211> LENGTH: 20
<212> TYPE: PRT
<213> ORGANISM: Artificial Sequence
<220> FEATURE:
<223> OTHER INFORMATION: PAS Sequence

<400> SEQUENCE: 16

Ala Ala Pro Ala Ser Pro Ala Pro Ala Ala Pro Ser Ala Pro Ala Pro
1               5                   10                  15

Ala Ala Pro Ser
            20

<210> SEQ ID NO 17
<211> LENGTH: 20
<212> TYPE: PRT
<213> ORGANISM: Artificial Sequence
<220> FEATURE:
<223> OTHER INFORMATION: PAS sequence

<400> SEQUENCE: 17

Ala Pro Ser Ser Pro Ser Pro Ser Ala Pro Ser Ser Pro Ser Pro Ala
1               5                   10                  15

Ser Pro Ser Ser
            20

<210> SEQ ID NO 18
<211> LENGTH: 19
<212> TYPE: PRT
<213> ORGANISM: Artificial Sequence
<220> FEATURE:
<223> OTHER INFORMATION: PAS Sequence

<400> SEQUENCE: 18

Ala Pro Ser Ser Pro Ser Pro Ser Ala Pro Ser Ser Pro Ser Pro Ala
1               5                   10                  15

Ser Pro Ser

<210> SEQ ID NO 19
<211> LENGTH: 20
<212> TYPE: PRT
```

```
<213> ORGANISM: Artificial Sequence
<220> FEATURE:
<223> OTHER INFORMATION: PAS Sequence

<400> SEQUENCE: 19

Ser Ser Pro Ser Ala Pro Ser Pro Ser Ser Pro Ala Ser Pro Ser Pro
1               5                   10                  15

Ser Ser Pro Ala
            20

<210> SEQ ID NO 20
<211> LENGTH: 24
<212> TYPE: PRT
<213> ORGANISM: Artificial Sequence
<220> FEATURE:
<223> OTHER INFORMATION: PAS Sequence

<400> SEQUENCE: 20

Ala Ala Ser Pro Ala Ala Pro Ser Ala Pro Pro Ala Ala Ala Ser Pro
1               5                   10                  15

Ala Ala Pro Ser Ala Pro Pro Ala
            20

<210> SEQ ID NO 21
<211> LENGTH: 20
<212> TYPE: PRT
<213> ORGANISM: Artificial Sequence
<220> FEATURE:
<223> OTHER INFORMATION: PAS Sequence

<400> SEQUENCE: 21

Ala Ser Ala Ala Ala Pro Ala Ala Ala Ser Ala Ala Ala Ser Ala Pro
1               5                   10                  15

Ser Ala Ala Ala
            20
```

ASSAYS TO MONITOR BLEEDING DISORDERS

RELATED APPLICATIONS

This application is a division of U.S. patent application Ser. No. 14/234,789, filed Aug. 19, 2014, which is a 35 U.S.C. § 371 filing of International Patent Application No. PCT/US2012/048191, which claims priority to U.S. Provisional Patent Application Ser. No. 61/668,911, filed Jul. 6, 2012; 61/596,902, filed Feb. 9, 2012; 61/568,986, filed Dec. 9, 2011; 61/522,560, filed Aug. 11, 2011; and 61/511,207, filed Jul. 25, 2011, the entire disclosures of which are hereby incorporated herein.

BACKGROUND OF THE INVENTION

Field of the Invention

The present invention relates generally to the field of therapeutics for hemostatic disorders.

BACKGROUND ART

Hemophilia is a bleeding disorder in which blood clotting is disturbed by a lack of certain plasma clotting factors. Hemophilia A and Hemophilia B are two different types of hemophilia that are caused by deficiencies in Factor VIII (FVIII) and Factor IX, respectively.

Hemophilia A is characterized by spontaneous hemorrhage and excessive bleeding after trauma. Over time, the repeated bleeding into muscles and joints, which often begins in early childhood, results in hemophilic arthropathy and irreversible joint damage. This damage is progressive and can lead to severely limited mobility of joints, muscle atrophy and chronic pain (Rodriguez-Merchan, E. C., Semin. Thromb. Hemost. 29:87-96 (2003), which is herein incorporated by reference in its entirety).

Hemophilia B (also known as Christmas disease) is one of the most common inherited bleeding disorders in the world. It results in decreased in vivo and in vitro blood clotting activity and requires extensive medical monitoring throughout the life of the affected individual. In the absence of intervention, the afflicted individual will suffer from spontaneous bleeding in the joints, which produces severe pain and debilitating immobility; bleeding into muscles results in the accumulation of blood in those tissues; spontaneous bleeding in the throat and neck may cause asphyxiation if not immediately treated; renal bleeding; and severe bleeding following surgery, minor accidental injuries, or dental extractions also are prevalent.

Treatment of a bleeding disorder, e.g., hemophilia is by replacement therapy targeting restoration of Factor VIII and Factor IX activity. Treatment of hemophilia A is by replacement therapy targeting restoration of FVIII activity to 1 to 5% of normal levels to prevent spontaneous bleeding (Mannucci, P. M., et al., N. Engl. J. Med. 344:1773-1779 (2001), which is herein incorporated by reference in its entirety). There are plasma-derived and recombinant FVIII products available to treat bleeding episodes on-demand or to prevent bleeding episodes from occurring by treating prophylactically. Based on the half-life of these products treatment regimens require frequent intravenous administration. Such frequent administration is painful and inconvenient.

Treatment of hemophilia B occurs by replacement of the missing clotting factor by exogenous factor concentrates highly enriched in Factor IX, but is also problematic. Generating such a concentrate from blood is fraught with technical difficulties. Purification of Factor IX from plasma (plasma derived Factor IX; pdFIX) almost exclusively yields active Factor IX. However, such purification of factor IX from plasma is very difficult because Factor IX is only present in low concentration in plasma (5 µg/mL. Andersson, Thrombosis Research 7: 451 459 (1975). Further, purification from blood requires the removal or inactivation of infectious agents such as HIV and HCV. In addition, pdFIX has a short half-life and therefore requires frequent dosing. Recombinant factor IX (rFIX) is also available, but suffers from the same short half-life and need for frequent dosing (e.g., 2-3 times per week for prophylaxis) as pdFIX. rFIX also has a lower incremental recovery (K value) compared to pdFIX, which necessitates the use of higher doses of rFIX than those for pdFIX.

Reduced mortality, prevention of joint damage and improved quality of life have been important achievements due to the development of plasma-derived and recombinant Factor VIII and Factor IX products. Prolonged protection from bleeding would represent another key advancement in the treatment of hemophilia patients. In order to address this need, recombinant Factor VIII and Factor IX proteins expressed as Fc fusions are in development. However, methods of determining appropriate dosage of these products, which have unique pharmacokinetic properties in humans have not yet been developed. Therefore, there remains a need for improved methods of treating hemophilia due to Factor VIII and Factor IX deficiencies that are more tolerable and more effective than current therapies.

BRIEF SUMMARY OF THE INVENTION

This disclosure provides a method for optimizing treatment for a bleeding disorder in a subject in need thereof comprising: (a) measuring ex vivo at least one property of clot formation in a blood sample taken from a patient having been administered an amount of Factor VIII or Factor IX chimeric polypeptide; and (b) comparing the at least one property against a corresponding standard ex vivo clot formation property, wherein said standard clot formation property is correlated with a therapeutically efficacious treatment.

This disclosure further provides a method for optimizing treatment for a bleeding disorder in a patient in need thereof comprising: (a) administering to the patient a Factor VIII or Factor IX chimeric polypeptide; (b) obtaining a blood sample from the patient; (c) measuring at least one property of clot formation in the sample, wherein at least one property is one or more of thrombin generation, kinetics of clot formation, strength of clot formation, and stability of clot formation; and (d) adjusting the amount of Factor VIII or Factor IX chimeric polypeptide in subsequent administrations relative to the activity of the measured property.

This disclosure further provides a method for determining the efficacy of treatment for a bleeding disorder comprising: (a) administering to the patient a Factor VIII or Factor IX chimeric polypeptide; (b) obtaining a blood sample from the patient; (c) measuring at least one property of clot formation in the sample, wherein the at least one property is one or more of thrombin generation, kinetics of clot formation, strength of clot formation, and stability of clot formation; and (d) comparing the measured property of (c) to the measured property of a known normal sample, wherein substantially similar properties between the normal and patient samples is indicative of therapeutic efficacy.

This disclosure further provides a method of treating a bleeding disorder in a patient comprising: a) obtaining a blood sample from a patient being evaluated or treated for a bleeding disorder; b) measuring a clot formation property in the blood sample; c) comparing the patient's clot formation results with a corresponding standard, wherein the standard correlates with a therapeutically efficacious treatment; and d) administering an optimized treatment to the patient, wherein the treatment is maintained or adjusted based on the relative difference between the patient's clot formation results and the corresponding standard.

This disclosure further provides a method of treating a bleeding disorder in a patient comprising: a) obtaining a blood sample from a patient being evaluated or treated for a bleeding disorder; b) submitting the blood sample for measurement of a clot formation property and comparison to a corresponding standard, wherein the standard correlates with a therapeutically efficacious treatment; and c) administering an optimized treatment to the patient, wherein the treatment is maintained or adjusted based on the relative difference between the patient's clot formation results and the corresponding standard.

This disclosure further provides a method of treating a bleeding disorder in a patient comprising: a) measuring a clot formation property in a blood sample obtained from a patient being evaluated or treated for a bleeding disorder; b) comparing the patient's clot formation results with a corresponding standard, wherein the standard correlates with a therapeutically efficacious treatment; and c) instructing a healthcare provider to maintain or adjust the patient's treatment, wherein the treatment is maintained or adjusted based on the relative difference between the patient's clot formation results and the corresponding standard.

This disclosure further provides a method for optimizing bleeding disorder therapy in a patient comprising: a) obtaining a blood sample from a patient being evaluated or treated for a bleeding disorder; b) measuring a clot formation property in the blood sample; c) comparing the patient's clot formation results with a corresponding standard, wherein the standard correlates with a therapeutically efficacious treatment; and d) administering an optimized treatment to the patient, wherein the treatment is maintained or adjusted based on the relative difference between the patient's clot formation results and the corresponding standard.

This disclosure further provides a method for optimizing bleeding disorder therapy in a patient comprising: a) obtaining a blood sample from a patient being evaluated or treated for a bleeding disorder; b) submitting the blood sample for measurement of a clot formation property and comparison to a corresponding standard, wherein the standard correlates with a therapeutically efficacious treatment; and c) administering an optimized treatment to the patient, wherein the treatment is maintained or adjusted based on the relative difference between the patient's clot formation results and the corresponding standard.

This disclosure further provides a method for optimizing bleeding disorder therapy in a patient comprising: a) measuring a clot formation property in a blood sample obtained from a patient being evaluated or treated for a bleeding disorder; b) comparing the patient's clot formation results with a corresponding standard, wherein the standard correlates with a therapeutically efficacious treatment; and c) instructing a healthcare provider to optimize the patient's treatment, wherein the treatment is maintained or adjusted based on the relative difference between the patient's clot formation results and the corresponding standard.

This disclosure further provides a method of determining efficacy of treatment for a bleeding disorder in a patient comprising: a) obtaining a blood sample from a patient being evaluated or treated for a bleeding disorder; b) measuring a clot formation property in the blood sample; c) comparing the patient's clot formation results with a corresponding standard, wherein the standard is representative of a therapeutically efficacious treatment, and wherein a similarity between the patient's results and the standard is indicative of efficacy of the patient's current treatment; and d) maintaining or adjusting the patient's treatment based on the relative difference between the patient's clot formation results and the corresponding standard.

This disclosure further provides a method of determining efficacy of treatment for a bleeding disorder in a patient comprising: a) obtaining a blood sample from a patient being evaluated or treated for a bleeding disorder; b) submitting the blood sample for measurement of a clot formation property and comparison to a corresponding standard, wherein the standard correlates with a therapeutically efficacious treatment, and wherein a similarity between the patient's results and the standard is indicative of efficacy of the patient's current treatment; and c) maintaining or adjusting the patient's treatment based on the relative difference between the patient's clot formation results and the corresponding standard.

This disclosure further provides a method of determining efficacy of treatment for a bleeding disorder in a patient comprising: a) measuring a clot formation property in a blood sample obtained from a patient being evaluated or treated for a bleeding disorder; b) comparing the patient's clot formation results with a corresponding standard, wherein the standard is representative of a therapeutically efficacious treatment, and wherein a similarity between the patient's results and the standard is indicative of the efficacy of patient's current treatment; and c) instructing a healthcare provider to maintain or adjust the patient's treatment based on the relative difference between the patient's clot formation results and the corresponding standard.

This disclosure further provides a method for standardizing hemostasis assay results, comprising: a) obtaining blood samples from a population of patients being treated for bleeding disorders; b) measuring a clot formation property in the blood samples, wherein the measurements are performed using standardized reagents and methods; c) comparing the patients' clot formation results with a corresponding standard, wherein the standard is representative of a therapeutically efficacious treatment, and wherein a similarity between the patients' results and the standard are indicative of efficacy of the patient's current treatments; and d) maintaining or adjusting the patients' treatments based on the relative difference between the patients' clot formation results and the corresponding standard.

This disclosure further provides a method for standardizing hemostasis assay results, comprising: a) obtaining blood samples from a population of patients being treated for bleeding disorders; b) submitting the blood samples for measurement of a clot formation property and comparison to a corresponding standard, wherein the measurements are performed using standardized reagents and methods, wherein the standard correlates with a therapeutically efficacious treatment, and wherein a similarity between the patients' results and the standard are indicative of efficacy of the patients' current treatments; and c) maintaining or adjusting the patients' treatments based on the relative difference between the patient's clot formation results and the corresponding standard.

This disclosure further provides a method for standardizing hemostasis assay results, comprising: a) measuring a clot formation property in a blood samples obtained from a population of patients being treated for a bleeding disorder; b) comparing the patients' clot formation results with a corresponding standard, wherein the standard is representative of a therapeutically efficacious treatment, wherein the measurements are performed using standardized reagents and methods, and wherein a similarity between the patients' results and the standard are indicative of the efficacy of patients current treatments; and c) instructing healthcare providers from whom the samples are obtained to maintain or adjust their patients' treatments based on the relative difference between the patients' clot formation results and the corresponding standard.

This disclosure further provides a method for standardizing results in a multi-site clotting factor clinical trial, comprising: a) obtaining blood samples from test subjects with bleeding disorders at multiple clinical trial sites; b) measuring a clot formation property in the blood samples, wherein the measurements are performed using common reagents and methods; c) comparing the patients' clot formation results with a corresponding standard, wherein the standard is representative of a therapeutically efficacious treatment, wherein a similarity between the patients' results and the standard are indicative of efficacy of the patient's current treatments, and wherein the variance of results between the multiple clinical trial sites is not statistically significant; and d) maintaining or adjusting the patients' treatments based on the relative difference between the patients' clot formation results and the corresponding standard.

This disclosure further provides a method for standardizing results in a multi-site clotting factor clinical trial, comprising: a) obtaining blood samples from test subjects with bleeding disorders at multiple clinical trial sites; b) submitting the blood samples for measurement of a clot formation property and comparison to a corresponding standard, wherein the measurements are performed using common reagents and methods, wherein the standard correlates with a therapeutically efficacious treatment, wherein a similarity between the patients' results and the standard are indicative of efficacy of the patients' current treatments, and wherein the variance of results between the multiple clinical trial sites is not statistically significant; and c) maintaining or adjusting the patients' treatments based on the relative difference between the patient's clot formation results and the corresponding standard.

This disclosure further provides a method for standardizing results in a multi-site clotting factor clinical trial, comprising: a) measuring a clot formation property in a blood samples obtained from test subjects with bleeding disorders at multiple clinical trial sites; b) comparing the patients' clot formation results with a corresponding standard, wherein the measurements are performed using common reagents and methods, wherein the standard correlates with a therapeutically efficacious treatment, wherein a similarity between the patients' results and the standard are indicative of efficacy of the patients' current treatments, and wherein the variance of results between the multiple clinical trial sites is not statistically significant; and c) instructing healthcare providers participating in the clinical trial, from whom the samples were obtained, to maintain or adjust the test subjects' treatments based on the relative difference between the patients' clot formation results and the corresponding standard.

In certain embodiments the at least one property is assessed by assaying one or more of thrombin generation, kinetics of clot formation, strength of clot formation, and stability of clot formation. In certain aspects the at least one property is measured by one or more of thrombin generation assay (TGA), thromboelastography (TEG), rotation thromboelastometry (ROTEM®), and waveform analysis.

In certain aspects the method further comprises adjusting the amount of Factor VIII or Factor IX chimeric polypeptide administered to the subject in subsequent administrations to achieve a more efficacious outcome. In certain aspects the Factor VIII or Factor IX chimeric polypeptide comprises a Fc domain, e.g., a human Fc domain.

In some embodiments, the Factor VIII chimeric polypeptide for use in the method provided comprises a B-domain deleted Factor VIII. The Factor VIII chimeric polypeptide can comprise SEQ ID NO:6 and or SEQ ID NO:2. In some embodiments the Factor IX chimeric polypeptide can comprise SEQ ID NO:14.

The blood sample for use in the method provided can be, e.g., whole blood or plasma.

This disclosure further provides a method of quantifying an amount of protein capable of exhibiting FIX activity which is in its activated form (activated FIX) in a test sample, the method comprising: measuring thrombin generation activity for the test sample in the presence of FIX-deficient plasma or FIX-deficient blood and in the presence of exogenous thrombin, wherein the exogenous thrombin is present at a concentration of not more than about 50 nM, wherein the measuring is performed in the absence of exogenous tissue factor (TF), and wherein the amount of activated FIX protein in the test sample is indicated by the thrombin generation activity measured for the test sample. In certain aspects the measuring is performed in the presence of phospholipids.

In certain aspects of this method, an activated FIX protein standard curve is used to determine the amount of activated FIX protein in the test sample. The standard curve can be constructed by, e.g., (a) providing at least two reference samples, each containing a different, known concentration of activated FIX reference protein; and (b) measuring thrombin generation activity for each reference sample in the presence of FIX-deficient plasma or FIX-deficient blood and in the presence of exogenous thrombin, wherein the exogenous thrombin is present at a concentration of not more than about 50 nM, wherein the measuring is performed in the absence of exogenous tissue factor (TF), and wherein the concentration of activated FIX reference protein in the reference sample is indicated by the thrombin generation activity measured for the reference sample. In certain aspects each reference sample comprises from about 0 pM to about 200 pM, or from about 0 pM to about 100 pM of activated FIX protein. The activated FIX reference protein can be, for example, plasma derived activated FIX protein.

In certain embodiments of this method, the exogenous thrombin can be present at a concentration of not more than about 40 nM, not more than about 30 nM, not more than about 20 nM, or not more than about 10 nM, e.g., a concentration of about 1 nM to about 10 nM, or about 5 nM.

In certain embodiments of this method, the FIX-deficient plasma can be human FIX-deficient plasma.

This method can be adapted to accurately measure, e.g., less than about 100 pM, less than about 90 pM, less than about 80 pM, less than about 70 pM, less than about 60 pM, less than about 50 pM, less than about 30 pM, less than about 20 pM, less than about 10 pM, or less than about 5 pM of activated FIX protein in the test sample.

In certain aspects the test sample comprises a total amount of protein capable of exhibiting factor IX activity, wherein a portion of the total amount is present in its activated form. For example, the test sample can comprise a total amount of protein capable of exhibiting FIX activity, where less than about 1 (w/w) of the total amount of the protein capable of exhibiting FIX activity is present in its activated form. For example in certain aspects the test sample contains less than 2 pM of activated FIX protein. In certain embodiments the protein having FIX activity comprises a heterologous moiety, e.g., an immunoglobulin constant (Fc) region or a portion thereof, albumin or a fragment thereof, a XTEN polypeptide, a straight or branched polyethylene glycol (PEG) moiety, a PAS sequence, or a hydroxyethyl starch (HES) moiety or a derivative thereof. In certain embodiments the heterologous moiety is a first Fc region and can comprise a second Fc region, wherein the second Fc region is associated with the first Fc region by a covalent bond or a non-covalent bond. In certain aspects the protein capable of exhibiting FIX activity is a recombinant Factor IX-Fc fusion (FIX-Fc) protein.

BRIEF DESCRIPTION OF THE FIGURES

FIG. 5. Pharmacokinetics of rFVIIIFc by one stage assay activity.

FIG. 10A and FIG. 10C: ROTEM® parameters at equivalent FIX levels were significantly different in two donor plasmas. FIG. 10B: Plasma of Donor 2 demonstrated longer clot time by aPTT compared to plasma of Donor 1.

FIG. 14: Performance of rFVIIIFc in Field Studies (One-Stage Clotting Assay, n=30 labs).

FIG. 15: Performance of rFVIIIFc in Field Studies (Chromogenic Assay, n=11 labs).

FIG. 16: Chromogenic/One-Stage Assay Ratio in Clinical Assays.

DETAILED DESCRIPTION OF THE INVENTION

Figure 1:
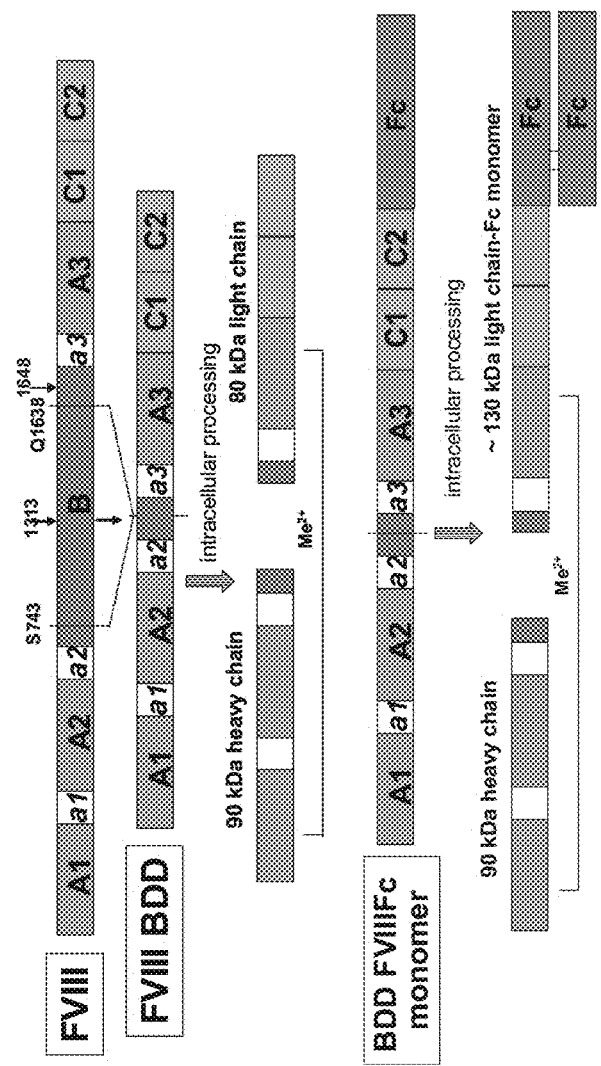
FIG. 1. Schematic Representation of rFVIIIFc protein.

Use of in vitro one stage clotting assays or chromogenic substrate assays are not reliably predictive of in vivo activity for long acting Factor VIII and Factor IX therapeutics. Therefore, this disclosure provides methods of optimizing dosing strategies for Factor VIII ("FVIII") and Factor IX ("FIX") therapeutics using global hemostasis assays. Certain FVIII and FIX polypeptides for use in the methods provided herein are described in International Application No. PCT/US2010/059136, filed Dec. 6, 2010, and in International Application No. PCT/US2011/043569, filed Jul. 11, 2011, each of which is herein incorporated by reference in its entirety.

Certain commercially-available FIX therapeutic compositions contain amounts of activated FIX protein (see, e.g., R. T. Peters et al. Prolonged activity of factor IX as a monomeric Fc fusion protein. *Blood* 2010; 115: 2057-2064), and certain assay formats used to determine the therapeutic potency/strength of FIX compositions (e.g., in quality control analyses) can produce misleading results due to the presence of activated FIX protein (e.g., residual activated FIX protein) in those compositions.

This disclosure provides assay procedures which can distinguish the in vitro biological activity derived from native FIX protein versus the in vitro activity derived from the corresponding activated (i.e., pre-activated) form of the FIX protein. Activated FIX protein in such preparations can be considered an impurity because the activated protein does not possess the same beneficial in vivo biological activities as the FIX protein which is activated in vivo. The assay procedures provided in this application can be used to detect the presence of activated FIX protein in a test sample, and can also be used to accurately measure very small concentrations (e.g., less than 100 pM) of activated FIX protein in a test sample (high-sensitivity assay).

In some aspects, this disclosure provides methods (e.g., high-sensitivity methods) of quantifying an amount (or determining the concentration of) protein having FIX activity which is in its activated form (pre-activated FIX protein) in a test sample. An exemplary method comprises: (i)

measuring thrombin generation activity for the test sample in the presence of FIX-deficient plasma or FIX-deficient blood and in the presence of exogenous thrombin, wherein the exogenous thrombin is present at a concentration of not more than about 50 nM (e.g., not more than about 30 nM, not more than about 10 nM, or about 5 nM), and wherein the measuring is performed in the absence of exogenous tissue factor (TF). The amount or concentration of activated FIX protein in the test sample is indicated by the thrombin generation activity measured for the test sample.

Another exemplary method comprises: (i) measuring thrombin generation activity in an assay mixture comprising the test sample, wherein the assay mixture further comprises FIX-deficient plasma or FIX-deficient blood and exogenous thrombin, wherein the exogenous thrombin is added to the assay mixture prior to measuring (e.g., prior to initiating thrombin generation) at a concentration of not more than about 50 nM (e.g., not more than about 50 nM, or not more than about 10 nM), and wherein the measuring is performed in the absence of exogenous tissue factor (TF). The amount or concentration of activated FIX protein in the test sample is indicated by the thrombin generation activity measured for the assay mixture.

Thrombin generation activity can be expressed, e.g., as the amount of thrombin generated or the peak thrombin concentration measured during the assay procedure. Thrombin generation activity can be determined, e.g., using a known thrombin generation assay (TGA) adapted according to the method above. An exemplar TGA is described in Example 1. Typical TGA assay results are depicted in FIG. 3A to FIG. 3F.

The test sample can be any sample containing a protein having FIX activity. In one example, the test sample is a pharmaceutical preparation containing a protein having FIX activity, e.g., recombinant protein having FIX activity (e.g., recombinant FIX, such as BENEFIX® or rFIX-Fc).

In one example, the test sample comprises a total amount of protein having FIX activity. The above method is useful to determine how much (if any) (e.g., percentage, ratio) of the total amount of protein having FIX activity in the test sample is present in its activated form. In another example, the test sample includes a total amount of protein having FIX activity, wherein a portion (e.g., less than 10%) of the total amount is present in its activated form. In another example, the test sample includes a total amount of protein having FIX activity, wherein essentially none (e.g., less than 0.2% w/w) of the total amount is present in its activated form.

The above method can further include: (ii) using an activated FIX protein standard curve to determine the concentration or the amount of activated FIX protein in the test sample.

In one example according to any of the above embodiments, the method further comprises prior to the measuring: contacting the test sample with the FIX-deficient plasma or blood. This can be accomplished, e.g., by spiking the test sample into a volume of FIX-deficient plasma or blood.

In one example according to any of the above embodiments, the FIX-deficient plasma is hemophilic plasma (e.g., plasma derived from FIX-deficient, e.g., hemophilic whole blood). In another example, the FIX-deficient plasma is human FIX-deficient or hemophilic plasma. In yet another example, the FIX-deficient blood is human FIX-deficient blood.

The term "absence of tissue factor" indicates that no exogenous TF is added as an assay reagent. However, small amounts of TF can be present in the assay mixture, e.g., as a result of using FIX-deficient plasma or blood, in which endogenous TF may be present. Hence, a low level of thrombin generation activity may be measured due to the presence of endogenous TF. However, any residual thrombin generation activity can be accounted for by constructing a standard curve as described herein below. In one example, the concentration of TF present during the measuring is less than about 5 pM, less than about 1 pM, less than about 0.5 pM, less than about 0.1 pM, less than about 0.05 pM, or less than about 0.01 pM.

Unexpectedly, the inventors have discovered that a small amount of thrombin added to the assay mixture at the outset of the assay (e.g., before the thrombin generation is initiated) significantly increases the sensitivity of the assay for measuring activated FIX protein present in a test sample.

For example, "exogenous thrombin" is added to the assay mixture prior to measuring thrombin generation, e.g., prior to initiating the thrombin generation reaction (e.g., prior to adding a reaction starter). In one example, the thrombin generation is initiated by adding calcium to the assay mixture (i.e., re-calcification). In one example according to any of the above embodiments, the exogenous thrombin is present (e.g., is added to the assay mixture prior to initiating the thrombin generation reaction) at a concentration of not more than about 90 nM, not more than about 80 nM, not more than about 70 nM, not more than about 60 nM, not more than about 50 nM, not more than about 40 nM, not more than about 30 nM, not more than about 20 nM, not more than about 10 nM, or from about 1 nM to about 20 nM. In another example according to any of the above embodiments, the exogenous thrombin is present (e.g., is added to the assay mixture) at a concentration of at least about 0.1 nM, at least about 0.2 nM, at least about 0.3 nM, at least about 0.5 nM, at least about 0.6 nM, at least about 0.7 nM, at least about 0.8 nM, at least about 0.8 nM, at least about 1 nM, at least about 2 nM, at least about 3 nM, at least about 4 nM, or at least about 5 nM. In another example, the thrombin is present at a concentration of about 1 nM to about 10 nM or from about 3 nM to about 8 nM. In yet another example, the exogenous thrombin is present at a concentration of about 5 nM.

In one example according to any of the above embodiments, the measuring is performed in the presence of phospholipids (PL). For example, the measuring is performed in the presence of at least about 0.5 µM, 1 µM, at least about 2 µM, at least about 3 µM, at least about 4 µM, at least about 5 µM, at least about 6 µM, at least about 7 µM, at least about 8 µM, at least about 9 µM, or at least about 10 µM of phospholipids. For example, the measuring is performed in the presence of from about 1 uM to about 10 µM, from about 2 µM to about 6 µM, about 3 to 5 µM, or about 4 µM phospholipids.

In another example according to any of the above embodiments, the protein having FIX activity can be any Factor IX protein, e.g., those described herein. In another example according to this method, the protein having FIX activity is a chimeric FIX protein comprising a heterologous moiety, e.g., selected from those described herein. In yet another example, the protein having FIX activity comprises a heterologous moiety selected from an immunoglobulin constant (Fc) region or a portion thereof, albumin or a fragment thereof, a XTEN polypeptide, a straight or branched polyethylene glycol (PEG) moiety, a PAS sequence, and a hydroxyethyl starch (HES) moiety or a derivative thereof. In a further example, the heterologous moiety contains at least one Fc region or a portion thereof. In another example, the heterologous moiety contains a first Fc region. In another example, the heterologous moiety contains a first Fc region and further comprises a second Fc region, wherein the second Fc region is associated with the first Fc region (e.g., by a covalent bond or a non-covalent bond).

In yet another example according to any of the above embodiments, the protein having FIX activity is a recombinant Factor IX-Fc fusion (FIX-Fc) protein, e.g., selected from those described herein.

In one example according to any of the above embodiments, the method further comprises (iii) constructing an activated FIX protein standard curve. In one example, the standard curve is constructed by (a) providing reference samples (e.g., at least two reference samples), each containing a different concentrations of activated FIX protein (e.g., exogenous FIX protein); and (b) measuring thrombin generation activity for each reference sample using the thrombin generation assay (TGA) described above. For example, the measuring is performed in the presence of FIX-deficient plasma or blood, the measuring is performed in the presence of exogenous thrombin, wherein the exogenous thrombin is present at a concentration of not more than about 100 nM, and the measuring is performed in the absence of tissue factor (TF) (e.g., exogenous TF).

The concentration/amount of activated FIX protein in the reference sample is indicated by the thrombin generation activity measured for the reference sample.

In another example, the standard curve is constructed by (a) mixing increasing amounts of activated FIX protein (e.g., exogenous plasma derived activated FIX protein) with FIX-deficient plasma or blood (e.g., spiking increasing concentrations of activated FIX protein into FIX-deficient plasma or blood) thereby creating a number of reference samples containing various concentrations of activated FIX protein; and (b) measuring thrombin generation activity for each reference sample using the thrombin generation assay (TGA) described above.

In one example according to any of the above embodiments, the reference samples used to construct the standard curve contain from about 0 pM to about 500 pM, from about 0 pM to about 400 pM, from about 0 pM to about 300 pM, from about 0 pM to about 200 pM of activated FIX protein. In another example, the reference samples used to construct the standard curve contain from about 0 pM to about 100 pM of activated FIX protein.

In yet another example according to any of the above embodiments, the above method further comprises (iv) using the standard curve to determine the concentration/amount of activated FIX protein in the test sample.

In yet another example according to any of the above embodiments, the method is useful to measure very low concentrations of activated FIX protein. In one example, the TGA is adapted to accurately (e.g., with not more than ±10% inter-assay variability) measure less than about 500 pM, less than about 400 pM, less than about 300 pM, less than about 200 pM, less than about 100 pM, less than about 90 pM, less than about 80 pM, less than about 70 pM, less than about 60 pM, less than about 50 pM, less than about 30 pM, less than about 20 pM, less than about 10 pM, or less than about 5 pM of activated FIX protein in the test sample or the reference sample.

In a further example according to any of the above embodiments, less than about 20%, less than about 10%, less than about 1% (w/w), less than about 0.9% (w/w), less than about 0.8% (w/w), less than about 0.7% (w/w), less than about 0.6% (w/w), less than about 0.5% (w/w), less than about 0.4% (w/w), less than about 0.3% (w/w), less than about 0.2% (w/w), or less than about 0.1% (w/w) of the total amount of the protein having FIX activity contained in the test sample, is present as its activated form.

In another example according to any of the above embodiments, less than about 20%, less than about 10%, less than about 1%, less than about 0.9%, less than about 0.8%, less than about 0.7%, less than about 0.6%, less than about 0.5%, less than about 0.4%, less than about 0.3%, less than about 0.2%, or less than about 0.1% of the total TGA activity of the test sample is due to the presence of activated FIX protein.

In yet another example, the test sample contains less than about 50 pM, less than about 40 pM, less than about 30 pM, less than about 20 pM, less than about 10 pM, less than about 9 pM, less than about 8 pM, less than about 7 pM, less than about 6 pM, less than about 5 pM, less than about 4 pM, less than about 3 pM, or less than about 2 pM of activated FIX protein.

I. Definitions

"Global hemostasis assays" as used herein, are assays that detect mechanical properties of clot formation. Such properties include the patterns of changes in shear elasticity of the developing clot, determination of the kinetics of clot formation, as well as the strength and stability of the formed clot. Included in the measured properties is thrombin generation. These properties can be measured by any assay known in the art, including but not limited to, thrombin generation assays (TGA), thromboelastography (TEG), rotation thromboelastometry (ROTEM®, instrumentation and methods available from Tem International GmbH, Munich, Germany), and waveform analyses. As is known in the art, thromboelastometry is a viscoelastometric method for hemostasis testing in whole blood. TEM measures the interactions of coagulation factors, inhibitors and cellular components during the phases of clotting and subsequent lysis over time. TEG is a method of testing the efficiency of coagulation in the blood. For example, TGA can be used to monitor the amount of active thrombin produced in patient plasma after recalcification, which represents a useful indication in the evaluation of coagulation capacity of hemophilic plasma.

"Exogenous" in connection with a substance used in an assay (e.g., TGA) procedure means that the substance (e.g., tissue factor, thrombin) is added to an assay solution or assay buffer (e.g., as a reagent). The same substance may or may not be endogenously present, e.g., when whole blood plasma is used for an assay. The term "exogenous thrombin" must be distinguished from the thrombin, which is generated in an assay (e.g., a thrombin generation assay). For example, "exogenous thrombin" is added to the assay mixture prior to initiating a thrombin generation reaction, e.g., by adding a reaction starter. In one example, a thrombin generation is initiated by adding calcium to the assay mixture (i.e., re-calcification). In another example, "exogenous thrombin" is added to the assay mixture prior to initiating the thrombin generation.

"Administering," as used herein, means to give a pharmaceutically acceptable Factor VIII or Factor IX polypeptide, including a chimeric polypeptide, to a subject via a pharmaceutically acceptable route. Routes of administration include intravenous, e.g., intravenous injection and intravenous infusion, e.g., via central venous access. Additional routes of administration include subcutaneous, intramuscular, oral, nasal, and pulmonary administration. In some embodiments, the administration is subcutaneous. Factor VIII and Factor IX chimeric polypeptides and hybrid proteins can be administered as part of a pharmaceutical composition comprising at least one excipient. Advantages of the present invention include: improved regimen compliance; reduced break through bleeds; increased protection of joints from bleeds; prevention of joint damage; reduced morbidity; reduced mortality; prolonged protection from bleeding; decreased thrombotic events; and improved quality of life.

"Culture," "to culture" and "culturing," as used herein, means to incubate cells under in vitro conditions that allow for cell growth or division or to maintain cells in a living state. "Cultured cells," as used herein, means cells that are propagated in vitro.

"Equivalent amount," as used herein, means the same amount of Factor VIII or Factor IX activity as expressed in International Units, which is independent of molecular weight of the polypeptide in question. One International Unit (IU) of Factor VIII or Factor IX activity corresponds approximately to the quantity of Factor VIII or Factor IX in one milliliter of normal human plasma. Several assays are available for measuring Factor VIII or Factor IX activity, including the European Pharmacopoeia chromogenic substrate assay and a one stage clotting assay.

"Polypeptide," "peptide" and "protein" are used interchangeably and refer to a polymeric compound comprised of covalently linked amino acid residues.

"Polynucleotide" and "nucleic acid" are used interchangeably and refer to a polymeric compound comprised of covalently linked nucleotide residues. Polynucleotides can be DNA, cDNA, RNA, single stranded, or double stranded, vectors, plasmids, phage, or viruses. Polynucleotides include those in SEQUENCE Table 1, which encode the polypeptides of SEQUENCE Table 2 (see SEQUENCE Table 1). Polynucleotides also include fragments of the polynucleotides of SEQUENCE Table 1, e.g., those that encode fragments of the polypeptides of SEQUENCE Table 2, such as Factor VIII, Factor IX, Fc, signal sequence, propeptide, 6His and other fragments of the polypeptides of SEQUENCE Table 2.

"Subject," as used herein means a human or a non-human mammal. Non-human mammals include mice, dogs, primates, bears, cats, horses, cows, pigs, and other domestic animals and small animals. Subjects also include pediatric humans. Pediatric human subjects are birth to 20 years, e.g., birth to 18 years, birth to 16 years, birth to 15 years, birth to 12 years, birth to 11 years, birth to 6 years, birth to 5 years, birth to 2 years, or 2 to 11 years of age.

The methods of the invention can be practiced on a subject in need of control or prevention of bleeding, bleeding episodes, or hemophilia disorders. Such subjects include those in need of control or prevention of bleeding in minor hemorrhage, hemarthroses, superficial muscle hemorrhage, soft tissue hemorrhage, moderate hemorrhage, intramuscle or soft tissue hemorrhage with dissection, mucous membrane hemorrhage, hematuria, major hemorrhage, hemorrhage of the pharynx, hemorrhage of the retropharynx, hemorrhage of the retroperitonium, hemorrhage of the central nervous system, bruises, cuts, scrapes, joint hemorrhage, nose bleed, mouth bleed, gum bleed, intracranial bleeding, intraperitoneal bleeding, minor spontaneous hemorrhage, bleeding after major trauma, moderate skin bruising, or spontaneous hemorrhage into joints, muscles, internal organs or the brain. Such subjects also include those need of pen-operative management, such as management of bleeding associated with surgery or dental extraction.

"Variant," as used herein, refers to a polynucleotide or polypeptide differing from the original polynucleotide or polypeptide, but retaining essential properties thereof, e.g., Factor VIII coagulant activity, Factor IX coagulant activity or Fc (FcRn binding) activity. Generally, variants are overall closely similar, and, in many regions, identical to the original polynucleotide or polypeptide. Variants include polypeptide and polynucleotide fragments, deletions, insertions, and modified versions of original polypeptides.

Variant polynucleotides can comprise, or alternatively consist of, a nucleotide sequence which is at least 85%, 90%, 95%, 96%, 97%, 98% or 99% identical to, for example, the nucleotide coding sequence in SEQ ID NO:1, 3, 5, 7, 9, 11, or 13 (the Factor VIII portion, the Factor IX portion, the Fc portion, individually or together) or the complementary strand thereto, the nucleotide coding sequence of known mutant and recombinant Factor VIII, Factor IX, or Fc such as those disclosed in the publications and patents cited herein or the complementary strand thereto, a nucleotide sequence encoding the polypeptide of SEQ ID NO:2, 4, 6, 8, 10, 12, or 14 (the Factor VIII portion, the Factor IX portion, the Fc portion, individually or together), and/or polynucleotide fragments of any of these nucleic acid molecules (e.g., those fragments described herein). Polynucleotides which hybridize to these nucleic acid molecules under stringent hybridization conditions or lower stringency conditions are also included as variants, as are polypeptides encoded by these polynucleotides as long as they are functional.

Variant polypeptides can comprise, or alternatively consist of, an amino acid sequence which is at least 85%, 90%, 95%, 96%, 97%, 98%, 99% identical to, for example, the polypeptide sequence shown in SEQ ID NO:2, 4, 8, 8, 10, 12, or 14 (the Factor VIII portion, the Factor IX portion, the Fc portion, individually or together), and/or polypeptide fragments of any of these polypeptides (e.g., those fragments described herein).

By a nucleic acid having a nucleotide sequence at least, for example, 95% "identical" to a reference nucleotide sequence, it is intended that the nucleotide sequence of the nucleic acid is identical to the reference sequence except that the nucleotide sequence can include up to five point mutations per each 100 nucleotides of the reference nucleotide sequence. In other words, to obtain a nucleic acid having a nucleotide sequence at least 95% identical to a reference nucleotide sequence, up to 5% of the nucleotides in the reference sequence can be deleted or substituted with another nucleotide, or a number of nucleotides up to 5% of the total nucleotides in the reference sequence can be inserted into the reference sequence. The query sequence can be, for example, the entire sequence shown in SEQ ID NO:1, 3, 5, 7, 9, 11, or 13, an ORF (open reading frame), or any fragment specified as described herein.

A polypeptide which is "isolated" is a polypeptide which is in a form not found in nature. Isolated polypeptides include those which have been purified to a degree that they are no longer in a form in which they are found in nature. In some embodiments, a polypeptide which is isolated is substantially pure.

A "recombinant" polypeptide or protein refers to a polypeptide or protein produced via recombinant DNA technology. Recombinantly produced polypeptides and proteins expressed in host cells are considered isolated for the purpose of the invention, as are native or recombinant polypeptides which have been separated, fractionated, or partially or substantially purified by any suitable technique. The polypeptides disclosed herein, e.g., clotting factors or procoagulant peptides, can be recombinantly produced using methods known in the art. Alternatively, proteins and peptides disclosed herein can be chemically synthesized.

A "conservative amino acid substitution" is one in which the amino acid residue is replaced with an amino acid residue having a similar side chain. Families of amino acid residues having similar side chains have been defined in the art, including basic side chains (e.g., Lys, Arg, His), acidic side chains (e.g., Asp, Glu), uncharged polar side chains (e.g., Gly, Asn, Gln, Ser, Thr, Tyr, Cys), nonpolar side chains (e.g., Ala, Val, Leu, Ile, Pro, Phe, Met, Trp), beta-branched side chains (e.g., Thr, Val, Ile) and aromatic side chains (e.g., Tyr, Phe, Trp, His). Thus, if an amino acid in a polypeptide is replaced with another amino acid from the same side chain family, the substitution is considered to be conservative. In another embodiment, a string of amino acids can be conservatively replaced with a structurally similar string that differs in order and/or composition of side chain family members.

Non-conservative substitutions include those in which (i) a residue having an electropositive side chain (e.g., Arg, His or Lys) is substituted for, or by, an electronegative residue (e.g., Glu or Asp), (ii) a hydrophilic residue (e.g., Ser or Thr) is substituted for, or by, a hydrophobic residue (e.g., Ala, Leu, He, Phe or Val), (iii) a cysteine or proline is substituted for, or by, any other residue, or (iv) a residue having a bulky hydrophobic or aromatic side chain (e.g., Val, He, Phe or Trp) is substituted for, or by, one having a smaller side chain (e.g., Ala, Ser) or no side chain (e.g., Gly).

The term "percent sequence identity" between two polynucleotide or polypeptide sequences refers to the number of identical matched positions shared by the sequences over a comparison window, taking into account additions or deletions (e.g., gaps) that must be introduced for optimal alignment of the two sequences. A matched position is any position where an identical nucleotide or amino acid is presented in both the target and reference sequence. Gaps presented in the target sequence are not counted since gaps are not nucleotides or amino acids. Likewise, gaps presented in the reference sequence are not counted since target sequence nucleotides or amino acids are counted, not nucleotides or amino acids from the reference sequence.

The percentage of sequence identity is calculated by determining the number of positions at which the identical amino-acid residue or nucleic acid base occurs in both sequences to yield the number of matched positions, dividing the number of matched positions by the total number of positions in the window of comparison and multiplying the result by 100 to yield the percentage of sequence identity. The comparison of sequences and determination of percent sequence identity between two sequences can be accomplished using readily available software both for online use and for download. Suitable software programs are available from various sources, and for alignment of both protein and nucleotide sequences. One suitable program to determine percent sequence identity is bl2seq, part of the BLAST suite of program available from the U.S. government's National Center for Biotechnology Information BLAST web site (blast.ncbi.nlm.nih.gov). Bl2seq performs a comparison between two sequences using either the BLASTN or BLASTP algorithm. BLASTN is used to compare nucleic acid sequences, while BLASTP is used to compare amino acid sequences. Other suitable programs are, e.g., Needle, Stretcher, Water, or Matcher, part of the EMBOSS suite of bioinformatics programs and also available from the European Bioinformatics Institute (EBI) at www.ebi.ac.uk/Tools/psa.

Different regions within a single polynucleotide or polypeptide target sequence that aligns with a polynucleotide or polypeptide reference sequence can each have their own percent sequence identity. It is noted that the percent sequence identity value is rounded to the nearest tenth. For example, 80.11, 80.12, 80.13, and 80.14 are rounded down to 80.1, while 80.15, 80.16, 80.17, 80.18, and 80.19 are rounded up to 80.2. It also is noted that the length value will always be an integer.

In certain embodiments, the percentage identity "X" of a first amino acid sequence to a second sequence amino acid is calculated as 100×(Y/Z), where Y is the number of amino acid residues scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be higher than the percent identity of the second sequence to the first sequence.

One skilled in the art will appreciate that the generation of a sequence alignment for the calculation of a percent sequence identity is not limited to binary sequence-sequence comparisons exclusively driven by primary sequence data. Sequence alignments can be derived from multiple sequence alignments. One suitable program to generate multiple sequence alignments is ClustalW2, available from www.clustal.org. Another suitable program is MUSCLE, available from www.drive5.com/muscle/. ClustalW2 and MUSCLE are alternatively available, e.g., from the EBI.

It will also be appreciated that sequence alignments can be generated by integrating sequence data with data from heterogeneous sources such as structural data (e.g., crystallographic protein structures), functional data (e.g., location of mutations), or phylogenetic data. A suitable program that integrates heterogeneous data to generate a multiple sequence alignment is T-Coffee, available at www.tcoffee.org, and alternatively available, e.g., from the EBI. It will also be appreciated that the final alignment used to calculate percent sequence identity can be curated either automatically or manually.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence can include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence can be inserted, deleted, (indels) or substituted with another amino acid. These alterations of the reference sequence can occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 85%, 90%, 95%, 96%, 97%, 98% or 99% identical to, for instance, the amino acid sequences of SEQ ID NO:2, SEQ ID NO:4, SEQ ID NO:6, or SEQ ID NO:14 (the factor VIII portion, the Factor IX portion, the Fc portion, individually or together), or a known Factor VIII or Factor IX or Fc polypeptide sequence, can be determined conventionally using known computer programs. One method for determining the best overall match between a query sequence (reference or original sequence) and a subject sequence, also referred to as a global sequence alignment, can be determined using the FASTDB computer program based on the algorithm of Brutlag et al., Comp. App. Biosci. 6:237-245 (1990), incorporated herein by reference in its entirety. In a sequence alignment the query and subject sequences are either both nucleotide sequences or both amino acid sequences. The result of said global sequence alignment is in percent identity. Typical parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence, are manually corrected for.

The polynucleotide variants can contain alterations in the coding regions, non-coding regions, or both. Examples include, without limitation polynucleotide variants containing alterations which produce silent substitutions, additions, or deletions, but do not alter the properties or activities of the encoded polypeptide. Nucleotide variants can be produced by silent substitutions due to the degeneracy of the genetic code. In addition, variants in which 5-10, 1-5, or 1-2 amino acids are substituted, deleted, or added in any combination are included. Polynucleotide variants can be produced for a variety of reasons, e.g., to optimize codon expression for a particular host (change codons in the human mRNA to those preferred by a bacterial host such as E. coli).

Naturally occurring variants are called "allelic variants," and refer to one of several alternate forms of a gene occupying a given locus on a chromosome of an organism (Genes II, Lewin, B., ed., John Wiley & Sons, New York (1985)). These allelic variants can vary at either the polynucleotide and/or polypeptide level and are included in the present invention. Alternatively, non-naturally occurring variants can be produced by mutagenesis techniques or by direct synthesis.

Using known methods of protein engineering and recombinant DNA technology, variants can be generated to improve or alter the characteristics of the polypeptides. For instance, one or more amino acids can be deleted from the N-terminus or C-terminus of the secreted protein without substantial loss of biological function. The authors of Ron et al., J. Biol. Chem. 268: 2984-2988 (1993), incorporated herein by reference in its entirety, reported variant KGF proteins having heparin binding activity even after deleting 3, 8, or 27 amino-terminal amino acid residues. Similarly, Interferon gamma exhibited up to ten times higher activity after deleting 8-10 amino acid residues from the carboxy terminus of this protein. (Dobeli et al., J. Biotechnology 7:199-216 (1988), incorporated herein by reference in its entirety.)

Moreover, ample evidence demonstrates that variants often retain a biological activity similar to that of the naturally occurring protein. For example, Gayle and coworkers (J. Biol. Chem. 268:22105-22111 (1993), incorporated herein by reference in its entirety) conducted extensive mutational analysis of human cytokine IL-la. They used random mutagenesis to generate over 3,500 individual IL-la mutants that averaged 2.5 amino acid changes per variant over the entire length of the molecule. Multiple mutations were examined at every possible amino acid position. The investigators found that "[m]ost of the molecule could be altered with little effect on either [binding or biological activity]." (See Abstract.) In fact, only 23 unique amino acid sequences, out of more than 3,500 nucleotide sequences examined, produced a protein that significantly differed in activity from wild type.

As stated above, polypeptide variants include modified polypeptides. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination.

The term "about" is used herein to mean approximately, roughly, around, or in the regions of. When the term "about" is used in conjunction with a numerical range, it modifies that range by extending the boundaries above and below the numerical values set forth. Thus, "about 10-20" means "about 10 to about 20." In general, the term "about" is used herein to modify a numerical value above and below the stated value by a variance of 10 percent, up or down (higher or lower).

As used herein, the term "healthcare provider" refers to individuals or institutions which directly interact and administer to living subjects, e.g., human patients. Non-limiting examples of healthcare providers include doctors, nurses, technicians, therapist, pharmacists, counselors, alternative medicine practitioners, medical facilities, doctor's offices, hospitals, emergency rooms, clinics, urgent care centers, alternative medicine clinics/facilities, and any other entity providing general and/or specialized treatment, assessment, maintenance, therapy, medication, and/or advice relating to all, or any portion of, a patient's state of health, including but not limited to general medical, specialized medical, surgical, and/or any other type of treatment, assessment, maintenance, therapy, medication and/or advice.

As used herein, the term "clinical laboratory" refers to a facility for the examination or processing of materials derived from a living subject, e.g., a human being. Non-limiting examples of processing include biological, biochemical, serological, chemical, immunohematological, hematological, biophysical, cytological, pathological, genetic, or other examination of materials derived from the human body for the purpose of providing information, e.g., for the diagnosis, prevention, or treatment of any disease or impairment of, or the assessment of the health of living subjects, e.g., human beings. These examinations can also include procedures to collect or otherwise obtain a sample, prepare, determine, measure, or otherwise describe the presence or absence of various substances in the body of a living subject, e.g., a human being, or a sample obtained from the body of a living subject, e.g., a human being. In certain aspects a clinical laboratory can be "centralized" or "local", meaning that a small number or a single laboratory makes all measurements of samples submitted from all outside sources. In other aspects, multiple clinical laboratories, also referred to as "satellite" or "global" laboratories, can be validated to all provide standard, reliable results that can be easily compared.

As used herein, the term "healthcare benefits provider" encompasses individual parties, organizations, or groups providing, presenting, offering, paying for in whole or in part, or being otherwise associated with giving a patient access to one or more healthcare benefits, benefit plans, health insurance, and/or healthcare expense account programs.

In some aspects, a healthcare provider can administer or instruct another healthcare provider to administer a therapy to treat a bleeding disease or disorder. A healthcare provider can implement or instruct another healthcare provider or patient to perform the following actions: obtain a sample, process a sample, submit a sample, receive a sample, transfer a sample, analyze or measure a sample, quantify a sample, provide the results obtained after analyzing/measuring/quantifying a sample, receive the results obtained after analyzing/measuring/quantifying a sample, compare/score the results obtained after analyzing/measuring/quantifying one or more samples, provide the comparison/score from one or more samples, obtain the comparison/score from one or more samples, administer a therapy or therapeutic agent (e.g., a clotting factor such as a factor VIII or factor IX polypeptide), commence the administration of a therapy, cease the administration of a therapy, continue the administration of a therapy, temporarily interrupt the administration of a therapy, increase the amount of an administered therapeutic agent, decrease the amount of an administered therapeutic agent, continue the administration of an amount of a therapeutic agent, increase the frequency of administration of a therapeutic agent, decrease the frequency of administration of a therapeutic agent, maintain the same dosing frequency on a therapeutic agent, replace a therapy or therapeutic agent by at least another therapy or therapeutic agent, combine a therapy or therapeutic agent with at least another therapy or additional therapeutic agent.

In some aspects, a healthcare benefits provider can authorize or deny, for example, collection of a sample, processing of a sample, submission of a sample, receipt of a sample, transfer of a sample, analysis or measurement a sample, quantification a sample, provision of results obtained after analyzing/measuring/quantifying a sample, transfer of results obtained after analyzing/measuring/quantifying a sample, comparison/scoring of results obtained after analyzing/measuring/quantifying one or more samples, transfer of the comparison/score from one or more samples, administration of a therapy or therapeutic agent, commencement of the administration of a therapy or therapeutic agent, cessation of the administration of a therapy or therapeutic agent, continuation of the administration of a therapy or therapeutic agent, temporary interruption of the administration of a therapy or therapeutic agent, increase of the amount of administered therapeutic agent, decrease of the amount of administered therapeutic agent, continuation of the administration of an amount of a therapeutic agent, increase in the frequency of administration of a therapeutic agent, decrease in the frequency of administration of a therapeutic agent, maintain the same dosing frequency on a therapeutic agent, replace a therapy or therapeutic agent by at least another therapy or therapeutic agent, or combine a therapy or therapeutic agent with at least another therapy or additional therapeutic agent.

In addition a healthcare benefits providers can, e.g., authorize or deny the prescription of a therapy, authorize or deny coverage for therapy, authorize or deny reimbursement for the cost of therapy, determine or deny eligibility for therapy, etc.

In some aspects, a clinical laboratory can, for example, collect or obtain a sample, process a sample, submit a sample, receive a sample, transfer a sample, analyze or measure a sample, quantify a sample, provide the results obtained after analyzing/measuring/quantifying a sample, receive the results obtained after analyzing/measuring/quantifying a sample, compare/score the results obtained after analyzing/measuring/quantifying one or more samples, provide the comparison/score from one or more samples, obtain the comparison/score from one or more samples, The above enumerated actions can be performed by a healthcare provider, healthcare benefits provider, or patient automatically using a computer-implemented method (e.g., via a web service or stand-alone computer system).

Abbreviations $AUC_{INF}$ Area under the concentration-time curve from zero to infinity $AUC_\alpha$ Area under the concentration-time curve over the distribution phase $AUC_\beta$ Area under the concentration-time curve over the elimination phase Alpha HL Distribution phase half-life Beta HL Elimination phase half-life; also referred to as $t_{1/2}$ C168 Estimated FIXFc activity above baseline at approximately 168 h after dose $C_{max}$ Maximum concentration, occurring at $T_{max}$ CV % Percent coefficient of variation Cl Clearance IVR in vivo recovery (%)
K-Value Incremental recovery
MRT Mean residence time
N Number
NC Not Calculable
NR Not Reported
SD Standard Deviation
SE Standard Error
TBLP1 Model-predicted time after dose when FIXFc activity has declined to approximately 1 IU/dL above baseline
TBLP3 Model-predicted time after dose when FIXFc activity has declined to approximately 3 IU/dL above baseline
TBLP5 Model-predicted time after dose when FIXFc activity has declined to approximately 5 IU/dL above baseline
$V_{SS}$ Volume of distribution at steady state
$V_1$ Volume of distribution of the central compartment
EXTEM Thromboelastometry using extrinsic activator such as tissue factor (TF)
INTEM Thromboelastometry using intrinsic activator such as ellagic acid
NATEM Thromboelastometry using natural activation after recalcification
ROTEM® Rotation thromboelastometry
PPP Platelet poor plasma

II. Factor VIII and Factor IX Polypeptides

A. Factor VIII Polypeptides

"Factor VIII," as used herein, means functional factor VIII polypeptide in its normal role in coagulation, unless otherwise specified. Thus, the term Factor VIII includes variant polypeptides that are functional. Factor VIII proteins include the human, porcine, canine, and murine factor VIII proteins. The full length polypeptide and polynucleotide sequences are known, as are many functional fragments, mutants and modified versions. Examples of human factor VIII sequences are shown as subsequences in SEQ ID NOs:2, 6, 8, 10, and 12 (SEQUENCE Table 2). Factor VIII polypeptides include, e.g., full-length factor VIII, full-length factor VIII minus Met at the N-terminus, mature factor VIII (minus the signal sequence), mature factor VIII with an additional Met at the N-terminus, and/or factor VIII with a full or partial deletion of the B domain. Factor VIII polypeptides include B domain deletions, whether partial or full deletions or single chain FVIII. Factor VIII can be made by recombinant means ("recombinant Factor VIII" or "rFVIII"), i.e., it is not naturally occurring or derived from plasma.

"B domain" of Factor VIII, as used herein, is the same as the B domain known in the art that is defined by internal amino acid sequence identity and sites of proteolytic cleavage by thrombin, e.g., residues Ser741-Arg1648 of full length human factor VIII. The other human factor VIII domains are defined by the following amino acid residues: A1, residues Ala1-Arg372; A2, residues Ser373-Arg740; A3, residues Ser1690-Ile2032; C1, residues Arg2033-Asn2172; C2, residues Ser2173-Tyr2332. The A3-C1-C2 sequence includes residues Ser1690-Tyr2332. The remaining sequence, residues Glu1649-Arg1689, is usually referred to as the factor VIII light chain activation peptide. The locations of the boundaries for all of the domains, including the B domains, for porcine, mouse and canine factor VIII are also known in the art. In certain aspects, the B domain of Factor VIII is deleted ("B domain deleted factor VIII" or "BDD FVIII"). An example of a BDD FVIII is REFACTO (recombinant BDD FVIII), which has the same sequence as the Factor VIII portion of the sequence in SEQUENCE Table 2A(i) (amino acids −19 to 1438 or 1 to 1438 of SEQ ID NO:2).

Figure 2:
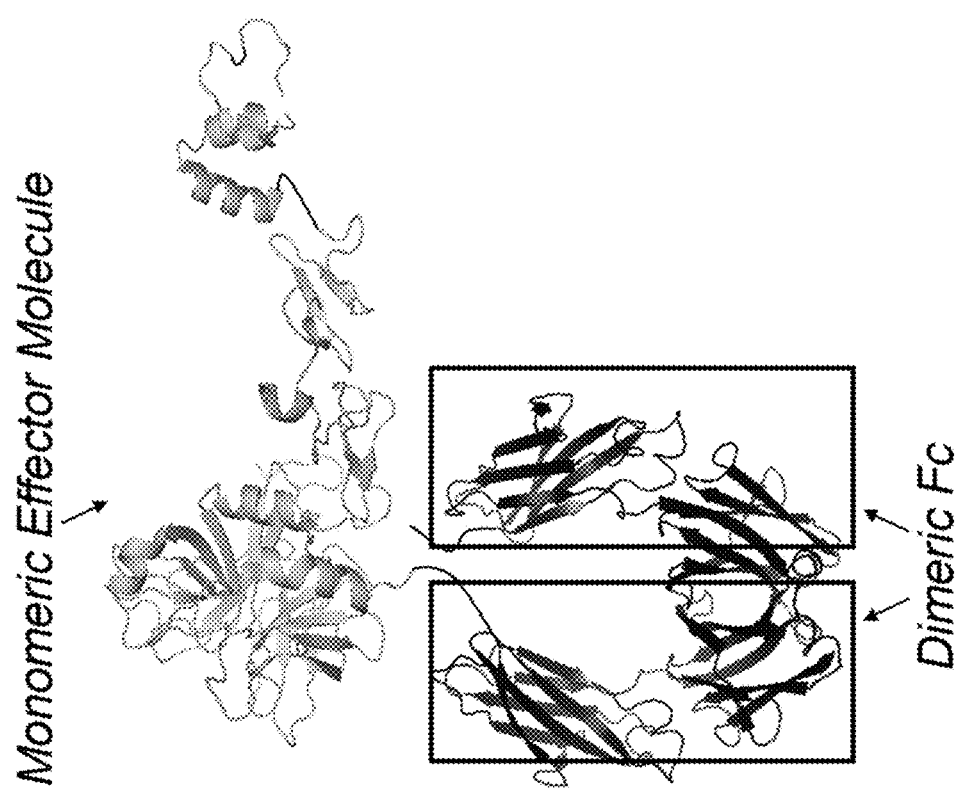
FIG. 2. Schematic of one type of Factor IX chimeric polypeptide, a rFIXFc protein.

A "B domain deleted factor VIII" can have the full or partial deletions disclosed in U.S. Pat. Nos. 6,316,226, 6,346,513, 7,041,635, 5,789,203, 6,060,447, 5,595,886, 6,228,620, 5,972,885, 6,048,720, 5,543,502, 5,610,278, 5,171,844, 5,112,950, 4,868,112, and 6,458,563, each of which is incorporated herein by reference in its entirety. In some embodiments, a B domain deleted factor VIII sequence of the present invention comprises any one of the deletions disclosed at col. 4, line 4 to col. 5, line 28 and examples 1-5 of U.S. Pat. No. 6,316,226 (also in U.S. Pat. No. 6,346,513). In some embodiments, a B domain deleted factor VIII of the present invention has a deletion disclosed at col. 2, lines 26-51 and examples 5-8 of U.S. Pat. No. 5,789,203 (also U.S. Pat. Nos. 6,060,447, 5,595,886, and 6,228,620). In some embodiments, a B domain deleted factor VIII has a deletion described in col. 1, lines 25 to col. 2, line 40 of U.S. Pat. No. 5,972,885; col. 6, lines 1-22 and example 1 of U.S. Pat. No. 6,048,720; col. 2, lines 17-46 of U.S. Pat. No. 5,543,502; col. 4, line 22 to col. 5, line 36 of U.S. Pat. No. 5,171,844; col. 2, lines 55-68, FIG. 2, and example 1 of U.S. Pat. No. 5,112,950; col. 2, line 2 to col. 19, line 21 and table 2 of U.S. Pat. No. 4,868,112; col. 2, line 1 to col. 3, line 19, col. 3, line 40 to col. 4, line 67, col. 7, line 43 to col. 8, line 26, and col. 11, line 5 to col. 13, line 39 of U.S. Pat. No. 7,041,635; or col. 4, lines 25-53, of U.S. Pat. No. 6,458,563. In some embodiments, a B domain deleted factor VIII has a deletion of most of the B domain, but still contains amino-terminal sequences of the B domain that are essential for in vivo proteolytic processing of the primary translation product into two polypeptide chain, as disclosed in WO 91/09122, which is incorporated herein by reference in its entirety. In some embodiments, a B domain deleted factor VIII is constructed with a deletion of amino acids 747-1638, e.g., virtually a complete deletion of the B domain. Hoeben R. C., et al. *J. Biol. Chem.* 265 (13): 7318-7323 (1990), incorporated herein by reference in its entirety. A B domain deleted factor VIII can also contain a deletion of amino acids 771-1666 or amino acids 868-1562 of factor VIII. Meulien P., et al. *Protein Eng.* 2(4): 301-6 (1988), incorporated herein by reference in its entirety. Additional B domain deletions that are part of the invention include, e.g., deletion of amino acids 982 through 1562 or 760 through 1639 (Toole et al., Proc. Natl. Acad. Sci. U.S.A. (1986) 83, 5939-5942)), 797 through 1562 (Eaton, et al. Biochemistry (1986) 25:8343-8347)), 741 through 1646 (Kaufman (PCT published application No. WO 87/04187)), 747-1560 (Sarver, et al., DNA (1987) 6:553-564)), 741 through 1648 (Pasek (PCT application No. 88/00831)), 816 through 1598 or 741 through 1689 (Lagner (Behring Inst. Mitt. (1988) No 82:16-25, EP 295597)), each of which is incorporated herein by reference in its entirety.

In other embodiments, BDD FVIII includes a FVIII polypeptide containing fragments of the B-domain that retain one or more N-linked glycosylation sites, e.g., residues 757, 784, 828, 900, 963, or optimally 943, which correspond to the amino acid sequence of the full-length FVIII sequence. Examples of the B-domain fragments include 226 amino acids or 163 amino acids of the B-domain as disclosed in Miao, H. Z., et al., Blood 103(a): 3412-3419 (2004), Kasuda, A, et al., J. Thromb. Haemost. 6: 1352-1359 (2008), and Pipe, S. W., et al., J. Thromb. Haemost. 9: 2235-2242 (2011) (e.g., the first 226 amino acids or 163 amino acids of the B domain are retained). In still other embodiments, BDD FVIII further comprises a point mutation at residue 309 (from Phe to Ser) to improve expression of the BDD FVIII protein. See Miao, H. Z., et al., Blood 103(a): 3412-3419 (2004). In still other embodiments, the BDD FVIII includes a FVIII polypeptide containing a portion of the B-domain, but not containing one or more furin cleavage sites (e.g., Arg1313 and Arg 1648). See Pipe, S. W., et al., J. Thromb. Haemost. 9: 2235-2242 (2011). The references are incorporated herein by reference, and each of the foregoing deletions can be made in any Factor VIII sequence.

In certain embodiments, FVIII includes a single chain FVIII polypeptide. In one embodiment, a single chain FVIII polypeptide can include one or more mutations or substitutions at R1645 or R1648 corresponding to full-length Factor VIII sequence or both. Additional examples of single chain FVIII polypeptides can be found at U.S. Provisional Application No. 61/668,889, filed Jul. 6, 2012, which is incorporated herein by reference in its entirety. In another embodiment, a single chain FVIII polypeptide contains a FVIII polypeptide having a deletion of R1645 and/or R1648 corresponding to full-length FVIII sequence or a deletion of a sequence containing R1645 and/or R1648 corresponding to full-length FVIII. For example, a single chain FVIII can contain a deletion of amino acid positions 746 to 1649, 746 to 1652, 746 to 1655, 758 to 1649, 758 to 1652, 758 to 1655, 765 to 1649, 765 to 1652, 765 to 1655, 748 to 1658, 755 to 1658, 762 to 1658, 769 to 1658, 776 to 1658, or 783 to 1658 corresponding to full-length FVIII sequence. Additional examples of single chain FVIII can be found at U.S. Pat. No. 7,041,635, filed Jan. 3, 2003, which is incorporated herein by reference in its entirety.

A great many functional factor VIII variants are known, as is discussed above and below. In addition, hundreds of nonfunctional mutations in factor VIII have been identified in hemophilia patients, and it has been determined that the effect of these mutations on factor VIII function is due more to where they lie within the 3-dimensional structure of factor VIII than on the nature of the substitution (Cutler et al., Hum. Mutat. 19:274-8 (2002), incorporated herein by reference in its entirety). In addition, comparisons between factor VIII from humans and other species have identified conserved residues that are likely to be required for function (Cameron et al., Thromb. Haemost. 79:317-22 (1998); U.S. Pat. No. 6,251,632), incorporated herein by reference in its entirety.

The human factor VIII gene was isolated and expressed in mammalian cells (Toole, J. J., et al., Nature 312:342-347 (1984); Gitschier, J., et al., Nature 312:326-330 (1984); Wood, W. I., et al., Nature 312:330-337 (1984); Vehar, G. A., et al., Nature 312:337-342 (1984); WO 87/04187; WO 88/08035; WO 88/03558; U.S. Pat. No. 4,757,006), each of which is incorporated herein by reference in its entirety and the amino acid sequence was deduced from cDNA. Capon et al., U.S. Pat. No. 4,965,199, incorporated herein by reference in its entirety, discloses a recombinant DNA method for producing factor VIII in mammalian host cells and purification of human factor VIII. Human factor VIII expression in CHO (Chinese hamster ovary) cells and BHKC (baby hamster kidney cells) has been reported. Human factor VIII has been modified to delete part of or the entire B domain (U.S. Pat. Nos. 4,994,371 and 4,868,112, each of which is incorporated herein by reference in its entirety), and replacement of the human factor VIII B domain with the human factor V B domain has been performed (U.S. Pat. No. 5,004,803, incorporated herein by reference in its entirety). The cDNA sequence encoding human factor VIII and predicted amino acid sequence are shown in SEQ ID NOs:1 and 2, respectively, of US Application Publ. No. 2005/0100990, incorporated herein by reference in its entirety.

U.S. Pat. No. 5,859,204, Lollar, J. S., incorporated herein by reference in its entirety, reports functional mutants of factor VIII having reduced antigenicity and reduced immunoreactivity. U.S. Pat. No. 6,376,463, Lollar, J. S., incorporated herein by reference in its entirety, also reports mutants of factor VIII having reduced immunoreactivity. US Application Publ. No. 2005/0100990, Saenko et al., incorporated herein by reference in its entirety, reports functional mutations in the A2 domain of factor VIII.

A number of functional factor VIII molecules, including B-domain deletions, are disclosed in the following U.S. Pat. Nos. 6,316,226 and 6,346,513, both assigned to Baxter; U.S. Pat. No. 7,041,635 assigned to In2Gen; U.S. Pat. Nos. 5,789,203, 6,060,447, 5,595,886, and 6,228,620 assigned to Chiron; U.S. Pat. Nos. 5,972,885 and 6,048,720 assigned to Biovitrum, U.S. Pat. Nos. 5,543,502 and 5,610,278 assigned to Novo Nordisk; U.S. Pat. No. 5,171,844 assigned to Immuno Ag; U.S. Pat. No. 5,112,950 assigned to Transgene S. A.; U.S. Pat. No. 4,868,112 assigned to Genetics Institute, each of which is incorporated herein by reference in its entirety.

The porcine factor VIII sequence is published, (Toole, J. J., et al., Proc. Natl. Acad. Sci. USA 83:5939-5942 (1986)), incorporated herein by reference in its entirety, and the complete porcine cDNA sequence obtained from PCR amplification of factor VIII sequences from a pig spleen cDNA library has been reported (Healey, J. F., et al., Blood 88:4209-4214 (1996), incorporated herein by reference in its entirety). Hybrid human/porcine factor VIII having substitutions of all domains, all subunits, and specific amino acid sequences were disclosed in U.S. Pat. No. 5,364,771 by Lollar and Runge, and in WO 93/20093, incorporated herein by reference in its entirety. More recently, the nucleotide and corresponding amino acid sequences of the A1 and A2 domains of porcine factor VIII and a chimeric factor VIII with porcine A1 and/or A2 domains substituted for the corresponding human domains were reported in WO 94/11503, incorporated herein by reference in its entirety. U.S. Pat. No. 5,859,204, Lollar, J. S., also discloses the porcine cDNA and deduced amino acid sequences. U.S. Pat. No. 6,458,563, incorporated herein by reference in its entirety assigned to Emory discloses a B-domain deleted porcine Factor VIII.

The Factor VIII (or Factor VIII portion of a chimeric polypeptide) can be at least 90% or 95% identical to a Factor VIII amino acid sequence shown in SEQUENCE Table 2 without a signal sequence (amino acids 1 to 1438 of SEQ ID NO:2; amino acids 1 to 2332 of SEQ ID NO:6; amino acids 1 to 740 of SEQ ID NO:8; amino acids 1 to 745 of SEQ ID NO:10; or amino acids 1 to 684 of SEQ ID NO:12). The Factor VIII (or Factor VIII portion of a chimeric polypeptide) can be identical to a Factor VIII amino acid sequence shown in SEQUENCE Table 2 without a signal sequence (amino acids 1 to 1438 of SEQ ID NO:2; amino acids 1 to 2332 of SEQ ID NO:6; amino acids 1 to 740 of SEQ ID NO:8; amino acids 1 to 745 of SEQ ID NO:10; or amino acids 1 to 684 of SEQ ID NO:12).

The Factor VIII (or Factor VIII portion of a chimeric polypeptide) can be at least 90% or 95% identical to a Factor VIII amino acid sequence shown in SEQUENCE Table 2 with a signal sequence (amino acids −19 to 1438 of SEQ ID NO:2; amino acids −19 to 2332 of SEQ ID NO:6; amino acids −19 to 740 of SEQ ID NO:8; amino acids −19 to 745 of SEQ ID NO:10; or amino acids −20 to 684 of SEQ ID NO:12). The Factor VIII (or Factor VIII portion of a chimeric polypeptide) can be identical to a Factor VIII amino acid sequence shown in SEQUENCE Table 2 with a signal sequence (amino acids −19 to 1438 of SEQ ID NO:2; amino acids −19 to 2332 of SEQ ID NO:6; amino acids −19 to 740 of SEQ ID NO:8; amino acids −19 to 745 of SEQ ID NO:10; or amino acids −20 to 684 of SEQ ID NO:12).

B. Factor IX Polypeptides

"Factor IX", "FIX", "protein having FIX activity", "FIX protein", or "FIX polypeptide" as used herein, means functional Factor IX polypeptide in its normal role in coagulation, unless otherwise specified. Thus, the term Factor IX includes variant polypeptides that are functional and the polynucleotides that encode such functional variant polypeptides. Factor IX polypeptides include the human, bovine, porcine, canine, feline, and murine Factor IX polypeptides. The full length polypeptide and polynucleotide sequences of Factor IX are known, as are many functional variants, e.g., fragments, mutants and modified versions. Factor IX polypeptides include full-length Factor IX, full-length Factor IX minus Met at the N-terminus, full-length Factor IX minus the signal sequence, mature Factor IX (minus the signal sequence and propeptide), and mature Factor IX with an additional Met at the N-terminus. Factor IX can be made by recombinant means ("recombinant Factor IX" or "rFIX"), i.e., it is not naturally occurring or derived from plasma.

A great many functional Factor IX variants are known. International publication number WO 02/040544 A3, which is herein incorporated by reference in its entirety, discloses mutants that exhibit increased resistance to inhibition by heparin at page 4, lines 9-30 and page 15, lines 6-31. International publication number WO 03/020764 A2, which is herein incorporated by reference in its entirety, discloses Factor IX mutants with reduced T cell immunogenicity in Tables 2 and 3 (on pages 14-24), and at page 12, lines 1-27. International publication number WO 2007/149406 A2, which is herein incorporated by reference in its entirety, discloses functional mutant Factor IX molecules that exhibit increased protein stability, increased in vivo and in vitro half-life, and increased resistance to proteases at page 4, line 1 to page 19, line 11. WO 2007/149406 A2 also discloses chimeric and other variant Factor IX molecules at page 19, line 12 to page 20, line 9. International publication number WO 08/118507 A2, which is herein incorporated by reference in its entirety, discloses Factor IX mutants that exhibit increased clotting activity at page 5, line 14 to page 6, line 5. International publication number WO 09/051717 A2, which is herein incorporated by reference in its entirety, discloses Factor IX mutants having an increased number of N-linked and/or O-linked glycosylation sites, which results in an increased half-life and/or recovery at page 9, line 11 to page 20, line 2. International publication number WO 09/137254 A2, which is herein incorporated by reference in its entirety, also discloses Factor IX mutants with increased numbers of glycosylation sites at page 2, paragraph [006] to page 5, paragraph [011] and page 16, paragraph [044] to page 24, paragraph [057]. International publication number WO 09/130198 A2, which is herein incorporated by reference in its entirety, discloses functional mutant Factor IX molecules that have an increased number of glycosylation sites, which result in an increased half-life, at page 4, line 26 to page 12, line 6. International publication number WO 09/140015 A2, which is herein incorporated by reference in its entirety, discloses functional mutant Factor IX mutants that an increased number of Cys residues, which can be used for polymer (e.g., PEG) conjugation, at page 11, paragraph [0043] to page 13, paragraph [0053].

In addition, hundreds of non-functional mutations in Factor IX have been identified in hemophilia patients, many of which are disclosed in Table 1, at pages 11-14 of International publication number WO 09/137254 A2, which is herein incorporated by reference in its entirety. Such non-functional mutations are not included in the invention, but provide additional guidance for which mutations are more or less likely to result in a functional Factor IX polypeptide.

The Factor IX (or Factor IX portion of a chimeric polypeptide) can be at least 90% or at least 95% or 100% identical to a Factor IX amino acid sequence shown in SEQUENCE Table 2 without a signal sequence and propeptide sequence (amino acids 1 to 415 of SEQ ID NO:14), or alternatively, with a propeptide sequence, or with a propeptide and signal sequence (full length Factor IX).

Factor IX coagulant activity is expresses as International Unit(s) (IU). One IU of Factor IX activity corresponds approximately to the quantity of Factor IX in one milliliter of normal human plasma. Several assays are available for measuring Factor IX activity, including the one stage clotting assay (activated partial thromboplastin time; aPTT), thrombin generation time (TGA) and rotational thromboelastometry (ROTEM®).

"Protein having FIX activity which is in its activated form", or "activated FIX protein" means the activated form of a corresponding FIX protein/polypeptide. The term "activated" in connection with an activated FIX protein/polypeptide is used according to its common meaning. For example, in vivo, Factor IX is produced as a zymogen, an inactive precursor. It is processed to remove a signal peptide, glycosylated and then cleaved, e.g., by factor XIa or factor VIIa to produce activated FIX (FIXa), a two-chain form where the two chains are linked by a disulfide bridge. For example, activated FIX protein can be formed during the production and/or purification of a recombinant FIX protein. In one example, in pharmaceutical FIX polypeptide compositions, the activated form of the FIX polypeptide can be considered an impurity.

III. Factor VIII and Factor IX Chimeric Polypeptides

"Chimeric polypeptide," as used herein, means a polypeptide that includes within it at least two moieties (or portions thereof such as subsequences or peptides) from different sources. Chimeric polypeptides can include two, three, four, five, six, seven, or more polypeptides or portions thereof from different sources, such as different genes, different cDNAs, or different animal or other species. Chimeric polypeptides can include one or more linkers joining the different polypeptides or portions thereof. Thus, the polypeptides or portions thereof can be joined directly or they can be joined indirectly, via linkers, or both, within a single chimeric polypeptide. Chimeric polypeptides can include additional peptides such as signal sequences and sequences such as 6His and FLAG that aid in protein purification or detection. In addition, chimeric polypeptides can have amino acid or peptide additions to the N- and/or C-termini.

In certain embodiments, a chimeric polypeptide is a long-acting clotting factor. "Long-acting clotting factor" such as long-acting FVIII or long-acting FIX is a Factor VIII or Factor IX having an increased half-life (also referred to herein as t½, t½ beta, elimination half-life and HL) over a reference Factor VIII or a reference Factor IX, respectively. The increased half-life of a long-acting Factor VIII or a long-acting Factor IX may be due to fusion to one or more non-Factor VIII or non-Factor IX polypeptides such as, e.g., Fc, XTEN, albumin, a PAS sequence, transferrin, CTP (28 amino acid C-terminal peptide (CTP) of hCG with its 4 O-glycans), polyethylene glycol (PEG), hydroxyethyl starch (HES), albumin binding polypeptide, albumin-binding small molecules, or two or more combinations thereof. The increased half-life may be due to one or more modification, such as, e.g., pegylation. Exemplary long-acting clotting factor polypeptides include, e.g., chimeric Factor VIII polypeptides comprising Fc, chimeric Factor VIII polypeptides comprising XTEN, chimeric Factor VIII polypeptides comprising albumin, chimeric Factor IX polypeptides comprising Fc, chimeric FIX polypeptide comprising XTEN, or chimeric Factor IX polypeptide comprising albumin. Additional exemplary long-acting Factor VIII polypeptides include, e.g., pegylated Factor VIII or pegylated Factor IX.

The "reference" polypeptide, in the case of a long-acting chimeric Factor VIII polypeptide, is a polypeptide consisting essentially of the Factor VIII portion of the chimeric polypeptide, e.g., the same Factor VIII portion without the Fc portion, without the XTEN portion, or without the albumin portion. The "reference" polypeptide, in the case of a long-acting chimeric Factor IX polypeptide, is a polypeptide consisting essentially of the Factor IX portion of the chimeric polypeptide, e.g., the same Factor IX portion without the Fc portion, without the XTEN portion, or without the albumin portion. Likewise, the reference polypeptide in the case of a modified Factor VIII or Factor IX is the same Factor VIII or Factor IX without the modification, respectively, e.g., a Factor VIII without the pegylation or a Factor IX without the pegylation.

In some embodiments, the chimeric polypeptide comprises a Factor VIII portion and a non-Factor VIII portion. In some embodiment, the chimeric polypeptide comprises a Factor IX portion and a non-Factor IX portion. Exemplary non-Factor VIII or non-Factor IX portions include, e.g., Fc, XTEN, and albumin. Exemplary chimeric polypeptides include, e.g., chimeric Factor VIII-Fc polypeptides, chimeric Factor IX-Fc polypeptides, chimeric Factor VIII-XTEN polypeptides, chimeric Factor IX-XTEN polypeptides, chimeric Factor VIII-albumin polypeptides, and chimeric Factor IX-albumin polypeptides.

"FcRn binding partner," "FcRn BP," or "Fc" as used herein, means functional neonatal Fc receptor (FcRn) binding partners, unless otherwise specified. An FcRn binding partner is any molecule that can be specifically bound by the FcRn receptor with consequent active transport by the FcRn receptor of the FcRn binding partner. Thus, the term FcRn BP or Fc includes any variants of IgG Fc that are functional. For example, the region of the Fc portion of IgG that binds to the FcRn receptor has been described based on X-ray crystallography (Burmeister et al. 1994, Nature 372:379, incorporated herein by reference in its entirety). The major contact area of the Fc with the FcRn is near the junction of the CH2 and CH3 domains. Fc-FcRn contacts are all within a single Ig heavy chain. FcRn BPs include whole IgG, the Fc fragment of IgG, and other fragments of IgG that include the complete binding region of FcRn. The major contact sites include amino acid residues 248, 250-257, 272, 285, 288, 290-291, 308-311, and 314 of the CH2 domain and amino acid residues 385-387, 428, and 433-436 of the CH3 domain. References made to amino acid numbering of immunoglobulins or immunoglobulin fragments, or regions, are all based on Kabat et al. 1991, Sequences of Proteins of Immunological Interest, U. S. Department of Public Health, Bethesda; MD, incorporated herein by reference in its entirety. (The FcRn receptor has been isolated from several mammalian species including humans. The sequences of the human FcRn, rat FcRn, and mouse FcRn are known (Story et al. 1994, J. Exp. Med. 180: 2377), incorporated herein by reference in its entirety.) An FcRn BP can comprise the CH2 and CH3 domains of an immunoglobulin with or without the hinge region of the immunoglobulin. Exemplary FcRn BP variants are provided in WO 2004/101740 and WO 2006/074199, incorporated herein by reference in its entirety.

FcRn BP also include albumin and fragments thereof that bind to the FcRn. In certain aspects the albumin is human albumin. Factor VIII or Factor IX can be fused to either the N-terminal end of the albumin or to the C-terminal end of the albumin, provided the Factor VIII or Factor IX component of the albumin fusion protein can be processed by an enzymatically-active proprotein convertase to yield a processed Factor VIII- or Factor IX-containing polypeptide. Examples of albumin, e.g., fragments thereof, which can be used in the present invention, are known. e.g., U.S. Pat. Nos. 7,592,010; 6,686,179; and Schulte, Thrombosis Res. 124 Suppl. 2:S6-S8 (2009), each of which is incorporated herein by reference in its entirety.

FcRn BP (or FcRn BP portion of a chimeric polypeptide) can contain one or more mutations, and combinations of mutations. FcRn BP (or FcRn BP portion of a chimeric polypeptide) can contain mutations conferring increased half-life such as M252Y, S254T, T256E, and combinations thereof, as disclosed in Oganesyan et al., Mol. Immunol. 46:1750 (2009), which is incorporated herein by reference in its entirety; H433K, N434F, and combinations thereof, as disclosed in Vaccaro et al., Nat. Biotechnol. 23:1283 (2005), which is incorporated herein by reference in its entirety; the mutants disclosed at pages 1-2, paragraph [0012], and Examples 9 and 10 of U.S. 2009/0264627 A1, which is incorporated herein by reference in its entirety; and the mutants disclosed at page 2, paragraphs [0014] to [0021] of U.S. 20090163699 A1, which is incorporated herein by reference in its entirety.

FcRn BP (or FcRn BP portion of a chimeric polypeptide) can also include, e.g., the following mutations: The Fc region of IgG can be modified according to well recognized procedures such as site directed mutagenesis and the like to yield modified IgG or Fc fragments or portions thereof that will be bound by FcRn. Such modifications include modifications remote from the FcRn contact sites as well as modifications within the contact sites that preserve or even enhance binding to the FcRn. For example the following single amino acid residues in human IgG1 Fc (Fcγ1) can be substituted without significant loss of Fc binding affinity for FcRn: P238A, S239A, K246A, K248A, D249A, M252A, T256A, E258A, T260A, D265A, S267A, H268A, E269A, D270A, E272A, L274A, N276A, Y278A, D280A, V282A, E283A, H285A, N286A, T289A, K290A, R292A, E293A, E294A, Q295A, Y296F, N297A, S298A, Y300F, R301A, V303A, V305A, T307A, L309A, Q311A, D312A, N315A, K317A, E318A, K320A, K322A, S324A, K326A, A327Q, P329A, A330Q, A330S, P331A, P331S, E333A, K334A, T335A, S337A, K338A, K340A, Q342A, R344A, E345A, Q347A, R355A, E356A, M358A, T359A, K360A, N361A, Q362A, Y373A, S375A D376A, A378Q, E380A, E382A, S383A, N384A, Q386A, E388A, N389A, N390A, Y391F, K392A, L398A, S400A, D401A, D413A, K414A, R416A, Q418A, Q419A, N421A, V422A, S424A, E430A, N434A, T437A, Q438A, K439A, S440A, S444A, and K447A, where for example P238A represents wild type proline substituted by alanine at position number 238. In addition to alanine other amino acids can be substituted for the wild type amino acids at the positions specified above. Mutations can be introduced singly into Fc giving rise to more than one hundred FcRn binding partners distinct from native Fc. Additionally, combinations of two, three, or more of these individual mutations can be introduced together, giving rise to hundreds more FcRn binding partners. Certain of these mutations can confer new functionality upon the FcRn binding partner. For example, one embodiment incorporates N297A, removing a highly conserved N-glycosylation site. The effect of this mutation is to reduce immunogenicity, thereby enhancing circulating half-life of the FcRn binding partner, and to render the FcRn binding partner incapable of binding to FcγRI, FcγRIIA, FcγRIIB, and FcγRIIIA, without compromising affinity for FcRn (Routledge et al. 1995, Transplantation 60:847, which is incorporated herein by reference in its entirety; Friend et al. 1999, Transplantation 68:1632, which is incorporated herein by reference in its entirety; Shields et al. 1995, J. Biol. Chem. 276:6591, which is incorporated herein by reference in its entirety). Additionally, at least three human Fc gamma receptors appear to recognize a binding site on IgG within the lower hinge region, generally amino acids 234-237. Therefore, another example of new functionality and potential decreased immunogenicity can arise from mutations of this region, as for example by replacing amino acids 233-236 of human IgG1 "ELLG" to the corresponding sequence from IgG2 "PVA" (with one amino acid deletion). It has been shown that FcγRI, FcγRII, and FcγRIII which mediate various effector functions will not bind to IgG1 when such mutations have been introduced (Ward and Ghetie 1995, Therapeutic Immunology 2:77, which is incorporated herein by reference in its entirety; and Armour et al. 1999, Eur. J. Immunol. 29:2613, which is incorporated herein by reference in its entirety). As a further example of new functionality arising from mutations described above, affinity for FcRn can be increased beyond that of wild type in some instances. This increased affinity can reflect an increased "on" rate, a decreased "off" rate or both an increased "on" rate and a decreased "off" rate. Mutations believed to impart an increased affinity for FcRn include T256A, T307A, E380A, and N434A (Shields et al. 2001, J. Biol. Chem. 276:6591, which is incorporated herein by reference in its entirety).

The FcRn BP (or FcRn BP portion of a chimeric polypeptide) can be at least 90% or at least 95% or 100% identical to the Fc amino acid sequence shown in SEQUENCE Table 2 without a signal sequence (amino acids 1 to 227 of SEQ ID NO:4), or alternatively, with a signal sequence (amino acids −20 to 227 of SEQ ID NO:4).

The Fc (or Fc portion of a chimeric polypeptide) can be at least 90%, at least 95%, or 100% identical to the Fc amino acid sequence shown in SEQUENCE Table 2 (amino acids 1439 to 1665 of SEQ ID NO:2; amino acids 2333 to 2559 of SEQ ID NO:6; amino acids 741 to 967 of SEQ ID NO:8; amino acids 746 to 972 of SEQ ID NO:10; amino acids 685 to 924 of SEQ ID NO:12).

Exemplary chimeric polypeptides include Factor VIII or Factor IX fused to one or more XTEN polypeptides. See, e.g., Schellenburger et al., Nat. Biotech. 27:1186-90 (2009), which is incorporated herein by reference in its entirety. Factor VIII or Factor IX can be fused to either the N-terminal end of the XTEN polypeptide or to the C-terminal end of the XTEN polypeptide, provided the Factor VIII or Factor IX component of the XTEN fusion protein can be processed by an protease to yield a processed Factor VIII or Factor IX containing polypeptide. A protease site can be included between the XTEN portion and the Factor VIII portion to allow such processing. XTEN polypeptides include, e.g., those disclosed in WO 2009/023270, WO 2010/091122, WO 2007/103515, US 2010/0189682, and US 2009/0092582, each of which is incorporated herein by reference in its entirety.

Exemplary chimeric polypeptides also include Factor VIII or Factor IX fused to one or more albumin polypeptides. The albumin can be human albumin. Factor VIII or Factor IX can be fused to either the N-terminal end of the albumin or to the C-terminal end of the albumin, provided the Factor VIII or Factor IX component of the albumin fusion protein can be processed by an enzymatically-active proprotein convertase to yield a processed Factor VIII- or Factor IX-containing polypeptide. Examples of albumin, e.g., fragments thereof, that can be used in the present invention are known. e.g., U.S. Pat. Nos. 7,592,010; 6,686, 179; and Schulte, Thrombosis Res. 124 Suppl. 2:S6-S8 (2009), each of which is incorporated herein by reference in its entirety.

In some embodiments, a chimeric polypeptide comprising a Factor VIII or Factor IX portion of a chimeric protein has an increased half-life (t½) over a polypeptide consisting of the same Factor VIII or Factor IX portion without the non-Factor VIII or Factor IX portion. A chimeric Factor VIII or Factor IX polypeptide with an increased t½ can be referred to herein as a long-acting Factor VIII or Factor IX. Long-acting chimeric Factor VIII or Factor IX polypeptides include, e.g., Factor VIII or Factor IX fused to Fc (including, e.g., chimeric Factor VIII or Factor IX polypeptides in the form of a hybrid such as a FVIIIFc monomer dimer hybrid; see e.g., FIGS. 1 and 2, and Table 2; and U.S. Pat. Nos. 7,404,956 and 7,348,004), Factor VIII or Factor IX fused to XTEN, and Factor VIII or Factor IX fused to albumin.

Exemplary chimeric Factor VIII polypeptides of the invention include, e.g., chimeric Factor VIII-Fc polypeptides, chimeric Factor VIII-XTEN polypeptides, and chimeric Factor VIII-albumin polypeptides. Exemplary chimeric Factor VIII-Fc polypeptides include, e.g., SEQ ID NOs:2, 6, 8, 10, and 12 (SEQUENCE Table 2), with or without their signal sequences and the chimeric Fc polypeptide of SEQ ID NO:4 (SEQUENCE Table 2). The chimeric polypeptide can comprise a sequence at least 90% or 95% identical to the Factor VIII and Fc amino acid sequence shown in SEQUENCE Table 2A(i) without a signal sequence (amino acids 1 to 1665 of SEQ ID NO:2) or at least 90% or 95% identical to the Factor VIII and Fc amino acid sequence shown in SEQUENCE Table 2A(i) with a signal sequence (amino acids −19 to 1665 of SEQ ID NO:2). The chimeric polypeptide can comprise a sequence identical to the Factor VIII and Fc amino acid sequence shown in SEQUENCE Table 2A(i) without a signal sequence (amino acids 1 to 1665 of SEQ ID NO:2) or identical to the Factor VIII and Fc amino acid sequence shown in SEQUENCE Table 2A(i) with a signal sequence (amino acids −19 to 1665 of SEQ ID NO:2).

Exemplary chimeric Factor IX polypeptides of the invention are Factor IX-FcRn BP chimeric polypeptides, e.g., Factor IX-Fc chimeric polypeptides such as the FIXFc in SEQ ID NO:2 (SEQUENCE Table 2), with or without its signal sequence and propeptide. Other exemplary chimeric polypeptides of the invention include, but are not limited to, Factor IX-XTEN chimeric polypeptides. Factor IX can be fused to either N-terminus or C-terminus of XTEN. The chimeric polypeptide can comprise a sequence at least 90% or at least 95% or 100% identical to the Factor IX and FcRn BP, e.g., the Fc amino acid sequence shown in SEQUENCE Table 2A without a signal sequence and propeptide sequence (amino acids 1 to 642 of SEQ ID NO:14), or alternatively, with a propeptide sequence, or alternatively with a signal sequence and a propeptide sequence.

PAS Sequence

In other embodiments, the heterologous moiety is a PAS sequence. A PAS sequence, as used herein, means an amino acid sequence comprising mainly alanine and serine residues or comprising mainly alanine, serine, and proline residues, the amino acid sequence forming random coil conformation under physiological conditions. Accordingly, the PAS sequence is a building block, an amino acid polymer, or a sequence cassette comprising, consisting essentially of, or consisting of alanine, serine, and proline which can be used as a part of the heterologous moiety in the chimeric polypeptide. Yet, the skilled person is aware that an amino acid polymer also can form random coil conformation when residues other than alanine, serine, and proline are added as a minor constituent in the PAS sequence. The term "minor constituent" as used herein means that amino acids other than alanine, serine, and proline can be added in the PAS sequence to a certain degree, e.g., up to about 12%, e.g., about 12 of 100 amino acids of the PAS sequence, up to about 10%, e.g. about 10 of 100 amino acids of the PAS sequence, up to about 9%, e.g., about 9 of 100 amino acids, up to about 8%, e.g., about 8 of 100 amino acids, about 6%, e.g., about 6 of 100 amino acids, about 5%, e.g., about 5 of 100 amino acids, about 4%, e.g., about 4 of 100 amino acids, about 3%, e.g., about 3 of 100 amino acids, about 2%, e.g., about 2 of 100 amino acids, about 1%, e.g., about 1 of 100 of the amino acids. The amino acids different from alanine, serine and proline can be selected from the group consisting of Arg, Asn, Asp, Cys, Gln, Glu, Gly, His, Ile, Leu, Lys, Met, Phe, Thr, Trp, Tyr, and Val.

Under physiological conditions, the PAS sequence stretch forms a random coil conformation and thereby can mediate an increased in vivo and/or in vitro stability to the VWF factor or the protein of coagulation activity. Since the random coil domain does not adopt a stable structure or function by itself, the biological activity of the polypeptide is essentially preserved. In other embodiments, the PAS sequences that form random coil domain are biologically inert, especially with respect to proteolysis in blood plasma, immunogenicity, isoelectric point/electrostatic behavior, binding to cell surface receptors or internalization, but are still biodegradable, which provides clear advantages over synthetic polymers such as PEG.

Non-limiting examples of the PAS sequences forming random coil conformation comprise an amino acid sequence selected from the group consisting of ASPAAPA-PASPAAPAPSAPA (SEQ ID NO:15), AAPASPAPAAP-SAPAPAAPS (SEQ ID NO: 16), APSSPSP-SAPSSPSPASPSS (SEQ ID NO: 17), APSPSPSAPSSPSPASPS (SEQ ID NO: 18), SSP-SAPSPSSPASPSPSSPA (SEQ ID NO: 19), AASPAAPSAP-PAAASPAAPSAPPA (SEQ ID NO: 20) and ASAAAPAAASAAASAPSAAA (SEQ ID NO: 21) or any combinations thereof. Additional examples of PAS sequences are known from, e.g., US Pat. Publ. No. 2010/0292130 A1 and PCT Appl. Publ. No. WO 2008/155134 A1.

Hydroxyethyl Starch (HES)

In certain embodiments, the heterologous moiety is a polymer, e.g., hydroxyethyl starch (HES) or a derivative thereof. Hydroxyethyl starch (HES) is a derivative of naturally occurring amylopectin and is degraded by alpha-amylase in the body. HES is a substituted derivative of the carbohydrate polymer amylopectin, which is present in corn starch at a concentration of up to 95% by weight. HES exhibits advantageous biological properties and is used as a blood volume replacement agent and in hemodilution therapy in the clinics (Sommermeyer et al., *Krankenhauspharmazie,* 8(8), 271-278 (1987); and Weidler et al., *Arzneim.-Forschung/Drug Res.,* 41, 494-498 (1991)).

Amylopectin contains glucose moieties, wherein in the main chain alpha-1,4-glycosidic bonds are present and at the branching sites alpha-1,6-glycosidic bonds are found. The physical-chemical properties of this molecule are mainly determined by the type of glycosidic bonds. Due to the nicked alpha-1,4-glycosidic bond, helical structures with about six glucose-monomers per turn are produced. The physico-chemical as well as the biochemical properties of the polymer can be modified via substitution. The introduction of a hydroxyethyl group can be achieved via alkaline hydroxyethylation. By adapting the reaction conditions it is possible to exploit the different reactivity of the respective hydroxy group in the unsubstituted glucose monomer with respect to a hydroxyethylation. Owing to this fact, the skilled person is able to influence the substitution pattern to a limited extent.

HES is mainly characterized by the molecular weight distribution and the degree of substitution. The degree of substitution, denoted as DS, relates to the molar substitution, is known to the skilled people. See Sommermeyer et al., Krankenhauspharmazie, 8(8), 271-278 (1987), as cited above, in particular p. 273.

In one embodiment, hydroxyethyl starch has a mean molecular weight (weight mean) of from 1 to 300 kD, from 2 to 200 kD, from 3 to 100 kD, or from 4 to 70kD. Hydroxyethyl starch can further exhibit a molar degree of substitution of from, e.g., 0.1 to 3, 0.1 to 2, 0.1 to 0.9, or 0.1 to 0.8, and a ratio between C2:C6 substitution in the range of from 2 to 20 with respect to the hydroxyethyl groups. A non-limiting example of HES having a mean molecular weight of about 130 kD is a HES with a degree of substitution of 0.2 to 0.8 such as 0.2, 0.3, 0.4, 0.5, 0.6, 0.7, or 0.8, e.g., of 0.4 to 0.7 such as 0.4, 0.5, 0.6, or 0.7. In a specific embodiment, HES with a mean molecular weight of about 130 kD is VOLUVEN® from Fresenius. VOLUVEN® is an artificial colloid, employed, e.g., for volume replacement used in the therapeutic indication for therapy and prophylaxis of hypervolemia. The characteristics of VOLUVEN® are a mean molecular weight of 130,000+/−20,000 D, a molar substitution of 0.4 and a C2:C6 ratio of about 9:1. In other embodiments, ranges of the mean molecular weight of hydroxyethyl starch are, e.g., 4 to 70 kD or 10 to 70 kD or 12 to 70 kD or 18 to 70 kD or 50 to 70 kD or 4 to 50 kD or 10 to 50 kD or 12 to 50 kD or 18 to 50 kD or 4 to 18 kD or 10 to 18 kD or 12 to 18 kD or 4 to 12 kD or 10 to 12 kD or 4 to 10 kD. In still other embodiments, the mean molecular weight of hydroxyethyl starch employed is in the range of from more than 4 kD and below 70 kD, such as about 10 kD, or in the range of from 9 to 10 kD or from 10 to 11 kD or from 9 to 11 kD, or about 12 kD, or in the range of from 11 to 12 kD) or from 12 to 13 kD or from 11 to 13 kD, or about 18 kD, or in the range of from 17 to 18 kD or from 18 to 19 kD or from 17 to 19 kD, or about 30 kD, or in the range of from 29 to 30, or from 30 to 31 kD, or about 50 kD, or in the range of from 49 to 50 kD or from 50 to 51 kD or from 49 to 51 kD.

In certain embodiments, the heterologous moiety can be mixtures of hydroxyethyl starches having different mean molecular weights and/or different degrees of substitution and/or different ratios of C2: C6 substitution. Therefore, mixtures of hydroxyethyl starches can be employed having different mean molecular weights and different degrees of substitution and different ratios of C2: C6 substitution, or having different mean molecular weights and different degrees of substitution and the same or about the same ratio of C2:C6 substitution, or having different mean molecular weights and the same or about the same degree of substitution and different ratios of C2:C6 substitution, or having the same or about the same mean molecular weight and different degrees of substitution and different ratios of C2:C6 substitution, or having different mean molecular weights and the same or about the same degree of substitution and the same or about the same ratio of C2:C6 substitution, or having the same or about the same mean molecular weights and different degrees of substitution and the same or about the same ratio of C2:C6 substitution, or having the same or about the same mean molecular weight and the same or about the same degree of substitution and different ratios of C2: C6 substitution, or having about the same mean molecular weight and about the same degree of substitution and about the same ratio of C2:C6 substitution.

IV. Factor VIII and Factor IX Hybrid Polypeptides

"Hybrid" polypeptides and proteins, as used herein, means a combination of a chimeric polypeptide with a second polypeptide. The chimeric polypeptide and the second polypeptide in a hybrid can be associated with each other via non-covalent protein-protein interactions, such as charge-charge or hydrophobic interactions. The chimeric polypeptide and the second polypeptide in a hybrid can be associated with each other via covalent bond(s) such as disulfide bonds. The chimeric peptide and the second peptide can be associated with each other via more than one type of bond, such as non-covalent and disulfide bonds. Hybrids are described in WO 2004/101740, WO2005/001025, U.S. Pat. Nos. 7,404,956, 7,348,004, and WO 2006/074199, each of which is incorporated herein by reference in its entirety. The second polypeptide can be a second copy of the same chimeric polypeptide or it can be a non-identical chimeric polypeptide.

In some embodiments, the second polypeptide is a polypeptide comprising an Fc. In some embodiments, the chimeric polypeptide is a chimeric Factor VIII-Fc polypeptide and the second polypeptide consists essentially of Fc, e.g., a rFVIIIFc recombinant fusion protein consisting of a single molecule of recombinant B-domain deleted human FVIII (BDD-rFVIII) fused to the dimeric Fc domain of the human IgG1, with no intervening linker sequence. This hybrid polypeptide is referred to herein as FVIIIFc monomeric Fc fusion protein, FVIIIFc monomer hybrid, monomeric FVIIIFc hybrid, and FVIIIFc monomer-dimer. In some embodiments, the chimeric polypeptide is a Factor IX-FcRn BP, e.g., Factor IX-Fc chimeric polypeptide, and the second polypeptide consists essentially of Fc. See, e.g., Table 2 (SEQ ID NOs:14 and 4). See, e.g., U.S. Pat. No. 7,404,956, which is incorporated herein by reference in its entirety.

The second polypeptide in a hybrid can comprise or consist essentially of a sequence at least 90% or at least 95%, or 100% identical to the amino acid sequence shown in SEQUENCE Table 2 without a signal sequence (amino acids 1 to 227 of SEQ ID NO:4), or alternatively, at least 90%, or at least 95%, or 100% identical to the amino acid sequence shown in SEQUENCE Table 2 with a signal sequence (amino acids −20 to 227 of SEQ ID NO:4).

FIG. 1 is a schematic showing the structure of a B domain deleted factor VIII-Fc chimeric polypeptide, and its association with a second polypeptide that is an Fc polypeptide.

To obtain this hybrid, the coding sequence of human recombinant B-domain deleted FVIII was obtained by reverse transcription-polymerase chain reaction (RT-PCR) from human liver poly A RNA (Clontech) using FVIII-specific primers. The FVIII sequence includes the native signal sequence for FVIII. The B-domain deletion was from serine 743 (S743; 2287 bp) to glutamine 1638 (Q1638; 4969 bp) for a total deletion of 2682 bp. Then, the coding sequence for human recombinant Fc was obtained by RT-PCR from a human leukocyte cDNA library (Clontech) using Fc specific primers. Primers were designed such that the B-domain deleted FVIII sequence was fused directly to the N-terminus of the Fc sequence with no intervening linker. The FVIIIFc DNA sequence was cloned into the mammalian dual expression vector pBUDCE4.1 (Invitrogen) under control of the CMV promoter. A second identical Fc sequence including the mouse Igk signal sequence was obtained by RT-PCR and cloned downstream of the second promoter, EF1α, in the expression vector pBUDCE4.1.

The rFVIIIFc expression vector was transfected into human embryonic kidney 293 cells (HEK293H; Invitrogen) using Lipofectamine 2000 transfection reagent (Invitrogen). Stable clonal cell lines were generated by selection with Zeocin (Invitrogen). One clonal cell line, 3C4-22 was used to generate FVIIIFc for characterization in vivo. Recombinant FVIIIFc was produced and purified (McCue et al. 2009) at the central site. The transfection strategy described above was expected to yield three products, monomeric rFVIIIFc hybrids, dimeric rFVIIIFc hybrids and dimeric Fc. However, there was essentially no dimeric rFVIIIFc detected in the conditioned medium from these cells. Rather, the conditioned medium contained Fc and monomeric rFVIIIFc. It is possible that the size of dimeric rFVIIIFc was too great and prevented efficient secretion from the cell. This result was beneficial since it rendered the purification of the monomer less complicated than if all three proteins had been present. The material used in these studies had a specific activity of approximately 9000 IU/mg.

V. Dosing and Administration of Factor VIII and Factor IX

"Dosing interval," as used herein, means the amount of time that elapses between multiple doses being administered to a subject. The comparison of dosing interval can be carried out in a single subject or in a population of subjects and then the average obtained in the population can be calculated.

The dosing interval when administering a chimeric Factor VIII or Factor IX polypeptide, e.g., a chimeric Factor VIII-Fc or Factor IX-Fc polypeptide (a polypeptide comprising a Factor VIII or Factor IX or a hybrid), can be at least about one and one-half times longer than the dosing interval required for an equivalent amount of said FVIII or FIX without the non-FVIII or non-FIX portion, e.g., without the Fc portion (a polypeptide consisting of said FVIII or FIX). The dosing interval can be at least about one and one-half to six times longer, one and one-half to five times longer, one and one-half to four times longer, one and one-half to three times longer, or one and one-half to two times longer, than the dosing interval required for an equivalent amount of said FVIII or FIX without the non-FVIII or FIX portion, e.g., without the Fc portion (a polypeptide consisting of said Factor VIII). The dosing interval can be at least about one and one-half, two, two and one-half, three, three and one-half, four, four and one-half, five, five and one-half or six times longer than the dosing interval required for an equivalent amount of said FVIII or FIX without the non-FVIII or FIX portion, e.g., without the Fc portion (a polypeptide consisting of said FVIII or FIX).

The dosing interval can be about every five, six, seven, eight, nine, ten, eleven, twelve, thirteen, or fourteen days or longer. The dosing interval can be at least about one and one-half to 5, one and one-half, 2, 3, 4, or 5 days or longer. For on-demand treatment, the dosing interval of said chimeric polypeptide or hybrid is about once every 24-36, 24-48, 24-72, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, or 72 hours or longer.

In certain aspects, the effective dose for Factor VIII is 25-65 IU/kg (25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 62, 64, or 65 IU/kg) and the dosing interval is once every 3-5, 3-6, 3-7, 3, 4, 5, 6, 7, or 8 or more days, or three times per week, or no more than three times per week. In one aspect, the effective dose is 65 IU/kg and the dosing interval is once weekly, or once every 6-7 days.

"Long-acting Factor VIII" is a Factor VIII having an increased half-life (also referred to herein as t½, t½ beta, elimination half-life and HL) over a reference Factor VIII. The increased half-life of a long-acting Factor VIII can be due to fusion to one or more non-Factor VIII polypeptides such as, e.g., Fc, XTEN or albumin. The increased half-life can be due to one or more modification, such as, e.g., pegylation. Exemplary long-acting Factor VIII polypeptides include, e.g., chimeric Factor VIII polypeptides comprising Fc, chimeric Factor VIII polypeptides comprising XTEN and chimeric Factor VIII polypeptides comprising albumin. Additional exemplary long-acting Factor VIII polypeptides include, e.g., pegylated Factor VIII.

The "reference" polypeptide, in the case of a long-acting chimeric Factor VIII polypeptide, is a polypeptide consisting essentially of the Factor VIII portion of the chimeric polypeptide, e.g., the same Factor VIII portion without the Fc portion, without the XTEN portion, or without the albumin portion. Likewise, the reference polypeptide in the case of a modified Factor VIII is the same Factor VIII without the modification, e.g., a Factor VIII without the pegylation.

In some embodiments, the long-acting Factor VIII has one or more of the following properties when administered to a subject:
  a mean residence time (MRT) (activity) in said subject of about 14-41.3 hours;
  a clearance (CL) (activity) in said subject of about 1.22-5.19 mL/hour/kg or less;
  a t½beta (activity) in said subject of about 11-26.4 hours;
  an incremental recovery (K value) (activity; observed) in said subject of about 1.38-2.88 IU/dL per IU/kg;
  a $V_{SS}$ (activity) in said subject of about 37.7-79.4 mL/kg; and
  an AUC/dose in said subject of about 19.2-81.7 IU*h/dL per IU/kg.

In some embodiments, the long-acting Factor VIII has one or more of the following properties when administered to a patient population:
  a mean incremental recovery (K-Value) (activity; observed) greater than 1.38 IU/dL per IU/kg;
  a mean incremental recovery (K-Value) (activity; observed) of at least about 1.5, at least about 1.85, or at least about 2.46 IU/dL per IU/kg;
  a mean clearance (CL) (activity) in said patient population of about 2.33±1.08 mL/hour/kg or less;
  a mean clearance (CL) (activity) in said patient population of about 1.8-2.69 mL/hour/kg;
  a mean clearance (CL) (activity) in said patient population that is about 65% of the clearance of a polypeptide comprising said Factor VIII without modification;
  a mean mean residence time (MRT) (activity) in said patient population of at least about 26.3±8.33 hours;
  a mean MRT (activity) in said patient population of about 25.9-26.5 hours;
  a mean MRT (activity) in said patent population that is about 1.5 fold longer than the mean MRT of a polypeptide comprising said Factor VIII without modification;
  a mean t½beta (activity) in said patient population of about 18.3±5.79 hours;
  a mean t½beta (activity) in said patient population that is about 18-18.4 hours;
  a mean t½beta (activity) in said patient population that is about 1.5 fold longer than the mean t½beta of a polypeptide comprising said Factor VIII without modification;
  a mean incremental recovery (K value) (activity; observed) in said patient population of about 2.01±0.44 IU/dL per IU/kg;
  a mean incremental recovery (K value) (activity; observed) in said patient population of about 1.85-2.46 IU/dL per IU/kg;
  a mean incremental recovery (K value) (activity; observed) in said patient population that is about 90% of the mean incremental recovery of a polypeptide comprising said Factor VIII without modification;
  a mean $V_{SS}$ (activity) in said patient population of about 55.1±12.3 mL/kg;
  a mean $V_{SS}$ (activity) in said patient population of about 45.3-56.1 mL/kg;
  a mean AUC/dose (activity) in said patient population of about 49.9±18.2 IU*h/dL per IU/kg;
  a mean AUC/dose (activity) in said patient population of about 44.8-57.6 IU*h/dL per IU/kg.

In some embodiments, the dosing interval for Factor IX is 6-18, 6-10, 9-18, at least 6, at least 7, at least 8, at least 9, at least 10, at least 11, at least 12, at least 13, at least 14, at least 15, at least 16, at least 17, or at least 18 days. The dosing interval can be at least about once weekly, and can be 6-10 days, e.g., about 7-10, about 7-9, about 7-8, about 8-10, about 9-10, about 6-7, about 8-9, about 6, about 7, about 8, about 9, or about 10 days.

The dosing interval can be 9-18 days, e.g., about 9-17, about 9-16, about 9-15, about 9-14, about 9-13, about 9-12, about 9-11, about 9-10 days, about 10-18, about 11-18, about 12-18, about 13-18, about 14-18, about 15-18, about 16-18, about 17-18 days, about 10-11, about 11-12, about 12-13, about 13-14, about 14-15, about 15-16, and about 16-17 days, about 9, about 10, about 11, about 12, about 13, about 14, about 15, about 16, about 17, or about 18 days. The dosing interval can be about 10-14 days. The dosing interval can be about every two weeks or twice monthly. The dosing interval can be longer than 18 days, e.g., about 19, about 20, about 21, about 22, about 23, about 24, about 25, about 26, about 27, about 28, about 29, about 30, about 31, about 32, about 33, about 34, about 35, about 36, about 37, about 38, about 39, or about 40 days. The dosing interval can be a fixed interval, e.g., 7 days for 25-50 IU/kg, 10-13 days for 50-100 IU/kg, or 14 days for 100-150 IU/kg. The fixed interval and dose are determined such that the combination of interval and dose will result in a trough of at least about 1-5 or at least about 1-3, or at least about 1, at least about 2, or at least about 3 IU/dl FIX activity in a population of subjects or in an individual subject. The fixed dosing interval can also be 7 days for 20-50 IU/kg, 10-14 days for 50-100 IU/kg, 14-16 days for 100-150 IU/kg, 7 days for 10-50 IU/kg, 10-13 days for 15-100 IU/kg, or 14-15 days for 50-150 IU/kg. The fixed dosing interval can also be 7 days for 10-30 IU/kg, 10 days 15-50 IU/kg, 11 days 20-70 IU/kg, 12 days 25-85 IU/kg, 13 days 30 to 100 IU/kg, 14 days 40 to 125 IU/kg, and 15 days for 50-150 IU/kg.

In certain embodiments, the dosing interval is 20 IU/kg once weekly, 40 IU/kg every 10 days, or 100 IU/kg every two weeks (twice monthly).

The dosing interval can be an individualized interval that is determined for each subject based on pharmacokinetic data or other information about that subject. The individualized dose/dosing interval combination can be the same as those for fixed interval regimens in the preceding paragraphs, or can differ. The regimen can initially be at a fixed dosing interval, and then it can change to an individualized dosing interval.

Bleeding disease or disorder, as used herein, means a genetically inherited or acquired condition characterized by a tendency to bleed, either spontaneously or as a result of trauma or surgery, due to an impaired ability or inability to form a fibrin clot. Bleeding disease or disorder can require on-demand treatment or prophylactic treatment. Exemplary bleeding disorders are hemophilia A and hemophilia B.

"On-demand treatment," as used herein, means treatment that is intended to take place over a short course of time and is in response to an existing condition, such as a bleeding episode, or a perceived short term need such as planned surgery. Conditions that can require on-demand treatment include a bleeding episode, hemarthrosis, muscle bleed, oral bleed, hemorrhage, hemorrhage into muscles, oral hemorrhage, trauma, trauma capitis, gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, or bleeding in the illiopsoas sheath. Bleeding episodes other than these are also included. The subject can be in need of surgical prophylaxis, pen-operative management, or treatment for surgery. Such surgeries include minor surgery, major surgery, tooth extraction, tonsillectomy, other dental/thoraco-facial surgeries, inguinal herniotomy, synovectomy, total knee replacement, other joint replacement, craniotomy, osteosynthesis, trauma surgery, intracranial surgery, intra-abdominal surgery, intrathoracic surgery. Surgeries other than these are also included.

Additional conditions that can require on-demand treatment include minor hemorrhage, hemarthroses, superficial muscle hemorrhage, soft tissue hemorrhage, moderate hemorrhage, intramuscle or soft tissue hemorrhage with dissection, mucous membrane hemorrhage, hematuria, major hemorrhage, hemorrhage of the pharynx, hemorrhage of the retropharynx, hemorrhage of the retroperitonium, hemorrhage of the central nervous system, bruises, cuts, scrapes, joint hemorrhage, nose bleed, mouth bleed, gum bleed, intracranial bleeding, intraperitoneal bleeding, minor spontaneous hemorrhage, bleeding after major trauma, moderate skin bruising, or spontaneous hemorrhage into joints, muscles, internal organs or the brain. Additional reasons for on-demand treatment include the need for peri-operative management for surgery or dental extraction, major surgery, extensive oral surgery, urologic surgery, hernia surgery, orthopedic surgery such as replacement of knee, hip, or other major joint.

In certain aspects, on-demand treatment resolves greater than 80% (greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98%, greater than 99%, or 100%) or 80-100%, 80-90%, 85-90%, 90-100%, 90-95%, or 95-100% of bleeds (e.g., spontaneous bleeds) in a single dose. In certain aspects, greater than 80% (greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98%, or 100%) or 80-100%, 80-90%, 85-90%, 90-100%, 90-95%, or 95-100% of bleeding episodes are rated excellent or good by physicians after on-demand treatment. In certain aspects, greater than 5%, (greater than 6%, greater than 7%, greater than 8%, greater than 9%, greater than 10%, greater than 11%, greater than 12%, greater than 13%, greater than 14%, greater than 15%, greater than 16%, greater than 17%, greater than 18%, greater than 19%, greater than 20%), or 5-20%, 5-15%, 5-10%, 10-20%, or 10-15% of bleeding episodes are rated as fair by physicians after on-demand treatment.

"Prophylactic treatment," or "prophylaxis" as used herein, means administering a Factor VIII or Factor IX polypeptide in multiple doses to a subject over a course of time to increase the level of Factor VIII or Factor IX activity in a subject's plasma. In certain aspects, the increased level is sufficient to decrease the incidence of spontaneous bleeding or to prevent bleeding in the event of an unforeseen injury. Prophylactic treatment decreases or prevents bleeding episodes, for example, those described under on-demand treatment. In some embodiments, prophylactic treatment is administered such that the plasma protein level in the subject does not fall below the baseline level for that subject or below the level of Factor VIII or Factor IX that characterizes severe hemophilia. Prophylactic treatment can be fixed or can be individualized, as discussed under "dosing interval", e.g., to compensate for inter-patient variability.

In certain aspects, the prophylaxis regimen is "tailored" to the individual patient, for example, by determining PK data for each patient and administering Factor VIII of the invention at a dosing interval that maintains a trough level of 1-3% FVIII activity. Adjustments can be made when a subject experiences unacceptable bleeding episodes defined as ≥2 spontaneous bleeding episodes over a rolling two-month period. In this case, adjustment will target trough levels of 3-5%. In certain aspects, prophylactic treatment results in prevention and control of bleeding, sustained control of bleeding, sustained protection from bleeding, and/or sustained benefit. Prophylaxis, e.g., sustained protection can be demonstrated by an increased AUC to last measured time point (AUC-LAST) and reduced clearance, resulting in increased terminal t½ compared to short acting FVIII. In certain aspects, prophylaxis is demonstrated by better Cmax, better Tmax, and/or greater mean residence time versus short-acting FVIII. In certain aspects, prophylaxis results in no spontaneous bleeding episodes within about 24, 36, 48, 72, or 96 hours (e.g., 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 96, 87, 88, 89, 90, 91, 92, 93, 94, 95, or 96 hours, for example, within 72 hours), after injection (e.g., the last injection). In certain aspects, prophylaxis results in greater than 30% (e.g., greater than 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 96, 87, 88, 89, or 90%, for example, greater than 50%), mean reduction in annualized bleeding episodes with once weekly dosing (e.g., at 65 IU/kg).

Pharmacokinetic (PK) parameters include the terms above and the following terms, which have their ordinary meaning in the art, unless otherwise indicated. Some of the terms are explained in more detail in the Examples. PK parameters can be based on FIX antigen level (often denoted parenthetically herein as "antigen") or FIX activity level (often denoted parenthetically herein as "activity"). In the literature, PK parameters are often based on FIX activity level due to the presence in the plasma of some patients of endogenous, inactive FIX, which interferes with the ability to measure administered (i.e., exogenous) FIX using antibody against FIX. However, when FIX is administered as part of a fusion protein containing a heterologous polypeptide such as a FcRn BP, administered (i.e., exogenous) FIX antigen can be accurately measured using antibody to the heterologous polypeptide. In addition, certain PK parameters can be based on model predicted data (often denoted parenthetically herein as "model predicted") or on observed data (often denoted parenthetically herein as "observed"), and can be based on observed data.

"Baseline," as used herein, is the lowest measured plasma FVIII or FIX level in a subject prior to administering a dose. "Baseline" can also be derived from control measurements made in patients with known disease severity, healthy individuals, or a combination thereof.

"Area under the plasma concentration versus time curve" ("AUC"), which, as used herein, is based upon the rate and extent of elimination of FVIII or FIX following administration. AUC is determined over a specified time period, such as 12, 18, 24, 36, 48, or 72 hours, or for infinity using extrapolation based on the slope of the curve. Unless otherwise specified herein, AUC is determined for infinity ($AUC_{INF}$). AUC can also be calculated on a per dose basis. As with many of the other PK parameters, the determination of AUC can be carried out in a single subject, or in a population of subjects for which the average is calculated. Therefore, the mean AUC/dose in a patient population can be about 26-40, about 26, about 27, about 28, about 29, about 30, about 31, about 32, about 33, about 34, about 35, about 36, about 37, about 38, about 39, or about 40 IU*h/dL per IU/kg.

"In vivo recovery" ("IVR") is represented by the incremental recovery (K-value), which is the observed peak activity minus predose level and then divided by the dose. IVR can also be calculated on a percentage basis. For clarity, the units (K value or IU/dl per IU/kg versus %) are used herein. The mean IVR can be determined in a patient population, or the individual IVR can be determined in a single subject. The chimeric polypeptide of the invention can exhibit an mean IVR in a patient population of 0.85-1.15 (e.g., about 0.85, about 0.86, about 0.87, about 0.88, about 0.89, about 0.90, about 0.91, about 0.92, about 0.93, about 0.94, about 0.95, about 0.96, about 0.97, about 0.98, about 0.99, about 1.0, about 1.05, about 1.10, about 1.15) and an IVR in a subject of at least about 0.6, about 0.7, 0.8, about 0.9, about 1.0, about 1.1, or about 1.2 IU/dl per IU/kg.

"Clearance rate" ("CL"), as used herein, is a measure of the body's ability to eliminate a drug, and is expressed as the volume of plasma cleared of drug over time. A chimeric polypeptide of the invention can exhibit a mean CL in a population of 3.0-3.72, 3.0, 3.1, 3.2, 3.3, 3.4, 3.5, 3.6, 3.7, or 3.72 mL/hour/kg.

"Mean residence time" ("MRT"), as used herein, is a measure of the average lifetime of drug molecules in the body. A chimeric polypeptide of the invention can exhibit a mean MRT in a population of 60-78, about 60, about 62, about 64, about 66, about 68, about 70, about 72, about 74, about 76, or about 78 hours and a MRT in a subject of at least about 50, about 55, about 60, about 65, about 70, about 75, about 80, about 85, or about 90 hours.

"$t_{1/2\beta}$," or "$t_{1/2\ beta}$," or "Beta HL," as used herein, is half-life associated with elimination phase, $t_{1/2\beta}$=(ln2)/elimination rate constant associated with the terminal phase. A chimeric polypeptide of the invention can exhibit an average $t_{1/2\beta}$ greater than about 47, about 48, about 49, about 50, about 51, about 52, about 53, about 54, about 55, about 56, about 57, about 58, about 59, or about 60 hours.

"Trough," as used herein, is the lowest plasma FVIII or FIX activity level reached after administering a dose of chimeric FVIII or FIX polypeptide and before the next dose is administered, if any. Trough is used interchangeably herein with "threshold." Baseline FVIII or FIX levels are subtracted from measured FVIII or FIX to calculate the trough level. In some embodiments, the trough is 1-5 or 1-3 IU/dl after about 6, about 7, about 8, about 9, about 10, about 11, about 12, about 13 or about 14 days. In some embodiments, the plasma level of the chimeric polypeptide reaches an average trough of at least about 1 IU/dl after at least about 6 days in at least about 70%, at least about 80%, at least about 90%, or about 100% of a patient population or reaches a trough of at least about 1, 2, 3, 4, or 5 IU/dl after at least about 6 days in a subject. In some embodiments, the plasma level of said chimeric polypeptide reaches an average trough of about 1-5 or 1-3 IU/dl. Such trough or average trough can be reached after about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, or about 40 days.

"Volume of distribution at steady state ($V_{SS}$)," as used herein, is the apparent space (volume) into which a drug distributes. $V_{SS}$=the amount of drug in the body divided by the plasma concentration at steady state. The mean $V_{SS}$ in a patient population can be 200-300, about 200, about 210, about 220, about 230, about 240, about 250, about 260, about 270, about 280, about 290, or about 300 mL/kg. The $V_{SS}$ for individual subjects can be about 145, about 150, about 160, about 170, about 180, about 190, about 200, about 210, about 220, about 230, about 240, about 250, about 260, about 270, about 280, about 290, about 300, about 310, about 320, about 330, about 340, about 350, about 360, or about 370 ml/kg.

"Therapeutic dose," as used herein, means a dose that achieves a therapeutic goal, as described herein.

The calculation of the required dosage of factor VIII is based upon the empirical finding that, on average, 1 IU of factor VIII per kg body weight raises the plasma factor VIII activity by approximately 2 IU/dL. The required dosage is determined using the following formula:

Required units=body weight (kg)×desired factor VIII rise (IU/dL or % of normal)×0.5 (IU/kg per IU/dL)

The therapeutic doses of FVIII that can be used in the methods of the invention are about 10-100 IU/kg, more specifically, 10-20, 20-30, 30-40, 40-50, 50-60, 60-70, 70-80, 80-90, or 90-100 IU/kg, and more specifically, 10, 15, 20, 25, 30, 35, 40, 45, 50, 55, 60, 65, 70, 75, 80, 85, 90, 95, or 100 IU/kg.

Additional therapeutic doses of FVIII that can be used in the methods of the invention are about 10 to about 150 IU/kg, more specifically, about 100-110, 110-120, 120-130, 130-140, 140-150 IU/kg, and more specifically, about 110, 115, 120, 125, 130, 135, 140, 145, or 150 IU/kg.

The calculation of the required dosage of plasma derived Factor IX (pdFIX) is based upon the empirical finding that, on average, 1 IU of pdFIX per kg body weight raises the plasma Factor IX activity by approximately 1 IU/dL (1%). On that basis, the required dosage is determined using the following formula:

Required units=body weight (kg)×desired Factor IX rise (IU/dL or % of normal)×1 (IU/kg per IU/dL)

Because FIXFc, e.g., as described in FIG. 1, has an incremental recovery similar to pdFIX (different from that of BENEFIX®), the required dose is determined using the formula above, or adjusting it slightly. For pediatric subjects using pdFIX, dosage guidance is the same as for adults. However, pediatric patients can have a lower incremental recovery, and the dosage can therefore need to be adjusted upwards.

The therapeutic doses that can be used in the methods of the invention are 10-180, 20-180, or 25-180 IU/kg, more specifically, exemplary doses for a 6-10 day dosing interval are as follows: about 25-110, about 30-110, about 40-110, about 50-110, about 60-110, about 70-110, about 80-110, about 90-110, and about 100-110; about 30-100, about 30-90, about 30-80, about 30-70, about 30-60, about 30-50, about 30-40 IU/kg; about 40-110, about 50-100, about 60-90, and about 70-80 IU/kg; about 40-50, about 50-60, about 60-70, about 70-80, about 80-90, about 90-100, and about 100-110 IU/kg; about 25, about 30, about 35, about 40, about 45, about 50, about 55, about 60, about 65, about 70, about 75, about 80, about 85, about 90, about 95, about 100, about 105, and about 110 IU/kg. A 6-10 day dosing interval includes a weekly dosing interval. Additional therapeutic doses for a 6-10 day, e.g., weekly, dosing interval include 20-50, 20-100, and 20-180 IU/kg, more specifically, exemplary doses for a 6-10 day, e.g., weekly, dosing interval are as follows: about 20-110, about 20-100, about 20-90, about 20-80, about 20-70, about 20-60, about 20-50, about 20-40, about 20-30, about 20-40, and about 20 IU/kg. Doses can be lower than 20 IU/kg if effective for a given patient, e.g., about 10, about 11, about 12, about 13, about 14, about 15, about 16, about 17, about 18, or about 19 IU/kg.

Exemplary therapeutic doses for a 9-18 day, e.g., two times monthly, dosing interval are as follows: about 50-180, about 60-180, about 70-180, about 80-180, about 90-180, about 100-180, about 110-180, about 120-180, about 130-180, about 140-180, about 150-180, about 160-180, and about 170-180 IU/kg; about 90-170, about 90-160, about 90-150, about 90-140, about 90-130, about 90-120, about 90-110, and about 90-100 IU/kg; about 100-170, about 110-160, about 120-150, and about 130-140 IU/kg; about 90-100, about 100-110, about 110-120, about 120-130, about 130-140, about 140-150, about 150-160, and about 160-170 IU/kg; about 60, about 70, about 80, about 90, about 95, about 100, about 105, about 110, about 115, about 120, about 125, about 130, about 135, about 140, about 145, about 150, about 155, about 160, about 165, about 170, about 175, and about 180 IU/kg.

Exemplary therapeutic doses are 10-50, 15-100, 20-100, 20-50, 50-100, 10, 20, 40, 50, and 100 IU/kg.

The therapeutic dose can be about 20-50, about 20-100, about 20-180, 25-110, about 30-110, about 40-110, about 50-110, about 60-110, about 70-110, about 80-110, about 90-110, about 100-110, about 30-100, about 30-90, about 30-80, about 30-70, about 30-60, about 30-50, about 30-40 IU/kg, about 40-110, about 50-100, about 60-90, about 70-80 IU/kg, about 40-50, about 50-60, about 60-70, about 70-80, about 80-90, about 90-100, about 100-110 IU/kg, about 20, about 25, about 30, about 35, about 40, about 45, about 50, about 55, about 60, about 65, about 70, about 75, about 80, about 85, about 90, about 95, about 100, about 105, and about 110 IU/kg. Such doses can be used for dosing intervals of about 6-10, about 7-10, about 7-9, about 7-8, about 8-10, about 9-10, about 6-7, about 8-9, about 6, about 7, about 8, about 9, and about 10 days, and once weekly.

The therapeutic dose can about 90-180, about 100-180, about 110-180, about 120-180, about 130-180, about 140-180, about 150-180, about 160-180, and about 170-180 IU/kg. The dose can be about 90-170, about 90-160, about 90-150, about 90-140, about 90-130, about 90-120, about 90-110, and about 90-100 IU/kg. The dose can be about 100-170, about 110-160, about 120-150, and about 130-140 IU/kg. The dose can be about 90-100, about 100-110, about 110-120, about 120-130, about 130-140, about 140-150, about 150-160, and about 160-170 IU/kg. The dose can be about 90, about 95, about 100, about 105, about 110, about 115, about 120, about 125, about 130, about 135, about 140, about 145, about 150, about 155, about 160, about 165, about 170, about 175, and about 180 IU/kg. Such doses can be used for dosing interval of about 9-18, about 9-17, about 9-16, about 9-15, about 9-14, about 9-13, about 9-12, about 9-11, about 9-10, about 10-18, about 11-18, about 12-18, about 13-18, about 14-18, about 15-18, about 16-18, about 17-18, about 10-11, about 11-12, about 12-13, about 13-14, about 14-15, about 15-16, and about 16-17 days, about 9, about 10, about 11, about 12, about 13, about 14, about 15, about 16, about 17, and about 18 days, one time monthly and two times monthly (every two weeks).

Exemplary therapeutic dose and dosing intervals are as follows: 20 IU/kg once weekly, 40 IU/kg every 10 days, and 100 IU/kg every two weeks (twice monthly). Additional combinations of dose and dose interval include: a dose at least about 50 IU/kg and a dosing interval at least about 7 days, a dose at least about 100 IU/kg and a dosing interval at least about 9 days, a dose at least about 100 IU/kg and a dosing interval at least about 12 days, a dose at least about 150 IU/kg and a dosing interval at least about 14 days, 20-50 or 20-100 IU/kg and said dosing interval is one time weekly, a dose of 20-50 IU/kg and a dosing interval of 7 days, a dose of 50-100 IU/kg and a dosing interval of 10-14 days, or a dose of 100-150 IU/kg and a dosing interval of 14-16 days. Exemplary combinations of dosing interval and dose also include 10-50 IU/kg for 7 days, 15-100 IU/kg for 10-13 days, 50-150 IU/kg for 14-15 days, 10-30 IU/kg for 7 days, 15-50 IU/kg for 10 days, 20-70 IU/kg for 11 days, 25-85

IU/kg for 12 days, 30 to 100 IU/kg for 13 days, 40 to 125 IU/kg for 14 days, and 50-150 IU/kg for 15 days.

VI. Testing for Clotting Activity in Patients

The methods and systems of the present disclosure can be applied to treating a patient or evaluating or determining whether a patient will benefit from administration of a therapeutically effective dose of a therapeutic agent that is capable of treating a bleeding disorder, for example, hemophilia A or hemophilia B. The application of the methods of systems disclosed herein can be used to apply more precise clotting factor dosing to patients.

In a further aspect, the methods and systems disclosed herein can be used to increase the power and effectiveness of clinical trials. Thus, individuals in a study can be monitored and dosages adjusted individually.

The present disclosure also provides methods of treating bleeding disorders by administration of a clotting factor, e.g., factor VIII or factor IX. Individualized treatment using the methods provided herein can result in fewer disease flare-ups, and thus provide a higher quality of life for the patient.

In order to treat a patient, samples from the patient can be obtained before or after the administration of a FVIII or FIX polypeptide. In some cases, successive samples can be obtained from the patient after clotting factor treatment has commenced or after treatment has ceased. Samples can, e.g., be requested by a healthcare provider (e.g., a doctor) or healthcare benefits provider, obtained and/or processed by the same or a different healthcare provider (e.g., a nurse, a hospital) or a clinical laboratory, and after processing, the results can be forwarded to yet another healthcare provider, healthcare benefits provider or the patient. Similarly, the measuring/determination of clotting times, the comparisons between time points, and treatment decisions can be performed by one or more healthcare providers, healthcare benefits providers, and/or clinical laboratories.

The methods described herein can be used for variety of evaluations, including without limitation, analysis of a patient's blood prior to treatment (or after complete washout of prior therapeutic treatment, to evaluate 'baseline' clot formation (which may correlate with severity of the disease) and 2) adding various therapeutic composition(s) such as recombinant FVII or FIX ex vivo to such blood in order to predict the individual's response to therapy.

In certain aspects of the disclosed methods, a blood sample is obtained from a patient or subject. The patient or subject can have a diagnosed bleeding disorder such as hemophilia, or can be a patient or subject where a bleeding disorder is suspected, but has not yet been diagnosed. A blood sample can be obtained by any known method including, but not limited to venipuncture, skin puncture, e.g., a finger stick with a lance or other device, or arterial sampling. The blood sample can be, e.g., whole blood, serum, or plasma. The blood sample may be stored for later clotting assessment, or may be assessed at the time of obtaining the blood sample. The blood sample can be obtained by the patient or subject, by a healthcare provider, or by a clinical laboratory. Once obtained, the blood sample can be assayed by a healthcare provider, or submitted to a clinical laboratory by a healthcare provider or the patient or subject.

In a further aspect of the disclosed methods, one or more clot formation properties of the obtained blood sample are measured. Such properties include any measurable phenotypic or physiological event associated with blood clotting. Clot formation properties that can be measured include, but are not limited to, the patterns of changes in shear elasticity of the developing clot, determination of the kinetics of clot formation, as well as the strength and stability of the formed clot. Other clot formation properties include the time and extent of thrombin generation or the time and extent of the generation of particular clotting factors such as FVIII or FIX. Any measurable clot formation property that can be used to assess hemostasis can be measured according to the methods provided herein. Exemplary methods to measure clot formation properties such as TGA, ROTEM®, ROTEG, and the like, are disclosed herein. In certain aspects, multiple measurements are made over time. One or more measurements can be made prior to treatment, throughout a course of treatment, or after treatment.

In certain aspects clot formation properties in one or more normal healthy subjects can be measured to provide baseline, standard, or normal results as negative controls. Similarly, clot formation properties can be measured in patients known to suffer from a particular bleeding disorder, or from a series of patients known to have bleeding disorders of different severities, to be used as positive controls. In certain aspects, clot formation properties can be measured in patients undergoing treatment with clotting factors before, during, and after treatment to provide "baseline" results corresponding to efficacious treatment. As will be appreciated, "baseline" results in bleeding disorder patients undergoing treatment can differ significantly for results obtained from normal health individuals, even if the treatment is very efficacious. As will be understood by those of ordinary skill in the art, results can vary significantly in a single subject or between subjects, even between healthy subjects. Accordingly, in certain aspects of the invention clot formation properties can be measured multiple times from a single obtained blood sample or from separately obtained blood samples, and for standards and controls, clot formation property measurements can be averaged over a population of subjects, e.g., 3 subjects, 5 subjects, 10 subjects, 50 subjects, or 100 or more subjects.

One or more clot formation properties can be measured by a healthcare provider, by a clinical laboratory, or by any other authorized facility. In certain aspects measurement of one or more clot formation properties can be ordered by a patient's primary or specialized healthcare provider. In certain aspects the patient or subject can ask the measurements to be taken. In certain aspects, measurement of one or more clot formation properties can be ordered by a healthcare benefits provider, e.g., prior to authorizing payment for treatment of a bleeding disorder.

In certain aspects of the disclosed methods, the results of the measurement of one or more clot formation properties as described above can be compared to one or more control measurements. Such control measurements can be, for example, an individual subject's baseline measurement, e.g., prior to or following treatment. Alternatively, control measurements can be measurements of clot formation properties of one or more normal healthy subjects, or measurements of clot formation properties of one or more known patients with a known bleeding disorder—either treated, untreated, or both.

In certain aspects, the control or baseline measurements are made at the same time and place as the measurements of clot formation properties of subject to be assessed. Having to perform such controls each time a measurement is made of a known or potential bleeding disorder patient can be inconvenient and expensive. Accordingly, in one aspect of the invention standardized baseline or control measurements are made at a centralized location and used to compare a patient's or potential patient's measurements. To insure that the measurements at the centralized location and those at various satellite locations can be standardized, common instruments, reagents and materials are provided to each satellite location. Control measurements can be made regularly at each satellite location to validate the accuracy of the measurements being made at that location. Validation of satellite laboratories for measurement of clot formation properties can provide a way to "globalize" measurements of clot formation properties. Such standardization can allow healthcare providers to more accurately determine and/or adjust therapeutic regimens for a given patient, or to determine that a subject does not require treatment.

In certain aspects the comparison with baseline or control measurements is carried out by a healthcare provider using patient data generated by the healthcare provider or provided from a satellite laboratory or a centralized laboratory and comparing the data to baseline or control data generated by the healthcare provider, a satellite laboratory, a centralized laboratory, or a combination thereof. In certain aspects the comparison is performed by a clinical laboratory (either a validated satellite facility or a centralized facility) using a patient blood sample provided by a healthcare provider, with comparison being made to data generated either at the satellite facility or a centralized facility.

In certain aspects, the methods disclosed herein provide healthcare providers and patients with a more accurate and reliable method of treating or evaluating bleeding disorders. Based on the date obtained from global hemostasis assays as provided herein, a subject can be determined to have, or to not have, a bleeding disorder. Furthermore, treatments can be more precisely adapted to the quality and severity of a patient's bleeding disorder. For example, a patient's therapy can be altered, increased, decreased, increased in frequency, decreased in frequency, or discontinued. In certain aspects, a patient with a known bleeding disorder who is contemplating a procedure such as surgery can be carefully monitored, and the patient's treatment can be adapted to whatever procedure is to be performed. In certain aspects, the methods provided herein provide a way to improve the results obtained from clinical trials of new bleeding disorder treatments, such as recombinant or synthetic clotting factors.

Treatment options indicated by the results obtained from the disclosed methods can be automatically generated upon comparison to the baseline control results, or the results can be sent to a healthcare provider who makes a decision on treatment options based on the results. In certain aspects where the treatment options are generated at a clinical laboratory, the results sent to a healthcare professional can include instructions to the healthcare provider to initiate, adjust, alter, optimize, or discontinue treatment in view of the assay results. In certain aspects such instructions can be based on statistical data obtained from a plurality of patients exhibiting similar results. While a healthcare provider is normally the ultimate decision maker as to treatment of a bleeding disorder, as used herein the concept of "instructing a healthcare provider to initiate, adjust, alter, optimize, or discontinue treatment" refers to, e.g., a report that would be provided to the healthcare provider indicating the recommended treatment options in view of the results.

By providing more standardized assays to measure clot formation properties, the methods provided herein provide patients and healthcare providers with more accurate and reliable tools to manage bleeding disorders.

Additional embodiments of the inventions include:

E1. A method of treating a bleeding disorder in a patient comprising:
 a) obtaining a blood sample from a patient being evaluated or treated for a bleeding disorder;
 b) measuring a clot formation property in the blood sample;
 c) comparing the patient's clot formation results with a corresponding standard, wherein the standard correlates with a therapeutically efficacious treatment; and
 d) administering an optimized treatment to the patient, wherein the treatment is maintained or adjusted based on the relative difference between the patient's clot formation results and the corresponding standard.

E2. A method of treating a bleeding disorder in a patient comprising:
 a) obtaining a blood sample from a patient being evaluated or treated for a bleeding disorder;
 b) submitting the blood sample for measurement of a clot formation property and comparison to a corresponding standard, wherein the standard correlates with a therapeutically efficacious treatment; and
 c) administering an optimized treatment to the patient, wherein the treatment is maintained or adjusted based on the relative difference between the patient's clot formation results and the corresponding standard.

E3. A method of treating a bleeding disorder in a patient comprising:
 a) measuring a clot formation property in a blood sample obtained from a patient being evaluated or treated for a bleeding disorder;
 b) comparing the patient's clot formation results with a corresponding standard, wherein the standard correlates with a therapeutically efficacious treatment; and
 c) instructing a healthcare provider to maintain or adjust the patient's treatment, wherein the treatment is maintained or adjusted based on the relative difference between the patient's clot formation results and the corresponding standard.

E4. A method for optimizing bleeding disorder therapy in a patient comprising:
 a) obtaining a blood sample from a patient being evaluated or treated for a bleeding disorder;
 b) measuring a clot formation property in the blood sample;
 c) comparing the patient's clot formation results with a corresponding standard, wherein the standard correlates with a therapeutically efficacious treatment; and
 d) administering an optimized treatment to the patient, wherein the treatment is maintained or adjusted based on the relative difference between the patient's clot formation results and the corresponding standard.

E5. A method for optimizing bleeding disorder therapy in a patient comprising:
 a) obtaining a blood sample from a patient being evaluated or treated for a bleeding disorder;
 b) submitting the blood sample for measurement of a clot formation property and comparison to a corresponding standard, wherein the standard correlates with a therapeutically efficacious treatment; and
 c) administering an optimized treatment to the patient, wherein the treatment is maintained or adjusted based on the relative difference between the patient's clot formation results and the corresponding standard.

E6. A method for optimizing bleeding disorder therapy in a patient comprising:
 a) measuring a clot formation property in a blood sample obtained from a patient being evaluated or treated for a bleeding disorder;

b) comparing the patient's clot formation results with a corresponding standard, wherein the standard correlates with a therapeutically efficacious treatment; and c) instructing a healthcare provider to optimize the patient's treatment, wherein the treatment is maintained or adjusted based on the relative difference between the patient's clot formation results and the corresponding standard.

E7. A method of determining efficacy of treatment for a bleeding disorder in a patient comprising:

a) obtaining a blood sample from a patient being evaluated or treated for a bleeding disorder;

b) measuring a clot formation property in the blood sample;

c) comparing the patient's clot formation results with a corresponding standard, wherein the standard is representative of a therapeutically efficacious treatment, and wherein a similarity between the patient's results and the standard is indicative of efficacy of the patient's current treatment; and d) maintaining or adjusting the patient's treatment based on the relative difference between the patient's clot formation results and the corresponding standard.

E8. A method of determining efficacy of treatment for a bleeding disorder in a patient comprising:

a) obtaining a blood sample from a patient being evaluated or treated for a bleeding disorder;

b) submitting the blood sample for measurement of a clot formation property and comparison to a corresponding standard, wherein the standard correlates with a therapeutically efficacious treatment, and wherein a similarity between the patient's results and the standard is indicative of efficacy of the patient's current treatment; and c) maintaining or adjusting the patient's treatment based on the relative difference between the patient's clot formation results and the corresponding standard.

E9. A method of determining efficacy of treatment for a bleeding disorder in a patient comprising:

a) measuring a clot formation property in a blood sample obtained from a patient being evaluated or treated for a bleeding disorder;

b) comparing the patient's clot formation results with a corresponding standard, wherein the standard is representative of a therapeutically efficacious treatment, and wherein a similarity between the patient's results and the standard is indicative of the efficacy of patient's current treatment; and c) instructing a healthcare provider to maintain or adjust the patient's treatment based on the relative difference between the patient's clot formation results and the corresponding standard.

E10. A method for standardizing hemostasis assay results, comprising:

a) obtaining blood samples from a population of patients being treated for bleeding disorders;

b) measuring a clot formation property in the blood samples, wherein the measurements are performed using standardized reagents and methods;

c) comparing the patients' clot formation results with a corresponding standard, wherein the standard is representative of a therapeutically efficacious treatment, and wherein a similarity between the patients' results and the standard are indicative of efficacy of the patient's current treatments; and d) maintaining or adjusting the patients' treatments based on the relative difference between the patients' clot formation results and the corresponding standard.

E11. A method for standardizing hemostasis assay results, comprising:

a) obtaining blood samples from a population of patients being treated for bleeding disorders;

b) submitting the blood samples for measurement of a clot formation property and comparison to a corresponding standard, wherein the measurements are performed using standardized reagents and methods, wherein the standard correlates with a therapeutically efficacious treatment, and wherein a similarity between the patients' results and the standard are indicative of efficacy of the patients' current treatments; and c) maintaining or adjusting the patients' treatments based on the relative difference between the patient's clot formation results and the corresponding standard.

E12. A method for standardizing hemostasis assay results, comprising:

a) measuring a clot formation property in a blood samples obtained from a population of patients being treated for a bleeding disorder;

b) comparing the patients' clot formation results with a corresponding standard, wherein the standard is representative of a therapeutically efficacious treatment, wherein the measurements are performed using standardized reagents and methods, and wherein a similarity between the patients' results and the standard are indicative of the efficacy of patients current treatments; and c) instructing healthcare providers from whom the samples are obtained to maintain or adjust their patients' treatments based on the relative difference between the patients' clot formation results and the corresponding standard.

E13. A method for standardizing results in a multi-site clotting factor clinical trial, comprising:

a) obtaining blood samples from test subjects with bleeding disorders at multiple clinical trial sites;

b) measuring a clot formation property in the blood samples, wherein the measurements are performed using common reagents and methods;

c) comparing the patients' clot formation results with a corresponding standard, wherein the standard is representative of a therapeutically efficacious treatment, wherein a similarity between the patients' results and the standard are indicative of efficacy of the patient's current treatments, and wherein the variance of results between the multiple clinical trial sites is not statistically significant; and d) maintaining or adjusting the patients' treatments based on the relative difference between the patients' clot formation results and the corresponding standard.

E14. A method for standardizing results in a multi-site clotting factor clinical trial, comprising:

a) obtaining blood samples from test subjects with bleeding disorders at multiple clinical trial sites;

b) submitting the blood samples for measurement of a clot formation property and comparison to a corresponding standard, wherein the measurements are performed using common reagents and methods, wherein the standard correlates with a therapeutically efficacious treatment, wherein a similarity between the patients' results and the standard are indicative of efficacy of the patients' current treatments, and wherein the variance of results between the multiple clinical trial sites is not statistically significant; and c) maintaining or adjusting the patients' treatments based on the relative difference between the patient's clot formation results and the corresponding standard.

E15. A method for standardizing results in a multi-site clotting factor clinical trial, comprising:
a) measuring a clot formation property in a blood samples obtained from test subjects with bleeding disorders at multiple clinical trial sites;
b) comparing the patients' clot formation results with a corresponding standard, wherein the measurements are performed using common reagents and methods, wherein the standard correlates with a therapeutically efficacious treatment, wherein a similarity between the patients' results and the standard are indicative of efficacy of the patients' current treatments, and wherein the variance of results between the multiple clinical trial sites is not statistically significant; and
c) instructing healthcare providers participating in the clinical trial, from whom the samples were obtained, to maintain or adjust the test subjects' treatments based on the relative difference between the patients' clot formation results and the corresponding standard.

E16. The method of any one of embodiments E1 to E15, wherein the treatment comprises administration of a Factor VIII protein or a fragment, variant, or derivative thereof, or a Factor IX protein or a fragment, variant, or derivative thereof.

E17. The method of embodiment E16, wherein the treatment comprises administration of a chimeric Factor VIII-Fc fusion protein or a chimeric Factor IX-Fc fusion protein.

E18. The method of embodiment E17, wherein the Fc portion of the chimeric Factor VIII or Factor IX protein comprises a human Fc domain.

E19. The method of any one of embodiments E16 to E18, wherein the chimeric Factor VIII protein comprises a B-domain deleted Factor VIII.

E20. The method of embodiment E19, wherein the chimeric Factor VIII protein comprises SEQ ID NO:6.

E21. The method of embodiment E19, wherein the chimeric Factor VIII protein SEQ ID NO:2.

E22. The method of embodiment E17 or embodiment E18, wherein the chimeric Factor IX protein comprises SEQ ID NO: 13.

E23. The method of any one of embodiments E1 to E22, wherein the clot formation property is thrombin generation, kinetics of clot formation, strength of clot formation, stability of clot formation or a combination thereof.

E24. The method of any one of embodiments E1 to E23, wherein said blood sample is whole blood.

E25. The method of any one of embodiments E1 to E23, wherein said blood sample is plasma.

E26. The method of any one of embodiments E1 to E25, wherein the clot formation property is measured by a thrombin generation assay (TGA), thromboelastography (TEG), rotation thromboelastometry (ROTEM®), waveform analysis, or a combination thereof.

E27. The method of embodiment E26, wherein the clot formation property is measured by TGA.

E28. The method of embodiment E26, wherein the clot formation property is measured by TEG.

E29. The method of embodiment E26, wherein the clot formation property is measured by ROTEM®.

E30. The method of embodiment E26 wherein the clot formation property is measured by wave form analysis.

E31. The method of any one of embodiments E1 to E9, further comprising adding, ex vivo, a range of doses of a clotting factor therapy to aliquots of the blood sample obtained from the patient, and comparing the range of clot formation results obtained with the added clotting factor therapy to the standard.

E32. The method of embodiment E31, wherein the standard is a standard curve of clot formation results obtained with increasing amounts of a clotting factor added to FVIII or FIX-deficient plasma.

E33. The method of any one of embodiments E1 to E9, wherein the patient has not yet been treated with a clotting factor.

E34. The method of any one of embodiments E1 to E9, wherein the patient has received prior clotting factor treatment, but the treatment has been discontinued for a time period sufficient to deplete the clotting factor treatment from the patient's blood.

Having now described the present invention in detail, the same will be more clearly understood by reference to the following examples, which are included herewith for purposes of illustration only and are not intended to be limiting of the invention. All patents and publications referred to herein are expressly incorporated by reference.

EXAMPLES

Example 1

Apparent Discrepancy in TGA Activity of rFIXFc Vs. BENEFIX® is Due to Higher FIXa Impurity in BENEFIX®

The thrombin generation assay (TGA), a global hemostasis assay that monitors the amount of active thrombin produced in patient plasma after re-calcification, represents a useful indication in the evaluation of coagulation capacity of hemophilic plasma.

Figure 3A:
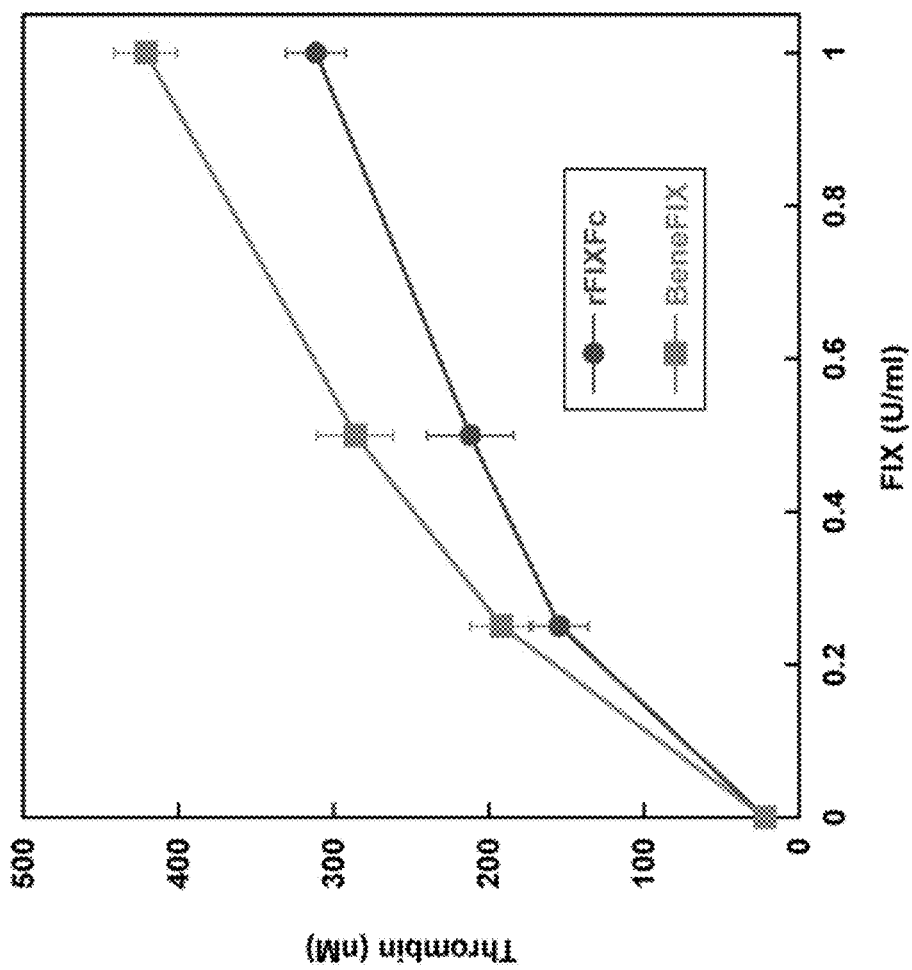
FIG. 3A. TGA Activity dose response curves for BENEFIX® and rFIXFc in FIX-deficient plasma.

Samples following rFIXFc or BENEFIX® (Pfizer) administration were analyzed by TGA. When equal units of rFIXFc and BENEFIX®, as determined by the one stage assay, were spiked into hemophilic plasma and their coagulation capacity was assessed by the TGA, BENEFIX® generated 2-fold higher peak thrombin and significantly left-shifted thrombin curve relative to rFIXFc in the presence of limiting tissue factor (TF) and 4 µM phospholipids (PL). As is shown in FIG. 3A, BENEFIX® appears to have twice the in vitro potency in standard TGA (1 pM TF+4 µM PL) compared to rFIXFc (1 IU/mL rFIXFc≈0.5 IU/mL BeneFIX®; IU/mL by aPTT).

Figure 3B:
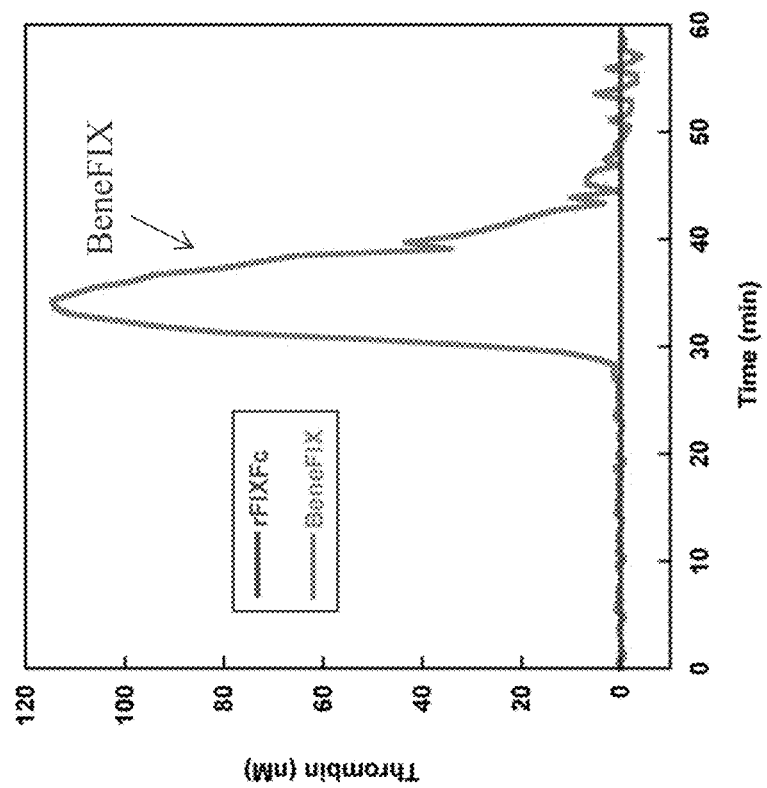
FIG. 3B. TGA Activity for BENEFIX® and rFIXFc in FIX-deficient plasma in the absence of tissue factor (auto-activation). Without tissue factor, BENEFIX® (1 IU/mL) generated a significant amount of thrombin whereas rFIXFc (1 IU/mL) demonstrated no thrombin generation.

In an assay control without tissue factor triggering, BENEFIX® demonstrated considerable thrombogenic activity, whereas rFIXFc was essentially inactive (FIG. 3B). BENEFIX® was observed to have a markedly higher level of FIXa impurity than rFIXFc in a factor IXa ELISA (see R. T. Peters et al. Prolonged activity of factor IX as a monomeric Fc fusion protein. *Blood* 2010; 115: 2057-2064). Factor IXa protease is known to be thrombogenic in an in vivo model (see, Gray E. et al. Measurement of activated Factor IX in Factor IX concentrates: correlation with in vivo thrombogenicity. *Thromb. Haemost.* 1995; 73(4):675-679; Buyue Y. et al. The heparin-binding exosite of factor IXa is a critical regulator of plasma thrombin generation and venous thrombosis. Blood 2008; 112(8):3234-3241.). It was therefore hypothesized that the enhanced in vitro thrombin generation profile of BeneFIX® is due to the presence of excess factor IXa.

Thrombin Generation Profile of BENEFIX® after Active Site Inhibition of Protease (FIXa)

Figure 3C:
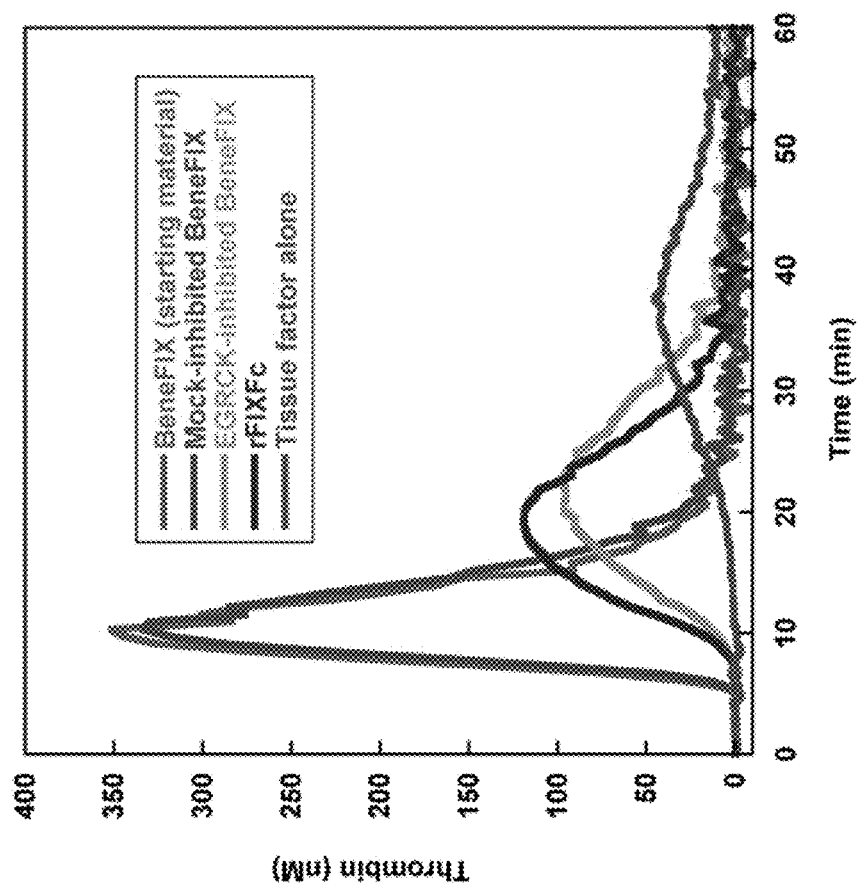
FIG. 3C. Thrombin generation profile of BENEFIX® after active site inhibition of protease (FIXa). Active site-inhibited BENEFIX® showed similar thrombin generation ability to rFIXFc.

To test the above hypothesis, BeneFIX® was incubated overnight with a serine protease active site blocker, EGR-chloromethyl ketone, and dialyzed by extensive buffer exchange. Thrombin generation was triggered with 1 pM tissue factor in the presence of 4 µM phospholipids in FIX-deficient plasma supplemented with 1 IU/mL of FIX material. The FIXa-blocked or active site-inhibited BENEFIX® showed a very similar thrombin generation profile (ETP, peak thrombin, time course and slope) to rFIXFc, confirming the role of FIXa in thrombin generation by BENEFIX® (FIG. 3C).

Titration of Plasma-Derived FIXa into FIX-Deficient Plasma in the Absence of Tissue Factor. Quantification of FIXa in BENEFIX® and rFIXFc Drug Products by TGA.

Figure 3D:
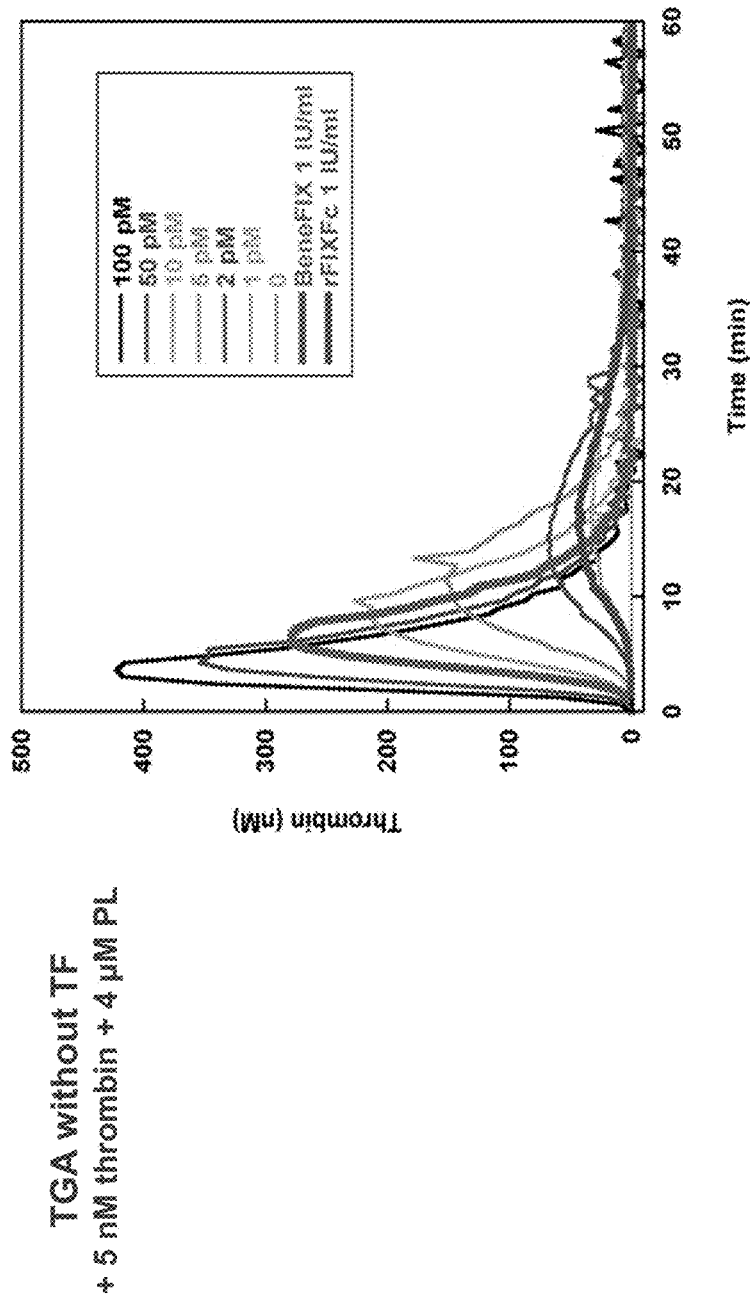
FIG. 3D. Titration of plasma-derived FIXa into FIX-deficient plasma in the absence of tissue factor.

FIXa can be more easily quantified in TGA without added (exogenous) TF, but primed with 5 nM thrombin, which is consumed during the reaction as seen by the '0 FIXa' control in FIG. 3D.

Figure 3E:
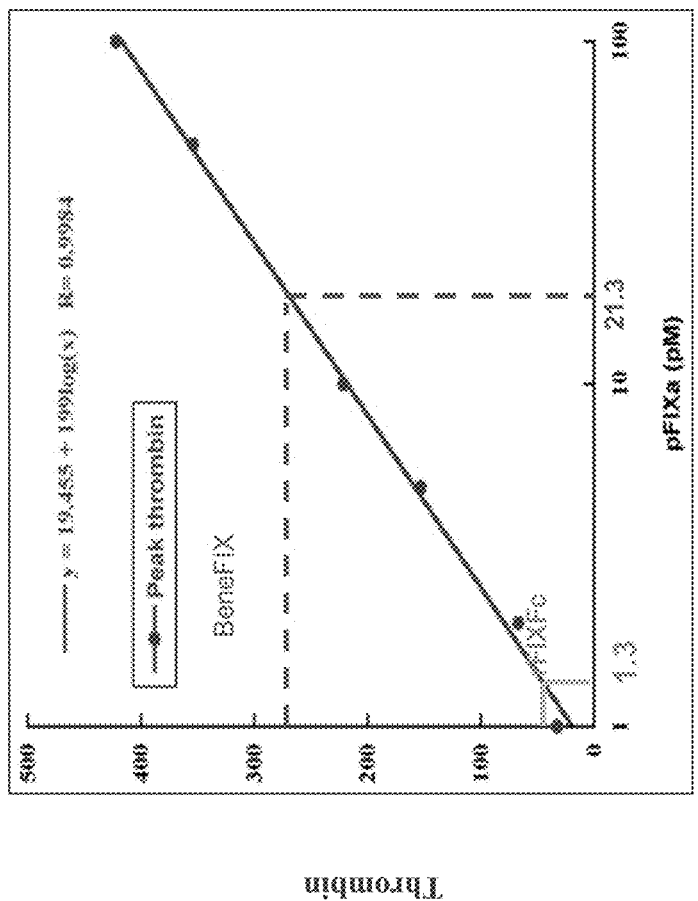
FIG. 3E. Quantification of FIXa in BeneFIX® and rFIXFc drug products by TGA (standard curve). Y axis=nM thrombin as in FIG. 3D.

To quantify the amount of active factor IXa in BENEFIX® and rFIXFc, a plasma-derived factor IXa (e.g., pFIXa, from Haematologic Technologies, Essex Junction, Vt.) standard curve was constructed by spiking increasing concentrations of factor IXa (0-100 pM) into human factor IX-deficient plasma in the presence of 4 µM phospholipids. Prior to starting the measurement, 5 nM thrombin was added to the assay in order to improve sensitivity (FIG. 3E).

A dose response was observed with a detection limit as low as 0.5 pM pFIXa in FIX-deficient plasma. BENEFIX®, FIXa-blocked BENEFIX® and rFIXFc of equal potency (1 IU/mL by the one-stage clotting assay) generated thrombin responses comparable to 20 pM, 1 pM and 2 pM pFIXa, respectively, indicating the amount of FIXa present in each FIX product. Representative curve and curve fitting are shown in FIGS. 3D and E. Similar results were observed in different lots of FIX-deficient plasmas (different single donors).

In a regular thrombin generation assay triggered with limiting TF, 1 IU/mL rFIXFc supplemented with 20 pM pFIXa demonstrated an equal peak thrombin and velocity index to 1 IU/mL BENEFIX®.

Figure 3F:
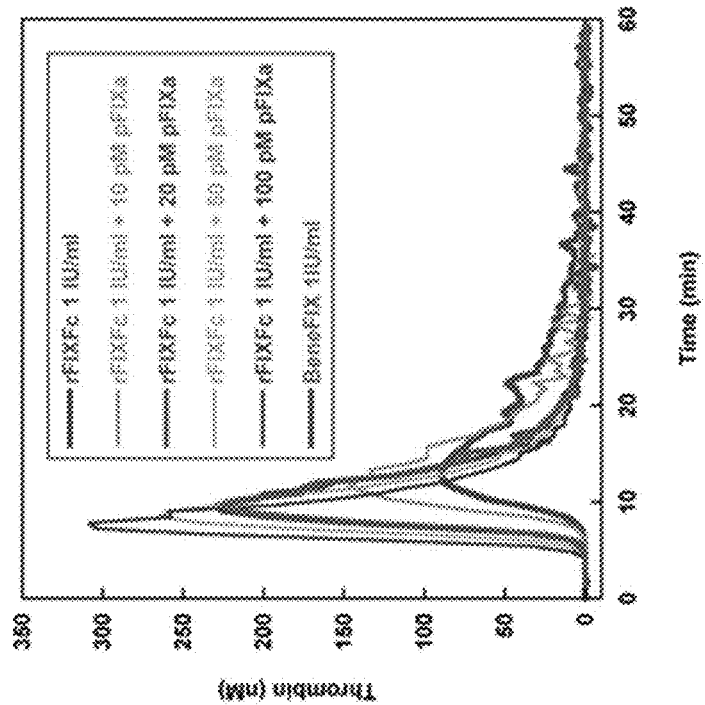
FIG. 3F. Tissue factor-triggered thrombin generation profile comparing BeneFIX® and rFIXFc, each supplemented with increasing plasma-derived FIXa.

Tissue Factor-Triggered Thrombin Generation Profile Comparison of BENEFIX® and rFIXFc Supplemented with Increasing Plasma-Derived FIXa To confirm the results from pFIXa titration, a tissue factor-triggered thrombin generation assay was performed by supplementing 1 IU/mL rFIXFc with increasing concentrations of pFIXa to FIX-deficient plasma and compared with 1 IU/mL BeneFIX® without FIXa (FIG. 3F). In this experiment, 1 IU/mL rFIXFc+20 pM pFIXa generated the same amount of thrombin 1 IU/mL BeneFIX® without added FIXa in thrombin generation response. The results are summarized in Table 1.

TABLE 1

Comparison of BENEFIX ® and rFIXFc supplemented with plasma-derived FIXa

| pFIXa (pM) Supplement | Lag time (min) | ETP (nM * min) | Peak thrombin (nM) | Peak time (min) |
|---|---|---|---|---|
| rFIXFc + 0 pM FIXa | 8.5 | 1175.5 | 90.37 | 13 |
| rFIXFc + 10 pM FIXa | 7.88 | 1301.5 | 143.58 | 11.75 |
| rFIXFc + 20 pM FIXa | 6.62 | 1452 | 231.47 | 9.62 |
| rFIXFc + 50 pM FIXa | 6.12 | 1548 | 268.13 | 8.75 |

TABLE 1-continued

Comparison of BENEFIX ® and rFIXFc supplemented with plasma-derived FIXa

| pFIXa (pM) Supplement | Lag time (min) | ETP (nM * min) | Peak thrombin (nM) | Peak time (min) |
|---|---|---|---|---|
| rFIXFc + 100 pM FIXa | 5.5 | 1600 | 314.68 | 7.5 |
| BeneFIX + 0 pM FIXa | 6.75 | 1430.5 | 224.61 | 9.62 |

Conclusion

These data suggest that: (1) minor amounts of FIXa in a FIX drug product (e.g., a trace amount of 0.1%) can trigger significant thrombin generation in global hemostasis assays (e.g., TGA); (2) the higher apparent peak thrombin and shortened time course in the thrombin generation profile for BENEFIX® relative to rFIXFc are caused entirely by the presence of factor IXa in BENEFIX®; and (3) discounting the rFIXa impurities in these drug products, BENEFIX® and rFIXFc have equivalent in vitro thrombin generation activity per unit of FIX activity.

Thus, comparing the potency of different products or FIX variants by TGA can be highly misleading if they contain different amounts of FIXa impurity. In vivo, FIXa is rapidly inactivated and does not contribute to the efficacy of the FIX drug product. Standardization of clinical TGA by spiking the FIX drug product into a baseline plasma sample may not be accurate, but no such effect of FIXa impurity on aPTT is seen due to rapid contact activation of FIX. Thus, FIXa can also affect ROTEM®/TEG assays when spiking FIX drug product into hemophilic blood.

From this data it can also be concluded that thrombin generation assays can be used to evaluate FIXa levels in FIX products with high sensitivity (0.5 pM FIXa per IU/ml FIX) when small amounts of thrombin are present during the measurement (e.g., in the assay buffer/assay solution).

Example 2

ROTEM® as a Global Assay for FVIII Activity Using Different Therapies

Figure 4:
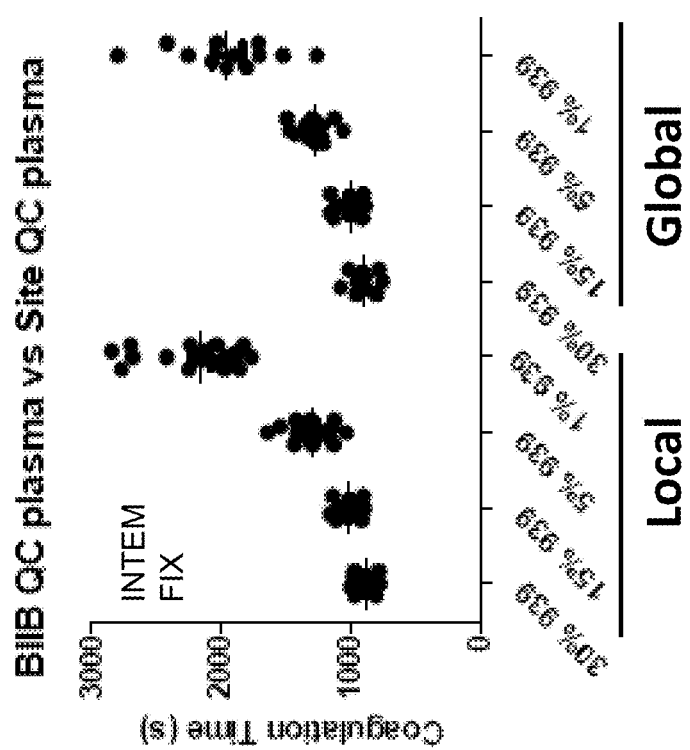
FIG. 4. Standardization of ROTEM® in a Factor VIII clinical trial.

As shown in FIG. 4, ROTEM® can be used to analyze FVIII clinical trial samples. Assays were performed at approximately 20 clinical sites. Platelet poor plasma controls were hemophilic plasma form a single donor (patient 939) spiked with 30%, 15%, 5%, and 1% of rFVIII These results were reproducible within a subject. Pharmacokinetics of rFVIIIFc activity against ADVATE® is shown in FIG. 5. Pharmacokinetics of rFVIIIFc is reproducible after 14 weeks.

Figure 6A:
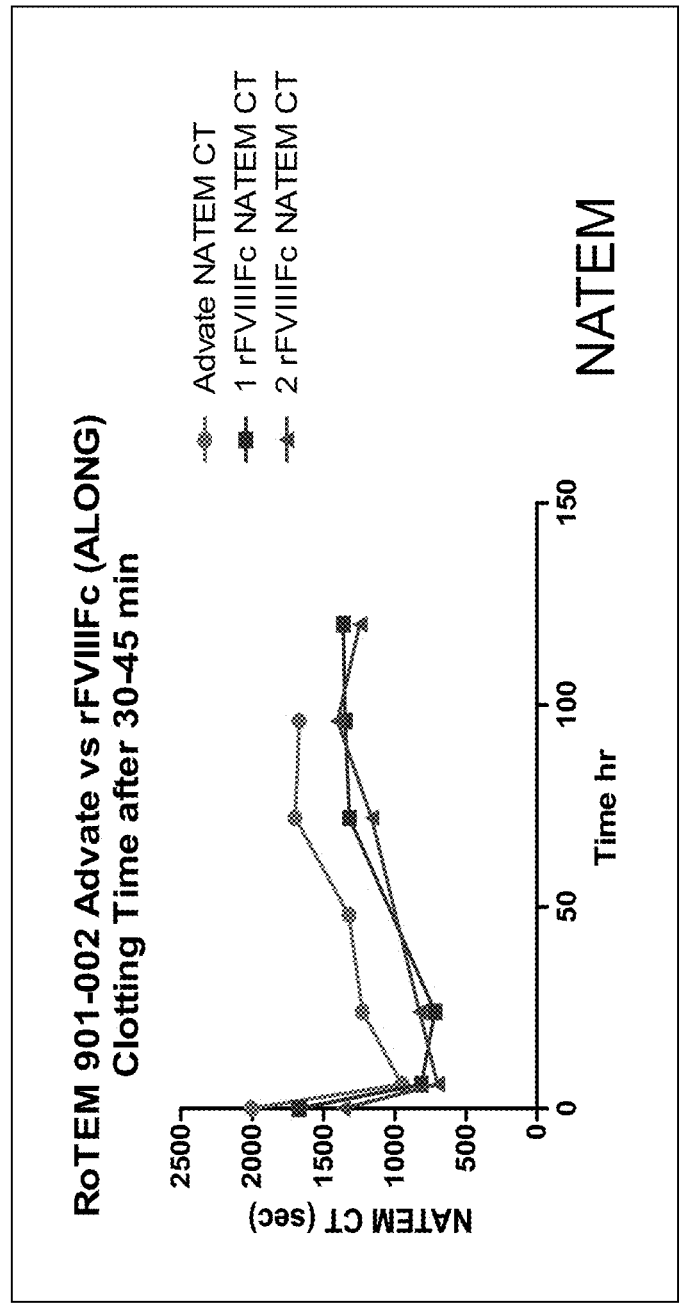
FIG. 6A.
Figure 6B:
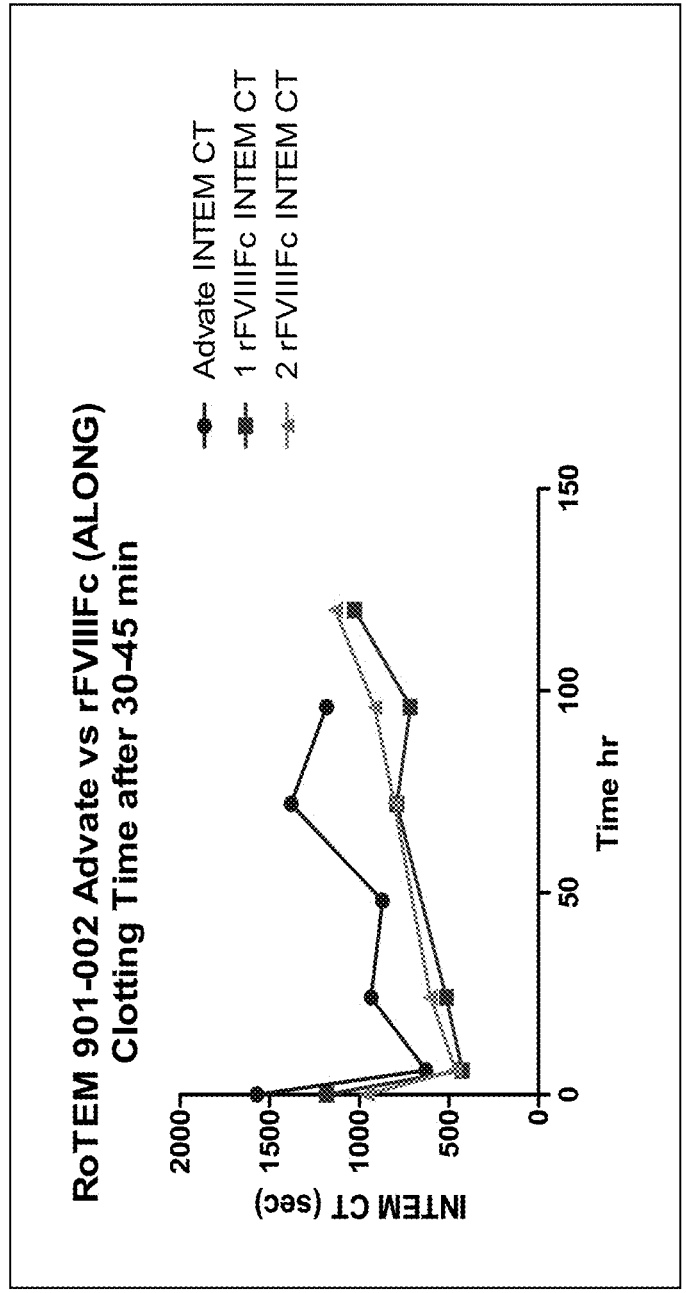
-FIG. 6C. rFVIIIFc ROTEM® results are reproducible within a subject. NATEM (6A): very sensitive assessment of the equilibrium of coagulation activation or inhibition; EXTEM (6C): Fast assessment of clot formation, fibrin polymerization and fibrinolysis via the extrinsic pathway; INTEM (6B): Fast assessment of clot formation, fibrin polymerization and fibrinolysis via the intrinsic pathway.
Figure 6C:
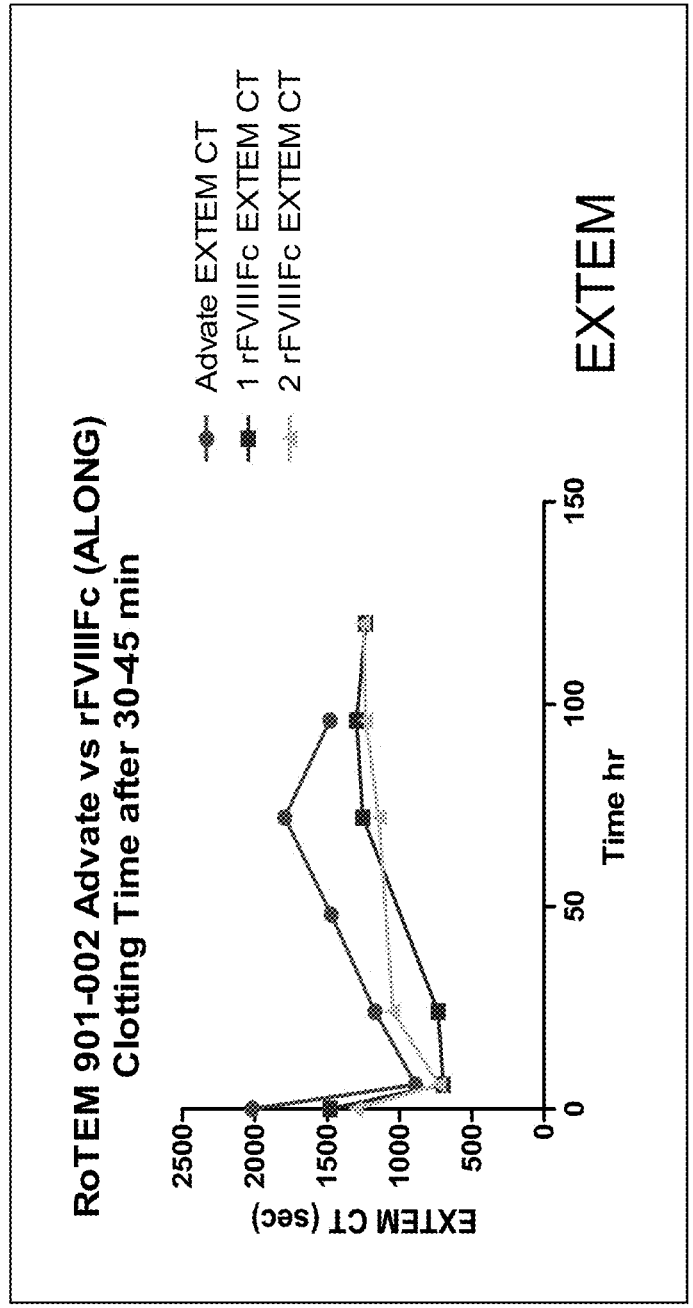
Figure 7A:
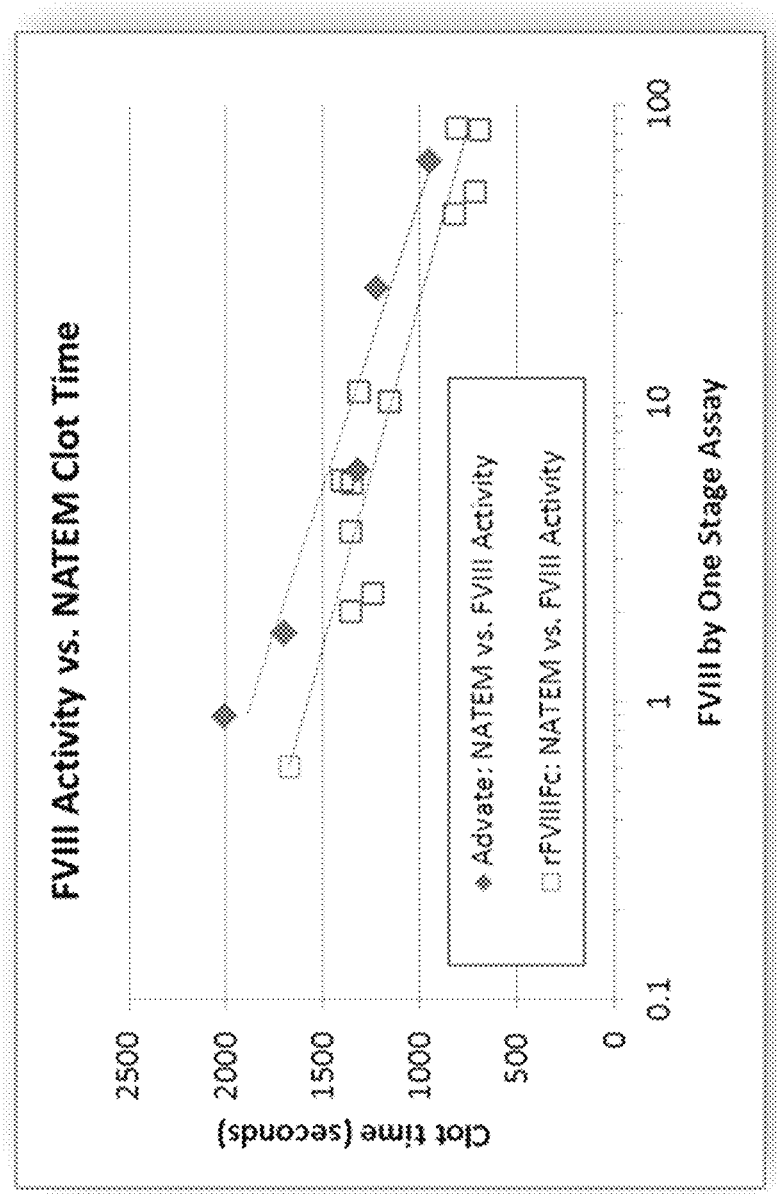
FIG. 7A-FIG. 7C. Correlation between FVIII activity and ROTEM® clot time. NATEM (7A): very sensitive assessment of the equilibrium of coagulation activation or inhibition; EXTEM (7C): Fast assessment of clot formation, fibrin polymerization and fibrinolysis via the extrinsic pathway; INTEM (7B): Fast assessment of clot formation, fibrin polymerization and fibrinolysis via the intrinsic pathway.
Figure 7B:
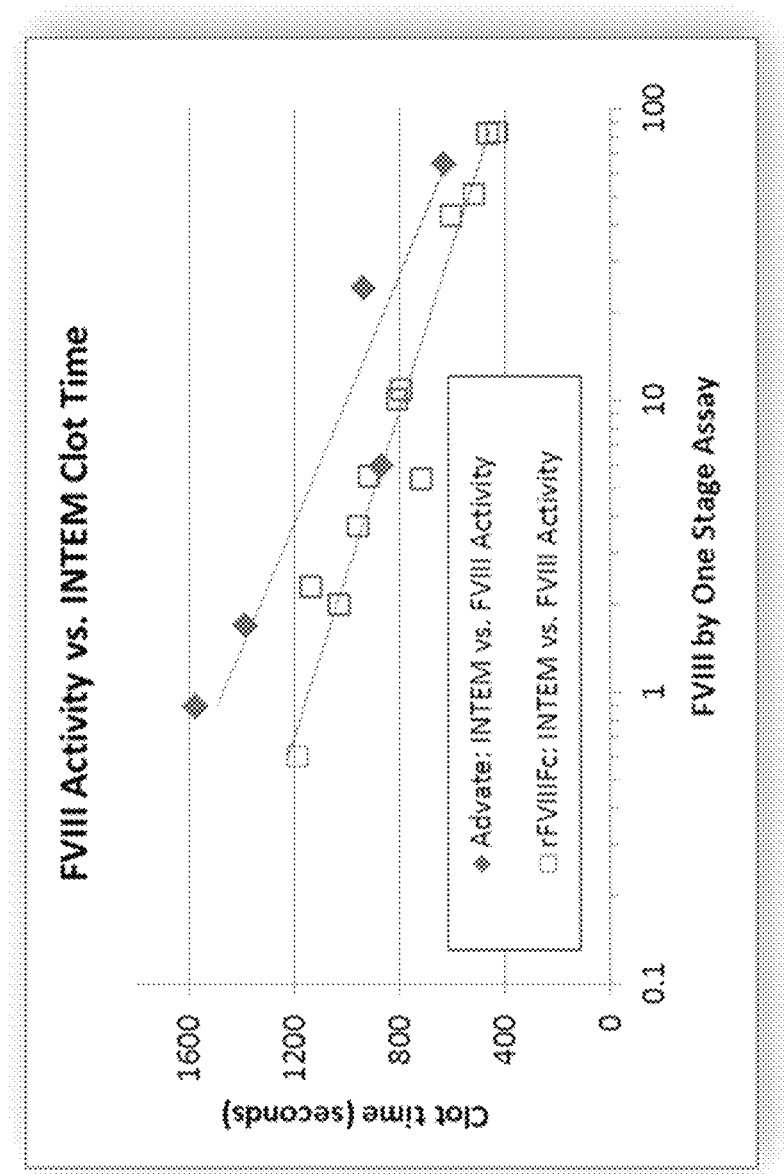
Figure 7C:
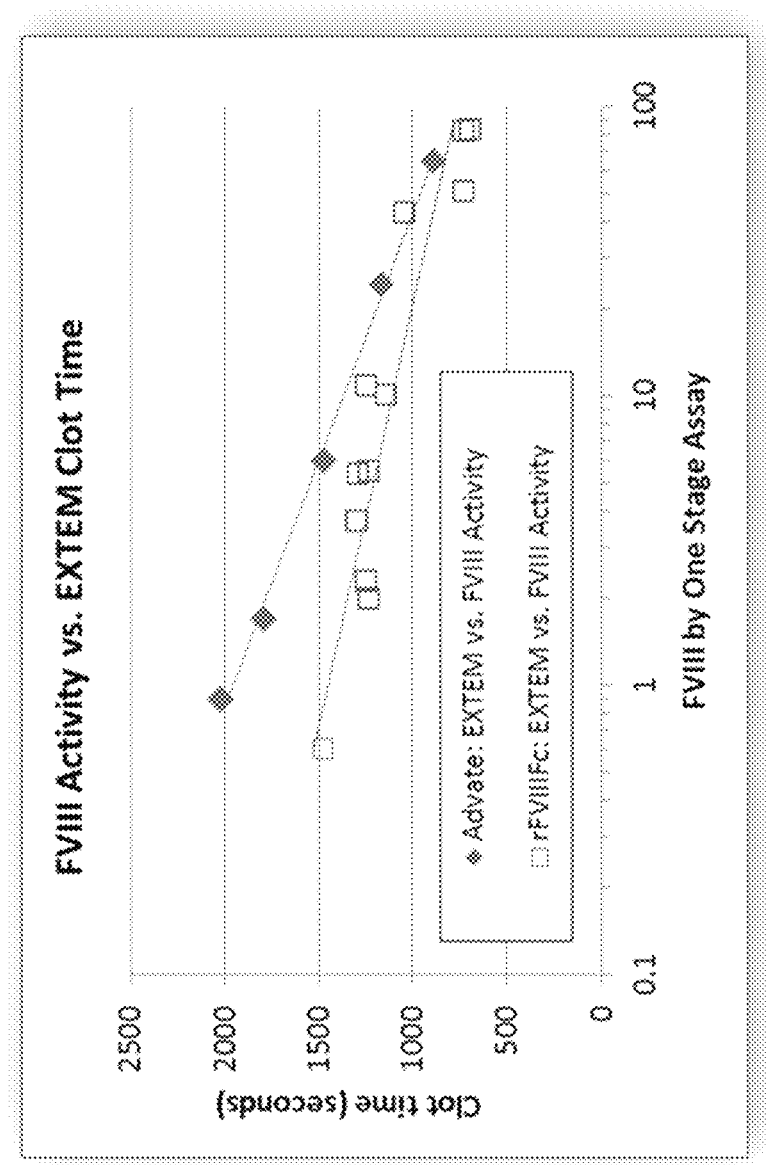

As shown in FIG. 6A to FIG. 6C, rVIIIFc improves clot formation (shortens clot time) for a longer period than ADVATE® (Baxter). ROTEM® results for initial rFVIIIFc PK (week 1) and repeat PK (week 14) also overlap. Importantly, this reproducibility within the same subject is critical for evaluation of inter-subject differences. These data were confirmed showing that there is good correlation between FVIII activity (via one-stage assay) and clot time by ROTEM®. As shown in FIG. 7A to FIG. 7C, at the same FVIII activity, rFVIIIFc appears to form clots more quickly than ADVATE®.

Example 3

Standardization of Global Hemostasis Assays Across Multiple Clinical Sites

Measurement of FVIII or FIX activity in clinical samples by the one-stage clotting assay has been the standard method for estimating the in vivo activity of current replacement factor products in the treatment of hemophilia. However, the one-stage clotting assay may not accurately predict the in vivo activity of novel FVIII and FIX products that have been modified for increased potency or longer half-life. Global hemostasis assays such as thromboelastography (TEG) and rotation thromboelastometry (ROTEM®) could provide additional information about the in vivo function of FVIII and FIX products since these whole blood assays are thought to more closely reflect in vivo coagulation.

The TEG and ROTEM® assays have not gained widespread acceptance in clinical use and have not been routinely used in hemophilia care mainly due to the lack of assay standardization, absence of reference materials appropriate for hemophilic patient samples and the time-consuming (low throughput) aspect of processing the blood samples. Nevertheless, if properly implemented as part of a clinical trial, these assays could provide a surrogate marker for in vivo activity of novel products where traditional factor assays can be of low predictive value.

The in vivo activity of long-lasting clotting factor IX Fc fusion protein (rFIXFc) can be more accurately measured using such method. Recombinant (r) FVIIIFc and rFIXFc are coagulation factors that are genetically fused to the Fc portion of human immunoglobulin G1 (IgG1). The resulting fusion proteins retain coagulation activity in the one-stage clotting and chromogenic assays.

Standardization of Assay to Measure FIXFc Activity In Vivo

The effectiveness of a standardized procedure for performing ROTEM® analysis at multiple clinical sites was evaluated in support of a phase 3 trial of long-lasting clotting factor IX Fc fusion protein.

Exemplary methods evaluate the process of blood coagulation and fibrinolysis by measuring the viscoelastic properties of the freshly collected blood over time, thus providing information about coagulation initiation and propagation kinetics, fibrin-platelet interaction, clot firmness and fibrinolysis. Exemplary parameters relevant to clot formation in hemophilic samples are clotting time (CT), clot formation time (CFT), α-angle (α), clot firmness (A5-AX), maximum clot firmness (MCF) and maximum clot lysis index (ML).

Comparison of ROTEM® results from individual subjects, e.g., across multiple clinical sites, requires a standardized procedure and a method for verifying consistent instrument, operator and reagent performance.

Prior to evaluating clinical samples, each participating site performed a set of quality control (QC) assays using the 'ROTROL N reagents provided by TEM Innovations GmbH and a set of frozen plasma controls that were prepared by the central site by spiking hemophilic plasma at 4 different levels of FIX drug product (1 IU/dL, 5 IU/dL, 15 IU/dL and 30 IU/dL).

Figure 8:
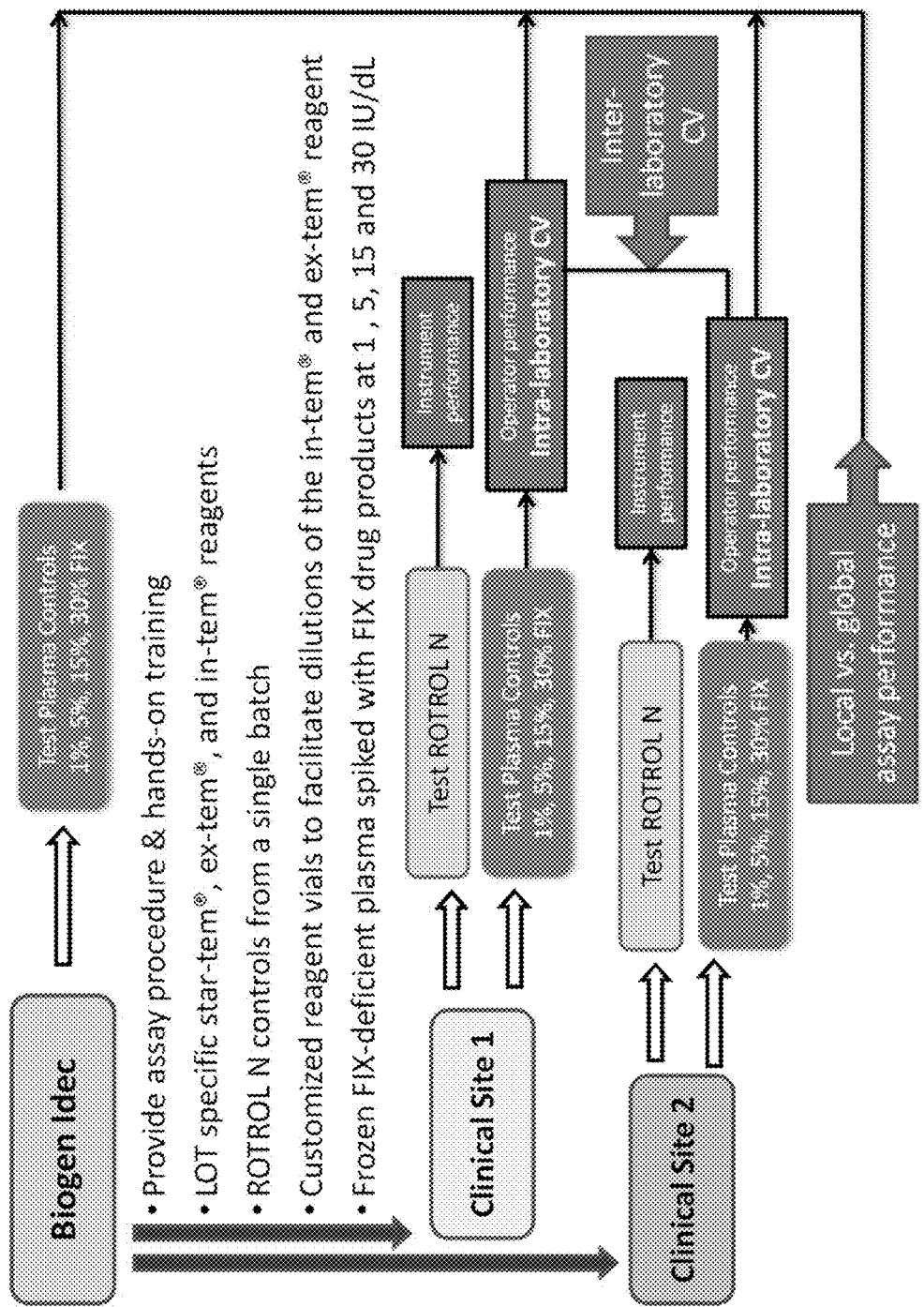
FIG. 8. Workflow diagram for standardization of ROTEM® in a Phase 3 clinical trial.

To verify reagent suitability and operator performance, including all reagent dilution steps, frozen plasma controls were prepared by the central site, which contain four levels of rFIX (FIG. 8). A detailed assay protocol and all reagents needed to perform the ROTEM®, including custom diluents, were provided to the sites by the central site in order to ensure a consistent method and reagent lot uniformity across all centers participating in this exploratory study. In addition, local operators at each site participated in hands-on training provided by the central site.

ROTROL N and plasma controls were tested on several occasions at each site over a period of at least 26 weeks. The data from the repeat assays were used to determine intra-laboratory and inter-laboratory variation. Analysis of variance (ANOVA) was performed for the inter-laboratory variance. A p-value<0.05 was considered statistically significant. A mixed effect model was utilized with covariates of center and plasma level. All statistical analyses were performed in TIBCO Spotfire S+8.2 (TIBCO Software Inc., Palo Alto, Calif.).

An interim analysis was performed on the QC data gathered from 6 clinical sites that performed a total of 44 QC runs for FIX on 8 ROTEM® instruments (7 model Gamma and 1 model Delta). Among the 4 ROTEM® parameters evaluated (clotting time, CT; clot formation rate, CFR; maximum clot firmness, MCF and alpha angle), CT was most reproducible, with a relatively small % CVs among the 5 sites, ranging from 8% to 24% across the 4 concentration levels of FIX (Table 2).

TABLE 2

Summary of ROTEM ® QC data (Clotting time (INTEM) for plasma control samples)

| | 30% FIX (n = 12) | 15% FIX (n = 11) | 5% FIX (n = 11) | 1% FIX (n = 10) |
|---|---|---|---|---|
| | Global Sites | | | |
| Mean | 901 | 1041 | 1342 | 2003 |
| Min, Max | 549, 1077 | 907, 1207 | 1127, 1737 | 936, 2750 |
| % CV | 17% | 8% | 13% | 24% |
| | Central Site | | | |
| | 30% FIX (n1 = 19) | 15% FIX (n1 = 19) | 5% FIX (n1 = 19) | 1% FIX (n1 = 19) |
| Mean | 893 | 1010 | 1295 | 2178 |
| Min, Max | 776, 1002 | 895, 1136 | 1033, 1640 | 1769, 2837 |
| % CV | 8% | 7% | 12% | 16% |

A mixed effect model was fitted for the ROTEM® global QC data (the response variable) with 'centers' and 'plasma FIX levels' as covariates. The center had no statistically significant effect on clotting time (p-value=0.57) and alpha angle (p-value=0.85), but a mild impact on MCF (p=0.12) and CFR (p-value=0.07). As expected, an increase in FIX concentration level was shown to significantly reduce the clotting times (p-value=0.001).

To further examine the standardization approach in controlling inter-site variability of ROTEM® data, two parameters, operator and instrument, were also evaluated. Comparison of the results obtained at the 5 clinical sites to replicate analysis at a single site (19 runs at each FIX level performed at the central site by a single operator on 6 model Delta instruments) indicated equivalent variability with an overall ANOVA p-value of 0.85 for CT (accounting for the correlation between ROTEM® data and FIX level) and a similar comparability for CFR, MCF and alpha angle.

Figure 9:
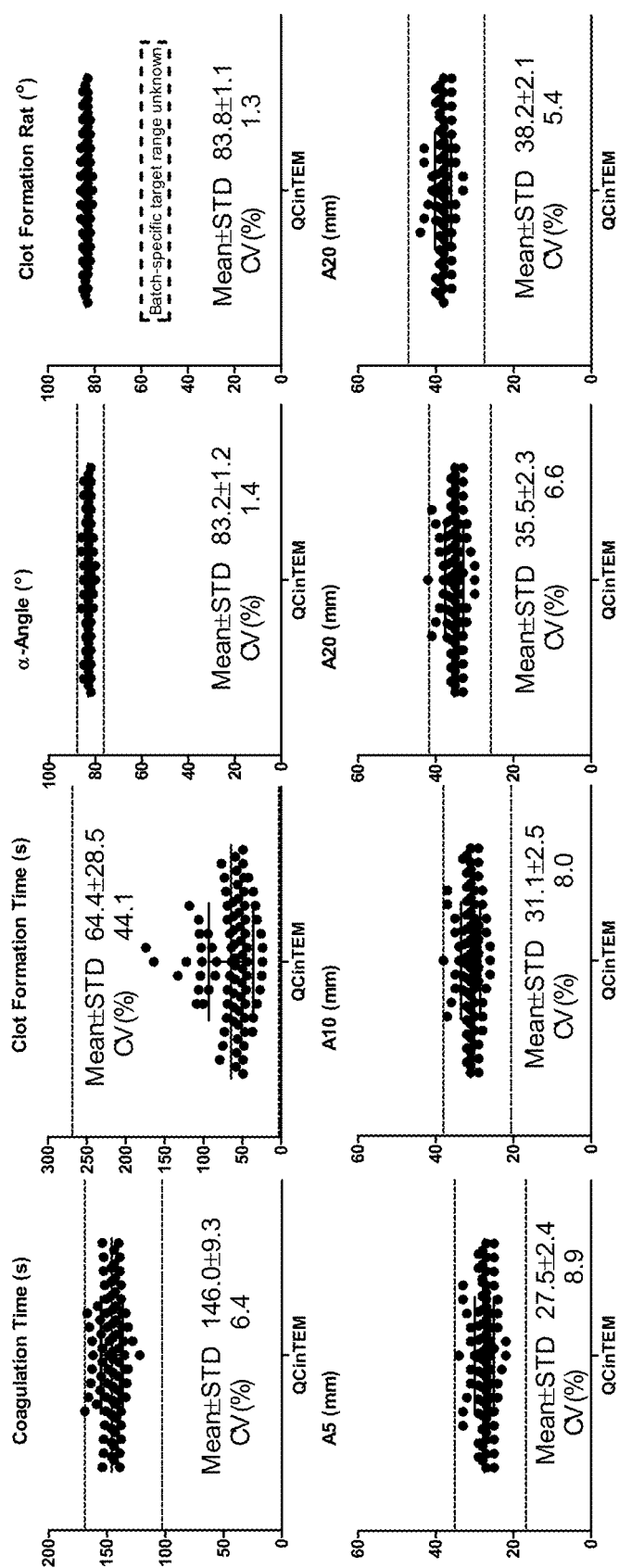
FIG. 9. Variability and range of ROTROL N results at 7 clinical sites.

To verify performance of each ROTEM® instrument in the multi-center study, the standardized ROTEM® QC INTEM method was tested using a single lot of ROTROL N, star-Tem® and in-Tem® reagents. Results are summarized in FIG. 9. The Batch-specific target ranges (dotted lines) could be confirmed by all participating sites, and there was no instrument-related clustering of results, e.g., when samples were assayed on multiple instruments at a single site by one operator. All instruments were maintained within the manufacturer's specification (per ROTROL N data). Thus, differences in instrument performance/calibration do not contribute significantly to the inter-site variability (e.g., operator and instrument variability is not a significant factor in the ROTEM® study).

Assuming the pre-analytical variables for the blood collection are also minimized in the standardized procedure, major differences in a subject's ROTEM® parameters will be a meaningful indicator of their hemostatic potential rather than simple assay variability between individual test sites.

Subject-Specific Differences in Coagulation Patterns of FIX-Deficient Plasma

Figure 10A:
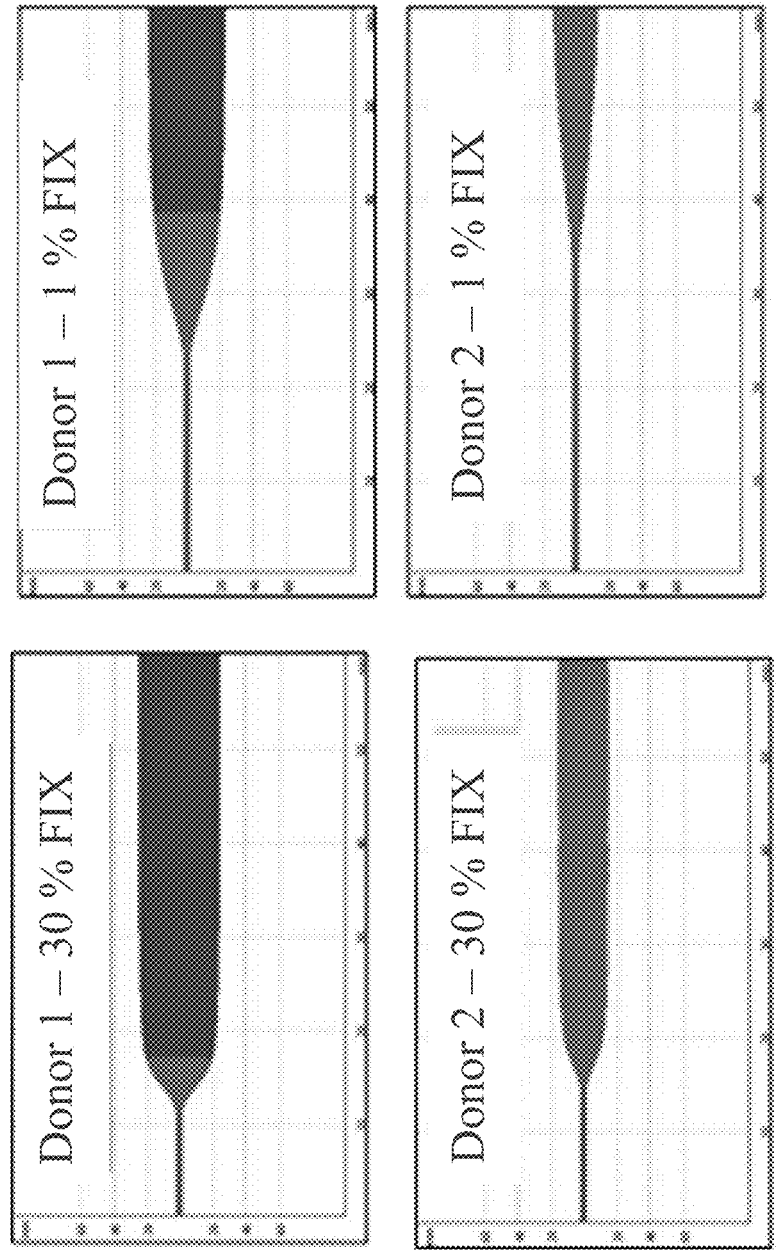
FIG. 10A-FIG. 10C. Subject-specific differences in coagulation patterns of FIX-deficient plasma.
Figure 10B:
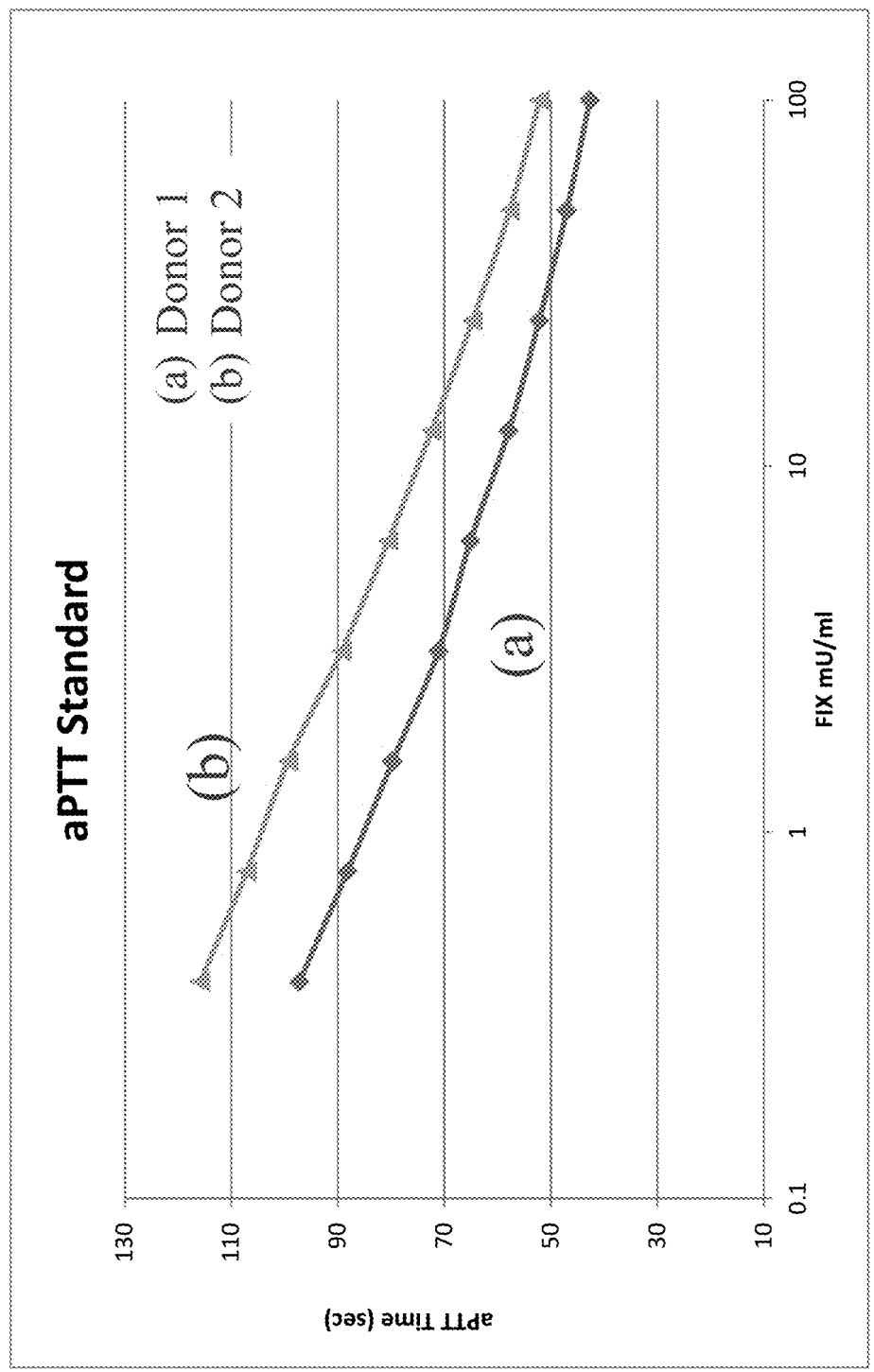
Figure 10C:
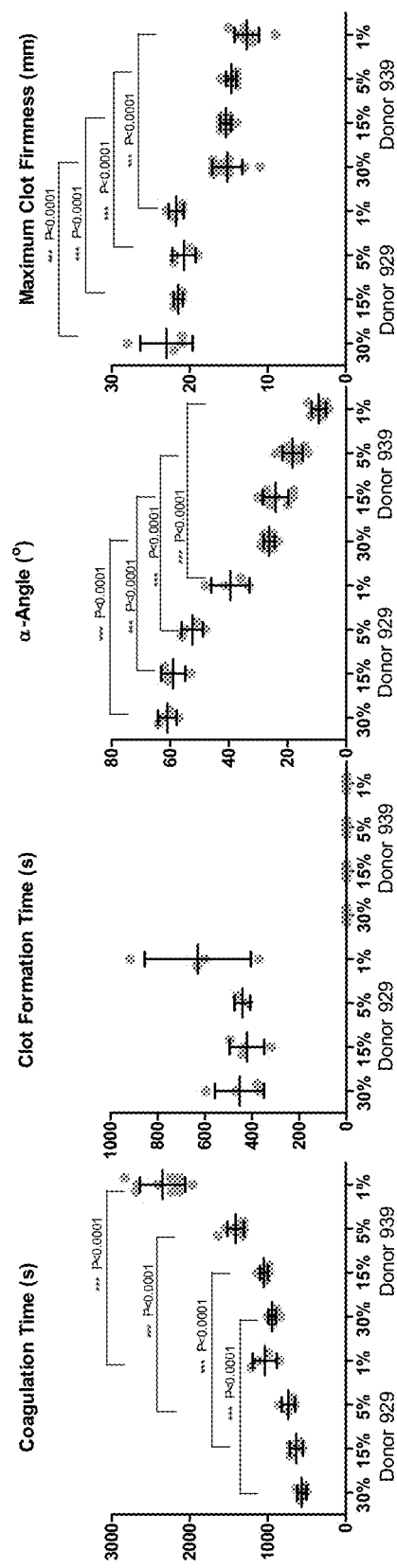

Plasma samples from two congenitally deficient donors showed <0.3% FIX and normal levels of FVII and FVIII activity (Table 3). ROTEM® parameters at equivalent FIX levels were significantly different in the two donor plasmas (FIG. 10A and FIG. 10C). Plasma from Donor 2 also demonstrated longer clot time by aPTT compared to plasma from Donor 1 (FIG. 10B). Plasma from Donor 2 was used to prepare control samples because of greater differentiation at lower FIX concentrations.

TABLE 3

| Assay | Clotting factor activity (%) | |
| --- | --- | --- |
| | Donor 1 | Donor 2 |
| FVII PT activity [IU/dL] | 65 | 59 |
| FVIII one-stage clotting activity [IU/dL] | 105 | 81 |
| FIX one-stage clotting activity [IU/dL] | <0.3 | <0.3 |

Comparison of Plasma Control Results Between Single Site and Global Sites

Figure 11:
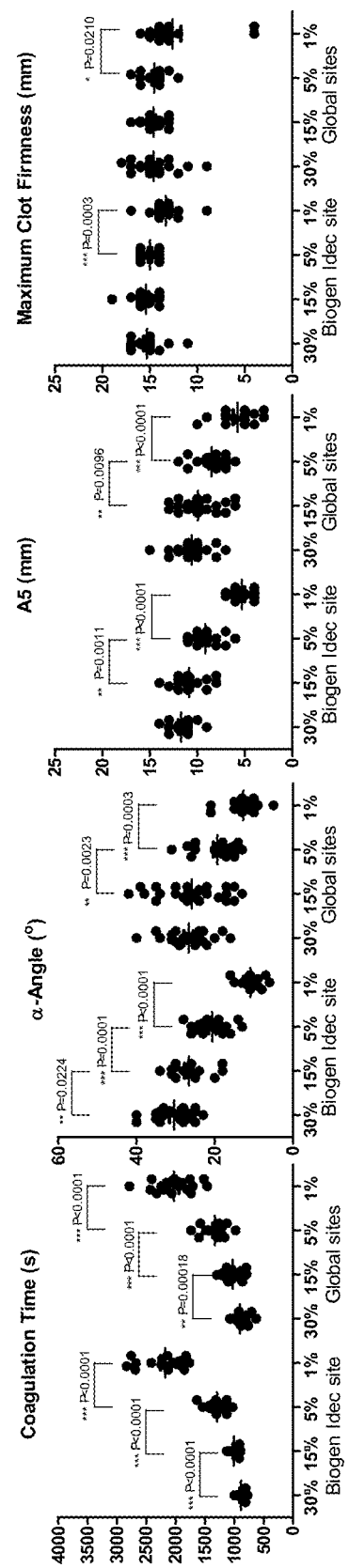
FIG. 11. ROTEM® coagulation results using plasma controls (FIX-deficient plasma spiked with 1 IU/dL, 5 IU/dL, 15 IU/Dl or 30 IU/dL or rFIX. Comparison of results between single (local) site and global sites.

A dose response from 1 UL/dL to 30 IU/dL in FIX-deficient plasma could be visualized by thromboelastometry parameters CT, α-Angle, A5, but not MCF. Increasing FIX concentrations significantly reduced the clotting times and increased the α-Angle. A mixed effect model showed that the centers had no statistically significant effect on clotting time (p-value=0.43), CFR (p-value=0.41), alpha (p-value=0.25), or MCF (p-value=0.83) compared to the single site (FIG. 11).

Standardization of Assay to Measure rFVIIIFc Activity In Vivo

The effectiveness of a standardized procedure for performing ROTEM® analysis at multiple clinical sites was evaluated in support of a phase 3 trial of long-lasting clotting factor VIII Fc fusion protein.

Comparison of ROTEM® results from individual subjects, e.g., across multiple clinical sites, requires a standardized procedure and a method for verifying consistent instrument, operator and reagent performance.

Prior to evaluating clinical samples, each participating site (14 sites) performed a set of quality control (QC) assays using the ROTROL N reagents provided by TEM Innovations GmbH. To verify reagent suitability and operator performance, including all reagent dilution steps, frozen plasma controls were prepared by the central site, which contain four levels of rFVIII (1%, 5%, 15% and 30%). A detailed assay protocol and all reagents needed to perform the ROTEM®, including custom diluents, custom controls, and other supplies were provided to the sites by the central site in order to ensure a consistent method and reagent lot uniformity across all centers participating in this exploratory study. In addition, local operators at each site participated in hands-on training provided by the central site. Eight tests were performed at each FVIII level at the central site, and a total of 35 tests per FVIII level were performed at the 14 clinical sites.

Figure 12:
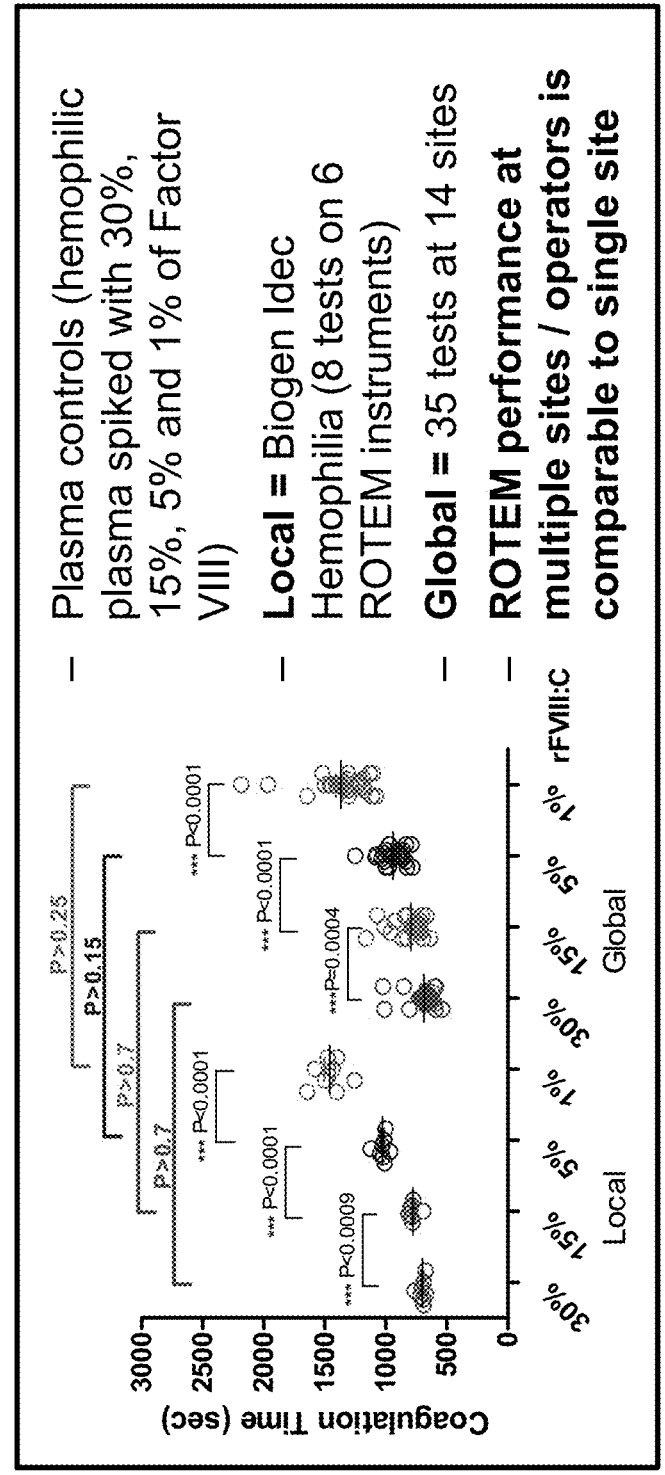
FIG. 12. ROTEM® coagulation times using plasma controls (hemophilic plasma spiked with 30%, 15%, 5% and 1% of Factor VIII). Comparison of results between single (local) site and global sites.

The results are shown in FIG. 12. No significant differences were found between the central site results and the global results at each FVIII concentration.

Conclusions

ROTEM® standardization across multiple sites in support of a global clinical trial is possible by providing detailed procedures, hands-on training and uniform reagents to each site ROTROL N and frozen plasma controls can be used instead of fresh whole blood to verify instrument and assay performance at each site.

Normalization of whole blood results against plasma standards as a method for improving comparability of clinical results, while useful, may not be needed with this level of procedural standardization. Even if not necessary, frozen plasma standards can be used to 'normalize' whole blood results caused by, e.g., site/instrument differences.

Assuming the pre-analytical variables for the blood collection are also minimized in the standardized procedure, we expect that major differences in ROTEM® parameters between individual subjects will be a meaningful indicator of their hemostatic potential rather than assay variability between individual test sites.

Example 4

Evaluation of Inter-Site Variability of the ROTEM® Assay

The one-stage clotting assay is the standard method for estimating the in vivo activity of replacement factor products in the treatment of hemophilia. A global hemostasis assay, such as rotation thromboelastometry (ROTEM®) could provide additional information about the in vivo function of FVIII product since this whole blood assay is thought to more closely reflect in vivo coagulation. However, ROTEM® has not been routinely used in hemophilia care, mainly due to the lack of assay standardization.

The effectiveness of a standardized ROTEM® procedure in support of the phase3 clinical trial of a long-lasting clotting factor VIII Fc fusion protein (rFVIIIFc). An interim analysis was performed on the QC data gathered from 10 clinical sites. Each site performed a set of assays using frozen plasma controls with different levels of FVIII drug product. Among the 4 ROTEM® parameters evaluated (CT, CFR, MCF and alpha angle), CT and MCF were most reproducible, with relatively small variation among all sites, ranging from 10% to 18% CV across the concentration levels. A mixed effect model was fitted for the ROTEM® global QC data (the response variable) with 'centers' and 'plasma FVIII levels' as covariates. The center had no statistically significant effect on clotting time. As expected, an increase in FVIII concentration level was shown to significantly reduce the clotting times (p<0.05). To further examine the standardization approach in controlling inter-site variability of ROTEM® data, two parameters, operator and instrument, were also evaluated. Comparison of the results obtained at the 10 clinical sites to a replicate analysis at a single site (8 runs at each FVIII level performed at the central site by a single operator on 4 model Delta instruments) indicated equivalent variability with an overall ANOVA p-value of 0.69 for CT (accounting for the correlation between ROTEM® data and FVIII level) and a similar comparability for CFR, MCF and alpha angle.

We conclude that the inter-site variability is not a significant factor in the ROTEM® study. Assuming the pre-analytical variables for the blood collection are also minimized in the standardized procedures, we expect that major differences in a subject's ROTEM® parameters will be a

Example 5

Figure 13:
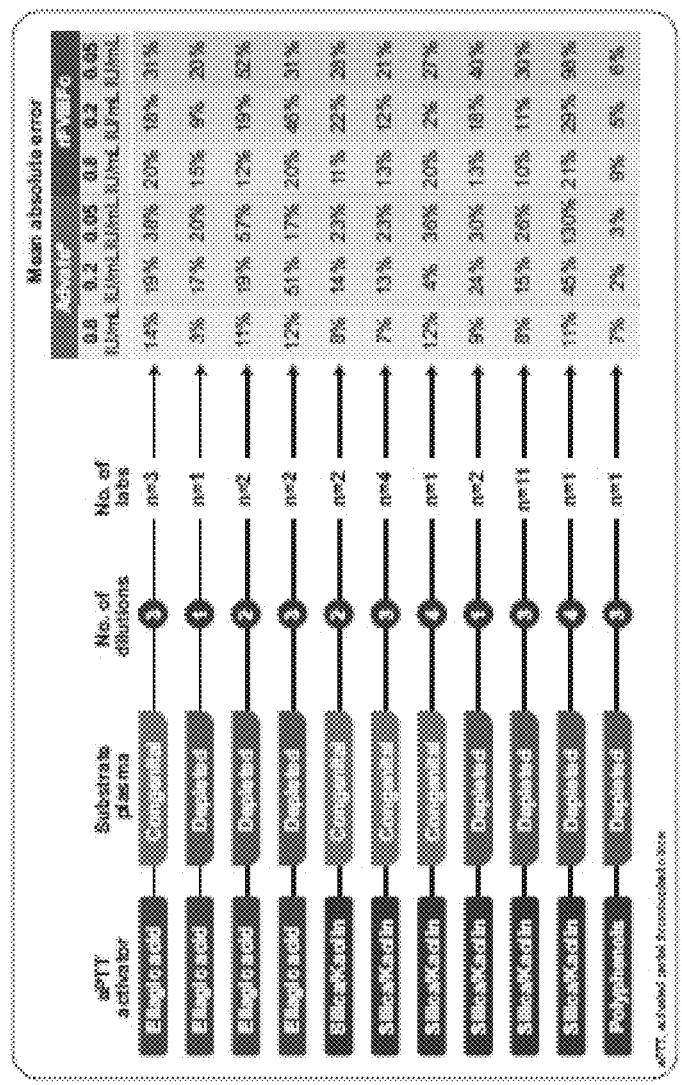
FIG. 13: one-stage assay reagents and critical steps in methodology employed by the 30 participating laboratories.

Comparative Field Study Evaluating the Activity of Recombinant Factor VIII-Fc Fusion Protein (rFVIIIFc) in Plasma Samples at Clinical Haemostasis Laboratories Congenital hemophilic plasma with no detectable FVIII activity was spiked with either ADVATE® or rFVIIIFc at nominal concentrations of 0.05 IU/mL, 0.2 IU/mL, or 0.8 IU/mL. Concentrations were based on the label potency for ADVATE® and rFVIIIFc drug product. Thirty participating clinical hemostasis laboratories in 7 countries received 3 sets of blinded samples to be tested on 3 separate days using their routine assays for measuring FVIII activity. Eleven labs also performed the chromogenic substrate assay for FVIII on an additional set of samples. Results were analyzed for intra-laboratory and inter-laboratory variation and any statistically significant correlations with particular assay reagents, standards, instrumentation, or methodology. FIG. 13 shows the array of one-stage assay reagents and critical steps in methodology employed by the 30 participating laboratories.

At 0.8 IU/mL, the mean recovery by the one-stage clotting assay in 30 clinical labs (90 test results per dose level) was 95% to 100% of expected for both ADVATE® and rFVIIIFc (FIG. 14). At 0.2 IU/mL, the average one-stage assay result was approximately 10% higher than expected for both products. This relative overestimation of FVIII activity increased to 20% at the 0.05-IU/mL level.

Intra-laboratory CVs for the one-stage assay (n=3 independent tests per level) were typically below 10% (FIG. 14). The overall assay performance was comparable for Advate® and rFVIIIFc. Inter-laboratory CV (comparing mean results from each lab) ranged from 10% to 16% at 0.8 IU/mL to over 30% at 0.05 IU/mL (FIG. 14), with some labs reporting over 2-fold higher or lower results compared with the consensus (FIG. 14).

Approximately normal distribution of results was seen for both products at each level. Normality tests (D'Agostino & Pearson, a=0.05) passed for ADVATE® at 0.8 and 0.2 IU/mL and for rFVIIIFc at 0.05 IU/mL. Laboratories that trended high (or low) for ADVATE® also reported correspondingly higher (or lower) than expected results for rFVIIIFc. This correlation was particularly significant at the 0.05-IU/mL level (P<0.05). Relative error in the estimated FVIII activity was not correlated with any obvious procedural or reagent differences (FIG. 13).

Eleven laboratories performed the FVIII chromogenic substrate assay. The average recovery by chromogenic FVIII activity was 107%±5% of label potency for ADVATE® across the 3 concentrations. For rFVIIIFc, the recovery by chromogenic activity was 124%±8% (FIG. 15).

The intra-laboratory CVs were generally lower for the chromogenic assay than for the one-stage assay, but the interlaboratory CVs were comparable between the 2 assays. Better dose linearity was observed for the chromogenic assay than for the one-stage clotting assay with no obvious overestimation at low FVIII levels by the chromogenic assay. The ratio of chromogenic to one-stage activity was somewhat higher for rFVIIIFc (range, 1.04-1.26) compared with ADVATE® (range, 0.86-1.12), which is likely due to the B-domain deleted nature of rFVIIIFc (FIG. 16).

Precision and accuracy were comparable for rFVIIIFc and ADVATE® using either the one-stage clotting assay or the chromogenic substrate assay in 30 and 11 clinical haemostasis labs, respectively. At low levels of ADVATE® or rFVIIIFc, most laboratories overestimated the activity in the one-stage clotting assay against the plasma reference standard. The ratio of chromogenic to one-stage activity was dependent on the factor level due to overestimation of the one-stage activity at low FVIII levels. The field study results show that rFVIIIFc can be monitored consistently among clinical hemostasis laboratories.

Sequence Tables

---

Sequence Table 1: Polynucleotide Sequences: FIX-Fc

A. B-Domain Deleted FVIIIF
(i) B-Domain Deleted FVIIIFc Chain DNA Sequence (FVIII signal peptide underlined, Fc region in bold) (SEQ ID NO: 1, which encodes SEQ ID NO: 2)

```
 661    A TGCAAATAGA GCTCTCCACC TGCTTCTTTC

721    TGTGCCTTTT GCGATTCTGC TTTAGTGCCA CCAGAAGATA CTACCTGGGT GCAGTGGAAC

781    TGTCATGGGA CTATATGCAA AGTGATCTCG GTGAGCTGCC TGTGGACGCA AGATTTCCTC

841    CTAGAGTGCC AAAATCTTTT CCATTCAACA CCTCAGTCGT GTACAAAAAG ACTCTGTTTG

901    TAGAATTCAC GGATCACCTT TTCAACATCG CTAAGCCAAG GCCACCCTGG ATGGGTCTGC

961    TAGGTCCTAC CATCCAGGCT GAGGTTTATG ATACAGTGGT CATTACACTT AAGAACATGG

1021    CTTCCCATCC TGTCAGTCTT CATGCTGTTG GTGTATCCTA CTGGAAAGCT TCTGAGGGAG

1081    CTGAATATGA TGATCAGACC AGTCAAAGGG AGAAAGAAGA TGATAAAGTC TTCCCTGGTG

1141    GAAGCCATAC ATATGTCTGG CAGGTCCTGA AAGAGAATGG TCCAATGGCC TCTGACCCAC

1201    TGTGCCTTAC CTACTCATAT CTTTCTCATG TGGACCTGGT AAAAGACTTG AATTCAGGCC

1261    TCATTGGAGC CCTACTAGTA TGTAGAGAAG GGAGTCTGGC CAAGGAAAAG ACACAGACCT

1321    TGCACAAATT TATACTACTT TTTGCTGTAT TTGATGAAGG GAAAAGTTGG CACTCAGAAA

1381    CAAAGAACTC CTTGATGCAG GATAGGGATG CTGCATCTGC TCGGGCCTGG CCTAAAATGC
```

Sequence Table 1: Polynucleotide Sequences: FIX-Fc

| | |
|---|---|
| 1441 | ACACAGTCAA TGGTTATGTA AACAGGTCTC TGCCAGGTCT GATTGGATGC CACAGGAAAT |
| 1501 | CAGTCTATTG GCATGTGATT GGAATGGGCA CCACTCCTGA AGTGCACTCA ATATTCCTCG |
| 1561 | AAGGTCACAC ATTTCTTGTG AGGAACCATC GCCAGGCGTC CTTGGAAATC TCGCCAATAA |
| 1621 | CTTTCCTTAC TGCTCAAACA CTCTTGATGG ACCTTGGACA GTTTCTACTG TTTTGTCATA |
| 1681 | TCTCTTCCCA CCAACATGAT GGCATGGAAG CTTATGTCAA AGTAGACAGC TGTCCAGAGG |
| 1741 | AACCCCAACT ACGAATGAAA ATAATGAAG AAGCGGAAGA CTATGATGAT GATCTTACTG |
| 1801 | ATTCTGAAAT GGATGTGGTC AGGTTTGATG ATGACAACTC TCCTTCCTTT ATCCAAATTC |
| 1861 | GCTCAGTTGC CAAGAAGCAT CCTAAAACTT GGGTACATTA CATTGCTGCT GAAGAGGAGG |
| 1921 | ACTGGGACTA TGCTCCCTTA GTCCTCGCCC CCGATGACAG AAGTTATAAA AGTCAATATT |
| 1981 | TGAACAATGG CCCTCAGCGG ATTGGTAGGA AGTACAAAAA AGTCCGATTT ATGGCATACA |
| 2041 | CAGATGAAAC CTTTAAGACT CGTGAAGCTA TTCAGCATGA ATCAGGAATC TTGGGACCTT |
| 2101 | TACTTTATGG GGAAGTTGGA GACACACTGT TGATTATATT TAAGAATCAA GCAAGCAGAC |
| 2161 | CATATAACAT CTACCCTCAC GGAATCACTG ATGTCCGTCC TTTGTATTCA AGGAGATTAC |
| 2221 | CAAAAGGTGT AAAACATTTG AAGGATTTTC CAATTCTGCC AGGAGAAATA TTCAAATATA |
| 2281 | AATGGACAGT GACTGTAGAA GATGGGCCAA CTAAATCAGA TCCTCGGTGC CTGACCCGCT |
| 2341 | ATTACTCTAG TTTCGTTAAT ATGGAGAGAG ATCTAGCTTC AGGACTCATT GGCCCTCTCC |
| 2401 | TCATCTGCTA CAAAGAATCT GTAGATCAAA GAGGAAACCA GATAATGTCA GACAAGAGGA |
| 2461 | ATGTCATCCT GTTTTCTGTA TTTGATGAGA ACCGAAGCTG GTACCTCACA GAGAATATAC |
| 2521 | AACGCTTTCT CCCCAATCCA GCTGGAGTGC AGCTTGAGGA TCCAGAGTTC CAAGCCTCCA |
| 2581 | ACATCATGCA CAGCATCAAT GGCTATGTTT TTGATAGTTT GCAGTTGTCA GTTTGTTTGC |
| 2641 | ATGAGGTGGC ATACTGGTAC ATTCTAAGCA TTGGAGCACA GACTGACTTC CTTTCTGTCT |
| 2701 | TCTTCTCTGG ATATACCTTC AAACACAAAA TGGTCTATGA AGACACACTC ACCCTATTCC |
| 2761 | CATTCTCAGG AGAAACTGTC TTCATGTCGA TGGAAAACCC AGGTCTATGG ATTCTGGGGT |
| 2821 | GCCACAACTC AGACTTTCGG AACAGAGGCA TGACCGCCTT ACTGAAGGTT TCTAGTTGTG |
| 2881 | ACAAGAACAC TGGTGATTAT TACGAGGACA GTTATGAAGA TATTTCAGCA TACTTGCTGA |
| 2941 | GTAAAAACAA TGCCATTGAA CCAAGAAGCT TCTCTCAAAA CCCACCAGTC TTGAAACGCC |
| 3001 | ATCAACGGGA ATAACTCGT ACTACTCTTC AGTCAGATCA AGAGGAAATT GACTATGATG |
| 3061 | ATACCATATC AGTTGAAATG AAGAAGGAAG ATTTTGACAT TTATGATGAG GATGAAAATC |
| 3121 | AGAGCCCCCG CAGCTTTCAA AAGAAAACAC GACACTATTT TATTGCTGCA GTGGAGAGGC |
| 3181 | TCTGGGATTA TGGGATGAGT AGCTCCCCAC ATGTTCTAAG AAACAGGGCT CAGAGTGGCA |
| 3241 | GTGTCCCTCA GTTCAAGAAA GTTGTTTTCC AGGAATTTAC TGATGGCTCC TTTACTCAGC |
| 3301 | CCTTATACCG TGGAGAACTA AATGAACATT TGGGACTCCT GGGGCCATAT ATAAGAGCAG |
| 3361 | AAGTTGAAGA TAATATCATG GTAACTTTCA GAAATCAGGC CTCTCGTCCC TATTCCTTCT |
| 3421 | ATTCTAGCCT TATTTCTTAT GAGGAAGATC AGAGGCAAGG AGCAGAACCT AGAAAAAACT |
| 3481 | TTGTCAAGCC TAATGAAACC AAAACTTACT TTTGGAAAGT GCAACATCAT ATGGCACCCA |
| 3541 | CTAAAGATGA GTTTGACTGC AAAGCCTGGG CTTATTTCTC TGATGTTGAC CTGGAAAAAG |
| 3601 | ATGTGCACTC AGGCCTGATT GGACCCCTTC TGGTCTGCCA CACTAACACA CTGAACCCTG |
| 3661 | CTCATGGGAG ACAAGTGACA GTACAGGAAT TTGCTCTGTT TTTCACCATC TTTGATGAGA |

| Sequence Table 1: Polynucleotide Sequences: FIX-Fc |  |  |  |  |
|---|---|---|---|---|
| 3721 | CCAAAAGCTG | GTACTTCACT | GAAAATATGG | AAAGAAACTG CAGGGCTCCC TGCAATATCC |
| 3781 | AGATGGAAGA | TCCCACTTTT | AAAGAGAATT | ATCGCTTCCA TGCAATCAAT GGCTACATAA |
| 3841 | TGGATACACT | ACCTGGCTTA | GTAATGGCTC | AGGATCAAAG GATTCGATGG TATCTGCTCA |
| 3901 | GCATGGGCAG | CAATGAAAAC | ATCCATTCTA | TTCATTTCAG TGGACATGTG TTCACTGTAC |
| 3961 | GAAAAAAGA | GGAGTATAAA | ATGGCACTGT | ACAATCTCTA TCCAGGTGTT TTTGAGACAG |
| 4021 | TGGAAATGTT | ACCATCCAAA | GCTGGAATTT | GGCGGGTGGA ATGCCTTATT GGCGAGCATC |
| 4081 | TACATGCTGG | GATGAGCACA | CTTTTTCTGG | TGTACAGCAA TAAGTGTCAG ACTCCCCTGG |
| 4141 | GAATGGCTTC | TGGACACATT | AGAGATTTTC | AGATTACAGC TTCAGGACAA TATGGACAGT |
| 4201 | GGGCCCCAAA | GCTGGCCAGA | CTTCATTATT | CCGGATCAAT CAATGCCTGG AGCACCAAGG |
| 4261 | AGCCCTTTTC | TTGGATCAAG | GTGGATCTGT | TGGCACCAAT GATTATTCAC GGCATCAAGA |
| 4321 | CCCAGGGTGC | CCGTCAGAAG | TTCTCCAGCC | TCTACATCTC TCAGTTTATC ATCATGTATA |
| 4381 | GTCTTGATGG | GAAGAAGTGG | CAGACTTATC | GAGGAAATTC CACTGGAACC TTAATGGTCT |
| 4441 | TCTTTGGCAA | TGTGGATTCA | TCTGGGATAA | ACACAATAT TTTTAACCCT CCAATTATTG |
| 4501 | CTCGATACAT | CCGTTTGCAC | CCAACTCATT | ATAGCATTCG CAGCACTCTT CGCATGGAGT |
| 4561 | TGATGGGCTG | TGATTTAAAT | AGTTGCAGCA | TGCCATTGGG AATGGAGAGT AAAGCAATAT |
| 4621 | CAGATGCACA | GATTACTGCT | TCATCCTACT | TTACCAATAT GTTTGCCACC TGGTCTCCTT |
| 4681 | CAAAAGCTCG | ACTTCACCTC | CAAGGGAGGA | GTAATGCCTG AGACCTCAG GTAATAATC |
| 4741 | CAAAAGAGTG | GCTGCAAGTG | GACTTCCAGA | AGACAATGAA AGTCACAGGA GTAACTACTC |
| 4801 | AGGGAGTAAA | ATCTCTGCTT | ACCAGCATGT | ATGTGAAGGA GTTCCTCATC TCCAGCAGTC |
| 4861 | AAGATGGCCA | TCAGTGGACT | CTCTTTTTC | AGAATGGCAA AGTAAAGGTT TTTCAGGGAA |
| 4921 | ATCAAGACTC | CTTCACACCT | GTGGTGAACT | CTCTAGACCC ACCGTTACTG ACTCGCTACC |
| 4981 | TTCGAATTCA | CCCCCAGAGT | TGGGTGCACC | AGATTGCCCT GAGGATGGAG GTTCTGGGCT |
| 5041 | GCGAGGCACA | GGACCTCTAC | GACAAAACTC ACACATGCCC ACCGTGCCCA GCTCCAGAAC |
| 5101 | TCCTGGGCGG | ACCGTCAGTC | TTCCTCTTCC | CCCCAAAACC CAAGGACACC CTCATGATCT |
| 5161 | CCCGGACCCC | TGAGGTCACA | TGCGTGGTGG | TGGACGTGAG CCACGAAGAC CCTGAGGTCA |
| 5221 | AGTTCAACTG | GTACGTGGAC | GGCGTGGAGG | TGCATAATGC CAAGACAAAG CCGCGGGAGG |
| 5281 | AGCAGTACAA | CAGCACGTAC | CGTGTGGTCA | GCGTCCTCAC CGTCCTGCAC CAGGACTGGC |
| 5341 | TGAATGGCAA | GGAGTACAAG | TGCAAGGTCT | CCAACAAAGC CCTCCCAGCC CCCATCGAGA |
| 5401 | AAACCATCTC | CAAAGCCAAA | GGGCAGCCCC | GAGAACCACA GGTGTACACC CTGCCCCCAT |
| 5461 | CCCGGGATGA | GCTGACCAAG | AACCAGGTCA | GCCTGACCTG CCTGGTCAAA GGCTTCTATC |
| 5521 | CCAGCGACAT | CGCCGTGGAG | TGGGAGAGCA | ATGGGCAGCC GGAGAACAAC TACAAGACCA |
| 5581 | CGCCTCCCGT | GTTGGACTCC | GACGGCTCCT | TCTTCCTCTA CAGCAAGCTC ACCGTGGACA |
| 5641 | AGAGCAGGTG | GCAGCAGGGG | AACGTCTTCT | CATGCTCCGT GATGCATGAG GCTCTGCACA |
| 5701 | ACCACTACAC | GCAGAAGAGC | CTCTCCCTGT | CTCCGGGTAA A |

(ii) Fc DNA sequence (mouse Igκ signal peptide underlined) (SEQ ID NO: 3, which encodes SEQ ID NO: 4)

| 7981 | <u>ATGGA GACAGACACA</u> |
|---|---|
| 8041 | <u>CTCCTGCTAT GGGTACTGCT GCTCTGGGTT CCAGGTTCCA CTGGTGACAA</u> AACTCACACA |
| 8101 | TGCCCACCGT GCCCAGCACC TGAACTCCTG GGAGGACCGT CAGTCTTCCT CTTCCCCCCA |
| 8161 | AAACCCAAGG ACACCCTCAT GATCTCCCGG ACCCCTGAGG TCACATGCGT GGTGGTGGAC |

Sequence Table 1: Polynucleotide Sequences: FIX-Fc

| | |
|---|---|
| 8221 | GTGAGCCACG AAGACCCTGA GGTCAAGTTC AACTGGTACG TGGACGGCGT GGAGGTGCAT |
| 8281 | AATGCCAAGA CAAAGCCGCG GGAGGAGCAG TACAACAGCA CGTACCGTGT GGTCAGCGTC |
| 8341 | CTCACCGTCC TGCACCAGGA CTGGCTGAAT GGCAAGGAGT ACAAGTGCAA GGTCTCCAAC |
| 8401 | AAAGCCCTCC CAGCCCCCAT CGAGAAAACC ATCTCCAAAG CCAAAGGGCA GCCCCGAGAA |
| 8461 | CCACAGGTGT ACACCCTGCC CCCATCCCGC GATGAGCTGA CCAAGAACCA GGTCAGCCTG |
| 8521 | ACCTGCCTGG TCAAAGGCTT CTATCCCAGC GACATCGCCG TGGAGTGGGA GAGCAATGGG |
| 8581 | CAGCCGGAGA ACAACTACAA GACCACGCCT CCCGTGTTGG ACTCCGACGG CTCCTTCTTC |
| 8641 | CTCTACAGCA AGCTCACCGT GGACAAGAGC AGGTGGCAGC AGGGGAACGT CTTCTCATGC |
| 8701 | TCCGTGATGC ATGAGGCTCT GCACAACCAC TACACGCAGA AGAGCCTCTC CCTGTCTCCG |
| 8761 | GGTAAA |

B. Full Length FVIIIFc
(i) Full Length FVIIIFc DNA Sequence (FVIII signal peptide underlined, Fc region in bold) (SEQ ID NO: 5, which encodes SEQ ID NO: 6)

| | |
|---|---|
| 661 | ATG CAAATAGAGC TCTCCACCTG |
| 721 | <u>CTTCTTTCTG TGCCTTTTGC GATTCTGCTT TAGT</u>GCCACC AGAAGATACT ACCTGGGTGC |
| 781 | AGTGGAACTG TCATGGGACT ATATGCAAAG TGATCTCGGT GAGCTGCCTG TGGACGCAAG |
| 841 | ATTTCCTCCT AGAGTGCCAA AATCTTTTCC ATTCAACACC TCAGTCGTGT ACAAAAAGAC |
| 901 | TCTGTTTGTA GAATTCACGG ATCACCTTTT CAACATCGCT AAGCCAAGGC CACCCTGGAT |
| 961 | GGGTCTGCTA GGTCCTACCA TCCAGGCTGA GGTTTATGAT ACAGTGGTCA TTACACTTAA |
| 1021 | GAACATGGCT TCCCATCCTG TCAGTCTTCA TGCTGTTGGT GTATCCTACT GGAAAGCTTC |
| 1081 | TGAGGGAGCT GAATATGATG ATCAGACCAG TCAAAGGGAG AAAGAAGATG ATAAAGTCTT |
| 1141 | CCCTGGTGGA AGCCATACAT ATGTCTGGCA GGTCCTGAAA GAGAATGGTC CAATGGCCTC |
| 1201 | TGACCCACTG TGCCTTACCT ACTCATATCT TTCTCATGTG GACCTGGTAA AAGACTTGAA |
| 1261 | TTCAGGCCTC ATTGGAGCCC TACTAGTATG TAGAGAAGGG AGTCTGGCCA GGAAAAGAC |
| 1321 | ACAGACCTTG CACAAATTTA TACTACTTTT TGCTGTATTT GATGAAGGGA AAAGTTGGCA |
| 1381 | CTCAGAAACA AAGAACTCCT TGATGCAGGA TAGGGATGCT GCATCTGCTC GGGCCTGGCC |
| 1441 | TAAAATGCAC ACAGTCAATG GTTATGTAAA CAGGTCTCTG CCAGGTCTGA TTGGATGCCA |
| 1501 | CAGGAAATCA GTCTATTGGC ATGTGATTGG AATGGGCACC ACTCCTGAAG TGCACTCAAT |
| 1561 | ATTCCTCGAA GGTCACACAT TTCTTGTGAG GAACCATCGC CAGGCGTCCT TGGAAATCTC |
| 1621 | GCCAATAACT TTCCTTACTG CTCAAACACT CTTGATGGAC CTTGGACAGT TTCTACTGTT |
| 1681 | TTGTCATATC TCTTCCCACC AACATGATGG CATGGAAGCT TATGTCAAAG TAGACAGCTG |
| 1741 | TCCAGAGGAA CCCCAACTAC GAATGAAAAA TAATGAAGAA GCGGAAGACT ATGATGATGA |
| 1801 | TCTTACTGAT TCTGAAATGG ATGTGGTCAG GTTTGATGAT GACAACTCTC CTTCCTTTAT |
| 1861 | CCAAATTCGC TCAGTTGCCA AGAAGCATCC TAAAACTTGG GTACATTACA TTGCTGCTGA |
| 1921 | AGAGGAGGAC TGGGACTATG CTCCCTTAGT CCTCGCCCCC GATGACAGAA GTTATAAAAG |
| 1981 | TCAATATTTG AACAATGGCC CTCAGCGGAT TGGTAGGAAG TACAAAAAAG TCCGATTTAT |
| 2041 | GGCATACACA GATGAAACCT TTAAGACTCG TGAAGCTATT CAGCATGAAT CAGGAATCTT |
| 2101 | GGGACCTTTA CTTTATGGGG AAGTTGGAGA CACACTGTTG ATTATATTTA AGAATCAAGC |
| 2161 | AAGCAGACCA TATAACATCT ACCCTCACGG AATCACTGAT GTCCGTCCTT TGTATTCAAG |
| 2221 | GAGATTACCA AAAGGTGTAA ACATTTGAA GGATTTTCCA ATTCTGCCAG GAGAAATATT |

| Sequence Table 1: Polynucleotide Sequences: FIX-Fc |
| --- |
| 2281 CAAATATAAA TGGACAGTGA CTGTAGAAGA TGGGCCAACT AAATCAGATC CTCGGTGCCT |
| 2341 GACCCGCTAT TACTCTAGTT TCGTTAATAT GGAGAGAGAT CTAGCTTCAG GACTCATTGG |
| 2401 CCCTCTCCTC ATCTGCTACA AAGAATCTGT AGATCAAAGA GGAAACCAGA TAATGTCAGA |
| 2461 CAAGAGGAAT GTCATCCTGT TTTCTGTATT TGATGAGAAC CGAAGCTGGT ACCTCACAGA |
| 2521 GAATATACAA CGCTTTCTCC CCAATCCAGC TGGAGTGCAG CTTGAGGATC CAGAGTTCCA |
| 2581 AGCCTCCAAC ATCATGCACA GCATCAATGG CTATGTTTTT GATAGTTTGC AGTTGTCAGT |
| 2641 TTGTTTGCAT GAGGTGGCAT ACTGGTACAT TCTAAGCATT GGAGCACAGA CTGACTTCCT |
| 2701 TTCTGTCTTC TTCTCTGGAT ATACCTTCAA ACACAAAATG GTCTATGAAG ACACACTCAC |
| 2761 CCTATTCCCA TTCTCAGGAG AAACTGTCTT CATGTCGATG GAAAACCCAG GTCTATGGAT |
| 2821 TCTGGGGTGC CACAACTCAG ACTTTCGGAA CAGAGGCATG ACCGCCTTAC TGAAGGTTTC |
| 2881 TAGTTGTGAC AAGAACACTG GTGATTATTA CGAGGACAGT TATGAAGATA TTTCAGCATA |
| 2941 CTTGCTGAGT AAAAACAATG CCATTGAACC AAGAAGCTTC TCCCAGAATT CAAGACACCC |
| 3001 TAGCACTAGG CAAAAGCAAT TTAATGCCAC CACAATTCCA GAAAATGACA TAGAGAAGAC |
| 3061 TGACCCTTGG TTTGCACACA GAACACCTAT GCCTAAAATA CAAAATGTCT CCTCTAGTGA |
| 3121 TTTGTTGATG CTCTTGCGAC AGAGTCCTAC TCCACATGGG CTATCCTTAT CTGATCTCCA |
| 3181 AGAAGCCAAA TATGAGACTT TTTCTGATGA TCCATCACCT GGAGCAATAG ACAGTAATAA |
| 3241 CAGCCTGTCT GAAATGACAC ACTTCAGGCC ACAGCTCCAT ACAGTGGGG CATGGTATT |
| 3301 TACCCCTGAG TCAGGCCTCC AATTAAGATT AAATGAGAAA CTGGGGACAA CTGCAGCAAC |
| 3361 AGAGTTGAAG AAACTTGATT TCAAAGTTTC TAGTACATCA AATAATCTGA TTTCAACAAT |
| 3421 TCCATCAGAC AATTTGGCAG CAGGTACTGA TAATACAAGT TCCTTAGGAC CCCCAAGTAT |
| 3481 GCCAGTTCAT TATGATAGTC AATTAGATAC CACTCTATTT GGCAAAAAGT CATCTCCCCT |
| 3541 TACTGAGTCT GGTGGACCTC TGAGCTTGAG TGAAGAAAAT AATGATTCAA AGTTGTTAGA |
| 3601 ATCAGGTTTA ATGAATAGCC AAGAAAGTTC ATGGGGAAAA AATGTATCGT CAACAGAGAG |
| 3661 TGGTAGGTTA TTTAAAGGGA AAAGAGCTCA TGGACCTGCT TGTTGACTA AAGATAATGC |
| 3721 CTTATTCAAA GTTAGCATCT CTTTGTTAAA GACAAACAAA ACTTCCAATA ATTCAGCAAC |
| 3781 TAATAGAAAG ACTCACATTG ATGGCCCATC ATTATTAATT GAGAATAGTC CATCAGTCTG |
| 3841 GCAAAATATA TTAGAAAGTG ACACTGAGTT TAAAAAAGTG ACACCTTTGA TTCATGACAG |
| 3901 AATGCTTATG GACAAAAATG CTACAGCTTT GAGGCTAAAT CATATGTCAA ATAAAACTAC |
| 3961 TTCATCAAAA AACATGGAAA TGGTCCAACA GAAAAAAGAG GGCCCCATTC CACCAGATGC |
| 4021 ACAAAATCCA GATATGTCGT TCTTTAAGAT GCTATTCTTG CCAGAATCAG CAAGGTGGAT |
| 4081 ACAAAGGACT CATGGAAAGA ACTCTCTGAA CTCTGGGCAA GGCCCCAGTC CAAAGCAATT |
| 4141 AGTATCCTTA GGACCAGAAA AATCTGTGGA AGGTCAGAAT TTCTTGTCTG AGAAAAACAA |
| 4201 AGTGGTAGTA GGAAGGGTG AATTTACAAA GGACGTAGGA CTCAAAGAGA TGGTTTTTCC |
| 4261 AAGCAGCAGA AACCTATTTC TTACTAACTT GGATAATTTA CATGAAAATA ATACACACAA |
| 4321 TCAAGAAAAA AAAATTCAGG AAGAAATAGA AAAGAAGGAA ACATTAATCC AAGAGAATGT |
| 4381 AGTTTTGCCT CAGATACATA CAGTGACTGG CACTAAGAAT TTCATGAAGA ACCTTTTCTT |
| 4441 ACTGAGCACT AGGCAAAATG TAGAAGGTTC ATATGACGGG GCATATGCTC CAGTACTTCA |
| 4501 AGATTTTAGG TCATTAAATG ATTCAACAAA TAGAACAAAG AAACACACAG CTCATTTCTC |

| Sequence Table 1: Polynucleotide Sequences: FIX-Fc | | | | |
|---|---|---|---|---|
| 4561 | AAAAAAAGGG | GAGGAAGAAA | ACTTGGAAGG | CTTGGGAAAT | CAAACCAAGC | AAATTGTAGA |
| 4621 | GAAATATGCA | TGCACCACAA | GGATATCTCC | TAATACAAGC | CAGCAGAATT | TTGTCACGCA |
| 4681 | ACGTAGTAAG | AGAGCTTTGA | AACAATTCAG | ACTCCCACTA | GAAGAAACAG | AACTTGAAAA |
| 4741 | AAGGATAATT | GTGGATGACA | CCTCAACCCA | GTGGTCCAAA | AACATGAAAC | ATTTGACCCC |
| 4801 | GAGCACCCTC | ACACAGATAG | ACTACAATGA | GAAGGAGAAA | GGGGCCATTA | CTCAGTCTCC |
| 4861 | CTTATCAGAT | TGCCTTACGA | GGAGTCATAG | CATCCCTCAA | GCAAATAGAT | CTCCATTACC |
| 4921 | CATTGCAAAG | GTATCATCAT | TTCCATCTAT | TAGACCTATA | TATCTGACCA | GGGTCCTATT |
| 4981 | CCAAGACAAC | TCTTCTCATC | TTCCAGCAGC | ATCTTATAGA | AGAAAGATT | CTGGGGTCCA |
| 5041 | AGAAAGCAGT | CATTTCTTAC | AAGGAGCCAA | AAAAATAAC | CTTTCTTTAG | CCATTCTAAC |
| 5101 | CTTGGAGATG | ACTGGTGATC | AAAGAGAGGT | TGGCTCCCTG | GGACAAGTG | CCACAAATTC |
| 5161 | AGTCACATAC | AAGAAAGTTG | AGAACACTGT | TCTCCCGAAA | CCAGACTTGC | CAAAACATC |
| 5221 | TGGCAAAGTT | GAATTGCTTC | CAAAAGTTCA | CATTTATCAG | AAGGACCTAT | TCCCTACGGA |
| 5281 | AACTAGCAAT | GGGTCTCCTG | GCCATCTGGA | TCTCGTGGAA | GGGAGCCTTC | TTCAGGGAAC |
| 5341 | AGAGGGAGCG | ATTAAGTGGA | ATGAAGCAAA | CAGACCTGGA | AAAGTTCCCT | TTCTGAGAGT |
| 5401 | AGCAACAGAA | AGCTCTGCAA | AGACTCCCTC | CAAGCTATTG | GATCCTCTTG | CTTGGGATAA |
| 5461 | CCACTATGGT | ACTCAGATAC | CAAAAGAAGA | GTGGAAATCC | CAAGAGAAGT | CACCAGAAAA |
| 5521 | AACAGCTTTT | AAGAAAAAGG | ATACCATTTT | GTCCCTGAAC | GCTTGTGAAA | GCAATCATGC |
| 5581 | AATAGCAGCA | ATAAATGAGG | GACAAAATAA | GCCCGAAATA | GAAGTCACCT | GGGCAAAGCA |
| 5641 | AGGTAGGACT | GAAAGGCTGT | GCTCTCAAAA | CCCACCAGTC | TTGAAACGCC | ATCAACGGGA |
| 5701 | AATAACTCGT | ACTACTCTTC | AGTCAGATCA | AGAGGAAATT | GACTATGATG | ATACCATATC |
| 5761 | AGTTGAAATG | AAGAAGGAAG | ATTTTGACAT | TTATGATGAG | GATGAAAATC | AGAGCCCCCG |
| 5821 | CAGCTTTCAA | AAGAAAACAC | GACACTATTT | TATTGCTGCA | GTGGAGAGGC | TCTGGGATTA |
| 5881 | TGGGATGAGT | AGCTCCCCAC | ATGTTCTAAG | AAACAGGGCT | CAGAGTGGCA | GTGTCCCTCA |
| 5941 | GTTCAAGAAA | GTTGTTTTCC | AGGAATTTAC | TGATGGCTCC | TTTACTCAGC | CCTTATACCG |
| 5001 | TGGAGAACTA | AATGAACATT | TGGGACTCCT | GGGGCCATAT | ATAAGAGCAG | AAGTTGAAGA |
| 6061 | TAATATCATG | GTAACTTTCA | GAAATCAGGC | CTCTCGTCCC | TATTCCTTCT | ATTCTAGCCT |
| 6121 | TATTTCTTAT | GAGGAAGATC | AGAGGCAAGG | AGCAGAACCT | AGAAAAAACT | TTGTCAAGCC |
| 6181 | TAATGAAACC | AAAACTTACT | TTTGGAAAGT | GCAACATCAT | ATGGCACCCA | CTAAAGATGA |
| 6241 | GTTTGACTGC | AAAGCCTGGG | CTTATTTCTC | TGATGTTGAC | CTGGAAAAAG | ATGTGCACTC |
| 6301 | AGGCCTGATT | GGACCCCTTC | TGGTCTGCCA | CACTAACACA | CTGAACCCTG | CTCATGGGAG |
| 6361 | ACAAGTGACA | GTACAGGAAT | TTGCTCTGTT | TTTCACCATC | TTTGATGAGA | CCAAAAGCTG |
| 6421 | GTACTTCACT | GAAAATATGG | AAAGAAACTG | CAGGGCTCCC | TGCAATATCC | AGATGGAAGA |
| 6481 | TCCCACTTTT | AAAGAGAATT | ATCGCTTCCA | TGCAATCAAT | GGCTACATAA | TGGATACACT |
| 6541 | ACCTGGCTTA | GTAATGGCTC | AGGATCAAAG | GATTCGATGG | TATCTGCTCA | GCATGGGCAG |
| 6601 | CAATGAAAAC | ATCCATTCTA | TTCATTTCAG | TGGACATGTG | TTCACTGTAC | GAAAAAAAGA |
| 6661 | GGAGTATAAA | ATGGCACTGT | ACAATCTCTA | TCCAGGTGTT | TTTGAGACAG | TGGAAATGTT |
| 6721 | ACCATCCAAA | GCTGGAATTT | GGCGGGTGGA | ATGCCTTATT | GGCGAGCATC | TACATGCTGG |
| 6781 | GATGAGCACA | CTTTTTCTGG | TGTACAGCAA | TAAGTGTCAG | ACTCCCCTGG | GAATGGCTTC |
| 6841 | TGGACACATT | AGAGATTTTC | AGATTACAGC | TTCAGGACAA | TATGGACAGT | GGGCCCCAAA |

| Sequence Table 1: Polynucleotide Sequences: FIX-Fc |
| --- |
| 6901 GCTGGCCAGA CTTCATTATT CCGGATCAAT CAATGCCTGG AGCACCAAGG AGCCCTTTTC |
| 6961 TTGGATCAAG GTGGATCTGT TGGCACCAAT GATTATTCAC GGCATCAAGA CCCAGGGTGC |
| 7021 CCGTCAGAAG TTCTCCAGCC TCTACATCTC TCAGTTTATC ATCATGTATA GTCTTGATGG |
| 7081 GAAGAAGTGG CAGACTTATC GAGGAAATTC CACTGGAACC TTAATGGTCT TCTTTGGCAA |
| 7141 TGTGGATTCA TCTGGGATAA AACACAATAT TTTTAACCCT CCAATTATTG CTCGATACAT |
| 7201 CCGTTTGCAC CCAACTCATT ATAGCATTCG CAGCACTCTT CGCATGGAGT TGATGGGCTG |
| 7261 TGATTTAAAT AGTTGCAGCA TGCCATTGGG AATGGAGAGT AAAGCAATAT CAGATGCACA |
| 7321 GATTACTGCT TCATCCTACT TTACCAATAT GTTTGCCACC TGGTCTCCTT CAAAAGCTCG |
| 7381 ACTTCACCTC CAAGGGAGGA GTAATGCCTG GAGACCTCAG GTGAATAATC CAAAAGAGTG |
| 7441 GCTGCAAGTG ACTTCCAGA AGACAATGAA AGTCACAGGA GTAACTACTC AGGGAGTAAA |
| 7501 ATCTCTGCTT ACCAGCATGT ATGTGAAGGA GTTCCTCATC TCCAGCAGTC AAGATGGCCA |
| 7561 TCAGTGGACT CTCTTTTTTC AGAATGGCAA AGTAAAGGTT TTTCAGGGAA ATCAAGACTC |
| 7621 CTTCACACCT GTGGTGAACT CTCTAGACCC ACCGTTACTG ACTCGCTACC TTCGAATTCA |
| 7681 CCCCCAGAGT TGGGTGCACC AGATTGCCCT GAGGATGGAG GTTCTGGGCT GCGAGGCACA |
| 7741 GGACCTCTAC GACAAAACTC ACACATGCCC ACCGTGCCCA GCTCCAGAAC TCCTGGGCGG |
| 7801 ACCGTCAGTC TTCCTCTTCC CCCCAAAACC CAAGGACACC CTCATGATCT CCCGGACCCC |
| 7861 TGAGGTCACA TGCGTGGTGG TGGACGTGAG CCACGAAGAC CCTGAGGTCA AGTTCAACTG |
| 7921 GTACGTGGAC GGCGTGGAGG TGCATAATGC CAAGACAAAG CCGCGGGAGG AGCAGTACAA |
| 7981 CAGCACGTAC CGTGTGGTCA GCGTCCTCAC CGTCCTGCAC CAGGACTGGC TGAATGGCAA |
| 8041 GGAGTACAAG TGCAAGGTCT CCAACAAAGC CCTCCCAGCC CCCATCGAGA AAACCATCTC |
| 8101 CAAAGCCAAA GGGCAGCCCC GAGAACCACA GGTGTACACC CTGCCCCCAT CCCGGGATGA |
| 8161 GCTGACCAAG AACCAGGTCA GCCTGACCTG CCTGGTCAAA GGCTTCTATC CCAGCGACAT |
| 8221 CGCCGTGGAG TGGGAGAGCA ATGGGCAGCC GGAGAACAAC TACAAGACCA CGCCTCCCGT |
| 8281 GTTGGACTCC GACGGCTCCT TCTTCCTCTA CAGCAAGCTC ACCGTGGACA AGAGCAGGTG |
| 8341 GCAGCAGGGG AACGTCTTCT CATGCTCCGT GATGCATGAG GCTCTGCACA ACCACTACAC |
| 8401 GCAGAAGAGC CTCTCCCTGT CTCCGGGTAA A |

C.
(i) Heavy Chain (HC)-Fc DNA sequence (no linker between HC and Fc) (signal peptide underlined, Fc region in bold) (SEQ ID NO: 7, which encodes SEQ ID NO: 8)

| | |
| --- | --- |
| 1 | <u>ATGCAAATAG AGCTCTCCAC CTGCTTCTTT CTGTGCCTTT TGCGATTCTG CTTTAGTGCC</u> |
| 61 | ACCAGAAGAT ACTACCTGGG TGCAGTGGAA CTGTCATGGG ACTATATGCA AAGTGATCTC |
| 121 | GGTGAGCTGC CTGTGGACGC AAGATTTCCT CCTAGAGTGC AAAATCTTT TCCATTCAAC |
| 181 | ACCTCAGTCG TGTACAAAAA GACTCTGTTT GTAGAATTCA CGGATCACCT TTTCAACATC |
| 241 | GCTAAGCCAA GGCCACCCTG GATGGGTCTG CTAGGTCCTA CCATCCAGGC TGAGGTTTAT |
| 301 | GATACAGTGG TCATTACACT TAAGAACATG GCTTCCCATC CTGTCAGTCT TCATGCTGTT |
| 361 | GGTGTATCCT ACTGGAAAGC TTCTGAGGGA GCTGAATATG ATGATCAGAC CAGTCAAAGG |
| 421 | GAGAAAGAAG ATGATAAAGT CTTCCCTGGT GGAAGCCATA CATATGTCTG GCAGGTCCTG |
| 481 | AAAGAGAATG GTCCAATGGC CTCTGACCCA CTGTGCCTTA CCTACTCATA TCTTTCTCAT |
| 541 | GTGGACCTGG TAAAAGACTT GAATTCAGGC CTCATTGGAG CCCTACTAGT ATGTAGAGAA |

| Sequence Table 1: Polynucleotide Sequences: FIX-Fc |
|---|
| 601  GGGAGTCTGG CCAAGGAAAA GACACAGACC TTGCACAAAT TTATACTACT TTTTGCTGTA |
| 661  TTTGATGAAG GGAAAAGTTG GCACTCAGAA ACAAAGAACT CCTTGATGCA GGATAGGGAT |
| 721  GCTGCATCTG CTCGGGCCTG GCCTAAAATG CACACAGTCA ATGGTTATGT AAACAGGTCT |
| 781  CTGCCAGGTC TGATTGGATG CCACAGGAAA TCAGTCTATT GGCATGTGAT TGGAATGGGC |
| 841  ACCACTCCTG AAGTGCACTC AATATTCCTC GAAGGTCACA CATTTCTTGT GAGGAACCAT |
| 901  CGCCAGGCGT CCTTGGAAAT CTCGCCAATA ACTTTCCTTA CTGCTCAAAC ACTCTTGATG |
| 961  GACCTTGGAC AGTTTCTACT GTTTTGTCAT ATCTCTTCCC ACCAACATGA TGGCATGGAA |
| 1021 GCTTATGTCA AAGTAGACAG CTGTCCAGAG AACCCCAAC TACGAATGAA AAATAATGAA |
| 1081 GAAGCGGAAG ACTATGATGA TGATCTTACT GATTCTGAAA TGGATGTGGT CAGGTTTGAT |
| 1141 GATGACAACT CTCCTTCCTT TATCCAAATT CGCTCAGTTG CCAAGAAGCA TCCTAAAACT |
| 1201 TGGGTACATT ACATTGCTGC TGAAGAGGAG GACTGGGACT ATGCTCCCTT AGTCCTCGCC |
| 1261 CCCGATGACA GAAGTTATAA AAGTCAATAT TTGAACAATG GCCCTCAGCA GATTGGTAGG |
| 1321 AAGTACAAAA AAGTCCGATT TATGGCATAC ACAGATGAAA CCTTTAAGAC TCGTGAAGCT |
| 1381 ATTCAGCATG AATCAGGAAT CTTGGGACCT TTACTTTATG GGGAAGTTGG AGACACACTG |
| 1441 TTGATTATAT TTAAGAATCA AGCAAGCAGA CCATATAACA TCTACCCTCA CGGAATCACT |
| 1501 GATGTCCGTC CTTTGTATTC AAGGAGATTA CCAAAAGGTG TAAAACATTT GAAGGATTTT |
| 1561 CCAATTCTGC CAGGAGAAAT ATTCAAATAT AAATGGACAG TGACTGTAGA AGATGGGCCA |
| 1621 ACTAAATCAG ATCCTCGGTG CCTGACCCGC TATTACTCTA GTTTCGTTAA TATGGAGAGA |
| 1681 GATCTAGCTT CAGGACTCAT TGGCCCTCTC CTCATCTGCT ACAAAGAATC TGTAGATCAA |
| 1741 AGAGGAAACC AGATAATGTC AGACAAGAGG AATGTCATCC TGTTTTCTGT ATTTGATGAG |
| 1801 AACCGAAGCT GGTACCTCAC AGAGAATATA CAACGCTTTC TCCCCAATCC AGCTGGAGTG |
| 1861 CAGCTTGAGG ATCCAGAGTT CCAAGCCTCC AACATCATGC ACAGCATCAA TGGCTATGTT |
| 1921 TTTGATAGTT TGCAGTTGTC AGTTTGTTTG CATGAGGTGG CATACTGGTA CATTCTAAGC |
| 1981 ATTGGAGCAC AGACTGACTT CCTTTCTGTC TTCTTCTCTG GATATACCTT CAAACACAAA |
| 2041 ATGGTCTATG AAGACACACT CACCCTATTC CCATTCTCAG GAGAAACTGT CTTCATGTCG |
| 2101 ATGGAAAACC CAGGTCTATG GATTCTGGGG TGCCACAACT CAGACTTTCG GAACAGAGGC |
| 2161 ATGACCGCCT TACTGAAGGT TTCTAGTTGT GACAAGAACA CTGGTGATTA TTACGAGGAC |
| 2221 AGTTATGAAG ATATTTCAGC ATACTTGCTG AGTAAAAACA ATGCCATTGA ACCAAGAGAC |
| 2281 AAAACTCACA CATGCCCACC GTGCCCAGCT CCAGAACTCC TGGGCGGACC GTCAGTCTTC |
| 2341 CTCTTCCCCC CAAAACCCAA GGACACCCTC ATGATCTCCC GGACCCCTGA GGTCACATGC |
| 2401 GTGGTGGTGG ACGTGAGCCA CGAAGACCCT GAGGTCAAGT TCAACTGGTA CGTGGACGGC |
| 2461 GTGGAGGTGC ATAATGCCAA GACAAAGCCG CGGGAGGAGC AGTACAACAG CACGTACCGT |
| 2521 GTGGTCAGCG TCCTCACCGT CCTGCACCAG GACTGGCTGA ATGGCAAGGA GTACAAGTGC |
| 2581 AAGGTCTCCA ACAAAGCCCT CCCAGCCCCC ATCGAGAAAA CCATCTCCAA AGCCAAAGGG |
| 2641 CAGCCCCGAG AACCACAGGT GTACACCCTG CCCCCATCCC GGGATGAGCT GACCAAGAAC |
| 2701 CAGGTCAGCC TGACCTGCCT GGTCAAAGGC TTCTATCCCA GCGACATCGC CGTGGAGTGG |
| 2761 GAGAGCAATG GGCAGCCGGA GAACAACTAC AAGACCACGC CTCCCGTGTT GGACTCCGAC |

Sequence Table 1: Polynucleotide Sequences: FIX-Fc

2821 GGCTCCTTCT TCCTCTACAG CAAGCTCACC GTGGACAAGA GCAGGTGGCA GCAGGGGAAC

2881 GTCTTCTCAT GCTCCGTGAT GCATGAGGCT CTGCACAACC ACTACACGCA GAAGAGCCTC

2941 TCCCTGTCTC CGGGTAAA

C.
(ii) Heavy Chain (HC)-Fc DNA sequence (5 amino acid linker between HC and Fc) (signal peptide underlined. Fc region in bold, 5 amino acid linker is double-underlined) (SEQ ID NO: 9, which encodes SEQ ID NO: 10)

```
   1   ATGCAAATAG AGCTCTCCAC CTGCTTCTTT CTGTGCCTTT TGCGATTCTG CTTTAGTGCC

61   ACCAGAAGAT ACTACCTGGG TGCAGTGGAA CTGTCATGGG ACTATATGCA AAGTGATCTC

121   GGTGAGCTGC CTGTGGACGC AAGATTTCCT CCTAGAGTGC AAAATCTTT TCCATTCAAC

181   ACCTCAGTCG TGTACAAAAA GACTCTGTTT GTAGAATTCA CGGATCACCT TTTCAACATC

241   GCTAAGCCAA GGCCACCCTG GATGGGTCTG CTAGGTCCTA CCATCCAGGC TGAGGTTTAT

301   GATACAGTGG TCATTACACT TAAGAACATG GCTTCCCATC CTGTCAGTCT TCATGCTGTT

361   GGTGTATCCT ACTGGAAAGC TTCTGAGGGA GCTGAATATG ATGATCAGAC CAGTCAAAGG

421   GAGAAAGAAG ATGATAAAGT CTTCCCTGGT GGAAGCCATA CATATGTCTG GCAGGTCCTG

481   AAAGAGAATG GTCCAATGGC CTCTGACCCA CTGTGCCTTA CCTACTCATA TCTTTCTCAT

541   GTGGACCTGG TAAAAGACTT GAATTCAGGC CTCATTGGAG CCCTACTAGT ATGTAGAGAA

601   GGGAGTCTGG CCAAGGAAAA GACACAGACC TTGCACAAAT TTATACTACT TTTTGCTGTA

661   TTTGATGAAG GGAAAAGTTG GCACTCAGAA ACAAAGAACT CCTTGATGCA GGATAGGGAT

721   GCTGCATCTG CTCGGGCCTG GCCTAAAATG CACACAGTCA ATGGTTATGT AAACAGGTCT

781   CTGCCAGGTC TGATTGGATG CCACAGGAAA TCAGTCTATT GGCATGTGAT TGGAATGGGC

841   ACCACTCCTG AAGTGCACTC AATATTCCTC GAAGGTCACA CATTTCTTGT GAGGAACCAT

901   CGCCAGGCGT CCTTGGAAAT CTCGCCAATA ACTTTCCTTA CTGCTCAAAC ACTCTTGATG

961   GACCTTGGAC AGTTTCTACT GTTTTGTCAT ATCTCTTCCC ACCAACATGA TGGCATGGAA

1021   GCTTATGTCA AAGTAGACAG CTGTCCAGAG GAACCCCAAC TACGAATGAA AAATAATGAA

1081   GAAGCGGAAG ACTATGATGA TGATCTTACT GATTCTGAAA TGGATGTGGT CAGGTTTGAT

1141   GATGACAACT CTCCTTCCTT TATCCAAATT CGCTCAGTTG CCAAGAAGCA TCCTAAAACT

1201   TGGGTACATT ACATTGCTGC TGAAGAGGAG GACTGGGACT ATGCTCCCTT AGTCCTCGCC

1261   CCCGATGACA GAAGTTATAA AAGTCAATAT TTGAACAATG GCCCTCAGCG GATTGGTAGG

1321   AAGTACAAAA AAGTCCGATT TATGGCATAC ACAGATGAAA CCTTTAAGAC TCGTGAAGCT

1381   ATTCAGCATG AATCAGGAAT CTTGGGACCT TTACTTTATG GGAAGTTGG AGACACACTG

1441   TTGATTATAT TTAAGAATCA AGCAAGCAGA CCATATAACA TCTACCCTCA CGGAATCACT

1501   GATGTCCGTC CTTTGTATTC AAGGAGATTA CCAAAAGGTG TAAAACATTT GAAGGATTTT

1561   CCAATTCTGC CAGGAGAAAT ATTCAAATAT AAATGGACAG TGACTGTAGA AGATGGGCCA

1621   ACTAAATCAG ATCCTCGGTG CCTGACCCGC TATTACTCTA GTTTCGTTAA TATGGAGAGA

1681   GATCTAGCTT CAGGACTCAT TGGCCCTCTC CTCATCTGCT ACAAAGAATC TGTAGATCAA

1741   AGAGGAAACC AGATAATGTC AGACAAGAGG AATGTCATCC TGTTTTCTGT ATTTGATGAG

1801   AACCGAAGCT GGTACCTCAC AGAGAATATA CAACGCTTTC TCCCCAATCC AGCTGGAGTG

1861   CAGCTTGAGG ATCCAGAGTT CCAAGCCTCC AACATCATGC ACAGCATCAA TGGCTATGTT

1921   TTTGATAGTT TGCAGTTGTC AGTTTGTTTG CATGAGGTGG CATACTGGTA CATTCTAAGC
```

Sequence Table 1: Polynucleotide Sequences: FIX-Fc

```
1981   ATTGGAGCAC AGACTGACTT CCTTTCTGTC TTCTTCTCTG GATATACCTT CAAACACAAA

2041   ATGGTCTATG AAGACACACT CACCCTATTC CCATTCTCAG GAGAAACTGT CTTCATGTCG

2101   ATGGAAAACC CAGGTCTATG GATTCTGGGG TGCCACAACT CAGACTTTCG GAACAGAGGC

2161   ATGACCGCCT TACTGAAGGT TTCTAGTTGT GACAAGAACA CTGGTGATTA TTACGAGGAC

2221   AGTTATGAAG ATATTTCAGC ATACTTGCTG AGTAAAAACA ATGCCATTGA CCAAGAAGC

2281   TTCTCCCAGA ATGACAAAAC TCACACATGC CCACCGTGCC CAGCTCCAGA ACTCCTGGGC

2341   GGACCGTCAG TCTTCCTCTT CCCCCCAAAA CCCAAGGACA CCCTCATGAT CTCCCGGACC

2401   CCTGAGGTCA CATGCGTGGT GGTGGACGTG AGCCACGAAG ACCCTGAGGT CAAGTTCAAC

2461   TGGTACGTGG ACGGCGTGGA GGTGCATAAT GCCAAGACAA AGCCGCGGGA GGAGCAGTAC

2521   AACAGCACGT ACCGTGTGGT CAGCGTCCTC ACCGTCCTGC ACCAGGACTG GCTGAATGGC

2581   AAGGAGTACA AGTGCAAGGT CTCCAACAAA GCCCTCCCAG CCCCCATCGA GAAAACCATC

2641   TCCAAAGCCA AAGGGCAGCC CCGAGAACCA CAGGTGTACA CCCTGCCCCC ATCCCGGGAT

2701   GAGCTGACCA AGAACCAGGT CAGCCTGACC TGCCTGGTCA AAGGCTTCTA TCCCAGCGAC

2761   ATCGCCGTGG AGTGGGAGAG CAATGGGCAG CCGGAGAACA ACTACAAGAC CACGCCTCCC

2821   GTGTTGGACT CCGACGGCTC CTTCTTCCTC TACAGCAAGC TCACCGTGGA CAAGAGCAGG

2881   TGGCAGCAGG GGAACGTCTT CTCATGCTCC GTGATGCATG AGGCTCTGCA CAACCACTAC

2941   ACGCAGAAGA GCCTCTCCCT GTCTCCGGGT AAA
```

C.
(iii) Light Chain (LC)-Fc DNA sequence (signal peptide underlined, Fc region in bold) (SEQ ID NO: 11, which encodes SEQ ID NO: 12)

```
  1   ATGGAGACAG ACACACTCCT GCTATGGGTA CTGCTGCTCT GGGTTCCAGG TTCCACTGGT

61   GAAATAACTC GTACTACTCT TCAGTCAGAT CAAGAGGAAA TTGACTATGA TGATACCATA

121   TCAGTTGAAA TGAAGAAGGA AGATTTTGAC ATTTATGATG AGGATGAAAA TCAGAGCCCC

181   CGCAGCTTTC AAAAGAAAAC ACGACACTAT TTTATTGCTG CAGTGGAGAG GCTCTGGGAT

241   TATGGGATGA GTAGCTCCCC ACATGTTCTA AGAAACAGGG CTCAGAGTGG CAGTGTCCCT

301   CAGTTCAAGA AAGTTGTTTT CCAGGAATTT ACTGATGGCT CCTTTACTCA GCCCTTATAC

361   CGTGGAGAAC TAAATGAACA TTTGGGACTC CTGGGGCCAT ATATAAGAGC AGAAGTTGAA

421   GATAATATCA TGGTAACTTT CAGAAATCAG GCCTCTCGTC CCTATTCCTT CTATTCTAGC

481   CTTATTTCTT ATGAGGAAGA TCAGAGGCAA GGAGCAGAAC TAGAAAAAAA CTTTGTCAAG

541   CCTAATGAAA CCAAAACTTA CTTTTGGAAA GTGCAACATC ATATGGCACC CACTAAAGAT

601   GAGTTTGACT GCAAAGCCTG GGCTTATTTC TCTGATGTTG ACCTGGAAAA AGATGTGCAC

661   TCAGGCCTGA TTGGACCCCT TCTGGTCTGC CACACTAACA CACTGAACCC TGCTCATGGG

721   AGACAAGTGA CAGTACAGGA ATTTGCTCTG TTTTTCACCA TCTTTGATGA GACCAAAAGC

781   TGGTACTTCA CTGAAAAATA TGGAAAGAAC TGCAGGGCTC CCTGCAATAT CCAGATGGAA

841   GATCCCACTT TTAAAGAGAA TTATCGCTTC CATGCAATCA ATGGCTACAT AATGGATACA

901   CTACCTGGCT TAGTAATGGC TCAGGATCAA AGGATTCGAT GGTATCTGCT CAGCATGGGC

961   AGCAATGAAA ACATCCATTC TATTCATTTC AGTGGACATG TGTTCACTGT ACGAAAAAAA

1021  GAGGAGTATA AAATGGCACT GTACAATCTC TATCCAGGTG TTTTTGAGAC AGTGGAAATG

1081  TTACCATCCA AAGCTGGAAT TTGGCGGGTG GAATGCCTTA TTGGCGAGCA TCTACATGCT

1141  GGGATGAGCA CACTTTTTCT GGTGTACAGC AATAAGTGTC AGACTCCCCT GGGAATGGCT
```

Sequence Table 1: Polynucleotide Sequences: FIX-Fc

```
1201    TCTGGACACA TTAGAGATTT TCAGATTACA GCTTCAGGAC AATATGGACA GTGGGCCCCA

1261    AAGCTGGCCA GACTTCATTA TTCCGGATCA ATCAATGCCT GGAGCACCAA GGAGCCCTTT

1321    TCTTGGATCA AGGTGGATCT GTTGGCACCA ATGATTATTC ACGGCATCAA GACCCAGGGT

1381    GCCCGTCAGA AGTTCTCCAG CCTCTACATC TCTCAGTTTA TCATCATGTA TAGTCTTGAT

1441    GGGAAGAAGT GGCAGACTTA TCGAGGAAAT TCCACTGGAA CCTTAATGGT CTTCTTTGGC

1501    AATGTGGATT CATCTGGGAT AAAACACAAT ATTTTTAACC CTCCAATTAT TGCTCGATAC

1561    ATCCGTTTGC ACCCAACTCA TTATAGCATT CGCAGCACTC TTCGCATGGA GTTGATGGGC

1621    TGTGATTTAA ATAGTTGCAG CATGCCATTG GGAATGGAGA GTAAAGCAAT ATCAGATGCA

1681    CAGATTACTG CTTCATCCTA CTTTACCAAT ATGTTTGCCA CCTGGTCTCC TTCAAAAGCT

1741    CGACTTCACC TCCAAGGGAG GAGTAATGCC TGGAGACCTC AGGTGAATAA TCCAAAAGAG

1801    TGGCTGCAAG TGGACTTCCA AAAGACAATG AAAGTCACAG GAGTAACTAC TCAGGGAGTA

1861    AAATCTCTGC TTACCAGCAT GTATGTGAAG GAGTTCCTCA TCTCCAGCAG TCAAGATGGC

1921    CATCAGTGGA CTCTCTTTTT TCAGAATGGC AAAGTAAAGG TTTTTCAGGG AAATCAAGAC

1981    TCCTTCACAC CTGTGGTGAA CTCTCTAGAC CCACCGTTAC TGACTCGCTA CCTTCGAATT

2041    CACCCCCAGA GTTGGGTGCA CCAGATTGCC CTGAGGATGG AGGTTCTGGG CTGCGAGGCA

2101    CAGGACCTCT ACGACAAAAC TCACACATGC CCACCGTGCC CAGCTCCAGA ACTCCTGGGC

2161    GGACCGTCAG TCTTCCTCTT CCCCCCAAAA CCCAAGGACA CCCTCATGAT CTCCCGGACC

2221    CCTGAGGTCA CATGCGTGGT GGTGGACGTG AGCCACGAAG ACCCTGAGGT CAAGTTCAAC

2281    TGGTACGTGG ACGGCGTGGA GGTGCATAAT GCCAAGACAA AGCCGCGGGA GGAGCAGTAC

2341    AACAGCACGT ACCGTGTGGT CAGCGTCCTC ACCGTCCTGC ACCAGGACTG GCTGAATGGC

2401    AAGGAGTACA AGTGCAAGGT CTCCAACAAA GCCCTCCCAG CCCCCATCGA GAAAACCATC

2461    TCCAAAGCCA AAGGGCAGCC CCGAGAACCA CAGGTGTACA CCCTGCCCCC ATCCCGGGAT

2521    GAGCTGACCA AGAACCAGGT CAGCCTGACC TGCCTGGTCA AAGGCTTCTA TCCCAGCGAC

2581    ATCGCCGTGG AGTGGGAGAG CAATGGGCAG CCGGAGAACA ACTACAAGAC CACGCCTCCC

2641    GTGTTGGACT CCGACGGCTC CTTCTTCCTC TACAGCAAGC TCACCGTGGA CAAGAGCAGG

2701    TGGCAGCAGG GGAACGTCTT CTCATGCTCC GTGATGCATG AGGCTCTGCA CAACCACTAC

2761    ACGCAGAAGA GCCTCTCCCT GTCTCCGGGT AAA
```

D. FIX-Fc Chain DNA Sequence (SEQ ID NO: 13, which encodes SEQ ID NO: 14)
pSYN-FIX-030 Nucleotide sequence (nt 1 to 7583):
FIX exon 1 (signal peptide, 1st amino acid propeptide): nt 690-777
FIX mini intron: nt 778-1076
FIX propeptide sequence: nt 1077-1126
Mature FIX sequence: nt 1127-2371
Fc: nt 2372-3052

```
gcgcgcgttgacattgattattgactagttattaatagtaatcaattacggggtcattagttcatagcccatatatgg
agttccgcgttacataacttacggtaaatggcccgcctggctgaccgcccaacgaccccccgcccattgacgtcaataa
tgacgtatgttcccatagtaacgccaatagggactttccattgacgtcaatgggtggagtatttacggtaaactgccc
acttggcagtacatcaagtgtatcatatgccaagtacgccccctattgacgtcaatgacggtaaatggcccgcctggc
attatgcccagtacatgaccttatgggactttcctacttggcagtacatctacgtattagtcatcgctattaccatgg
tgatgcggttttggcagtacatcaatgggcgtggatagcggtttgactcacggggatttccaagtctccaccccattg
acgtcaatgggagtttgttttggcaccaaaatcaacgggactttccaaaatgtcgtaacaactccgccccattgacgc
aaatgggcggtaggcgtgtacggtgggaggtctatataagcagagctctctggctaactagagaacccactgcttact
ggcttatcgaaattaatacgactcactatagggagacccaagcttcgcgacgtacggccgccaccatgcagcgcgtga
acatgatcatggcagaatcaccaggcctcatcaccatctgccttttaggatatctactcagtgctgaatgtacaggtt
tgtttccttttttaaaatacattgagtgcttgcctttagatatagaaatatctgatgctgtcttcttcactaaat
tttgattacatgatttgacagcaatattgaagagtctaacagccagcacgcaggttggtaagtactgtgggaacatca
cagattttggctccatgccctaaagagaaattggctttcagattatttggattaaaaacaaagactttcttaagagat
gtaaaattttcatgatgtttctttttgctaaaactaaagaattattcttttacatttcagttttcttgatcatga
aaacgccaacaaaattctgaatcggccaaagaggtataattcaggtaaattggaagagtttgttcaagggaatctaga
gagagaatgtatggaagaaaagtgtagttttgaagaagcacgagaagtttttgaaaacactgaaagaacaactgaatt
```

-continued

Sequence Table 1: Polynucleotide Sequences: FIX-Fc

```
ttggaagcagtatgttgatggagatcagtgtgagtccaatccatgtttaaatggcggcagttgcaaggatgacattaa
ttcctatgaatgttggtgtcccttttgatttgaaggaaagaactgtgaattagatgtaacatgtaacattaagaatgg
cagatgcgagcagttttgtaaaaatagtgctgataacaaggtggtttgctcctgtactgagggatatcgacttgcaga
aaaccagaagtcctgtgaaccagcagtgccatttccatgtggaagagtttctgtttcacaaacttctaagctcacccg
tgctgagactgttttcctgatgtggactatgtaaattctactgaagctgaaaccattttggataacatcactcaaag
cacccaatcatttaatgacttcactcggggttgttggtggagaagatgccaaaccaggtcaattcccttggcaggttgt
tttgaatggtaaagttgatgcattctgtgtgaggctctatcgttaatgaaaaatggattgtaactgctgcccactgtgt
tgaaactggtgttaaaattacagttgtcgcaggtgaacataatattgaggagacagaacatacagagcaaaagcgaaa
tgtgattcgaattattcctcaccacaactacaatgcagctattaataagtacaaccatgacattgccttctgaact
ggacgaaccctagtgctaaacagctacgttacacctatttgcattgctgacaaggaatacacgaacatcttcctcaa
atttggatctggctatgtaagtggctggggaagagtcttccacaaagggagatcagctttagttcttcagtaccttag
agttccacttgttgaccgagccacatgtcttcgatctacaaagttcacatctataacaacatgttctgtgctggctt
ccatgaaggaggtagagattcatgtcaaggagatagtgggggaccccatgttactgaagtggaagggaccagtttctt
aactggaattattagctggggtgaagagtgtgcaatgaaaggcaaatatggaatatataccaaggtgtcccggtatgt
caactggattaaggaaaaaacaaagctcactgacaaaactcacacatgcccaccgtgcccagctccggaactcctggg
cggaccgtcagtcttcctcttccccccaaaacccaaggacaccctcatgatctcccggacccctgaggtcacatgcgt
ggtggtggacgtgagccacgaagaccctgaggtcaagttcaactggtacgtggacggcgtggaggtgcataatgccaa
gacaaagccgcggggaggagcagtacaacagcacgtaccgtgtggtcagcgtcctcaccgtcctgcaccaggactggct
gaatggcaaggagtacaagtgcaaggtctccaacaaagcccctcccagccccatcgagaaaaccatctccaaagccaa
agggcagccccgagaaccacaggtgtacaccctgcccccatcccgggatgagctgaccaagaaccaggtcagcctgac
ctgcctggtcaaaggcttctatcccagcgacatcgccgtggagtgggagagcaatgggcagccggagaacaactacaa
gaccacgcctcccgtgttggactccgacggctccttcttcctctacagcaagctcaccgtggacaagagcaggtggca
gcaggggaacgtcttctcatgctccgtgatgcatgaggctctgcacaaccactacacgcagaagagcctctccctgtc
tccgggtaaatgagaattcagacatgataagatacattgatggctgtggatgaaccacaactagaatgcagtgaaaaa
aatgctttatttgtgaaatttgtgatgctattgctttatttgtaaccattataagctgcaataaacaagttggggtgg
gcgaagaactccagcatgagatccccgcgctggaggatcatccagccggcgtcccggaaaacgattccgaagcccaac
cttttcatagaaggcggcggtggaatcgaaatctcgtagcacgtgtcagtcctgctcctcggccacgaagtgcacgcag
ttgccggccgggtcgcgcagggcgaactcccgcccccacggctgctcgccgatctcggtcatggccggcccggaggcg
tcccggaagttcgtggacacgacctccgaccactcggcgtacagctcgtccaggccgcgcacccacaccaggccagg
gtgttgtccggcaccacctggtcctggaccgcgctgatgaacagggtcacgtcgtcccggaccacaccggcgaagtcg
tcctccacgaagtcccgggagaacccgagccggtcggtccagaactcgaccgctccggcgacgtcgcgcgcggtgagc
accggaacggcactggtcaacttggccatggtttagttcctcaccttgtcgtattatactatgccgatatactatgcc
gatgattaattgtcaacacgtgctgatcagatccgaaaatggatatacaagctcccgggagcttttttgcaaaagccta
ggcctccaaaaaagcctcctcactacttctggaatagctcagaggcagaggcggcctcggcctctgcataaataaaaa
aaattagtcagccatggggcggagaatgggcggaactgggcggagttaggggcgggatgggcggagttaggggcggga
ctatggttgctgactaattgagatgcatgctttgcatacttctgcctgctggggagcctggggacttttccacacctgg
ttgctgactaattgagatgcatgctttgcatacttctgcctgctgtggggacccttgggggactttccacaccctcgtcgag
ctagcttcgtgaggctccggtgcccgtcagtgggcagagcgcacatcgcccacagtccccgagaagttggggggaggg
gtcggcaattgaaccggtgcctagagaaggtggcgcggggtaaactgggaaagtgatgtcgtgtactggctccgcctt
tttcccgagggtgggggagaaccgtatataagtgcagtagtcgccgtgaacgttcttttttcgcaacgggtttgccgcc
agaacacaggtaagtgccgtgtgtggttcccgcgggcctggcctctttacgggttatggccctttgcgtgccttgaatt
acttccacctggctccagtacgtgattcttgatcccgagctggagccaggggcgggccttgcgctttaggagcccctt
cgcctcgtgcttgagttgaggcctggcctgggcgctggggccgccgcgtgcgaatctggtggcaccttcgcgcctgtc
tcgctgctttcgataagtctctagccatttaaaatttttgatgacctgctgcgacgctttttttctggcaagatagtc
ttgtaaatgcgggccaggatctgcacactggtatttcggttttgggtttttggggccgcgatgacggggcccgtgcgtccc
agcgcacatgttcggcgaggcgggggcctgcgagcgcggccaccgagaatcggacgggggtagtctcaagctggccggc
ctgctctggtgcctggcctcgcgccgcgtgtatcgccccgccctgggcggcaaggctgccggtcggccaccagttg
cgtgagcggaaagatggccgcttcccggccctgctccaggggggctcaaaatggaggacgcggcgctcgggagagcggg
cgggtgagtcacccacacaaaggaaaggggcctttccgtcctcagccgtcgcttcatgtgactccacggagtaccggg
cgccgtccaggcacctcgattagttctggagctttttggagtacgtcgtctttaggttgggggggaggggtttttatgcga
tggagtttccccacactgagtgggtggagactgaagttaggccagcttggcacttgatgtaattctccttggaatttg
ccctttttgagtttggatcttggttcattctcaagcctcagacagtggttcaaagtttttttcttccatttcaggtgt
cgtgaacacgtggtcgcggccgcgccgccaccatggagacagacacactcctgctatgggtactgctgctctggtgggttc
caggttccactggtgacaaaactcacacatgcccaccgtgcccagcacctgaactcctgggaggaccgtcagtcttcc
tcttccccccaaaacccaaggacaccctcatgatctcccggacccctgaggtcacatgcgtggtggtggacgtgagcc
acgaagaccctgaggtcaagttcaactggtacgtggacggcgtggaggtgcataatgccaagacaaagccgcggggagg
agcagtacaacagcacgtaccgtgtggtcagcgtcctcaccgtcctgcaccaggactggctgaatggcaaggagtaca
agtgcaaggtctccaacaaagcccctcccagccccatcgagaaaaccatctccaaagccaaagggcagccccgagaac
cacaggtgtacaccctgcccccatcccgcgatgagctgaccaagaaccaggtcagcctgacctgcctggtcaaaggct
tctatcccagcgacatcgccgtggagtgggagagcaatgggcagccggagaacaactacaagaccacgcctcccgtgt
tggactccgacggctccttcttcctctacagcaagctcaccgtggacaagagcaggtggcagcaggggaacgtcttct
catgctccgtgatgcatgaggctctgcacaaccactacacgcagaagagcctctccctgtctccgggtaaatgactcg
agagatctggccggctgggcccgtttcgaaggtaagcctatccctaaccctctcctcggtctcgattctacgcgtacc
ggtcatcatccatcaccattgagtttaaacccgctgatcagcctcgactgtgccttctagttgccagccatctgtt
gtttgcccctcccccgtgccttccttgaccctggaaggtgccactcccactgtcctttcctaataaaatgaggaaatt
gcatcgcattgtctgagtaggtgtcattctattctggggggtgggtggggcaggacagcaagggggaggattgggaa
gacaatagcaggcatgctggggatgcggtgggctctatggcttctgaggcggaaagaaccagtggcggtaatacggtt
atccacagaatcaggggataacgcaggaaagaacatgtgagcaaaaggccagcaaaaggccaggaaccgtaaaaaggc
cgcgttgctggcgtttttccataggctccgcccccctgacgagcatcacaaaaatcgacgctcaagtcagaggtggcg
aaacccgacaggactataaagataccaggcgtttccccctggaagctccctcgtgcgctctcctgttccgaccctgcc
gcttaccggatacctgtccgcctttctcccttcgggaagcgtggcgctttctcatagctcacgctgtaggtatctcag
ttcggtgtaggtcgttcgctccaagctgggctgtgtgcacgaaccccccgttcagcccgaccgctgcgccttatccgg
taactatcgtcttgagtccaacccggtaagacacgacttatcgccactggcagcagccactggtaacaggattagcag
agcgaggtatgtaggcggtgctacagagttcttgaagtggtggcctaactacggctacactagaagaacagtatttgg
tatctgcgctctgctgaagccagttaccttcggaaaaagagttggtagctcttgatccggcaaacaaaccaccgctgg
tagcggtggtttttttgtttgcaagcagcagattacgcgcagaaaaaaaggatctcaagaagatcctttgatcttttc
tacggggtctgacgctcagtggaacgaaaactcacgttaagggattttggtcatgacattaacctataaaaataggcg
```

| Sequence Table 1: Polynucleotide Sequences: FIX-Fc |
|---|
| tatcacgaggcccttt cgtctcgcgcgtttcggtgatgacggtgaaaacctctgacacatgcagctcccggagacggt
cacagcttgtctgtaagcggatgccgggagcagacaagcccgtcagggcgcgtcagcgggtgttggcgggtgtcgggg
ctggcttaactatgcggcatcagagcagattgtactgagagtgcaccatatgcggtgtgaaataccgcacagatgc
gtaaggagaaaataccgcatcaggcgccattcgccattcaggctgcgcaactgttgggaagggcgatcggtgcgggcc
tcttcgctattacgcca B. Fc DNA sequence (mouse IgK signal peptide underlined) (SEQ ID NO: 3, which
encodes SEQ ID NO: 4) This is the Fc cassette from pSYN-FIX-030. In addition,
there is a separate Fc expression cassette that was transfected into the cell
line in plasmid pSYN-Fc-015 that encodes the same amino acid sequence, but
contains a few noncoding changes. The second copy of Fc encoding sequence
enables a better monomer: dimer ratio.
<u>atggagacagacacactcctgctatgggtactgctgctctgggttccaggttccactggt</u>gacaaaactcacacatgcc
caccgtgcccagcacctgaactcctgggaggaccgtcagtcttcctcttccccccaaaacccaaggacaccctcatgat
ctcccggacccctgaggtcacatgcgtggtggtggacgtgagccacgaagaccctgaggtcaagttcaactggtacg
tggacggcgtggaggtgcataatgccaagacaaagccgcgggaggagcagtacaacagcacgtaccgtgtggtca
gcgtcctcaccgtcctgcaccaggactggctgaatggcaaggagtacaagtgcaaggtctccaacaaagccctccca
gcccccatcgagaaaaccatctccaaagccaaagggcagccccgagaaccacaggtgtacaccctgcccccatccc
gcgatgagctgaccaagaaccaggtcagcctgacctgcctggtcaaaggcttctatcccagcgacatcgccgtggagt
gggagagcaatgggcagccggagaacaactacaagaccacgcctcccgtgttggactccgacggctccttcttcctct
acagcaagctcaccgtggacaagagcaggtggcagcaggggaacgtcttctcatgctccgtgatgcatgaggctctg
cacaaccactacacgcagaagagcctctccctgtctccgggtaaa |

| Sequence Table 2: Polypeptide Sequences |
|---|
| A. B-Domain Deleted FVIII-Fc Monomer Hybrid (BDD FVIIIFc monomer
dimer): created by coexpressing BDD FVIIIFc and Fc chains.
Construct = HC-LC-Fc fusion. An Fc expression cassette is cotransfected
with BDDFVIII-Fc to generate the BDD FVIIIFc monomer-. For the BDD
FVIIIFc chain, the Fc sequence is shown in bold; HC sequence is shown
in double underline; remaining B domain sequence is shown in italics.
Signal peptides are underlined.
i) B domain deleted FVIII-Fc chain (19 amino acid signal sequence
underlined) (SEQ ID NO: 2)
<u>MQIELSTCFFLCLLRFCFS</u>
<u>ATRRYYLGAVELSWDYMQSDLGELPVDARFPPRVPKSFPFNTSVVYKKTLFVEFTDHLFNIAKPR</u>
<u>PPWMGLLGPTIQAEVYDTVVITLKNMASHPVSLHAVGVSYWKASEGAEYDDQTSQREKEDDKVFP</u>
<u>GGSHTYVWQVLKENGPMASDPLCLTYSYLSHVDLVKDLNSGLIGALLVCREGSLAKEKTQTLHKF</u>
<u>ILLFAVFDEGKSWHSETKNSLMQDRDAASARAWPKMHTVNGYVNRSLPGLIGCHRKSVYWHVIGM</u>
<u>GTTPEVHSIFLEGHTFLVRNHRQASLEISPITFLTAQTLLMDLGQFLLFCHISSHQHDGMEAYVK</u>
<u>VDSCPEEPQLRMKNNEEAEDYDDDLTDSEMDVVRFDDDNSPSFIQIRSVAKKHPKTWVHYIAAEE</u>
<u>EDWDYAPLVLAPDDRSYKSQYLNNGPQRIGRKYKKVRFMAYTDETFKTREAIQHESGILGPLLYG</u>
<u>EVGDTLLIIFKNQASRPYNIYPHGITDVRPLYSRRLPKGVKHLKDFPILPGEIFKYKWTVTVEDG</u>
<u>PIKSDPRCLTRYYSSFVNMERDLASGLIGPLLICYKESVDQRGNQIMSDKRNVILFSVFDENRSW</u>
<u>YLTENIQRFLPNPAGVQLEDPEFQASNIMHSINGYVFDSLQLSVCLHEVAYWYILSIGAQTDFLS</u>
<u>VFFSGYTFKHKMVYEDTLTLFPFSGETVFMSMENPGLWILGCHNSDFRNRGMTALLKVSSCDKNT</u>
<u>GDYYEDSYEDISAYLLSKNNAIEPR</u>*SFSQNPPVLKRHQR*EITRTTLQSDQEEIDYDDTISVEMKK
EDFDIYDEDENQSPRSFQKKTRHYFIAAVERLWDYGMSSSPHVLRNRAQSGSVPQFKKVFQEFT
DGSFTQPLYRGELNEHLGLLGPYIRAEVEDNIMVTFRNQASRPYSFYSSLISYEEDQRQGAEPRK
NFVKPNETKTYFWKVQHHMAPTKDEFDCKAWAYFSDVDLEKDVHSGLIGPLLVCHTNTLNPAHGR
QVTVQEFALFFTIFDETKSWYFTENMERNCRAPCNIQMEDPTFKENYRFHAINGYIMDTLPGLVM
AQDQRIRWYLLSMGSNENIHSIHFSGHVFTVRKKEEYKMALYNLYPGVFETVEMLPSKAGIWRVE
CLIGEHLHAGMSTLFLVYSNKCQTPLGMASGHIRDFQITASGQYGQWAPKLARLHYSGSINAWST
KEPFSWIKVDLLAPMIIHGIKTQGARQKFSSLYISQFIIMYSLDGKKWQTYRGNSTGTLMVFFGN
VDSSGIKHNIFNPPIIARYIRLHPTHYSIRSTLRMELMGCDLNSCSMPLGMESKAISDAQITASS
YFTNMFATWSPSKARLHLQGRSNAWRPQVNNPKEWLQVDFQKTMKVTGVTTQGVKSLLTSMYVKE
FLISSSQDGHQWTLFFQNGKVKVFQGNQDSFTPVVNSLDPPLLTRYLRIHPQSWVHQIALRMEVL
GCEAQDLYDKTHTCPPCPAPELLGGPSVFLFPPKPKDTLMISRTPEVTCVVVDVSHEDPEVKFNW
YVDGVEVHNAKTKPREEQYNSTYRVVSVLTVLHQDWLNGKEYKCKVSNKALPAPIEKTISKAKGQ
PREPQVYTLPPSRDELTKNQVSLTCLVKGFYPSDIAVEWESNGQPENNYKTTPPVLDSDGSFFLY
SKLTVDKSRWQQGNVFSCSVMHEALHNHYTQKSLSLSPGK ii) Fc chain (20 amino acid heterologous signal peptide from mouse IgK
chain underlined) (SEQ ID NO: 4)
<u>METDTLLLWVLLLWVPGSTG</u>
DKTHTCPPCPAPELLGGPSVFLFPPKPKDTLMISRTPEVTCVVVDVSHEDPEVKFNWYVDGVEVH
NAKTKPREEQYNSTYRVVSVLTVLHQDWLNGKEYKCKVSNKALPAPIEKTISKAKGQPREPQVYT
LPPSRDELTKNQVSLTCLVKGFYPSDIAVEWESNGQPENNYKTTPPVLDSDGSFFLYSKLTVDKS
RWQQGNVFSCSVMHEALHNHYTQKSLSLSPGK |

Sequence Table 2: Polypeptide Sequences

B. Full length FVIIIFc monomer hybrid (Full length FVIIIFc monomer dimer): created by coexpressing FVIIIFc and Fc chains.
Construct HC-B-LC-Fc fusion. An Fc expression cassette is cotransfected with full length FVIII-Fc to generate the full length FVIIIFc monomer. For the FVIIIFc chain, the Fc sequence is shown in bold; HC sequence is shown in double underline; B domain sequence is shown in italics. Signal peptides are underlined.
i) Full length FVIIIFc chain (FVIII signal peptide underlined (SEQ ID NO: 6)
MQIELSTCFFLCLLRFCFS
ATRRYYLGAVELSWDYMQSDLGELPVDARFPPRVPKSFPFNTSVVYKKTLFVEFTDHLFNIAKPR
PPWMGLLGPTIQAEVYDTVVITLKNMASHPVSLHAVGVSYWKASEGAEYDDQTSQREKEDDKVFP
GGSHTYVWQVLKENGPMASDPLCLTYSYLSHVDLVKDLNSGLIGALLVCREGSLAKEKTQTLHKF
ILLFAVFDEGKSWHSETKNSLMQDRDAASARAWPKMHTVNGYVNRSLPGLIGCHRKSVYWHVIGM
GTTPEVHSIFLEGHTFLVRNHRQASLEISPITFLTAQTLLMDLGQFLLFCHISSHQHDGMEAYVK
VDSCPEEPQLRMKNNEEAEDYDDDLTDSEMDVVRFDDDNSPSFIQIRSVAKKHPKTWVHYIAAEE
EDWDYAPLVLAPDDRSYKSQYLNNGPQRIGRKYKKVRFMAYTDETFKTREAIQHESGILPLLYG
EVGDTLLIIFKNQASRPYNIYPHGITDVRPLYSRRLPKGVKHLKDFPILPGEIFKYKWTVTVEDG
PIKSDPRCLTRYYSSFVNMERDLASGLIGPLLICYKESVDQRGNQIMSDKRNVILFSVFDENRSW
YLTENIQRFLPNPAGVQLEDPEFQASNIMHSINGYVFDSLQLSVCLHEVAYWYILSIGAQTDFLS
VFFSGYTFKHKMVYEDTLTLFPFSGETVFMSMENPGLWILGCHNSDFRNRGMTALLKVSSCDKNT
GDYYEDSYEDISAYLLSKNNAIEPRSFSQNSRHPSTRQKQFNATTIPENDIEKTDPWFAHRTPMP
KIQNVSSSDLLMLLRQSPTPHGLSLSDLQEAKYETFSDDPSPGAIDSNNSLSEMTHFRPQLHHSG
DMVFTPESGLQLRLNEKLGTTAATELKKLDFKVSSTSNNLISTIPSDNLAAGTDNTSSLGPPSMP
VHYDSQLDTTLFGKKSSPLTESGGPLSLSEENNDSKLLESGLMNSQESSWGKNVSSTESGRLFKG
KRAHGPALLTKDNALFKVSISLLKTNKTSNNSATNRKTHIDGPSLLIENSPSVWQNILESDTEFK
KVTPLIHDRKLMDKNATALRLNHMSNKTTSSKNMEMVQQKKEGPIPPDAQNPDMSFFKKLFLPES
ARWIQRTHGKNSLNSGQGPSPKQLVSLGPEKSVEGQNFLSEKNKVVVGKGEFTKDVGLKEMVFPS
SRNLFLTNLDNLHENNTHNQEKKIQEEIEKKETLIQENVVLPQIHTVTGTKNFMKNLFLLSTRQN
VEGSYDGAYAPVLQDFRSLNDSTNRTKKHTAHFSKKGEEENLEGLGNQTKQIVEKYACTTRISPN
TSQQNFVTQRSKRALKQFRLPLEETELEKRIIVDDTSTQWSKNMKHLTPSTLTQIDYNEKEKGAI
TQSPLSDCLTRSHSIPQANRSPLPIAKVSSFPSIRPIYLTRVLFQDNSSHLPAASYRKKDSGVQE
SSHFLQGAKKNNLSLAILTLEMTGDQREVGSLGTSATNSVTYKKVENTVLPKPDLPKTSGKVELL
PKVHIYQKDLFPTETSNGSPGHLDLVEGSLLQGTEGAIKWNEANRPGKVPFLRVATESSAKTPSK
LLDPLAWDNHYGTQIPKEEWKSQEKSPEKTAFKKKDTILSLNACESNHAIAAINEGQNKPEIEVT
WAKQGRTERLCSQNPPVLKRHQREITRTTLQSDQEEIDYDDTISVEMKKEDFDIYDEDENQSPRS
FQKKTRHYFIAAVERLWDYGMSSSPHVLRNRAQSGSVPQFKKVVFQEFTDGSFTQPLYRGELNEH
LGLLGPYIRAEVEDNIMVTFRNQASRPYSFYSSLISYEEDQRQGAEPRKNFVKPNETKTYFWKVQ
HHMAPTKDEFDCKAWAYFSDVDLEKDVHSGLIGPLLVCHTNTLNPAHGRQVTVQEFALFFTIFDE
TKSWYFTENMERNCRAPCNIQMEDPTFKENYRFHAINGYIMDTLPGLVMAQDQRIRWYLLSMGSN
ENIHSIHFSGHVFTVRKKEEYKMALYNLYPGVFETVEMLPSKAGIWRVECLIGEHLHAGMSTLFL
VYSNKCQTPLGMASGHIRDFQITASGQYGQWAPKLARLHYSGSINAWSTKEPFSWIKVDLLAPMI
IHGIKTQGARQKFSSLYISQFIIMYSLDGKKWQTYRGNSTGTLMVFFGNVDSSGIKHNIFNPPII
ARYIRLHPTHYSIRSTLRMELMGCDLNSCSMPLGMESKAISDAQITASSYFTNMFATWSPSKARL
HLQGRSNAWRPQVNNPKEWLQVDFQKTMKVTGVITQGVKSLLTSMYVKEFLISSSQDGHQWILFF
QNGKVKVFQGNQDSFTPVVNSLDPPLLTRYLRIHPQSWVHQIALRMEVLGCEAQDLYDKTHTCPP
CPAPELLGGPSVFLFPPKPKDTLMISRTPEVTCVVVDVSHEDPEVKFNWYVDGVEVHNAKTKPRE
EQYNSTYRVVSVLTVLHQDWLNGKEYKCKVSNKALPAPIEKTISKAKGQPREPQVYTLPPSRDEL
TKNQVSLTCLVKGFYPSDIAVEWESNGQPENNYKTTPPVLDSDGSFFLYSKLTVDKSRWQQGNVF
SCSVMHEALHNHYTQKSLSLSPGK ii) Fc chain (20 amino acid heterologous signal peptide from mouse IgK chain underlined) (SEQ ID NO: 4)
METDTLLLWVLLLWVPGSTG
DKTHTCPPCPAPELLGGPSVFLFPPKPKDTLMISRTPEVTCVVVDVSHEDPEVKFNWYVDGVEVH
NAKTKPREEQYNSTYRVVSVLTVLHQDWLNGKEYKCKVSNKALPAPIEKTISKAKGQPREPQVYT
LPPSRDELTKNQVSLTCLVKGFYPSDIAVEWESNGQPENNYKTTPPVLDSDGSFFLYSKLTVDKS
RWQQGNVFSCSVMHEALHNHYTQKSLSLSPGK C. FVIII-Fc Heterodimer Hybrid
This is made by cotransfecting HC-Fc and LC-Fc constructs. Two HC-Fc constructs have been made. One has no linker between HC and Fc (HC-Fc) while the other has a 5 amino acid linker between HC and Fc (HC + 5-Fc).
The FVIII signal peptide was used for the HC-Fc constructs, while the mouse IgK signal sequence was used for the LC-Fc construct.
(i) HC-Fc (Fc sequence is shown in bold, signal peptide underlined) (SEQ ID NO: 8)
MQIELSTCFFLCLLRFCFS
ATRRYYLGAVELSWDYMQSDLGELPVDARFPPRVPKSFPFNTSVVYKKTLFVEFTDHLFNIAKPR
PPWMGLLGPTIQAEVYDTVVITLKNMASHPVSLHAVGVSYWKASEGAEYDDQTSQREKEDDKVFP
GGSHTYVWQVLKENGPMASDPLCLTYSYLSHVDLVKDLNSGLIGALLVCREGSLAKEKTQTLHKF
ILLFAVFDEGKSWHSETKNSLMQDRDAASARAWPKMHTVNGYVNRSLPGLIGCHRKSVYWHVIGM
GTTPEVHSIFLEGHTFLVRNHRQASLEISPITFLTAQTLLMDLGQFLLFCHISSHQHDGMEAYVK
VDSCPEEPQLRMKNNEEAEDYDDDLTDSEMDVVRFDDDNSPSFIQIRSVAKKHPKTWVHYIAAEE
EDWDYAPLVLAPDDRSYKSQYLNNGPQRIGRKYKKVRFMAYTDETFKTREAIQHESGILPLLYG
EVGDTLLIIFKNQASRPYNIYPHGITDVRPLYSRRLPKGVKHLKDFPILPGEIFKYKWTVTVEDG Sequence Table 2: Polypeptide Sequences PIKSDPRCLTRYYSSFVNMERDLASGLIGPLLICYKESVDQRGNQIMSDKRNVILFSVFDENRSW
YLTENIQRFLPNPAGVQLEDPEFQASNIMHSINGYVFDSLQLSVCLHEVAYWYILSIGAQTDFLS
VFFSGYTFKHKMVYEDTLTLFPFSGETVFMSMENPGLWILGCHNSDFRNRGMTALLKVSSCDKNT
GDYYEDSYEDISAYLLSKNNAIEPR**DKTHTCPPCPAPELLGGPSVFLFPPKPKDTLMISRTPEVT
CVVVDVSHEDPEVKFNWYVDGVEVHNAKTKPREEQYNSTYRVVSVLTVLHQDWLNGKEYKCKVSN
KALPAPIEKTISKAKGQPREPQVYTLPPSRDELTKNQVSLTCLVKGFYPSDIAVEWESNGQPENN
YKTTPPVLDSDGSFFLYSKLTVDKSRWQQGNVFSCSVMHEALHNHYTQKSLSLSPGK**

(ii) HC + 5-Fc (Fc sequence is shown in bold, 5 amino acid linker
sequence (from the B domain of FVIII) is shown in italics, signal
peptide underlined.) (SEQ ID NO: 10)
<u>MQIELSTCFFLCLLRFCFS</u>
ATRRYYLGAVELSWDYMQSDLGELPVDARFPPRVPKSFPFNTSVVYKKTLFVEFTDHLFNIAKPR
PPWMGLLGPTIQAEVYDTVVITLKNMASHPVSLHAVGVSYWKASEGAEYDDQTSQREKEDDKVFP
GGSHTYVWQVLKENGPMASDPLCLTYSYLSHVDLVKDLNSGLIGALLVCREGSLAKEKTQTLHKF
ILLFAVFDEGKSWHSETKNSLMQDRDAASARAWPKMHTVNGYVNRSLPGLIGCHRKSVYWHVIGM
GTTPEVHSIFLEGHTFLVRNHRQASLEISPITFLTAQTLLMDLGQFLLFCHISSHQHDGMEAYVK
VDSCPEEPQLRMKNNEEAEDYDDDLTDSEMDVVRFDDDNSPSFIQIRSVAKKHPKTWVHYIAAEE
EDWDYAPLVLAPDDRSYKSQYLNNGPQRIGRKYKKVRFMAYTDETFKTREAIQHESGILGPLLYG
EVGDTLLIIFKNQASRPYNIYPHGITDVRPLYSRRLPKGVKHLKDFPILPGEIFKYKWTVTEDG
PIKSDPRCLTRYYSSFVNMERDLASGLIGPLLICYKESVDQRGNQIMSDKRNVILFSVFDENRSW
YLTENIQRFLPNPAGVQLEDPEFQASNIMHSINGYVFDSLQLSVCLHEVAYWYILSIGAQTDFLS
VFFSGYTFKHKMVYEDTLTLFPFSGETVFMSMENPGLWILGCHNSDFRNRGMTALLKVSSCDKNT
GDYYEDSYEDISAYLLSKNNAIEPR*SFSQN***DKTHTCPPCPAPELLGGPSVFLEPPKPKDTLMISR
TPEVTCVVVDVSHEDPEVKFNWYVDGVEVHNAKTKPREEQYNSTYRVVSVLTVLHQDWLNGKEYK
CKVSNKALPAPIEKTISKAKGQPREPQVYTLPPSRDELTKNQVSLTCLVKGFYPSDIAVEWESNG
QPENNYKTTPPVLDSDGSFELYSKLTVDKSRWQQGNVESCSVMHEALHNHYTQKSLSLSPGK**

(iii) LC-Fc6His (Fc sequence is shown in bold, signal peptide under-
lined.) (SEQ ID NO: 12)
<u>METDTLLLWVLLLWVPGSTG</u>
EITRTTLQSDQEEIDYDDTISVEMKKEDFDIYDEDENQSPRSFQKKTRHYFIAAVERLWDYGMSS
SPHVLRNRAQSGSVPQFKKVVFQEFTDGSFTQPLYRGELNEHLGLLGPYIRAEVEDNIMVTFRNQ
ASRPYSFYSSLISYEEDQRQGAEPRKNFVKPNETKTYFWKVQHHMAPTKDEFDCKAWAYFSDVDL
EKDVHSGLIGPLLVCHTNTLNPAHGRQVTVQEFALFFTIFDETKSWYFTENMERNCRAPCNIQME
DPIFKENYRFHAINGYIMDTLPGLVMAQDQRIRWYLLSMGSNENIHSIHFSGHVFTVRKKEEYKM
ALYNLYPGVFETVEMLPSKAGIWRVECLIGEHLHAGMSTLFLVYSNKCQTPLGMASGHIRDFQIT
ASGQYGQWAPKLARLHYSGSINAWSTKEPFSWIKVDLLAPMIIHGIKTQGARQKFSSLYISQFII
MYSLDGKKWQTYRGNSTGTLMVFFGNVDSSGIKHNIFNPPIIARYIRLHPTHYSIRSTLRMELMG
CDLNSCSMPLGMESKAISDAQITASSYFTNMFATWSPSKARLHLQGRSNAWRPQVNNPKEWLQVD
FQKTMKVTGVTTQGVKSLLTSMYVKEFLISSSQDGHQWTLFFQNGKVKVFQGNQDSFTPVVNSLD
PPLLTRYLRIHPQSWVHQIALRMEVLGCEAQDLY**DKTHTCPPCPAPELLGGPSVFLFPPKPKDTL
MISRTPEVTCVVVDVSHEDPEVKFNWYVDGVEVHNAKTKPREEQYNSTYRVVSVLTVLHQDWLNG
KEYKCKVSNKALPAPIEKTISKAKGQPREPQVYTLPPSRDELTKNQVSLTCLVKGFYPSDIAVEW
ESNGQPENNYKTTPPVLDSDGSFELYSKLTVDKSRWQQGNVESCSVMHEALHNHYTQKSLSLSPG
K**

D. FIX-Fc Chain (SEQ ID NO:14):

(28 amino acid signal sequence underlined, 18 amino acid propeptide double underlined, Fc portion in italics.) The C-terminal lysine is not present in either subunit; this processing is often observed in recombinant proteins produced in mammalian cell culture, as well as with plasma derived proteins.

FIXFC-SC Subunit:

```
FIX Signal Peptide: -46 MQRVNMIMAE SPGLITICLL GYLLSAEC

FIX Propeptide: -18 TVFLDHENAN KILNRPKR
              1    YNSGKLEEFV QGNLERECME EKCSFEEARE VFENTERTTE FWKQYVDGDQ

51    CESNPCLNGG SCKDDINSYE CWCPFGFEGK NCELDVTCNI KNGRCEQFCK

101    NSADNKVVCS CTEGYRLAEN QKSCEPAVPF PCGRVSVSQT SKLTRAETVF

151    PDVDYVNSTE AETILDNITQ STQSFNDFTR VVGGEDAKPG QFPWQVVLNG

201    KVDAFCGGSI VNEKWIVTAA HCVETGVKIT VVAGEHNIEE TEHTEQKRNV

251    IRIIPHHNYN AAINKYNHDI ALLELDEPLV LNSYVTPICI ADKEYTNIFL

301    KFGSGYVSGW GRVFHKGRSA LVLQYLRVPL VDRATCLRST KFTIYNNMFC

351    AGFHEGGRDS CQGDSGGPHV TEVEGTSFLT GIISWGEECA MKGKYGIYTK

401    VSRYVNWIKE KTKLTDKTHT CPPCPAPELL GGPSVFLFPP KPKDTLMISR

451    TPEVTCVVVD VSHEDPEVKF NWYVDGVEVH NAKTKPREEQ YNSTYRVVSV
```

```
501    LTVLHQDWLN GKEYKCKVSN KALPAPIEKT ISKAKGQPRE PQVYTLPPSR

551    DELTKNQVSL TCLVKGFYPS DIAVEWESNG QPENNYKTTP PVLDSDGSFF

601    LYSKLTVDKS RWQQGNVFSC SVMHEALHNH YTQKSLSLSP GK
```

B. Fc chain (SEQ ID NO: 4)
20 amino acid heterologous mouse Igκ light chain signal peptide
(underlined):

```
-20    METDTLLLWV LLLWVPGSTG
```

Mature Fc sequence (corresponding to human IgG1 amino acids 221 to 447,
EU numbering)

```
  1    DKTHTCPPCP APELLGGPSV FLFPPKPKDT LMISRTPEVT CVVVDVSHED

51    PEVKFNWYVD GVEVHNAKTK PREEQYNSTY RVVSVLTVLH QDWLNGKEYK

101    CKVSNKALPA PIEKTISKAK GQPREPQVYT LPPSRDELTK NQVSLTCLVK

151    GFYPSDIAVE WESNGQPENN YKTTPPVLDS DGSFFLYSKL TVDKSRWQQG

201    NVFSCSVMHE ALHNHYTQKS LSLSPGK
```

ASPAAPAPASPAAPAPSAPA (SEQ ID NO: 15),

AAPASPAPAAPSAPAPAAPS (SEQ ID NO: 16),

APSSPSPSAPSSPSPASPSS (SEQ ID NO: 17),

APSSPSPSAPSSPSPASPS (SEQ ID NO: 18),

SSPSAPSPSSPASPSPSSPA (SEQ ID NO: 19),

AASPAAPSAPPAAASPAAPSAPPA (SEQ ID NO: 20) and

ASAAAPAAASAAASAPSAAA (SEQ ID NO: 21)

What is claimed is:

1. A method of quantifying an amount of protein capable of exhibiting FIX activity which is in its activated form (activated FIX protein) in a test sample, the method comprising:
   (i) measuring thrombin generation activity for the test sample in the presence of FIX-deficient plasma or FIX-deficient blood and in the presence of exogenous thrombin, wherein the exogenous thrombin is present at a concentration of about 5 nM, and
   (ii) comparing the thrombin generation activity to a standard curve plotting known activated FIX protein levels to thrombin generation activity;
   wherein the measuring is performed in the absence of exogenous tissue factor (TF).

2. The method of claim 1, wherein the standard curve is constructed by
   (a) providing at least two reference samples, each containing a different, known concentration of activated FIX reference protein; and
   (b) measuring thrombin generation activity for each reference sample in the presence of FIX-deficient plasma or FIX-deficient blood and in the presence of exogenous thrombin, wherein the exogenous thrombin is present at a concentration of about 5 nM,
   wherein the measuring is performed in the absence of exogenous tissue factor (TF).

3. The method of claim 2, wherein the reference samples comprise from about 0 pM to about 200 pM of activated FIX protein.

4. The method of claim 2, wherein the reference samples comprise plasma derived activated FIX protein.

5. The method of claim 1, wherein the FIX-deficient plasma is human FIX-deficient plasma.

6. The method of claim 1, wherein the method is adapted to accurately measure less than about 100 pM.

7. The method of claim 1, wherein the test sample comprises a total amount of protein capable of exhibiting factor IX activity, wherein a portion of the total amount is present in its activated form.

8. The method of claim 1, wherein less than about 1% (w/w) of the total amount of the protein capable of exhibiting FIX activity is present in its activated form.

9. The method of claim 1, wherein the test sample contains less than 2 pM of activated FIX protein.

10. The method of claim 1, wherein the protein capable of exhibiting FIX activity comprises a heterologous moiety.

11. The method of claim 10, wherein the heterologous moiety comprises an immunoglobulin constant (Fc) region or a portion thereof, albumin or a fragment thereof, a straight or branched polyethylene glycol (PEG) moiety, a PAS sequence, and a hydroxyethyl starch (HES) moiety or a derivative thereof, or a combination thereof.

12. The method of claim 10, wherein the heterologous moiety comprises a first Fc region.

13. The method of claim 12, wherein the heterologous moiety further comprises a second Fc region, wherein the second Fc region is associated with the first Fc region by a covalent bond or a non-covalent bond.

14. The method of claim 10, wherein the protein capable of exhibiting FIX activity is a recombinant Factor IX-Fc fusion (FIX-Fc) protein.

15. The method of claim 1, wherein the measuring is performed in the presence of phospholipids.

\* \* \* \* \*